(12) United States Patent
Adamski-Werner et al.

(10) Patent No.: US 9,475,803 B2
(45) Date of Patent: *Oct. 25, 2016

(54) SWEET FLAVOR MODIFIER

(71) Applicant: Senomyx, Inc., San Diego, CA (US)

(72) Inventors: Sara Adamski-Werner, San Diego, CA (US); Vincent Darmohusodo, Encinitas, CA (US); Catherine Tachdjian, San Diego, CA (US); Donald Karanewsky, Escondido, CA (US); Goran Petrovic, San Diego, CA (US); Rachel Kimmich, San Diego, CA (US); Joseph Fotsing, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/768,167

(22) PCT Filed: Feb. 19, 2014

(86) PCT No.: PCT/US2014/017060
§ 371 (c)(1),
(2) Date: Aug. 14, 2015

(87) PCT Pub. No.: WO2014/130513
PCT Pub. Date: Aug. 28, 2014

(65) Prior Publication Data
US 2015/0376176 A1    Dec. 31, 2015

Related U.S. Application Data

(60) Provisional application No. 61/766,652, filed on Feb. 19, 2013.

(51) Int. Cl.
| C07D 417/14 | (2006.01) |
| C07D 417/12 | (2006.01) |
| A23L 1/226  | (2006.01) |
| A23L 1/302  | (2006.01) |
| C07D 471/04 | (2006.01) |
| C07D 473/00 | (2006.01) |
| C07D 498/04 | (2006.01) |

(52) U.S. Cl.
CPC ......... *C07D 417/12* (2013.01); *A23L 1/22685* (2013.01); *A23L 1/302* (2013.01); *C07D 417/14* (2013.01); *C07D 471/04* (2013.01); *C07D 473/00* (2013.01); *C07D 498/04* (2013.01); *A23V 2002/00* (2013.01)

(58) Field of Classification Search
CPC ........................... C07D 417/14; C07D 417/12
USPC ....................................................... 544/11
See application file for complete search history.

(56) References Cited

U.S. PATENT DOCUMENTS

| 3,278,532 A | 10/1966 | Houlihan |
| 3,843,804 A | 10/1974 | Evers et al. |
| 3,845,770 A | 11/1974 | Theeuwes et al. |
| 3,857,972 A | 12/1974 | Evers et al. |
| 3,916,899 A | 11/1975 | Theeuwes et al. |
| 3,957,783 A | 5/1976 | Hirohashi et al. |
| 3,960,860 A | 6/1976 | Katz et al. |
| 3,966,965 A | 6/1976 | Sellstedt et al. |
| 4,036,837 A | 7/1977 | Sellstedt et al. |
| 4,137,325 A | 1/1979 | Sellstedt et al. |
| 4,146,716 A | 3/1979 | Cox et al. |
| 4,196,207 A | 4/1980 | Webber et al. |
| 4,377,580 A | 3/1983 | Ueda et al. |
| 4,765,539 A | 8/1988 | Noakes et al. |
| 4,960,870 A | 10/1990 | Lehmann |
| 5,112,598 A | 5/1992 | Biesalski |

(Continued)

FOREIGN PATENT DOCUMENTS

| CN | 1033624 | 7/1989 |
| CN | 101035442 | 9/2007 |

(Continued)

OTHER PUBLICATIONS

Abdel-Megied et al., 1998, Synthesis of 5,6-Dihydronaphtho[1',2':4,5]Thieno[2,3-*d*]Pyrimidines, 5,6-Dihydronaphtho[1',2':4,5]Thieno [3,2-*e*] [1,2,4] Triazolo[1,5-*c*]Pyrimidines, and Some of Their Nucleosides, Sulfur Letters, 21(6):269-284.
Abdelrazek et al., 1992, Heterocyclic Synthesis With Nitriles: Synthesis of Some Novel Thiophene and Thieno[2,3-D]Pyrimidine Derivatives, Phosphorus, Sulfur and Silicon and the Related Elements, 72(1-4):93-97.
Albrecht et al., 1979, Synthesis of 1,2,6-Thiadiazine 1,1-Dioxides via Isoxazolylsulfamides, J. Org. Chem., 44:4191-4194.
Alderman, 1984, A Review of Cellulose Ethers in Hydrophilic Matrices for Oral Controlled-Release Dosage Forms, Int. J. Pharm. Tech. & Prod. Mfr., 5(3):1-9.

(Continued)

*Primary Examiner* — Kahsay Habte
(74) *Attorney, Agent, or Firm* — Knobbe Martens Olson & Bear LLP

(57) ABSTRACT

The present invention includes compounds having structural formula (Ia):

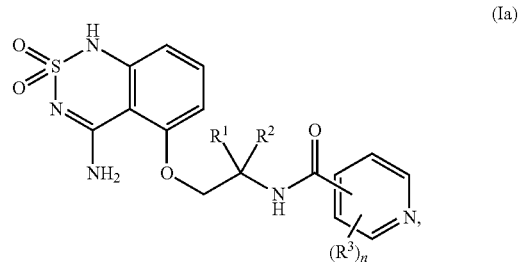

or salts or solvates thereof. These compounds are useful as sweet flavor modifiers. The present invention also includes compositions comprising the present compounds and methods of enhancing the sweet taste of compositions.

30 Claims, No Drawings

(56) References Cited

U.S. PATENT DOCUMENTS

| | | |
|---|---|---|
| 5,192,785 A | 3/1993 | Lo et al. |
| 5,380,541 A | 1/1995 | Beyts et al. |
| 5,504,095 A | 4/1996 | Nakane et al. |
| 5,556,611 A | 9/1996 | Biesalski |
| 5,698,155 A | 12/1997 | Grosswald et al. |
| 5,801,180 A | 9/1998 | Takase et al. |
| 5,950,619 A | 9/1999 | van der Linden et al. |
| 5,954,047 A | 9/1999 | Armer et al. |
| 5,970,974 A | 10/1999 | van der Linden et al. |
| 5,990,117 A | 11/1999 | Pamukcu et al. |
| 6,046,206 A | 4/2000 | Pamukcu et al. |
| 6,110,920 A | 8/2000 | Rochus et al. |
| 6,316,454 B1 | 11/2001 | Uckun et al. |
| 6,316,565 B1 | 11/2001 | Jung et al. |
| 6,475,544 B1 | 11/2002 | Hiramoto et al. |
| 6,852,862 B2 | 2/2005 | Nishizawa et al. |
| 7,105,650 B2 | 9/2006 | Adler |
| 7,476,399 B2 | 1/2009 | Tachdjian et al. |
| 7,915,410 B2 | 3/2011 | Johnson et al. |
| 7,928,111 B2 | 4/2011 | Tachdjian et al. |
| 8,541,421 B2 | 9/2013 | Tachdjian et al. |
| 8,586,733 B2 | 11/2013 | Tachdjian et al. |
| 8,633,186 B2 | 1/2014 | Tachdjian et al. |
| 8,968,708 B2 | 3/2015 | Tachdjian et al. |
| 9,000,054 B2 | 4/2015 | Tachdjian et al. |
| 9,000,151 B2 * | 4/2015 | Adamski-Werner . C07D 417/14 544/11 |
| 9,138,013 B2 | 9/2015 | Tachdjian et al. |
| 9,181,276 B2 | 11/2015 | Tachdjian et al. |
| 2002/0025366 A1 | 2/2002 | Jager et al. |
| 2003/0008344 A1 | 1/2003 | Adler et al. |
| 2003/0054448 A1 | 3/2003 | Adler et al. |
| 2003/0232407 A1 | 12/2003 | Zoller et al. |
| 2004/0127435 A1 | 7/2004 | Carson et al. |
| 2004/0197453 A1 | 10/2004 | Hirao et al. |
| 2005/0032158 A1 | 2/2005 | Adler et al. |
| 2005/0084506 A1 | 4/2005 | Tachdjian et al. |
| 2005/0196503 A1 | 9/2005 | Srivastava |
| 2006/0045953 A1 | 3/2006 | Tachdjian et al. |
| 2006/0083695 A1 | 4/2006 | Mori |
| 2006/0134693 A1 | 6/2006 | Servant et al. |
| 2006/0135552 A1 | 6/2006 | Malherbe et al. |
| 2006/0257543 A1 | 11/2006 | Tachdjian et al. |
| 2006/0257550 A1 | 11/2006 | Mori |
| 2007/0003680 A1 | 1/2007 | Tachdjian et al. |
| 2007/0010480 A1 | 1/2007 | Rusing et al. |
| 2007/0104701 A1 | 5/2007 | Ueda et al. |
| 2007/0104709 A1 | 5/2007 | Li et al. |
| 2008/0249189 A1 | 10/2008 | Atwal |
| 2008/0306053 A1 | 12/2008 | Tachdjian et al. |
| 2008/0306093 A1 | 12/2008 | Servant et al. |
| 2009/0286863 A1 | 11/2009 | Bruge et al. |
| 2011/0195170 A1 | 8/2011 | Shigemura et al. |
| 2011/0224155 A1 | 9/2011 | Tachdjian et al. |
| 2011/0230502 A1 | 9/2011 | Tachdjian et al. |
| 2011/0245353 A1 | 10/2011 | Tachdjian et al. |
| 2012/0041078 A1 | 2/2012 | Tachdjian et al. |
| 2014/0094453 A1 | 4/2014 | Tachdjian et al. |
| 2015/0257422 A1 | 9/2015 | Adamski-Werner et al. |
| 2015/0374020 A1 | 12/2015 | Tachdjian et al. |
| 2015/0376176 A1 | 12/2015 | Adamski-Werner et al. |

FOREIGN PATENT DOCUMENTS

| | | |
|---|---|---|
| CN | 101505601 | 8/2009 |
| DE | 22 58 403 | 6/1973 |
| EP | 0 227 450 | 7/1987 |
| EP | 0 530 994 | 3/1993 |
| EP | 0 584 797 | 3/1994 |
| EP | 0 887 344 | 12/1998 |
| ES | 0472163 | 3/1979 |
| ES | 8507558 | 12/1985 |
| GB | 951651 | 3/1964 |
| JP | 59-051290 | 3/1984 |
| JP | 63-87959 | 4/1988 |
| JP | 02-238856 | 9/1990 |
| WO | WO 89/00563 | 1/1989 |
| WO | WO 93/13104 | 7/1993 |
| WO | WO 98/06722 | 2/1998 |
| WO | WO 00/28952 | 5/2000 |
| WO | WO 00/71524 | 11/2000 |
| WO | WO 01/04086 | 1/2001 |
| WO | WO 03/001876 | 1/2003 |
| WO | WO 03/004992 | 1/2003 |
| WO | WO 03/007734 | 1/2003 |
| WO | WO 03/022214 | 3/2003 |
| WO | WO 03/051878 | 6/2003 |
| WO | WO 03/055866 | 7/2003 |
| WO | WO 03/076427 | 9/2003 |
| WO | WO 2004/056365 | 7/2004 |
| WO | WO 2005/015158 | 2/2005 |
| WO | WO 2005/016889 | 2/2005 |
| WO | WO 2005/116069 | 12/2005 |
| WO | WO 2005/123724 | 12/2005 |
| WO | WO 2006/076102 | 7/2006 |
| WO | WO 2006/084184 | 8/2006 |
| WO | WO 2006/113422 | 10/2006 |
| WO | WO 2006/113432 | 10/2006 |
| WO | WO 2007/004709 | 1/2007 |
| WO | WO 2007/047988 | 4/2007 |
| WO | WO 2007/071963 | 6/2007 |
| WO | WO 2008/003378 | 1/2008 |
| WO | WO 2008/154221 | 12/2008 |
| WO | WO 2012/001547 | 1/2012 |
| WO | WO 2012/021837 | 2/2012 |
| WO | WO 2012/054526 | 4/2012 |

OTHER PUBLICATIONS

Bamba et al., 1979, Release Mechanisms in Gelforming Sustained Release Preparations, Int. J. Pharm., 2:307-315.

Bancroft, 1978, Synthesis and Reduction of some 1H-2,1,3-Benzothiadiazin-4(3H)one 2,2-Dioxides, J. Heterocyclic Chem., 15:1521-1523.

Bandurco et al., 1987, Synthesis and Cardiotonic Activity of a Series of Substituted 4-Alkyl-2(1H)-quinazolinones 1421, J. Med. Chem., 30(8):1421-1426.

Belikov, 1993, Pharmaceutical Chemistry, High School, vol. 1, pp. 43-47.

Bellur et al., 2006, Synthesis of 4-(3-hydroxyalkyl)pyrimidines by ring transformation reactions of 2-alkylidenetetrahydrofurans with amidines, Tetrahedron, 62:5426-5434.

Berge et al., 1977, Pharmaceutical Salts, J. Pharm. Sci., 66(1):1-19.

Bhattacharya et al., 1994, Thieno[3',2':4,5][1]benzothieno[2,3-d]pyrimidine Derivatives: Synthesis and Conformation, Journal of the Chemical Society, Perkin Transactions 1: Organic and Bio-Organic Chemistry, 6:689-693.

Blackburn et al., 2006, Identification and characterization of amino-piperidinequinolones and quinazolinones as MCHr1 antagonists, Bioorg. & Med. Chem. Lett., 16:2621-2627.

Blanksma, 1908, Bereiding der oxymethyl (oxyethyl) cyaan-nitrobenzolen, Chemisch Weekblad, 5(44):789-795.

Boarland et al., 1951, Monosubstituted Pyrimidines, and the Action of Thiourea on Chloropyrimidines, J. Chem. Soc., 1218-1221.

Brodsky et al., 2005, Oxaziridine-mediated catalytic hydroxylation of unactivated 3° C-H bonds using hydrogen peroxide, J. Am. Chem. Soc., 127:15391-15393, and Supporting Material (16 pp.).

Brown, et al., 1990, Evolution of a Series of Peptidoleukotriene Antagonists: Synthesis and Structure-Activity Relationships of 1,6-Disubstituted Indoles and Indazoles, J. Med. Chem., 33(6):1771-1781.

Buck et al., 1991, A Novel Multigene Family May Encode Odorant Receptors: A Molecular Basis for Odor Recognition, Cell, 65(1):175-187.

Calkins, May 2010, 2,1-Benzothiazines: Preparation and Reactivity, PhD thesis, University of Missouri-Columbia, https://mospace.umsystem.edu/xmlui/handle/10355/830; 290 pp.

Campillo et al., 1998, A Novel Tetracyclic System Containing the 1,2,6-Thiadiazine Ring: Synthesis, Structural Assignment and Tautomeric Studies, Heterocycles, 48(9):1833-1840.

(56) References Cited

OTHER PUBLICATIONS

Campillo et al., 2004, A study of peculiar tautomerism of pyrido[2,3-c][1,2,6]thiadiazine 2,2-dioxide system, J. Mol. Struct., 678:83-89.
Chandrashekar et al., 2000, T2Rs Function as Bitter Taste Receptors, Cell, 100:703-711.
Chemical Abstracts Service, Registry No. 501002-78-4, Entered STN Mar. 31, 2003.
Cheng et al., 1958, Potential Purine Antagonists. XII. Synthesis of 1-Alkyl(aryl)-4,6-disubstituted Pyrazolo [3,4-d]pyrimidines, J. Org. Chem., 23:852-861.
Chien et al., 2004, Nucleosides XI. Synthesis and Antiviral Evaluation of 5'-Alkylthio-5'-deoxy Quinazolinone Nucleoside Derivatives as S-Adenosyl-L-homocysteine Analogs, Chem. Pharm. Bull., 52(12):1422-1426.
Clauss et al., 1970, Cycloadditionen Von Halogensulfonylisocyanaten an Acetylene, Tetrahedron Lett., 2:119-122.
Corbett et al., 2000, Novel 2,2-Dioxide-4,4-disubstituted-1,3-H-2,1,3-benzothiadiazines as Non-Nucleside Reverse Transcriptase Inhibitors, Bioorg. Med. Chem. Lett., 10:193-195.
Da Settimo et al., 2005, Naphtho[1,2-d]isothiazole Acetic Acid Derivatives as a Novel Class of Selective Aldose Reductase Inhibitors, J. Med. Chem., 48(22):6897-6907.
Dominguez et al., 2000, Efficient synthesis of 4,4-disubstituted-3,4-dihydro-1H-2,1,3-benzothiadiazine 2,2-dioxides, Tetrahedron Lett., 41:9825-9828.
Dorwald, 2005, Side Reactions in Organic Synthesis: A Guide to Successful Synthesis Design, Weinheim: Wiley-VCH Verlag GmbH & Co. KGaA, Preface.
Doucet-Personeni et al., 2001, A Structure-Based Design Approach to the Development of Novel, Reversible AChE Inhibitors, J. Med. Chem., 44(20):3203-3215.
During et al., 1989, Controlled Release of Dopamine from a Polymeric Brain Implant: In Vivo Characterization, Ann. Neurol., 25:351-356.
Elmegeed et al., 2005, Novel synthesizes aminosteroidal heterocycles intervention for inhibiting iron-induced oxidative stress, Eur. J. Med. Chem., 40:1283-1294.
El-Sherbeny et al., 2000, Novel Pyridothienopyrimidine and Pyridothienothiazine Derivatives as Potential Antiviral and Antitumor Agents, Med. Chem. Res., 10:122-135.
Etter et al., 1986, An Enolized Sulfonamide Formed by Strong Hydrogen Bonding to Triphenylphosphine Oxide, J. Org. Chem., 51(26):5405-5408.
Fan et al., 2004, Transient Silylation of the Guanosine O6 and Amino Groups Facilitates N-Acylation, Org. Lett., 6(15):2555-2557.
Francis et al., 1991, Anxiolytic Properties of Certain Annelated [1,2,4]Triazolo[1,5-c]pyrimidin-5(6H)-ones, J. Med. Chem., 34(9):2899-2906.
Frauli et al., 2006, Amino-Pyrrolidine Tricarboxylic Acids Give New Insight into Group III Metabotropic Glutamate Receptor Activation Mechanism, Molecular Pharmacology, 72(3):704-712.
Freidlander, et al., 1912, Uber brom- und methoxyderivate des indigos, Justus Liebigs Annalen der Chemie, 388:23-49.
Fuentes-Cabrera et al., 2005, Size-expanded DNA bases: an ab initio study of their structural and electronic properties, J. Phys. Chem. B, 109(44):21135-21139.
Garcia-Munoz et al., 1976, Synthesis of Purine-Like Ring Systems Derived From 1,2,6-Thiadiazine 1,1-Dioxide, J. Heterocyclic Chem., 13:793-796.
Goya et al., 1988, Synthesis and Cytostatic Screening of an $SO_2$ Analogue of Doridosine, Arch. Pharm. (Weinheim), 321:99-101.
Goya et al., 1988, Pteridine Analogues; Synthesis and Physico-Chemical Properties of 7-Oxopyrazino [2,3-c][1,2,6]thiadiazine 2,2-Dioxides, Liebigs Ann. Chem., 121-124.
Goya et al., 1986, Aminopyrido [2,3-c] [1,2,6]Thiadiazine 2,2-Dioxides: Synthesis and Physico-chemical Properties, Chemica Scripta, 26:607-611.
Goya et al., 1984, Fused 1,2,6-Thiadiazines: Tetrahydrobenzo[b]thieno[2,3-c] [1,2,6]thiadiazine 2,2-Dioxides, Arch. Pharm. (Weinheim), 317:777-781.
Goya et al., 1986, N-Glucosyl-5-Amino-4-Carbamoyl- and 4-Ethoxycarbonylimidazoles as Potential Precursors of 4-Oxoimidazo[4,5-c]-1,2,6-Thiadiazine 2,2-Dioxides, Heterocycles, 24:3451-3458.
Goya et al., 1987, Synthesis of 2S-Dioxo Isosteres of Purine and Pyrimidine Nucleosides IV. Selective Glycosylation of 4-Amino-5H-Imidazo [4,5-c]-1,2,6-Thiadiazine 2,2-Dioxide, Nucleosides & Nucleotides, 6(3), 631-642.
Goya et al., 1985, Fused thiadiazines, CAPLUS Accession No. 1987:18628, 2 pages, abstract of ES 531159 A1.
Guedira et al., 1992, Ambident behavior of ketone enolate anions in $S_NAr$ substitutions on Fluorobenzonitrile Substrates, J. Org. Chem., 57(21):5577-5585, and Supporting Material.
Harris et al., 1990, Antifolate and Antibacterial Activities of 5-Substituted 2,4-diaminoquinazolines, J. Med. Chem., 33(1):434-444.
Hauser et al., 1953, Synthesis of 5-Phenyl-4,6-Dimethyl-2-Pyrimidol and Derivatives From the Cyclization of Urea With 3-Phenyl-2,4-Pentanedione, J. Org. Chem., 18:588-593.
Hirohashi et al., 1975, Nuclear Magnetic Resonance Studies of Bicyclic Thiophene Derivatives. I. Ring Current Effects of the Benzene Ring on the Hα and Hβ signals of the Thiophene Ring in Benzoylthiophene, Thienopyrimidine, and Thienodiazepine Derivatives, Bull. Chem. Soc. Jpn., 48(1):147-156.
Hirota et al., 2003, Synthesis and Biological Evaluation of 2,8-Disubstituted 9-Benzyladenines: Discovery of 8-Mercaptoadenines as Potent Interferon-Inducers, Bioorg. Med. Chem., 11:2715-2722.
Hoon et al., 1991, Putative Mammalian Taste Receptors: A Class of Taste-Specific GPCRs with Distinct Topographic Selectivity. Cell, 96:541-551.
Howard et al., 1989, Intracerebral drug delivery in rats with lesion-induced memory deficits, J. Neurosurg., 71:105-112.
Hu et al., 2004, Organic Reactions in Ionic Liquids: Gewald Synthesis of 2-Aminothiophenes Catalyzed by Ethylenediammonium Diacetate, Synth. Commun., 34(20):3801-3806.
Jordan, 2003, Tamoxifen: A Most Unlikely Pioneering Medicine, Nature Reviews: Drug Discovery, 2003, 2:205-213.
Jung et al., 2006, Discovery of Novel and Potent thiazoloquinazolines as Selective Aurora A and B Kinase Inhibitors, J. Med. Chem., 49(3):955-970.
Justoni et al., 1951, Studi Su Sostanze a Presumibile Azione Chemioterapica Antitubercolare, II Farmaco, 6:849-858.
Kamal et al., 1988, Cyclization of 2-(Carbamoyloxy)- and 2-(Sulfamoyloxy)benzoates Mediated by Liver Microsomes, J. Org. Chem., 53(17):4112-4114.
Kamal et al., 1989, Enzymatic Cyclization of 2-(Carbamoyloxy)Benzoates, 2-(Sulfamoyloxy)-Benzoates and 2-(Carbamoyloxy)Benzopenones With Yeast and Lipase, Heterocycles, 29(7):1391-1397.
Kanbe et al., 2006, Discovery of thiochroman derivatives bearing a carboxy-containing side chain as orally active pure antiestrogens, Bioorg. & Med. Chem. Lett., 16:4090-4094.
Kanuma et al., 2005, Lead optimization of 4-(dimethylamino)quinazolines, potent and selective antagonists for the melanin-concentrating hormone receptor 1, Bioorg. & Med. Chem. Lett., 15:3853-3856.
Khabnadideh et al., 2005, Design, synthesis and evaluation of 2,4-diaminoquinazolines as inhibitors of trypanosomal and leishmanial dihydrofolate reductase, Bioorg. Med. Chem., 13:2637-2649.
Khatoon et al., 2004, Pyrido [2,3-d]pyrimidines and their ribofuranosides: synthesis and antimicrobial evaluations, Indian J. Heterocycl. Chem., 13(4):331-334.
Klaubert et al., 1982, N-(Aminophenyl)oxamic Acids and Esters as Potent, Orally Active Antiallergy Agents, J. Med. Chem., 24(6):742-748.
Klinger et al., 2006, Inhibition of Carbonic Anhydrase-II by Sulfamate and Sulfamide Groups: An Investigation Involving Direct Thermodynamic Binding Measurements, J. Med. Chem., 49(12):3496-3500.

(56) References Cited

OTHER PUBLICATIONS

Kokrashvili et al., 2009, Taste signaling elements expressed in gut enteroendocrine cells regulate nutrient-responsive secretion of gut hormones, Am. J. Clin Nutr., 90(suppl):1S-4S.
Kyriazis et al., 2012, Sweet taste receptor signaling in beta cells mediates fructose-induced potentation of glucose-stimulated insulin secretion, PNAS Early Edition, 9 pp. and Supporting Material.
Kyte et al., 1982, A Simple Method for Displaying the Hydropathic Character of a Protein, J. Mol. Biol., 157:105-132.
Langer et al., 1983, Chemical and Physical Structure of Polymers as Carriers for Controlled Release of Bioactive Agents: A Review, J. Macromol. Sci., Rev. Macromol. Chem. Phys., C23(1):61-126.
Langer, 1990, New Methods of Drug Delivery, Science, 249:1527-1533.
Lee et al., 2006, Acetonitrile-Mediated Synthesis of 2,4-Dichloroquinoline from 2-Ethynyl-aniline and 2,4-Dichloroquinazoline from Anthranilonitrile, Synlett, 1:65-68.
Leistner et al., 1989, Polycyclic azines with heteroatoms in the 1- and 3-positions, Part 22. A facile synthesis of 2-(alkylthio)-4-aminothieno[2,3-d]pyrimidines, Archiv. der Pharmazie (Weinheim, Germany), 322(4):227-230.
Levy et al., 1985, Inhibition of Calcification of Bioprosthetic Heart Valves by Local Controlled-Release Diphosphonate, Science, 228:190-192.
Li et al., 2002, Human receptors for sweet and umami taste, Proc. Natl. Acad. Sci. USA, 99(7):4692-4696.
Li et al., Preformulation studies for the Development of a Parenteral Liquid Formulation of an Antitumor Agent, AG337, PDA Journal of Pharmaceutical Science and Technology, 51(5):181-186.
Linkies et al., 1990, Ein neues Verfahren zur Herstellung von 6-Methyl-1,2,3-oxathiazin-4(3H)-on-2,2-dioxid Kaliumsalz (Acesulfam-K), Synthesis, 405-406.
Liu et al., 2007, Discovery of a new class of 4-anilinopyrimidines as potent c-Jun N-terminal kinase inhibitors: Synthesis and SAR studies, Bioorg. & Med. Chem. Lett., 17:668-672.
Martinez et al., 2000, Benzothiadiazine Dioxide Dibenzyl Derivatives as Potent Human Cytomegalovirus Inhibitors: Synthesis and Comparative Molecular Field Analysis, J. Med. Chem., 43(17):3218-3225.
Meyer et al., 1979, Synthesis of fused [1,2,6]Thiadiazine 1,1-Dioxides as Potential Transition-State Analogue Inhibitors of Xanthine Oxidase and Guanase, J. Med. Chem., 22(8):944-948.
Naganawa et al., 2006, Further optimization of sulfonamide analogs as EP1 receptor antagonists: Synthesis and evaluation of bioisosteres for the carboxylic acid group, Bioorg. Med. Chem., 14:7121-7137.
Nie et al., 2005, Distinct Contributions of T1R2 and T1R3 Taste Receptor Subunits to the Detection of Sweet Stimuli, Curr. Biol., 15(21):1948-1952.
Pal et al., 2005, Synthesis and Cyclooxygenase-2 (COX-2) Inhibiting Properties of 1,5-Diarylpyrazoles Possessing N-Substitution on the Sulfonamide (-$SO_2NH_2$) Moiety, Letters in Drug Design & Discovery 2:329-340.
Patil, 1980, The synthesis of Thieno[2,3-d]pyrimidine Nucleosides related to the Naturally Occurring Nucleosides Cytidine and Uridine, Journal of the Chemical Society, Perkin Transactions 1: Organic and Bio-Organic Chemistry, 9:1853-1858.
Petersen et al., 1996, Synthesis of Heterocycles Containing Two Cytosine or Two Guanine Base-Pairing Sites: Novel Tectons for Self-Assembly, Bioorg. Med. Chem., 4(7):1107-1112.
PubChemCompound, datasheets, retrieved from internet: cm Nos. 12715714 (Feb. 8, 2007), 12715732 (Feb. 8, 2007); 12715736 (Feb. 8, 2007); 13320183 (Feb. 8, 2007); 19818639 (Dec. 5, 2007); 19851977 (Dec. 5, 2007); 22136223 (Dec. 5, 2007); 22664816 (no longer available online); 24777415-24777421 (May 12, 2008); 24777776-24777778 (May 12, 2008).
Rad-Moghadam et al., 2006, One-pot Three-component Synthesis of 2-Substituted 4-Aminoquinazolines, J. Heterocyclic Chem., 43:913-916.

Raleigh et al., 1999, Pharmacokinetics of Isotretinoin (ISO) in Rats Following Oral Dosing or Aerosol Inhalation, British J. Cancer 80, Suppl. 2:96 Abstract No. P269.
Rasmussen et al., 1978, The Electrophilic Addition of Chlorosulfonyl Isocyanate to Ketones. A Convenient Synthesis of Oxazines, Oxathiazines, and Uracils, J. Org. Chem., 38(11):2114-2115.
Reddy et al., 1988, An Efficient Synthesis of 3,4-Dihydro-4-Imino-2(1H)-Quinazolinones, Synthetic Commun., 18:525-530.
Robinson et al., 2006, Sulfonamide Ligands Attained Through Opening of Saccharin Derivatives, Eur. J. Org. Chem., 19:4483-4489.
Rodriguez-Hahn et al., 1984, A Study of the Thorpe-Ziegler Reaction in Very Mild Conditions, Synthetic Commun., 14:967-972.
Rosowsky et al., 1966, Quinazolines. III. Synthesis of 1,3-Diaminobenzo[f]quinazoline and Related Compounds, J. Org. Chem., 31:2607-2613.
Roy et al., 2006, Auto-Redox Reaction: Tin(II) Chloride-Mediated One-Step Reductive Cyclization Leading to the Synthesis of Novel Biheterocyclic 5,6-Dihydro-quinazolino[4,3-b]quinazolin-8-ones with Three-Point Diversity, J. Org. Chem., 71(1):382-385.
Saudek et al., 1989, A Preliminary Trial of the Programmable Implantable Medication System for Insulin Delivery, N. Engl. J. Med., 321(9):574-579.
Seijas et al., 2000, Microwave enhanced synthesis of 4-aminoquinazolines, Tetrahedron Lett., 41:2215-2217.
Sharma et al., 2006, Synthesis and QSAR studies on 5-[2-(2-methylprop 1-enyl)-1H benzimidazol-1yl]-4,6-diphenyl-pyrimidin-2-(5H)-thione derivatives as antibacterial agents, Eur. J. Med. Chem., 41:833-840.
Silve et al., 2005, Delineating a $Ca^{2+}$ Binding Pocket within the Venus Flytrap Module of the Human Calcium Sensing Receptor, J. Biol. Chem., 280(45):37917-37923.
Smith et al., 2001, March's Advanced Organic Chemistry, pp. 479-480, 506-507, 510-511, 576-577, 862-865,1179-1180 and 1552-1553, $5^{th}$ Edition, John Wiley & Sons, Inc.
Spatola, 1983, Peptide Backbone Modifications: A Structure-Activity Analysis of Peptides Containing Amide Bond Surrogates, In Chemistry and Biochemistry of Amino Acids, Peptides and Proteins, 7:267-357, Marcell Dekker, NY.
Srivastava et al., 1999, Solid Phase Synthesis of Structurally Diverse Pyrimido[4,5-d] Pyrimidines for the Potential Use in Combinatorial Chemistry, Bioorg. Med. Chem. Lett., 9:965-966.
Thurmond et al., 2008, Synthesis and Biological Evaluation of Novel 2,4-Diaminoquinazoline Derivatives as SMN2 Promoter Activator for the Potential Treatment of Spinal Muscular Atrophy, J. Med. Chem., 51(3):449-469.
Tripathi et al., 1987, Reaction of Flavanones with Chlorosulphonyl Isocyanate, Indian J. Chem. Sect. B, 26B:1082-1083.
Trivedi et al., 1989, $C2,N^6$—Distributed Adenosines: Synthesis and Structure-Activity Relationships, J. Med. Chem., 32(8):1667-1673.
Tunaley, 1989, Chapter 11. Perceptual Characteristics of Sweeteners, in Progress in Sweeteners, Greby ed., Elsevier Applied Science, London and New York. pp. 291-309.
Uehling et al., 2006, Biarylaniline Phenethanolamines as Potent and Selective $\beta_3$ Adrenergic Receptor Agonists, J. Med. Chem., 49(9):2758-2771.
Verma et al., 2000, Osmotically Controlled Oral Drug Delivery, Drug Dev. Ind. Pharm., 26(7):695-708.
Vippagunta et al., 2001, Crystalline solids, Adv. Drug Deliv. Rev., 48:3-26.
Wiet et al., 1993, Fat Concentration Affects Sweetness and Sensory Profiles of Sucrose, Sucralose, and Aspartame, J. Food Sci., 58(3):599-602.
Wiet et al., 1997, Does chemical modification of tastants merely enhance their intrinsic taste qualities? Food Chem., 58(4):305-311.
Wilson et al., 2007, Synthesis of 5-deazaflavin derivatives and their activation of p53 in cells, Bioorg. & Med. Chem. 15:77-86.
Wilson, 2000, Traceless Solid-Phase Synthesis of 2,4-Diaminoquinazolines, Org. Lett., 3:585-588.
Winkler et al., 2005, Synthesis and microbial transformation of β-amino nitriles, Tetrahedron, 61:4249-4260.

(56) References Cited

OTHER PUBLICATIONS

Wright, 1965, The Synthesis of 2,1,3-Benzothiadiazine 2,2-Dioxides and 1,2,3-Benzoxathiazine 2,2-Dioxides, J. Org. Chem., 30(11):3960-3962.

Xu et al., 2006, Oxidative cyclization of N-alkyl-o-methyl-arenesulfonamides to biologically important saccharin derivatives, Tetrahedron, 62:7902-7910.

Xu et al., 1999, Purine and Pyrididine Nucleotides Inhibit a Noninactivating K+ Current and Depolarize Adrenal Cortical Cells through a G Protein-coupled Receptor, Mol. Pharmacol., 55:364-376.

Yamada et al., 2005, Discovery of Novel and Potent Small-Molecule Inhibitors of NO and Cytokine Production as Antisepsis Agents: Synthesis and Biological Activity of Alkyl 6-(N-Substituted sulfamoyl)cyclohex-1-ene-1-carboxylate, J. Med. Chem., 48(23):7457-7467.

Yoshizawa et al., 2002, Efficient solvent-free Thorpe reactions, Green Chem., 4:68-70.

Zunszain et al., 2005, Search for the pharmacophore in prazosin for Transport-P, Bioorg. & Med. Chem., 13:3681-3689.

Office Action dated Oct. 26, 2015 in U.S. Appl. No. 14/670,202.

International Search Report dated Jun. 23, 2014 in PCT/US14/017060.

CAS Registry No. 92932-14-4, May 18, 2016.

Zhu et al., 2006, The chemical development of CHIR-258, Chimia, 60(9):584-592.

\* cited by examiner

SWEET FLAVOR MODIFIER

CROSS-REFERENCE TO RELATED APPLICATION

This application claims benefit of priority to U.S. Provisional Application No. 61/766,652, filed on Feb. 19, 2013 and entitled "Sweet Flavor Modifier", the content of which are hereby incorporated by reference in its entirety for all purposes.

FIELD OF THE INVENTION

The invention relates to compounds suitable for modifying receptors and their ligands associated with chemosensory or chemosensory related sensation or reaction.

BACKGROUND OF THE INVENTION

The taste system provides sensory information about the chemical composition of the external world. Taste transduction is one of the most sophisticated forms of chemical-triggered sensation in animals. Signaling of taste is found throughout the animal kingdom, from simple metazoans to the most complex of vertebrates. Mammals are believed to have five basic taste modalities: sweet, bitter, sour, salty, and umami (the taste of monosodium glutamate, a.k.a. savory taste).

Obesity, diabetes, and cardiovascular disease are health concerns on the rise globally, but are growing at alarming rates in the United States. Sugar and calories are key components that can be limited to render a positive nutritional effect on health. High-intensity sweeteners can provide the sweetness of sugar, with various taste qualities. Because they are many times sweeter than sugar, much less of the sweetener is required to replace the sugar.

High-intensity sweeteners have a wide range of chemically distinct structures and hence possess varying properties, such as, without limitation, odor, flavor, mouthfeel, and aftertaste. These properties, particularly flavor and aftertaste, are well known to vary over the time of tasting, such that each temporal profile is sweetener-specific (Tunaley, A., "Perceptual Characteristics of Sweeteners", Progress in Sweeteners, T. H. Grenby, Ed. Elsevier Applied Science, 1989).

Sweeteners such as saccharin and 6-methyl-1,2,3-oxathiazin-4(3H)-one-2,2-dioxide potassium salt (acesulfame potassium) are commonly characterized as having bitter and/or metallic aftertastes. Products prepared with 2,4-dihydroxybenzoic acid are claimed to display reduced undesirable aftertastes associated with sweeteners, and do so at concentrations below those concentrations at which their own tastes are perceptible. Also, high intensity sweeteners such as sucralose and aspartame are reported to have sweetness delivery problems, i.e., delayed onset and lingering of sweetness (S. G. Wiet, et al., J. Food Sci., 58(3):599-602, 666 (1993)).

It has been reported that an extra-cellular domain, e.g., the Venus flytrap domain of a chemosensory receptor, especially one or more interacting sites within the Venus flytrap domain, is a suitable target for compounds or other entities to modulate the chemosensory receptor and/or its ligands. Certain compounds have been reported to be modulators of the chemosensory receptors in T1R family and/or their ligands and are described in the four patent applications listed below.

(1) U.S. patent application Ser. No. 11/760,592, entitled "Modulation of Chemosensory Receptors and Ligands Associated Therewith", filed Jun. 8, 2007; (2) U.S. Pat. No. 7,928,111, entitled "Modulation of Chemosensory Receptors and Ligands Associated Therewith", issued Apr. 19, 2011; and (3) International Application No. PCT/US2008/065650, entitled "Modulation of Chemosensory Receptors and Ligands Associated Therewith", filed Jun. 3, 2008. The content of these applications are herein incorporated by reference in their entirety for all purposes.

There is a need in the art to develop novel and inventive compounds suitable for modifying receptors and/or their ligands associated with chemosensory or chemosensory related sensation or reaction.

SUMMARY OF THE INVENTION

In one embodiment, the present invention provides a compound having structural Formula (I):

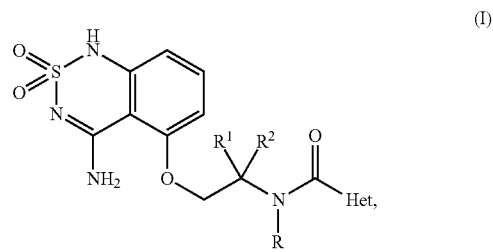

or a salt or solvate thereof; wherein, $R^1$ and $R^2$ are independently C1 to C4 alkyl; or alternatively, $R^1$ and $R^2$, together with the carbon atom to which they are attached, form a C3 to C7 cycloalkyl; R is hydrogen or C1 to C6 alkyl; and Het is heteroaryl or substituted heteroaryl.

In another embodiment, the present invention provides an ingestible composition comprising a compound of the present invention; and optionally an ingestibly acceptable excipient.

In another embodiment, the present invention provides a method of increasing the sweet taste of an ingestible composition comprising contacting the ingestible composition thereof with a compound of the present invention to form a modified ingestible composition. In the method, the present compound can be a chemosensory receptor modifier, a chemosensory receptor ligand modifier, or both, i.e., a partial chemosensory receptor modifier and partial chemosensory receptor ligand modifier. For example, the present compound can be a sweet receptor agonist, or a sweet enhancer, or a partial sweet receptor agonist and partial sweet enhancer.

In another embodiment, the present invention provides a sweet enhancing composition, comprising a compound of the present invention in an amount effective to provide sweetening in combination with a first amount of sweetener, wherein the sweetening is more than the sweetening provided by the first amount of sweetener without the compound.

In another embodiment, the present invention provides a flavoring concentrate formulation comprising i) as flavor modifying ingredient, a compound of the present invention; ii) a carrier; and iii) optionally at least one adjuvant.

DETAILED DESCRIPTION OF THE INVENTION

These and other embodiments, advantages, and features of the present invention are provided in the sections below.

Unless defined otherwise, all technical and scientific terms used herein have the same meaning as commonly understood by one of ordinary skill in the art to which this invention belongs.

Definitions

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. The term "alkyl" includes "cycloalkyl" as defined herein below. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 12 carbon atoms ($C_1$-$C_{12}$ alkyl). In still other embodiments, an alkyl group comprises from 1 to 6 carbon atoms ($C_1$-$C_6$ alkyl). It is noted that when an alkyl group is further connected to another atom, it becomes an "alkylene" group. In other words, the term "alkylene" refers to a divalent alkyl. For example, —$CH_2CH_3$ is an ethyl, while —$CH_2CH_2$— is an ethylene. That is, "Alkylene," by itself or as part of another substituent, refers to a saturated or unsaturated, branched, straight-chain or cyclic divalent hydrocarbon radical derived by the removal of two hydrogen atoms from a single carbon atom or two different carbon atoms of a parent alkane, alkene or alkyne. The term "alkylene" includes "cycloalkylene" as defined herein below. The term "alkylene" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanylene," "alkenylene," and "alkynylene" are used. In some embodiments, an alkylene group comprises from 1 to 20 carbon atoms ($C_1$-$C_{20}$ alkylene). In other embodiments, an alkylene group comprises from 1 to 12 carbon atoms ($C_1$-$C_{12}$ alkylene). In still other embodiments, an alkylene group comprises from 1 to 6 carbon atoms ($C_1$-$C_6$ alkylene).

"Alkanyl," by itself or as part of another substituent, refers to a saturated branched, straight-chain or cyclic alkyl radical derived by the removal of one hydrogen atom from a single carbon atom of a parent alkane. The term "alkanyl" includes "cycloakanyl" as defined herein below. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The term "alkenyl" includes "cycloalkenyl" as defined herein below. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. "Alkoxy," by itself or as part of another substituent, refers to a radical of the formula —O—$R^{199}$, where $R^{199}$ is alkyl or substituted alkyl as defined herein.

"Acyl" by itself or as part of another substituent refers to a radical —$C(O)R^{200}$, where $R^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl), i.e., 6- to 20-membered aryl ring. In other embodiments, an aryl group comprises from 6 to 15 carbon atoms ($C_6$-$C_{15}$ aryl), i.e., 6- to 15-membered aryl ring. In still other embodiments, an aryl group comprises from 6 to 15 carbon atoms ($C_6$-$C_{10}$ aryl), i.e., 6- to 10-membered aryl ring.

"Arylalkyl" or "aralkyl" by itself or as part of another substituent, refers to an acyclic alkyl group in which one of the hydrogen atoms bonded to a carbon atom, typically a terminal or $sp^3$ carbon atom, is replaced with an aryl group as, as defined herein. That is, an arylalkyl or aralkyl group is composed of an aryl group connected to an alkylene group which is further attached to other portion of a molecule. The alkylene group in the arylalkyl or aralkyl group can be an alkylene having 1 to 12 carbon atoms, or 1 to 6 carbon atoms, or 1 to 3 carbon atoms. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Cycloalkyl," or "Carbocyclyl," by itself or as part of another substituent, refers to a saturated or unsaturated cyclic alkyl radical, as defined herein. Similarly, "Cycloalkylene," or "Carbocyclylene," by itself or as part of another substituent, refers to a saturated or unsaturated cyclic alkylene radical, as defined herein. Where a specific level of saturation is intended, the nomenclature "cycloalkanyl", "cycloalkenyl", or "cycloalkynyl" is used. Typical cycloalkyl groups include, but are not limited to, groups derived from cyclopropane, cyclobutane, cyclopentane, cyclohexane, and the like. In some embodiments, the cycloalkyl group comprises from 3 to 10 ring atoms ($C_3$-$C_{10}$ cycloalkyl). In other embodiments, the cycloalkyl group comprises from 3 to 7 ring atoms ($C_3$-$C_7$ cycloalkyl). The cycloalkyl may be further substituted by one or more heteroatoms including, but not limited to, N, P, O, S, and Si, which attach to the carbon atoms of the cycloalkyl via monovalent or multivalent bond.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Similarly, "Heteroalkylene," "Heteroalkanylene," "Heteroalkenylene" and "Heteroalkynylene," by themselves or as part of other substituents, refer to alkylene, alkanylene, alkenylene and alkynyenel groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof.

The heteroatoms or heteroatomic groups may be placed at any interior position of the alkyl, alkenyl or alkynyl groups. Typical heteroatomic groups which can be included in these groups include, but are not limited to —O—, —S—, —O—O—, —S—S—, —O—S—, —NR$^{201}$R$^{202}$—, =N—N=, —N=N—, —N=N—NR$^{203}$R$^{204}$, —PR$^{205}$—, —P(O)$_2$—, —POR$^{206}$—, —O—P(O)$_2$—, —SO—, —SO$_2$—, —SnR$^{207}$R$^{208}$— and the like, where R$^{201}$, R$^{202}$, R$^{203}$, R$^{204}$, R$^{205}$, R$^{206}$, R$^{207}$ and R$^{208}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Cycloheteroalkyl," or "Heterocyclyl," by itself or as part of another substituent, refers to a saturated or unsaturated cyclic alkyl radical in which one or more carbon atoms (and optionally any associated hydrogen atoms) are independently replaced with the same or different heteroatom. Similarly, "Cycloheteroalkylene," or "Heterocyclylene," by itself or as part of another substituent, refers to a saturated or unsaturated cyclic alkylene radical in which one or more carbon atoms (and optionally any associated hydrogen atoms) are independently replaced with the same or different heteroatom. The cycloheteroalkyl may be further substituted by one or more heteroatoms including, but not limited to, N, P, O, S, and Si, which attach to the carbon atoms of the cycloheteroalkyl via monovalent or multivalent bond. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, and the like. In some embodiments, the cycloheteroalkyl group comprises from 3 to 10 ring atoms (3-10 membered cycloheteroalkyl) In other embodiments, the cycloalkyl group comprise from 5 to 7 ring atoms (5-7 membered cycloheteroalkyl). A cycloheteroalkyl group may be substituted at a heteroatom, for example, a nitrogen atom, with a ($C_1$-$C_6$) alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteroalkyl group may be attached to the remainder of the molecule via a ring carbon atom or a ring heteroatom. In one embodiment, heterocyclyl includes "azacyclyl" which denotes a heterocycle having one or more nitrogen atoms in the ring. An azacyclyl may also contain additional other heteroatom(s), such as oxygen and sulfur. An azacyclyl may be a four, five, six, seven, or eight-membered ring having one or more nitrogen atoms, such as azetidine, imidazolidine, morpholine, piperazine, piperidine, pyrazolidine, pyrrolidone, diazepane, azepane, diazocane, and azocane.

"Amine" refers to a moiety having structural formula of —NH$_2$. "Substituted amine" refers to a moiety having structural formula of —NR$^X$R$^Y$, wherein R$^X$ and R$^Y$ are independently hydrogen (provided that R$^X$ and R$^Y$ are not both hydrogen), alkyl, substituted alkyl, heteroalkyl, substituted heteroalkyl, aryl, substituted aryl, arylalkyl, substituted arylalkyl, heteroaryl, substituted heteroaryl, heteroarylalkyl, substituted heteroarylalkyl, carbocyclyl, substituted carbocyclyl, heterocyclyl, substituted heterocyclyl, acyl, substituted acyl, imine, substituted imine, amidine, e.g., —C(NH)—NH$_2$, or substituted amidine. In one embodiment of —NR$^X$R$^Y$, R$^X$ is hydrogen, and R$^Y$ is alkyl, substituted alkyl, heteroalkyl, substituted heteroalkyl, aryl, substituted aryl, arylalkyl, substituted arylalkyl, heteroaryl, substituted heteroaryl, heteroarylalkyl, substituted heteroarylalkyl, carbocyclyl, substituted carbocyclyl, heterocyclyl, substituted heterocyclyl, acyl, substituted acyl, imine, substituted imine, amidine, e.g., —C(NH)—NH$_2$, or substituted amidine.

"Compounds" refers to compounds encompassed by structural formulae disclosed herein, such as (I), (Ia), and (Ib) and includes any subgeneric and specific compounds within these formulae whose structures are disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The term "tautomer" as used herein refers to isomers that change into one another with great ease so that they can exist together in equilibrium. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

"Halo," by itself or as part of another substituent refers to a radical —F, —Cl, —Br or —I.

"Heteroaryl," by itself or as part of another substituent, refers to a monovalent heteroaromatic or partial heteroaromatic radical derived by the removal of one hydrogen atom from a single atom of a parent heteroaromatic or partial heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. That is, a heteroarylalkyl group is composed of a heteroaryl group connected to an alkylene group which is further attached to other portion of a molecule. The alkylene group in the heteroarylalkyl group can be an alkylene having 1 to 12 carbon atoms, or 1 to 6 carbon atoms, or 1 to 3 carbon atoms. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanylene, alkenylene or alkynylene moiety of the heteroarylalkyl is ($C_1$-$C_6$) alkylene and the heteroaryl moiety is a 5-15-membered heteroaryl. In other embodiments, the heteroarylalkyl is a 6-13 membered heteroarylalkyl, e.g., the alkanylene, alkenylene or alkynylene moiety is ($C_1$-$C_3$) alkylene and the heteroaryl moiety is a 5-10 membered heteroaryl.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate" means a compound formed by solvation (the combination of solvent molecules with molecules or ions of the solute), or an aggregate that consists of a solute ion or molecule, i.e., a compound of the present invention, with one or more solvent molecules. When water is the solvent, the corresponding solvate is "hydrate".

"N-oxide", also known as amine oxide or amine-N-oxide, means a compound that derives from a compound of the present invention via oxidation of an amine group of the compound of the present invention. An N-oxide typically contains the functional group $R_3N^+$—$O^-$ (sometimes written as $R_3N$=O or $R_3N{\rightarrow}O$) or $R_2N^+$—$O^-$ (sometimes written as $R_2N$=O or $R_2N{\rightarrow}O$) when the two R groups are in a heteroaryl ring system.

"Substituted," when used to modify a specified group or radical, means that one or more hydrogen atoms of the specified group or radical are each, independently of one another, replaced with the same or different substituent(s). The term "optionally substituted" means substitued or non-substituted (i.e., unsubstituted). For example, an optionally substituted azacyclic ring means the azacyclic ring can be substituted or nonsubstituted. Substituent groups useful for substituting saturated carbon atoms in the specified group or radical include, but are not limited to —$R^3$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-$C(O)OR^b$, -alkylene-$C(O)NR^bR^b$, and —$CH_2$—$CH_2$—C(O)—$CH_3$. The one or more substituent groups, taken together with the atoms to which they are bonded, may form a cyclic ring including cycloalkyl and cycloheteroalkyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^3$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined. Substituent groups from the above lists useful for substituting other specified groups or atoms will be apparent to those of skill in the art.

The above-referenced substituents as represented by chemical formulas are also readily recognized by their chemical names known to one skilled in the art. For example, those substituents include alkyl, heteroalkyl, halo, hydroxyl, alkoxy, amino, alkylamino, cyano, nitro, haloalkyl, carboxylic acid, amide, ester, acyl, thiol, alkylthio, sulfonamide, and etc.

The substituents used to substitute a specified group can be further substituted, typically with one or more of the same or different groups selected from the various groups specified above.

"Vehicle" refers to a diluent, adjuvant, excipient or carrier with which a compound is administered.

As used herein, an "ingestible composition" includes any substance that, either alone or together with another substance, can be taken by mouth whether intended for consumption or not. The ingestible composition includes both "food or beverage products" and "non-edible products". By "Food or beverage products", it is meant any edible product intended for consumption by humans or animals, including solids, semi-solids, or liquids (e.g., beverages). The term "non-edible products" or "noncomestible composition" includes any product or composition that can be taken by humans or animals for purposes other than consumption or as food or beverage. For example, the non-edible product or noncomestible composition includes supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as sweetened lip balms and other personal care products that may or may not contain any sweetener.

A "ingestibly acceptable carrier or excipient" is a medium and/or composition that is used to prepare a desired dispersed dosage form of the inventive compound, in order to administer the inventive compound in a dispersed/diluted form, so that the biological effectiveness of the inventive compound is maximized. The medium and/or composition may be in any form depending on the intended use of a product, e.g., solid, semi-solid, liquid, paste, gel, lotion, cream, foamy material, suspension, solution, or any combinations thereof (such as a liquid containing solid contents). The solid can be in various forms, such as powders or granules, which may be prepared by crystallization, condensation, evaporation, or spray-dry process, or any combination thereof. Ingestibly acceptable carriers includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids and their alkyl esters, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids; surface active agents; isotonic agents; thickening or emulsifying agents, preservatives; solid binders; lubricants and the like.

According to the present invention, a chemosensory receptor can be any receptor associated with chemosensory sensation or chemosensory ligand triggered signal transduction, e.g., via taste receptors or taste related receptors expressed in taste bud or internal organs of the body, such as gastrointestinal tract, etc. In one embodiment, a chemosensory receptor is a receptor that belongs to the 7-transmembrane receptor superfamily or G protein-coupled receptors (GPCRs). In another embodiment, a chemosensory receptor is a receptor carrying out signal transduction via one or more G proteins. In yet another embodiment, a chemosensory receptor is a receptor that belongs to family C or class C of GPCRs. In yet another embodiment, a chemosensory receptor is a receptor that belongs to the T1R family. In yet another embodiment, a chemosensory receptor is a receptor of T1R1, T1R2, T1R3, or their equivalences or variances or a combination thereof. In still another embodiment, a chemosensory receptor is a hetero-dimer of T1R2 and T1R3, or their equivalences or variances.

An "enhancer" herein refers to a compound, or an ingestibly acceptable salt or solvate thereof, that modulates (increases) the activation of a particular receptor, preferably the chemosensory, e.g., T1R2/T1R3 receptor. Herein such enhancers will enhance the activation of a chemosensory receptor by its ligand. Typically the "enhancer" will be specific to a particular ligand, i.e., it will not enhance the activation of a chemosensory receptor by chemosensory ligands other than the particular chemosensory ligand or ligands closely related thereto. Some enhancers, at its ligand enhancing concentration, do not result in activation of the particular receptor by themselves. That is, the ligand enhancing concentrations of these enhancers are concentration levels of the enhancers that increase or enhance the activation of a particular receptor by a ligand without substantially activating the particular receptor by the enhancers themselves. In some embodiments, certain enhancers, when used at a concentration higher than the ligand enhancing concentration, can also activate a particular receptor by themselves in addition to modulating (e.g., increase or enhancement) the activation of the receptor. For example, certain enhancers, when used at a concentration higher than the ligand enhancing concentration, can be sweeteners (i.e., sweet flavoring agent/entity) as well. In other embodiments, certain enhancers can activate a particular receptor by themselves in addition to modulating (e.g., increase or enhancement) the activation of the receptor simultaneously at the same concentration. In other words, certain enhancers are also sweeteners (i.e., sweet flavoring agent/entity) at the same time.

A "flavor" herein refers to the perception of taste in a subject, which include sweet, sour, salty, bitter and umami. The subject may be a human or an animal.

A "flavoring agent" herein refers to a compound or the ingestibly acceptable salt or solvate thereof that induces a flavor or taste in an animal or a human. The flavoring agent can be natural, semi-synthetic, or synthetic.

A "flavor modifier" or "flavor modifying agent" herein refers to a compound or the ingestibly acceptable salt or solvate thereof that modulates, including enhancing or potentiating, and/or inducing, the tastes of a flavoring agent in an animal or a human.

A "flavor enhancer" herein refers to a compound or ingestibly acceptable salt thereof that enhances and/or multiplies the tastes of a flavoring agent, or an ingestible composition comprising the flavoring agent.

A "sweet flavor" refers to the sweet taste typically induced by sugar, such as fructose, in an animal or a human.

A "sweet flavoring agent", "sweet flavor entity", "sweetener", or "sweet compound" herein refers to a compound or ingestibly acceptable salt thereof that elicits a detectable sweet flavor in a subject, e.g., fructose or a compound that activates a T1R2/T1R3 receptor in vitro. The subject may be a human or an animal.

A "sweet flavor modifier" or "sweet flavor modifying agent" herein refers to a compound or ingestibly acceptable salt or solvate thereof that modulates, including enhancing or potentiating, inducing, or blocking, the sweet taste of a sweet flavoring agents in an animal or a human. The sweet flavor modifier includes both sweet flavor enhancer and sweet flavoring agent.

A "sweet flavor enhancer" or "sweet flavor enhancing agent" herein refers to an enhancer of a sweet flavor wherein the term enhancer is the same as defined above.

A "sweet receptor activating compound" or "sweet receptor agonist" herein refers to a compound that activates a sweet receptor, such as a T1R2/T1R3 receptor. One example of a sweet receptor activating compound is a sweetener, such as fructose.

A "sweet receptor modulating compound" herein refers to a compound that modulates (activates, block, or enhances/reduces activation of) a sweet receptor such as a T1R2/T1R3 receptor.

A "sweet receptor enhancing compound" herein refers to a compound that enhances or potentiates the effect of a sweet receptor activating compound, e.g., fructose.

The present sweet receptor enhancing compounds or sweet flavor enhancers, at its ligand enhancing concentration of use, may or may not result in activation of the particular receptor by themselves. Some of the sweet receptor enhancing compounds or sweet flavor enhancers, can also activate a particular receptor by themselves in addition to modulating (increase) the activation of the receptor. For example, some of the sweet receptor enhancing compounds or sweet flavor enhancerscan also activate a sweet receptor, such as a T1R2/T1R3 receptor, acting as the receptor agonists.

A "sweet flavor modulating amount" herein refers to an amount of a compound of Formula (I) that is sufficient to alter (either increase or decrease) sweet taste in an ingestible composition, or a precursor thereof, sufficiently to be perceived by a human subject. In many embodiments of the invention, at least about 0.001 ppm of the present compound would need to be present in order for most human subjects to perceive a modulation of the sweet flavor of an ingestible composition comprising the present compound. A broad range of concentration that would typically be employed in order to economically provide a desirable degree of sweet flavor modulation can be from about 0.001 ppm to 100 ppm, or a narrow range from about 0.1 ppm to about 10 ppm. Alternative ranges of sweet flavor modulating amounts can be from about 0.01 ppm to about 30 ppm, from about 0.05 ppm to about 15 ppm, from about 0.1 ppm to about 5 ppm, or from about 0.1 ppm to about 3 ppm.

A "sweet flavor enhancing amount" herein refers to an amount of a compound that is sufficient to enhance the taste of flavoring agents, e.g., fructose, in a ingestible composition, as perceived by an animal or a human. A broad range of a sweet flavor enhancing amount can be from about 0.001 ppm to 100 ppm, or a narrow range from about 0.1 ppm to about 10 ppm. Alternative ranges of sweet flavor enhancing amounts can be from about 0.01 ppm to about 30 ppm, from about 0.05 ppm to about 15 ppm, from about 0.1 ppm to about 5 ppm, or from about 0.1 ppm to about 3 ppm. In some embodiments, sweet flavor enhancing amount is the amount corresponding to ligand enhancing concentration(s) of a sweet flavor enhancer of the present invention.

A "sweet receptor modulating amount" herein refers to an amount of a compound that is sufficient to modulate (activate, enhance or block) a sweet taste receptor protein. In many embodiments of the invention, a sweet receptor modulating amount is at least about 10 nM, or at least about 100 nM (i.e. about 0.1 µM), or at least about 1 µM, or at least about 10 µM. A "T1R2/T1R3 receptor modulating or activating amount" is an amount of compound that is sufficient to modulate or activate a T1R2/T1R3 receptor. A "sweet receptor" is a taste receptor that can be modulated by a sweet compound. Preferably a sweet receptor is a G protein coupled receptor, and more preferably the sweet receptor is a T1R2/T1R3 receptor.

Compounds

In one embodiment, the present invention provides a compound having structural Formula (I):

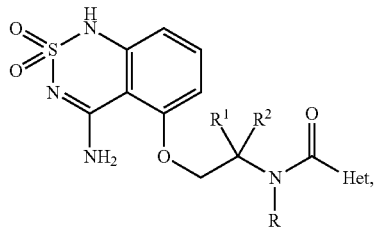

(I)

or a salt or solvate thereof; wherein, $R^1$ and $R^2$ are independently C1 to C4 alkyl; or alternatively, $R^1$ and $R^2$, together with the carbon atom to which they are attached, form a C3 to C7 cycloalkyl; R is hydrogen or C1 to C6 alkyl; and Het is heteroaryl or substituted heteroaryl.

In one embodiment of Formula (I), R is hydrogen.

In one embodiment of Formula (I), $R^1$ and $R^2$ are both methyl, ethyl, or propyl. That is, $R^1$ and $R^2$ are the same and are methyl, ethyl, or propyl.

In one embodiment of Formula (I), wherein $R^1$ and $R^2$, together with the carbon atom to which they are attached, form cyclopropyl, cyclobutyl, cylclopentyl, or cyclohexyl.

In one embodiment of Formula (I), wherein Het is an optionally substituted monocyclic five or six-membered heteroaryl containing one or more heteroatoms selected from the group of N, O, and S. By "optionally substituted", it is meant that the monocyclic five or six-membered heteroaryl can be unsubstituted or substituted.

In one embodiment of Formula (I), wherein Het is selected from the group consisting of pyridine, substituted pyridine, pyrimidine, substituted pyrimidine, pyrazine, substituted pyrazine, pyridazine, substituted pyridazine, triazine, and substituted triazine.

In one embodiment of Formula (I), wherein Het is an optionally substituted bicyclic eight to twelve-membered heteroaryl containing one or more heteroatoms selected from the group of N, O, and S. By "optionally substituted", it is meant that the bicyclic eight to twelve-membered heteroaryl can be unsubstituted or substituted.

In one embodiment of Formula (I), wherein Het is tetrazolopyridine, e.g., tetrazolo[1,5-a]pyridine; triazolopyridine, e.g., [1,2,4]triazolo[4,3-a]pyridine; purine, e.g., 9H-purine; pyrazolopyridine, e.g., 1H-pyrazolo[3,4-b]pyridine; quinoline, isoquinoline, isoxazolopyridine, e.g., isoxazolo[5,4-b]pyridine; or quinolinone, e.g., quinolin-2(1H)-one; each of which is optionally substituted. By "optionally substituted", it is meant that the Het can be unsubstituted or substituted.

In one embodiment of Formula (I), Het is unsubstituted or substituted with one, two, three, or four substituents independently selected from the group consisting of halo, cyano, hydroxyl, N-oxide, amine, substituted amine, alkoxy, substituted alkoxy, aryloxy, substituted aryloxy, acyl, sulfonamide, ester, alkyl, substituted alkyl, heteroalkyl, substituted heteroalkyl, aryl, substituted aryl, arylalkyl, substituted aryl, arylalkyl, substituted heteroaryl, heteroarylalkyl, substituted heteroarylalkyl, carbocyclyl, substituted carbo-cyclyl, heterocyclyl, and substituted heterocyclyl; or alternatively, two of the substituents, taken together with the ring atoms of Het to which they are bound, form a carbocyclyl or heterocyclyl.

In one embodiment of Formula (I), the compound is represented by structural Formula (Ia):

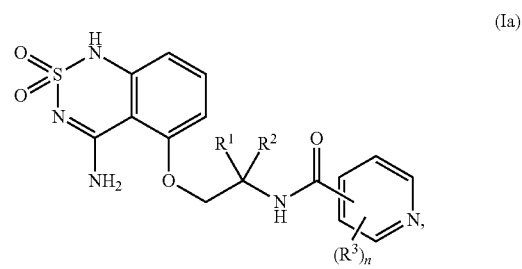

(Ia)

wherein, $R^1$ and $R^2$ are independently C1 to C4 alkyl; or alternatively, $R^1$ and $R^2$, together with the carbon atom to which they are attached, form a C3 to C7 cycloalkyl; n is 0, 1, 2, or 3; and $R^3$ is halo, cyano, hydroxyl, amine, substituted amine, alkoxy, substituted alkoxy, aryloxy, substituted aryloxy, acyl, sulfonamide, ester, alkyl, substituted alkyl, heteroalkyl, substituted heteroalkyl, aryl, substituted aryl, arylalkyl, substituted arylalkyl, heteroaryl, substituted heteroaryl, heteroarylalkyl, substituted heteroarylalkyl, carbocyclyl, substituted carbocyclyl, heterocyclyl, or substituted heterocyclyl.

In one embodiment of Formula (Ia), $R^1$ and $R^2$ are both methyl, ethyl, or propyl. That is, $R^1$ and $R^2$ are the same and are methyl, ethyl, or propyl.

In one embodiment of Formula (Ia), $R^1$ and $R^2$, together with the carbon atom to which they are attached, form cyclopropyl, cyclobutyl, cylclopentyl, or cyclohexyl.

In one embodiment of Formula (Ia), the compound is represented by structural Formula (Ib):

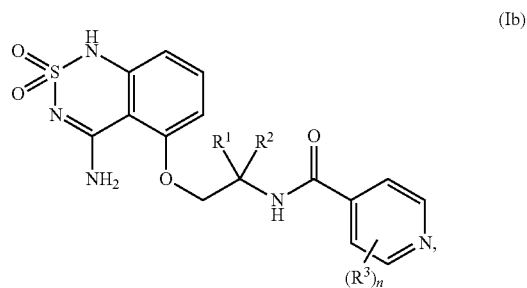

(Ib)

wherein, $R^1$ and $R^2$ are both methyl, ethyl, or propyl; or alternatively, $R^1$ and $R^2$, together with the carbon atom to which they are attached, form cyclopropyl, cyclobutyl, cylclopentyl, or cyclohexyl; n is 0, 1, 2, or 3; and $R^3$ is halo, cyano, hydroxyl, amine, substituted amine, alkoxy, substituted alkoxy, aryloxy, substituted aryloxy, acyl, sulfonamide, ester, alkyl, substituted alkyl, heteroalkyl, substituted heteroalkyl, aryl, substituted aryl, arylalkyl, substituted arylalkyl, heteroaryl, substituted heteroaryl, heteroarylalkyl, substituted heteroarylalkyl, carbocyclyl, substituted carbocyclyl, heterocyclyl, or substituted heterocyclyl.

In certain specific embodiments, the compounds of the present invention are selected from the group consisting of

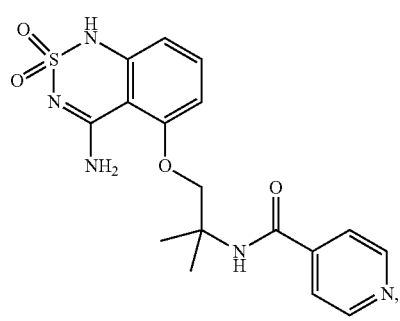
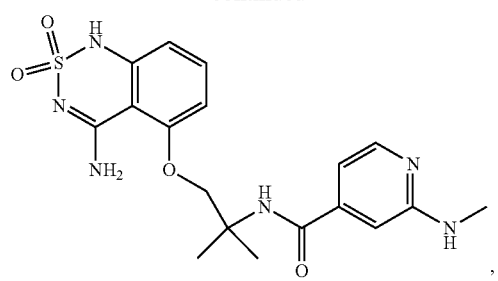
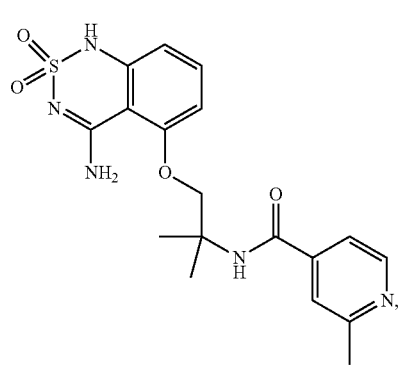
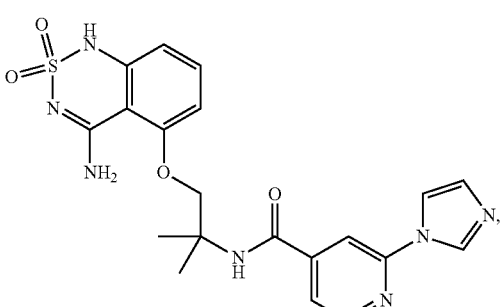
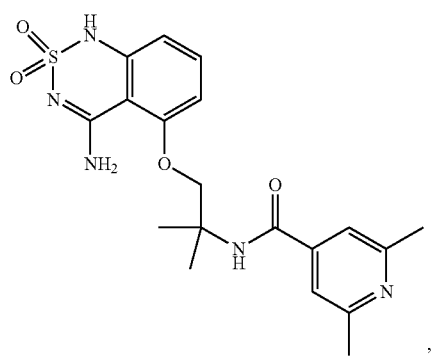
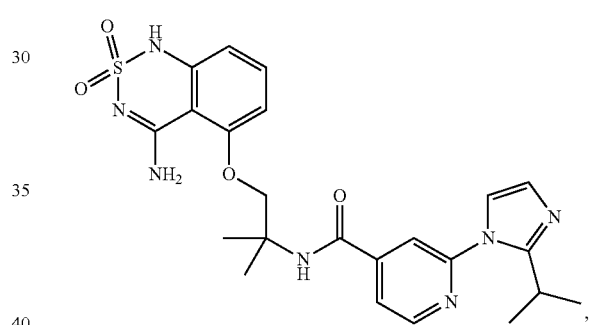
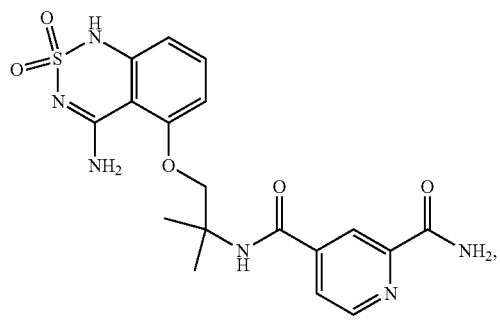
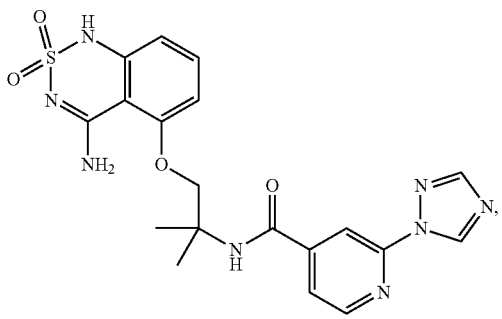
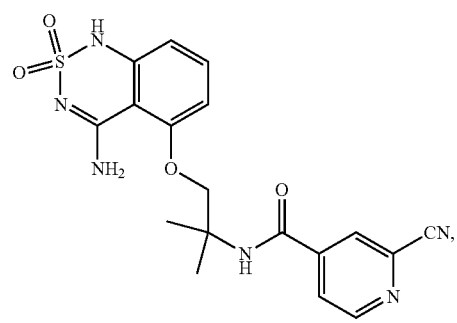
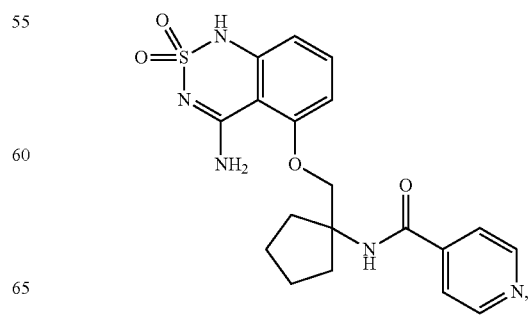

17
-continued
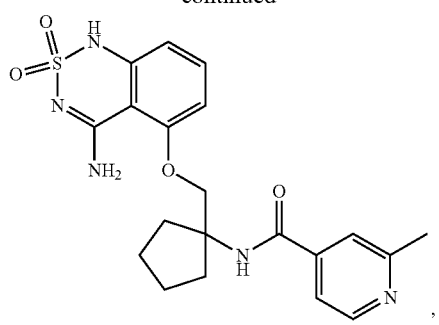
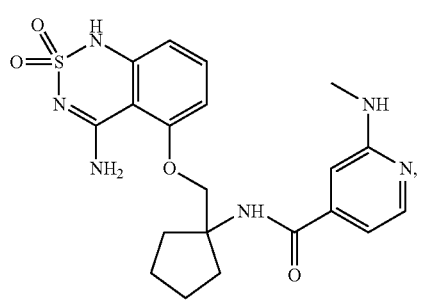
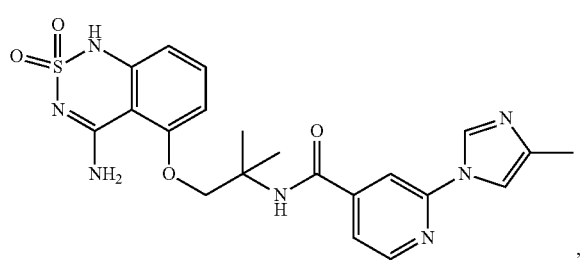
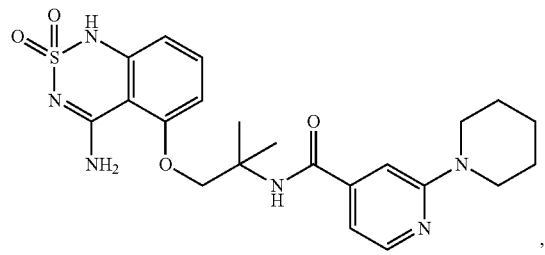
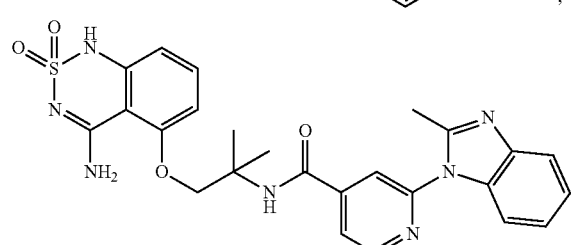
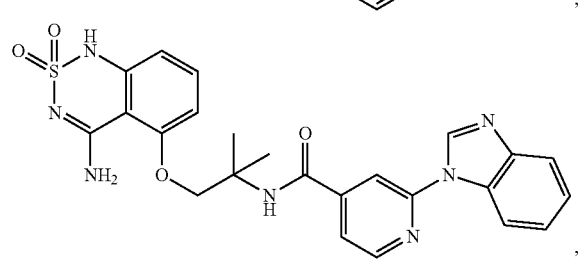
18
-continued
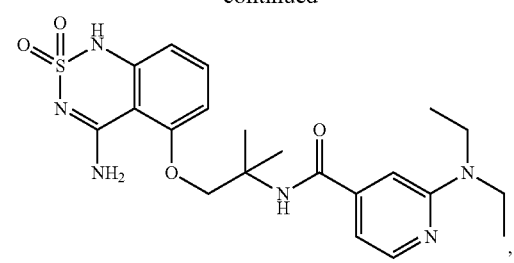
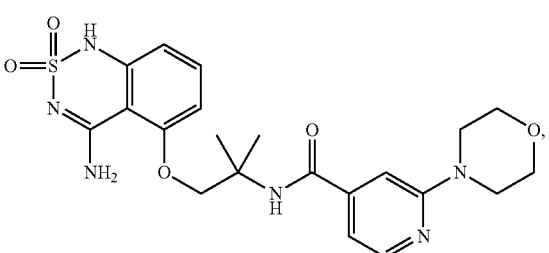
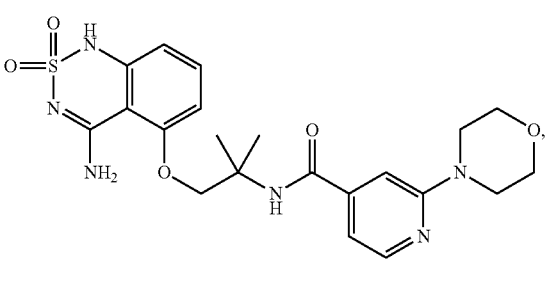
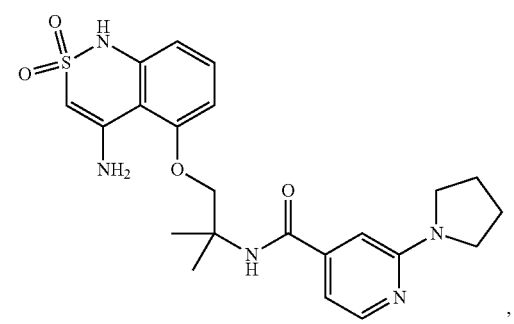
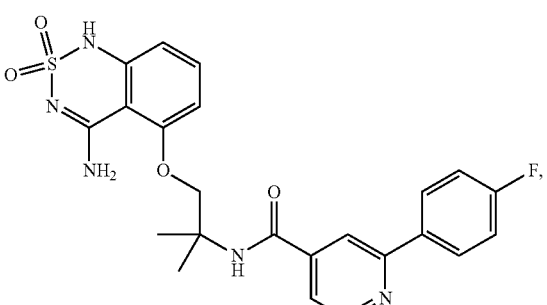
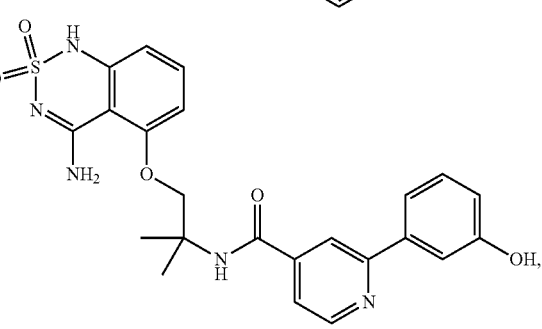

-continued
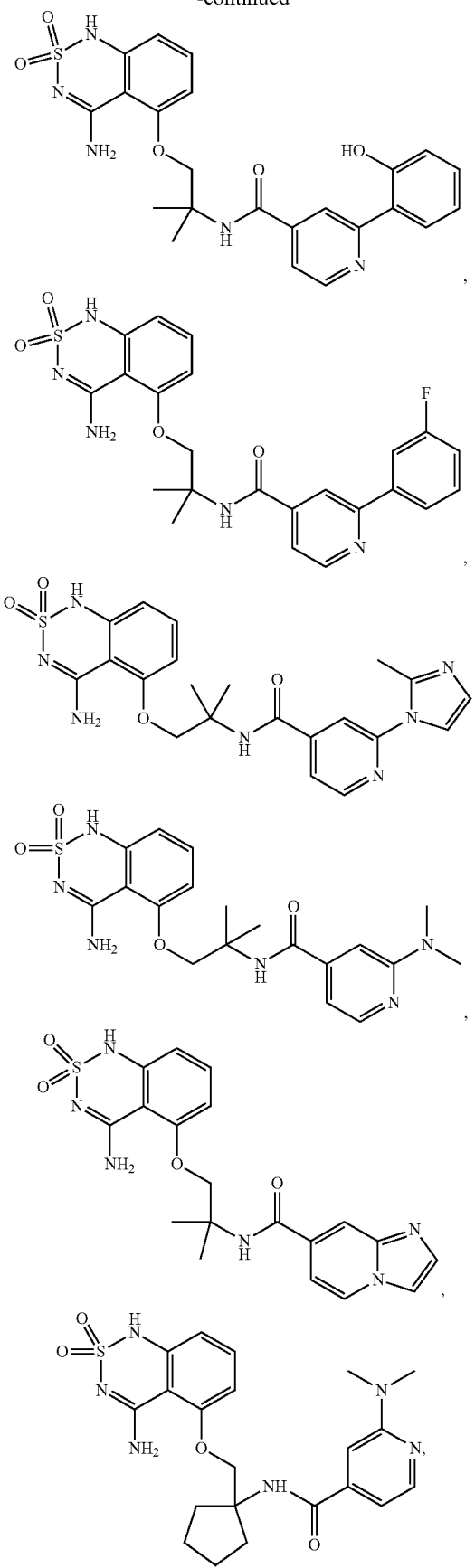
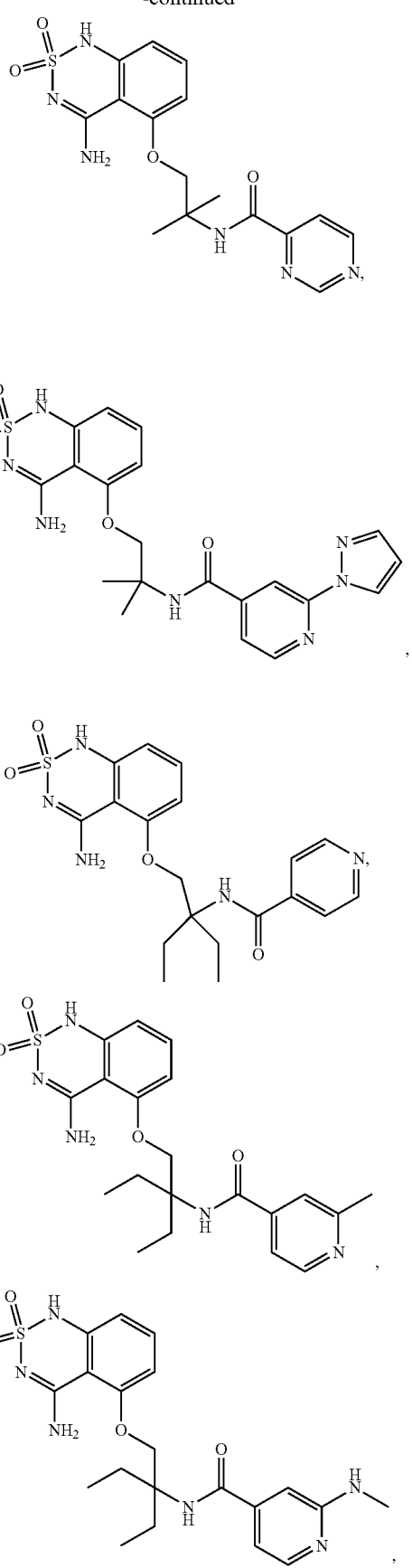

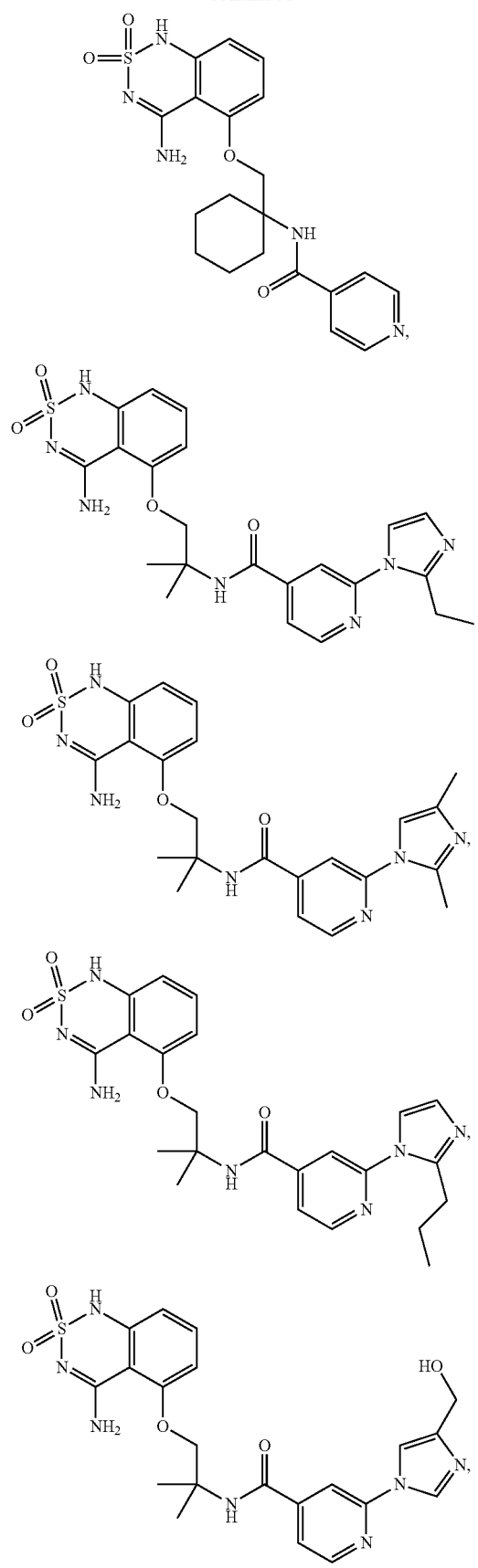
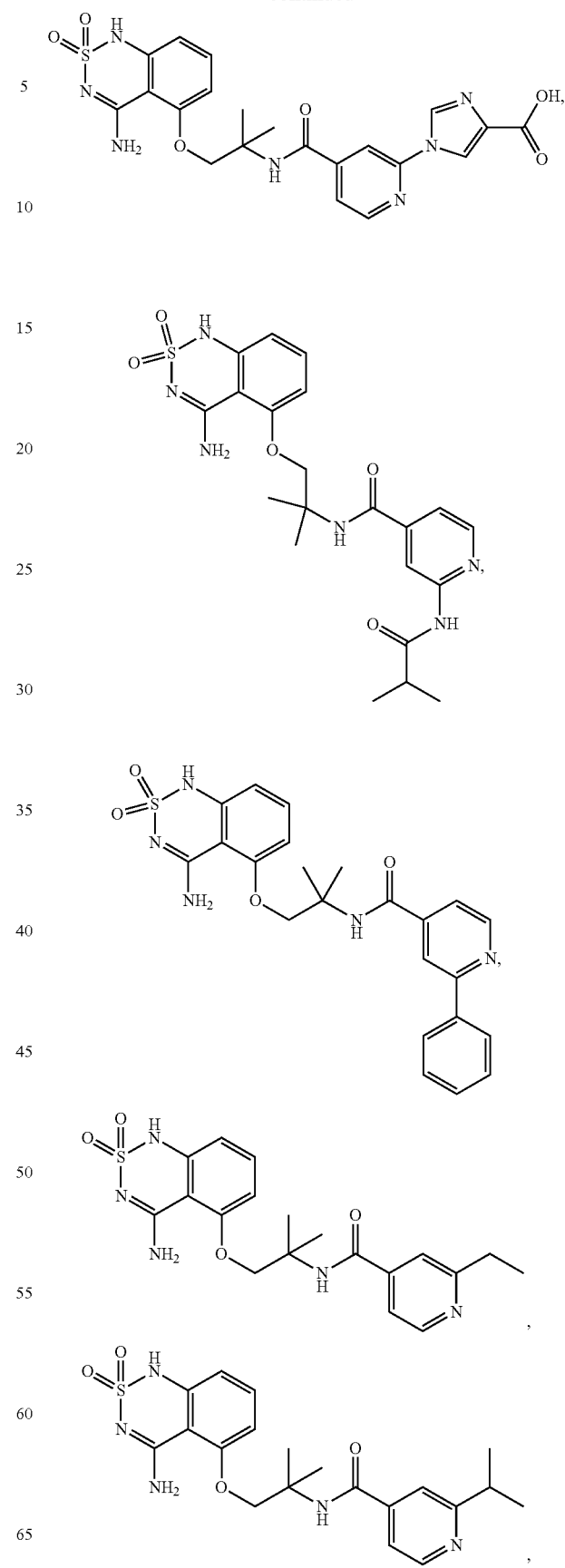

23
-continued
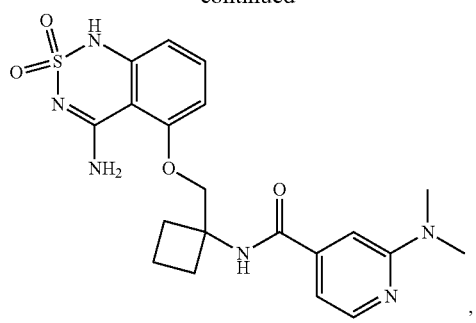
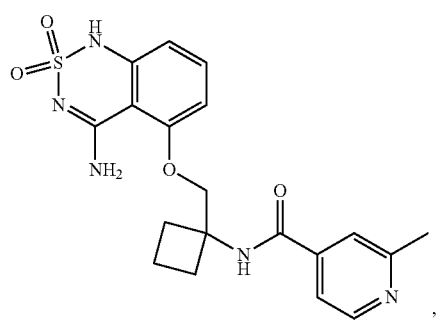
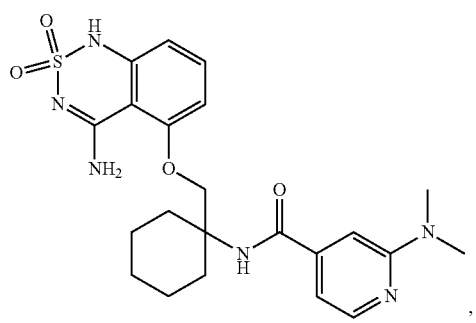
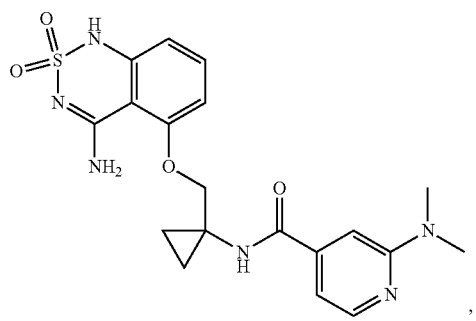
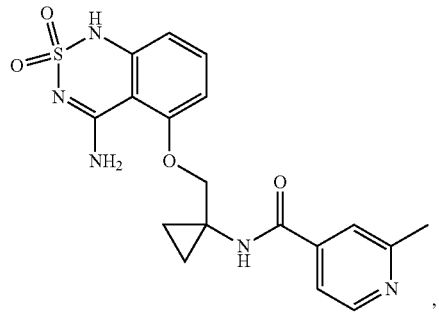
24
-continued
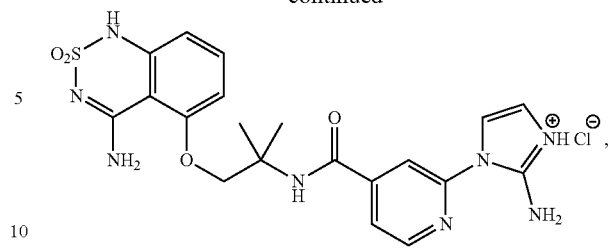
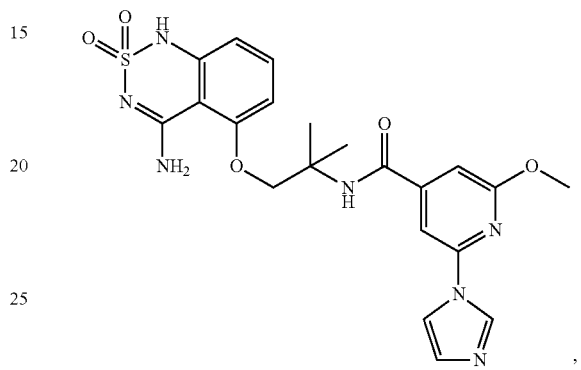
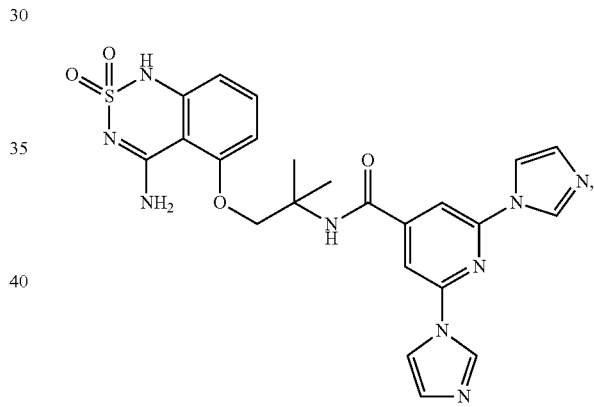
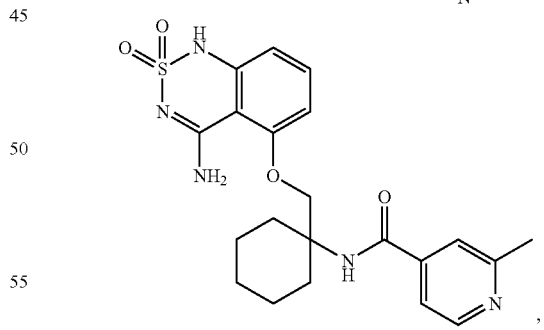
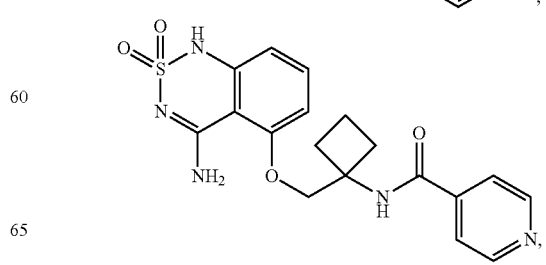

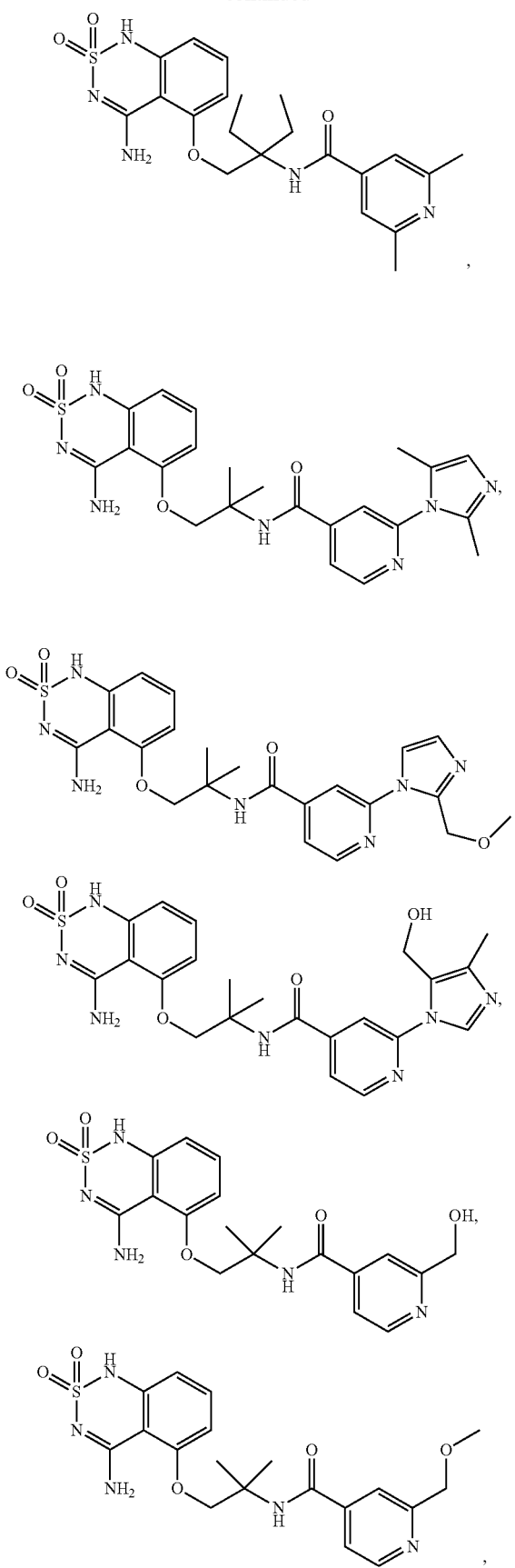
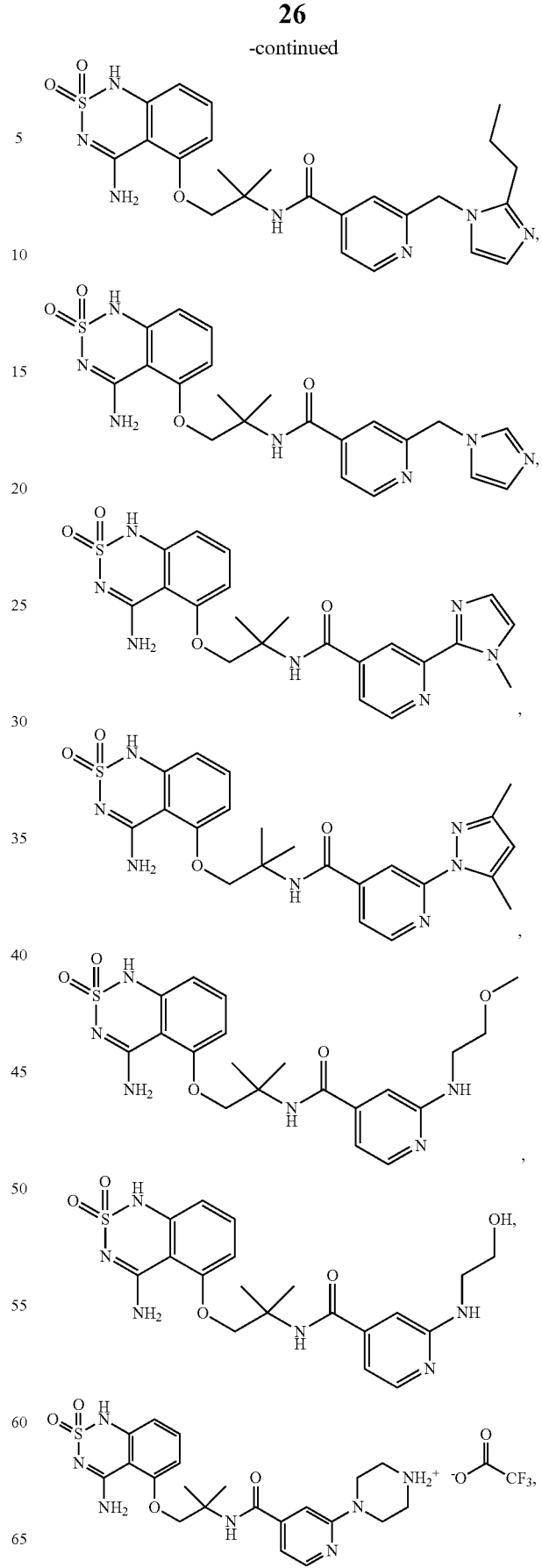

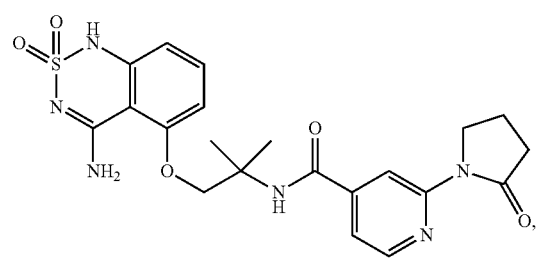
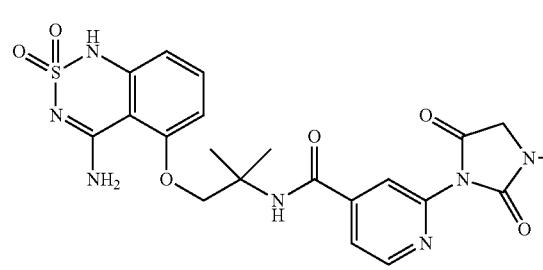
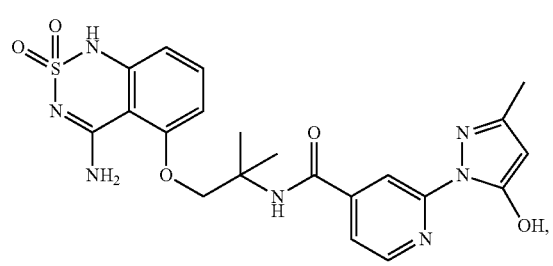
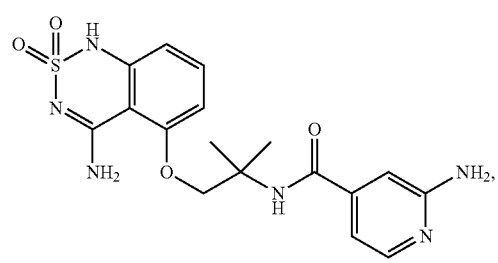
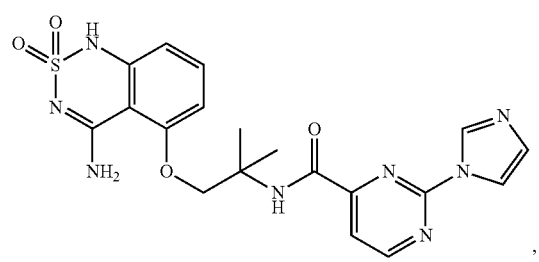
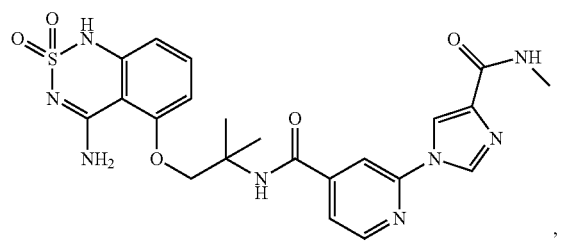
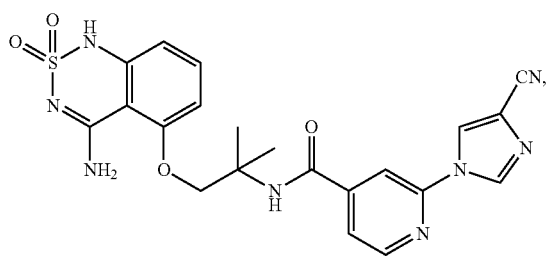
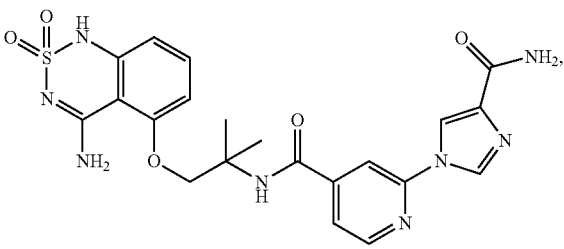
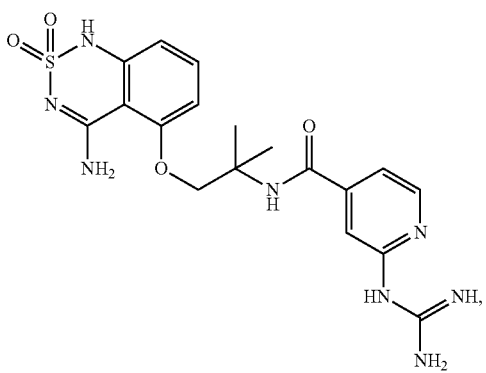
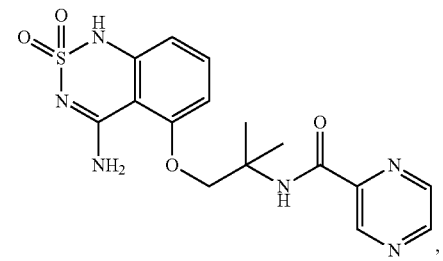
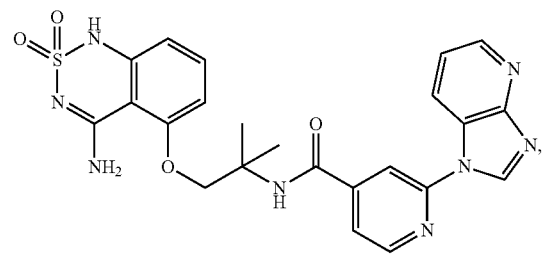
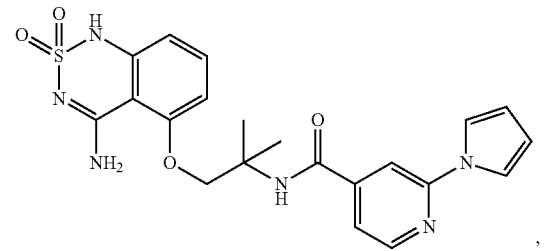

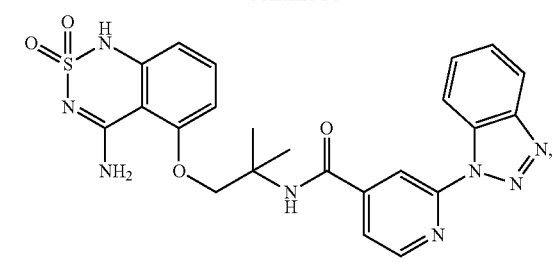
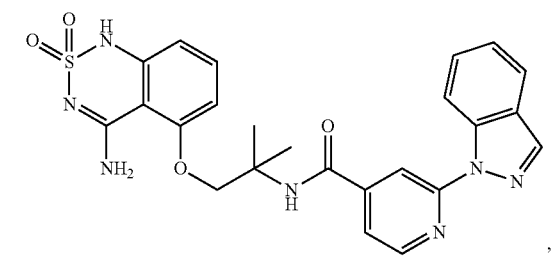
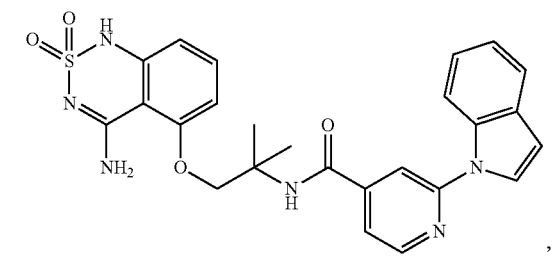
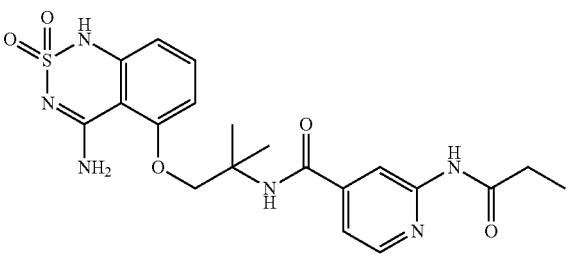
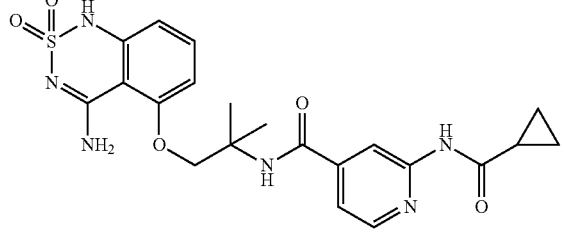
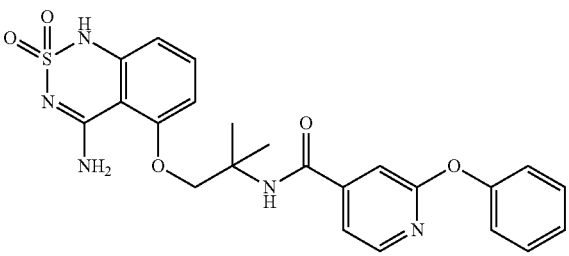
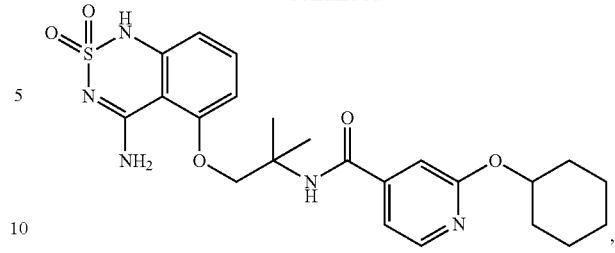
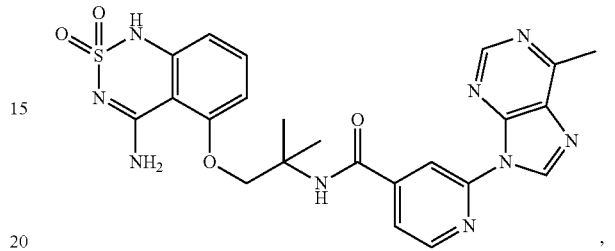
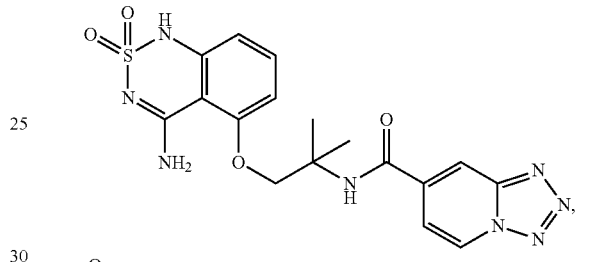
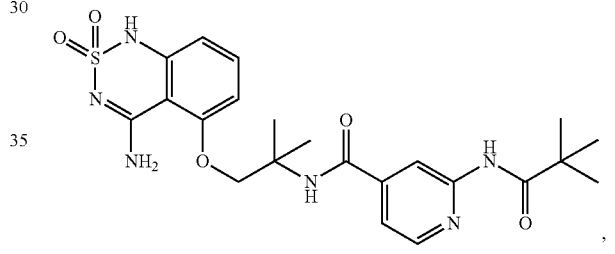
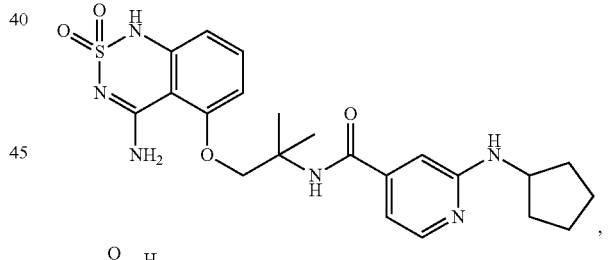
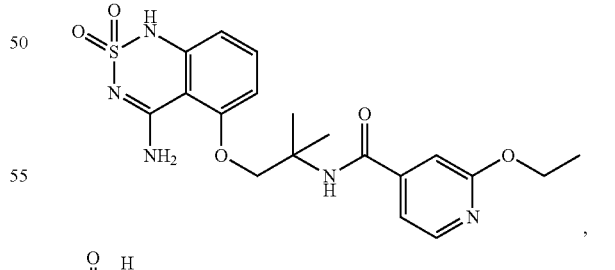
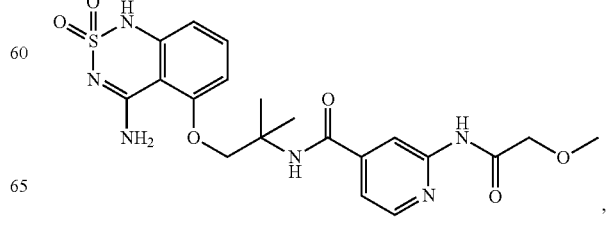

31
-continued
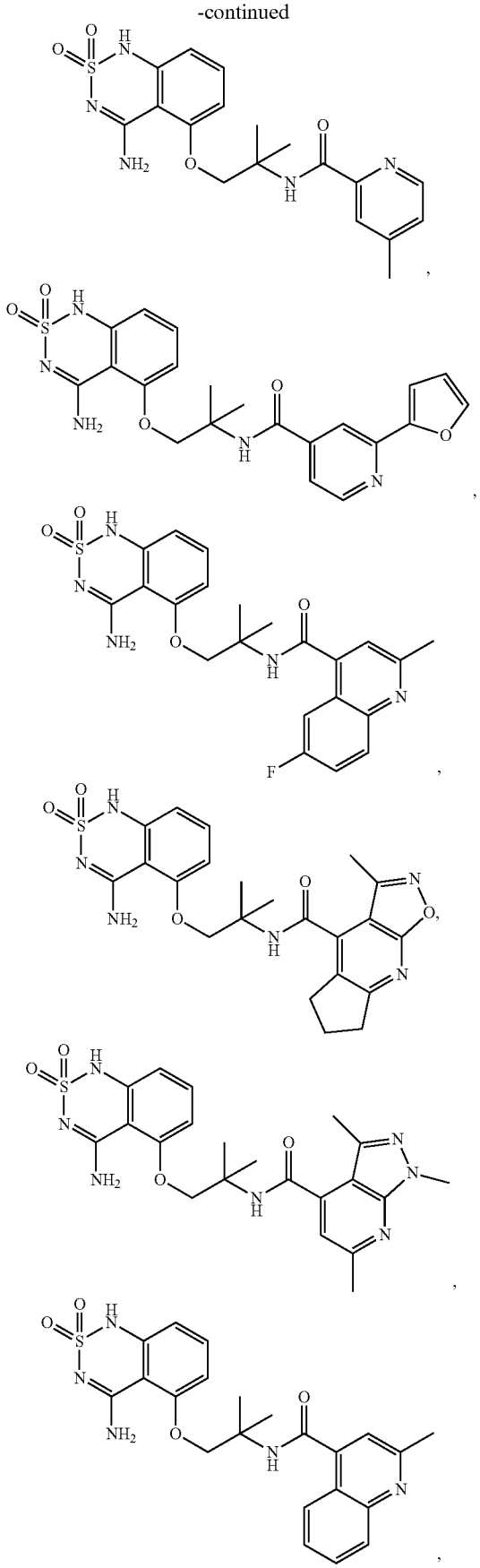
32
-continued
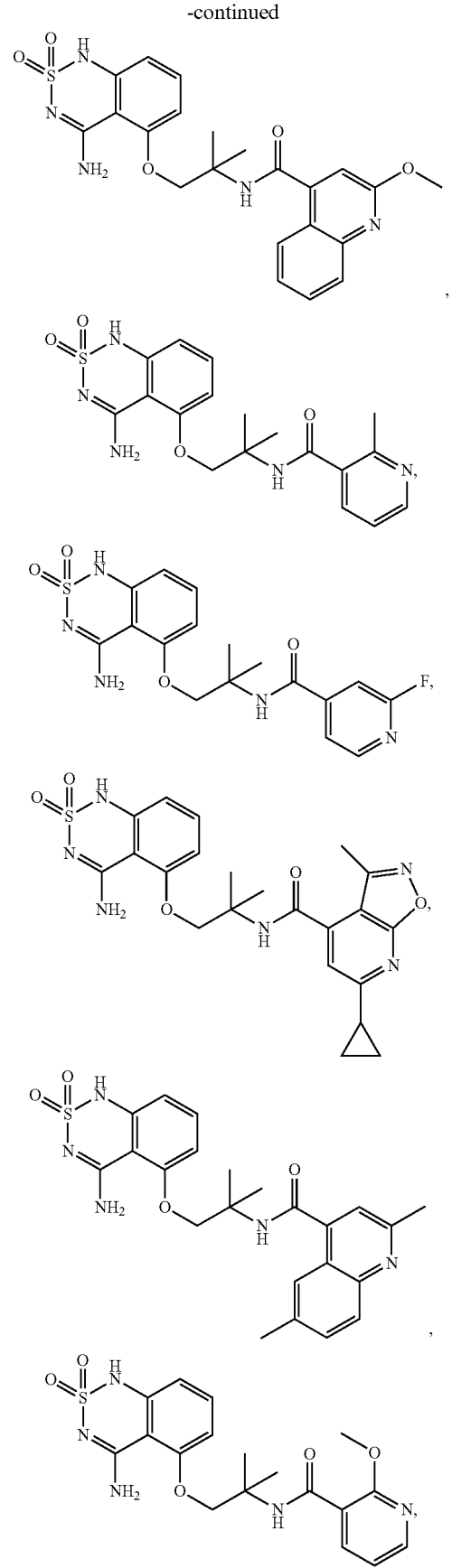

-continued
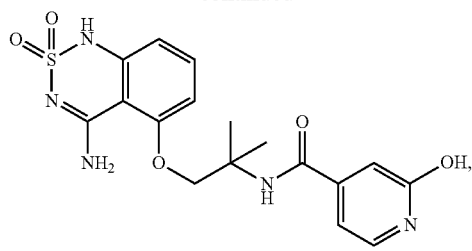

-continued
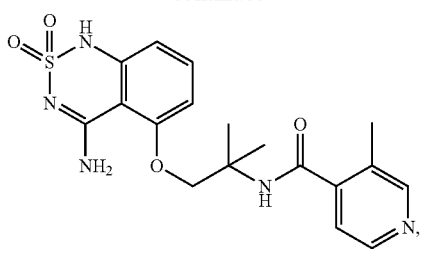
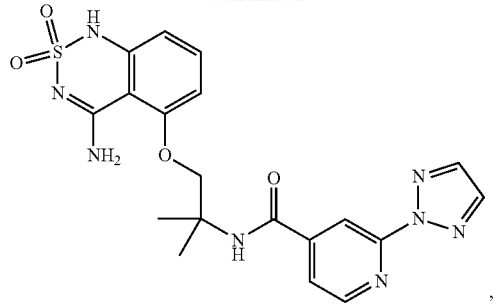
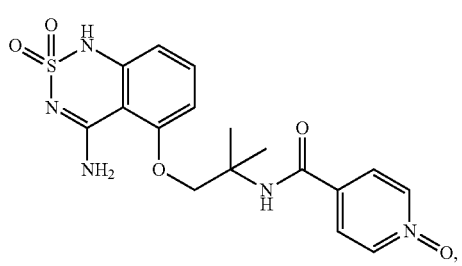
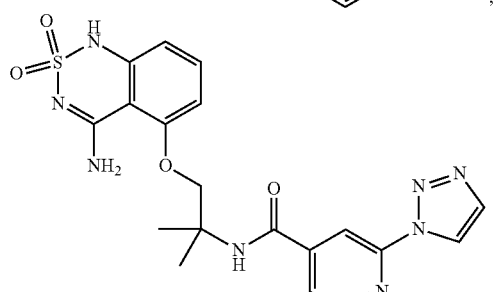
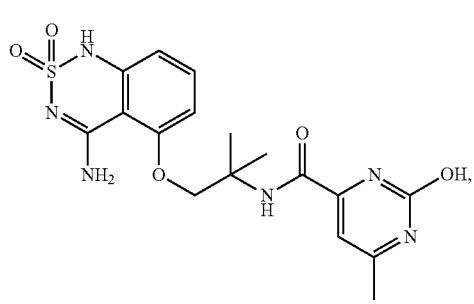
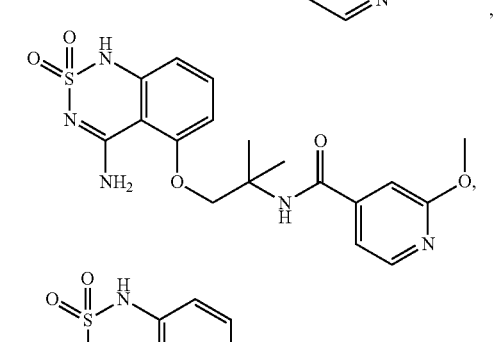
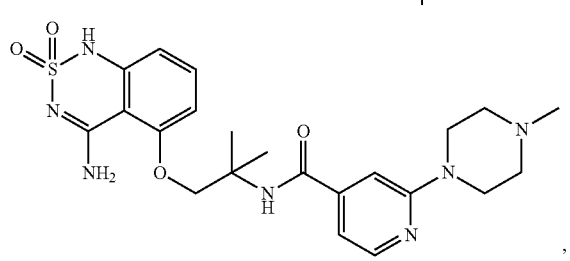
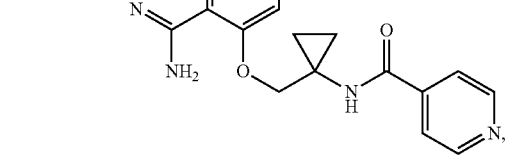
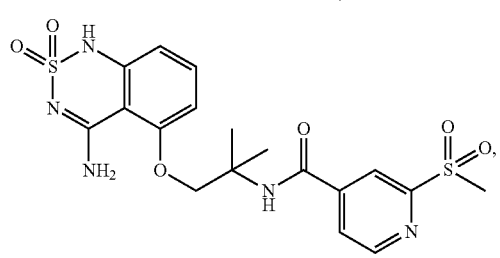
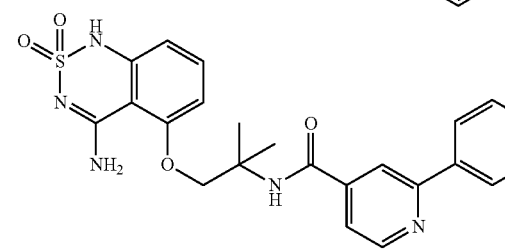
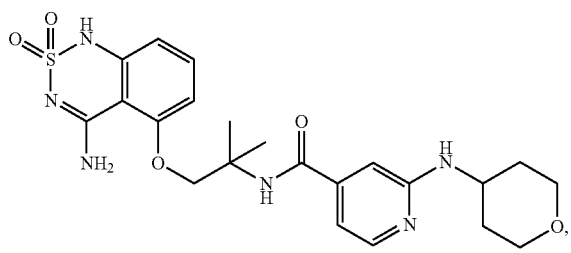
Compositions
The present compounds can be used for one or more methods of the present invention, e.g., modifying receptors and their ligands associated with chemosensory or chemosensory related sensation or reaction. According to the present invention, a method of modulating a chemosensory receptor and/or its ligand includes modulating the activity, structure, function, expression, and/or modification of a chemosensory receptor. In one embodiment, the method includes increasing or enhancing sweet flavor. In general, the compounds of the present invention, individually or in combination, can be provided in a composition, such as, e.g., an ingestible composition. In one embodiment, the present compound can impart a more sugar-like temporal profile and/or flavor profile to a sweetener composition by combining one or more present compound with one or more sweetener in the sweetener composition. In another embodiment, the present compound can increase or enhance the sweet taste of a composition by contacting the composition thereof with one or more present compound to form a modified composition.

The compounds of Formula (I), (Ia), (Ib), and its various subgenuses and species, and their salts and/or solvates, should preferably be comestibly acceptable, e.g., deemed suitable for consumption in food or drink from the perspective of giving unmodified comestible compositions an improved and/or pleasing sweet taste, and would not be significantly toxic or causes unpleasant or undesirable pharmacological or toxicological effects on an animal or human at the typical concentrations they are employed as flavoring agents for the comestible compositions.

One of the methods of demonstrating that a flavorant compound is comestibly acceptable is to have the compound tested and/or evaluated by an Expert Panel of the Flavor and Extract Manufacturers Association (FEMA) and declared as to be "Generally Recognized As Safe" ("GRAS"). The FEMA/GRAS evaluation process for flavorant compounds is complex but well known to those of ordinary skill in the food product preparation arts, as is discussed by Smith, et al. in an article entitled "GRAS Flavoring Substances 21," Food Technology, 57(5), pgs 46-59, May 2003, the entire contents of which are hereby incorporated herein by reference. In addition to the FEMA expert panel, an independent, qualified panel of experts in pertinent scientific disciplines may be formed by the manufacturer to evaluate the safety of a specific compound for GRAS status. This process is known as a "self determination of GRAS status." Another method of demonstrating that a flavorant compound is comestibly acceptable is to obtain favorable review by the WHO/FAO Joint Expert Committee on Food Additives, or JECFA. There are also other evaluation methods, such as independent review by the regulatory agency, which are generally known to those of ordinary skill in the food product preparation arts.

In one embodiment, the compounds of the present invention can be used at its ligand enhancing concentrations, e.g., very low concentrations on the order of a few parts per million, in combination with one or more known sweeteners, natural or artificial, so as to reduce the concentration of the known sweetener required to prepare an ingestible composition having the desired degree of sweetness.

In one embodiment, the present compounds can enhance the sweetness of a sweetener under a broad range of pH, e.g., from lower pH to neutral pH. The lower and neutral pH includes, but is not limited to, a pH from about 2.5 to about 8.5; from about 2.5 to about 8.0; from about 2.8 to about 7.5; from about 3.0 to about 7, and from about 3.5 to about 7. In certain embodiments, the present compounds can enhance the perceived sweetness of a fixed concentration of a sweetener in taste tests at a compound concentration of about 50 µM, 40 µM, 30 µM, 20 µM, or 10 µM at both low to neutral pH value. In certain embodiments, the enhancement factor of the present compounds at the lower pH is substantially similar to the enhancement factor of the compounds at neutral pH. Furthermore, in some embodiments, the present compounds demonstrate enhanced photostability. That is, when exposed to a light source, the presnet compounds have stability and less prone to degradation. Such photostability and consistent sweet enhancing property under a broad range of pH render the present compounds good candidates for a broad use in a wide variety of foods and beverages.

Commonly used known or artificial sweeteners for use in such combinations of sweeteners include but are not limited to the common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources, semi-synthetic "sugar alcohol" sweeteners such as erythritol, isomalt, lactitol, mannitol, sorbitol, xylitol, maltodextrin, and the like, and artificial sweeteners such as aspartame, saccharin, acesulfame-K, cyclamate, sucralose, and alitame. Sweeteners also include cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners, etc. The term "sweeteners" also includes combinations of sweeteners as disclosed herein.

In one embodiment, the present compound is added to a noncomestible composition or non-edible product, such as supplements, nutraceuticals, functional food products (e.g., any fresh or processed food claimed to have a health-promoting and/or disease-preventing properties beyond the basic nutritional function of supplying nutrients), pharmaceutical product, over the counter (OTC) product, oral care product, cosmetic products such as sweetened lip balms, and other personal care products.

In general, over the counter (OTC) product and oral care product generally refer to product for household and/or personal use which may be sold without a prescription and/or without a visit to a medical professional. Examples of the OTC products include, but are not limited to Vitamins and dietary supplements; Topical analgesics and/or anesthetic; Cough, cold and allergy remedies; Antihistamines and/or allergy remedies; and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anesthetic include any topical creams/ointments/gels used to alleviate superficial or deep-seated aches and pains, e.g. muscle pain; teething gel; patches with analgesic ingredient; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. Examples of oral care product include, but are not limited to mouth cleaning strips, toothpaste, toothbrushes, mouthwashes/dental rinses, denture care, mouth fresheners at-home teeth whiteners, dentifrices, and dental floss.

In another embodiment, the present compounds are added to food or beverage products or formulations. Examples of food and beverage products or formulations include, but are not limited to sweet coatings, frostings, or glazes for comestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionary category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups).

The Dehydrated and Culinary Food Category usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee; tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionary category generally refers to edible product that is sweet to the taste. Examples of confectionary include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles. The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is note limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for comestible composition, particularly food and beverage products or formulations, are provided as follows. Exemplary comestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarized gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary comestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary comestible compositions also include breakfast cereals, sweet beverages or solid or liquid concentrate compositions for preparing beverages, ideally so as to enable the reduction in concentration of previously known saccharide sweeteners, or artificial sweeteners.

Typically at least a sweet receptor modulating amount, a sweet receptor ligand modulating amount, a sweet flavor modulating amount, a sweet flavoring agent amount, or a sweet flavor enhancing amount one or more of the present compounds will be added to the ingestible composition, optionally in the presence of known sweeteners, e.g., so that the sweet flavor modified ingestible composition has an increased sweet taste as compared to the ingestible composition prepared without the compounds of the present invention, as judged by human beings or animals in general, or in the case of formulations testing, as judged by a majority of a panel of at least eight human taste testers, via procedures commonly known in the field.

The concentration of sweet flavoring agent needed to modulate or improve the flavor of the ingestible composition will of course depend on many variables, including the specific type of the ingestible composition and its various other ingredients, especially the presence of other known sweet flavoring agents and the concentrations thereof, the natural genetic variability and individual preferences and health conditions of various human beings tasting the compositions, and the subjective effect of the particular compound on the taste of such chemosensory compounds.

One application of the present compounds is for modulating (inducing, enhancing or inhibiting) the sweet taste or other taste properties of other natural or synthetic sweet tastants, and ingestable compositions made therefrom. In one embodiment, the compounds of the present invention is used or provided in its ligand enhancing concentration(s). For example, a broad but also low range of concentrations of the compounds or entities of the present invention would typically be required, i.e., from about 0.001 ppm to 100 ppm, or narrower alternative ranges from about 0.1 ppm to about 10 ppm, from about 0.01 ppm to about 30 ppm, from about 0.05 ppm to about 10 ppm, from about 0.01 ppm to about 5 ppm, or from about 0.02 ppm to about 2 ppm, or from about 0.01 ppm to about 1 ppm.

In one embodiment, the present invention provides a sweet enhancing composition. The sweet enhancing composition comprises a compound of the present invention in an amount effective to provide sweetening, e.g., sweet flavor enhancing amount in combination with a first amount of sweetener, wherein the sweetening is more than the sweetening provided by the first amount of sweetener without the compound.

In one embodiment, the present invention provides an ingestible composition which comprises the sweet enhancing composition of the present invention. In certain embodiments, the present ingestible composition is in the form of a food or beverage product, a pharmaceutical composition, a nutritional product, a dietary supplement, over-the-counter medication, or oral care product.

In one embodiment, the present invention provides a sweetener replacement composition which comprises one or more compounds of the present invention in an amount effective to provide sweetening, e.g., at a concentration higher than their ligand enhancing concentration in the absence of a sweetener, e.g., sucrose other than the present compound(s).

According to another aspect of the invention, the compounds of the present invention are provided in a flavoring concentrate formulation, e.g., suitable for subsequent processing to produce a ready-to-use (i.e., ready-to-serve) product. By "a flavoring concentrate formulation", it is meant a formulation which should be reconstituted with one or more diluting medium to become a ready-to-use composition. The term "ready-to-use composition" is used herein interchangeably with "ingestible composition", which denotes any substance that, either alone or together with another substance, can be taken by mouth whether intended for consumption or not. In one embodiment, the ready-to-use composition includes a composition that can be directly consumed by a human or animal. The flavoring concentrate formulation is typically used by mixing with or diluted by one or more diluting medium, e.g., any consumable or ingestible ingredient or product, to impart or modify one or more flavors to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a soft drink syrup concentrate can be reconstituted with water or other aqueous medium by a manufacture in large industrial scales to produce the ready-to-use soft drinks. Since the flavoring concentrate formulation has the flavoring agent or flavor modifying agent in a concentration higher than the ready-to-use composition, the flavoring concentrate formulation is typically not suitable for being consumed directly without reconstitution. There are many benefits of using and producing a flavoring concentrate formulation. For example, one benefit is the reduction in weight and volume for transportation as the flavoring concentrate formulation can be reconstituted at the time of usage by the addition of suitable solvent, solid or liquid.

In one embodiment, the flavoring concentrate formulation comprises i) as flavor modifying ingredient, a compound of the present invention; ii) a carrier; and iii) optionally at least one adjuvant. The term "as flavor modifying ingredient" denotes that the compound of the present invention acts as a flavoring agent or a flavor modifying agent (such as a flavor enhancer) in the formulation. The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the flavoring concentrate formulation; and in other embodiments, the carrier is different from the diluting medium. The term "carrier" as used herein includes, but is not limited to, ingestibly acceptable carrier.

In one embodiment, the flavoring concentrate formulation comprises more than about 10% or 15% by weight of a compound of the present invention. In another embodiment, the flavoring concentrate formulation comprises about 20%, 25%, 30%, 35%, or 40% by weight or any amount in between of the present compound. In another embodiment, the flavoring concentrate formulation comprises more than about 40%, 45%, 50%, 55%, 60%, or 65% by weight or any amount in between of the present compound. In another embodiment, the flavoring concentrate formulation comprises more than about 65% by weight of the present compound.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French vanilla, peanut butter, chai, or combinations thereof. In another embodiment, the at least one adjuvant comprises one or more sweeteners. The one or more sweeteners can be any of the sweeteners described in this application. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the contents of which are hereby incorporated by reference in its entirety for all purposes.

In one embodiment, the present flavoring concentrate formulation can be in a form selected from the group consisting of liquid including solution and suspension, solid, foamy material, paste, gel, cream, and a combination thereof, such as a liquid containing certain amount of solid contents. In one embodiment, the flavoring concentrate formulation is in form of a liquid including aqueous-based and nonaqueous-based. The present flavoring concentrate formulation can be carbonated or non-carbonated.

The flavoring concentrate formulation may further comprise a freezing point depressant, nucleating agent, or both as the at least one adjuvant. The freezing point depressant is a ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes a ingestibly acceptable compound or agent which is able to facilitate nucleation. The presence of nucleating agent in the flavoring concentrate formulation can improve the mouthfeel of the frozen slushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In one embodiment, the flavoring concentrate formulation is formulated to have a low water activity for extended shelf life. Water activity is the ratio of the vapor pressure of water in a formulation to the vapor pressure of pure water at the same temperature. In one embodiment, the flavoring concentrate formulation has a water activity of less than about 0.85. In another embodiment, the flavoring concentrate formulation has a water activity of less than about 0.80. In another embodiment, the flavoring concentrate formulation has a water activity of less than about 0.75.

In one embodiment, the flavoring concentrate formulation has the present compound in a concentration that is at least 2 times of the concentration of the compound in a ready-to-use composition. In one embodiment, the flavoring concentrate formulation has the present compound in a concentration that is at least 5 times of the concentration of the compound in a ready-to-use composition. In one embodiment, the flavoring concentrate formulation has the present compound in a concentration that is at least 10 times of the concentration of the compound in a ready-to-use composition. In one embodiment, the flavoring concentrate formulation has the present compound in a concentration that is at least 15 times of the concentration of the compound in a ready-to-use composition. In one embodiment, the flavoring concentrate formulation has the present compound in a concentration that is at least 20 times of the concentration of the compound in a ready-to-use composition. In one embodiment, the flavoring concentrate formulation has the present compound in a concentration that is at least 30 times of the concentration of the compound in a ready-to-use composition. In one embodiment, the flavoring concentrate formulation has the present compound in a concentration that is at least 40 times of the concentration of the compound in a ready-to-use composition. In one embodiment, the flavoring concentrate formulation has the present compound in a concentration that is at least 50 times of the concentration of the compound in a ready-to-use composition. In one embodiment, the flavoring concentrate formulation has the present compound in a concentration that is at least 60 times of the concentration of the compound in a ready-to-use composition. In one embodiment, the flavoring concentrate formulation has the present compound in a concentration that is up to 100 times of the concentration of the compound in a ready-to-use composition.

Preparations

The starting materials used in preparing the compounds of the invention, i.e. the various structural subclasses and species of the compounds of the synthetic precursors of the present compounds of Formula (I), are often known compounds, or can be synthesized by known methods described in the literature, or are commercially available from various sources well known to those of ordinary skill in the art, such as for example, Sigma-Aldrich Corporation of St. Louis, Mo. USA and their subsidiaries Fluka and Riedel-de Haen, at their various other worldwide offices, and other well known chemical suppliers such as Fisher Scientific, TCI America of Philadelphia, Pa., ChemDiv of San Diego, Calif., Chembridge of San Diego, Calif., Asinex of Moscow, Russia, SPECS/BIOSPECS of the Netherlands, Maybridge of Cornwall, England, Acros, TimTec of Russia, Comgenex of South San Francisco, Calif., and ASDI Biosciences of Newark, Del.

It is recognized that the skilled artisan in the art of organic chemistry can readily carry out the synthesis of many starting materials and subsequent manipulations without further direction, that is, it is well within the scope and practice of the skilled artisan to carry out many desired manipulations. These include reduction of carbonyl compounds to their corresponding alcohols, oxidations, acylations, aromatic substitutions, both electrophilic and nucleophilic, etherifications, esterification, saponification, nitrations, hydrogenations, reductive animation and the like. These manipulations are discussed in standard texts such as March's Advanced Organic Chemistry (3d Edition, 1985, Wiley-Interscience, New York), Feiser and Feiser's Reagents for Organic Synthesis, and in the various volumes and editions oẗMethoden der Organischen Chemie (Houben-Weyl), and the like. Many general methods for preparation of starting materials comprising variously substituted heterocyclic, hetereoaryl, and aryl rings (the precursors of Ar, $hAr^1$, and/or $hAr^2$) can be found in Methoden der Organischen Chemie (Houben-Weyl), whose various volumes and editions are available from Georg Thieme Verlag, Stuttgart. The entire disclosures of the treatises recited above are hereby incorporated by reference in their entireties for their teachings regarding methods for synthesizing organic compounds and their precursors.

The skilled artisan will also readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts, Protecting Groups in Organic Synthesis, $3^r$ Ed., John Wiley & Sons (1999).

Some exemplary synthetic methods useful for preparing the present compounds or the intermediates thereof are described below. As shown in Scheme 1 below, commercially available 2,6-dinitrobenzonitrile 1 can be coupled with an appropriately substituted amino alcohol where R and $R_1$ are alkyl or linked cycloalkyl substituents. Further reaction of the resulting primary amine 2 with isonicotinic acid 4 under standard coupling conditions provides the desired amide 6 where $R_2$ is alkyl, aryl, alkoxy, amino or amido. Those aforementioned isonicotinic acid analogs 4 that are not commercially available may be derived from chloro, bromo or iodo isonicotinic acid 3 through either halogen displacement or metal-catalyzed coupling (Suzuki, Buchwald-Hartwig, Negishi or Ullmann coupling conditions, etc). Alternatively, isonicotinic acid 4 can be converted into acid chloride 5 and coupled with amine 2 to provide amide 6. Subsequent conversion of 6 to aniline 7 through catalytic hydrogenation or iron reduction, followed by reaction with sulfamoyl chloride in DMA, and ring closure with NaOH in water provides the desired final compound 13. Additionally, advanced intermediate 6 can be accessed by reaction of 2-amino-6-fluorobenzonitrile with an appropriately substituted amino alcohol in the presence of sodium hydride, followed by coupling with isonicotinic acid 4 using TBTU and diisopropylethyl amine.

Scheme 1:

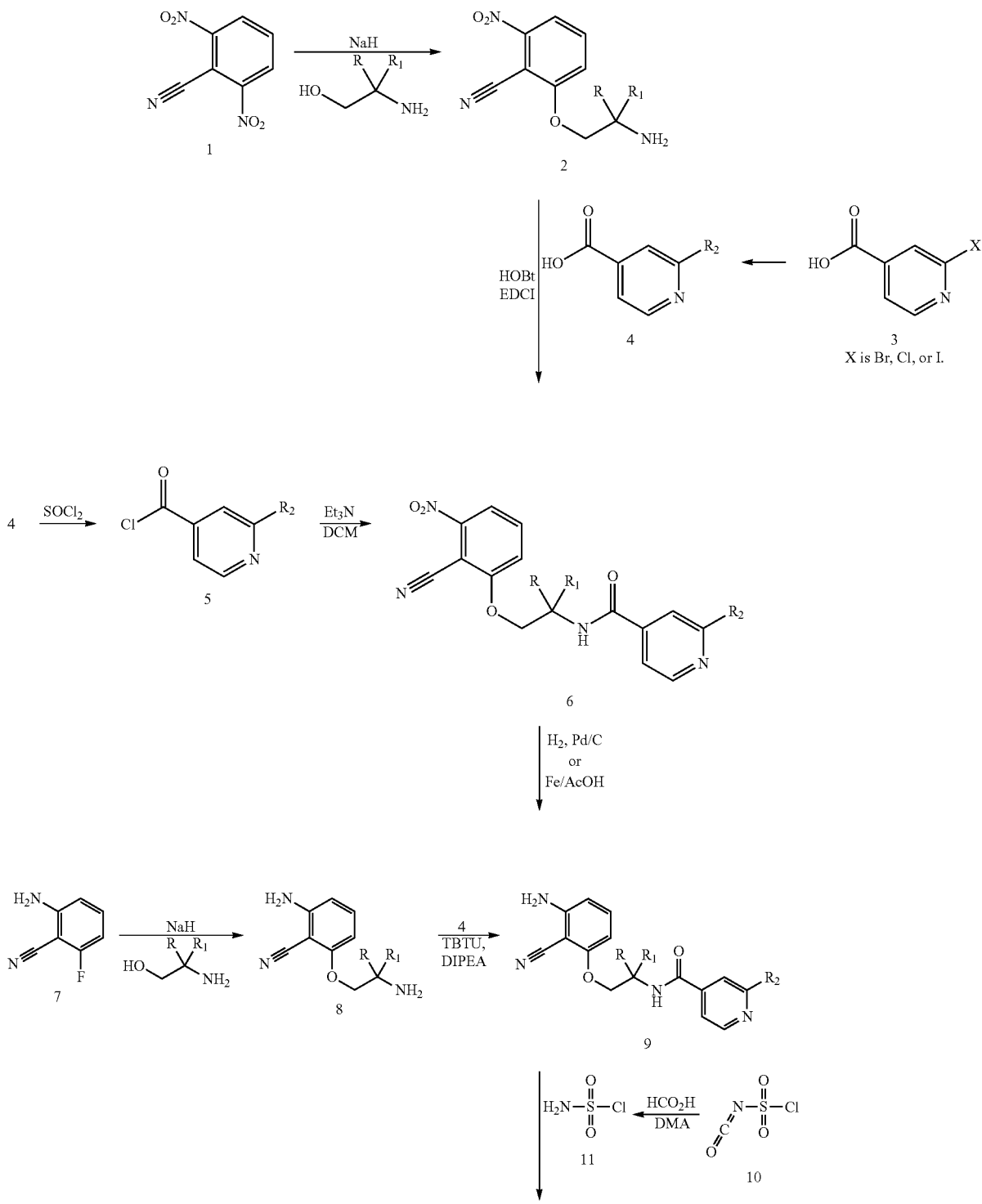

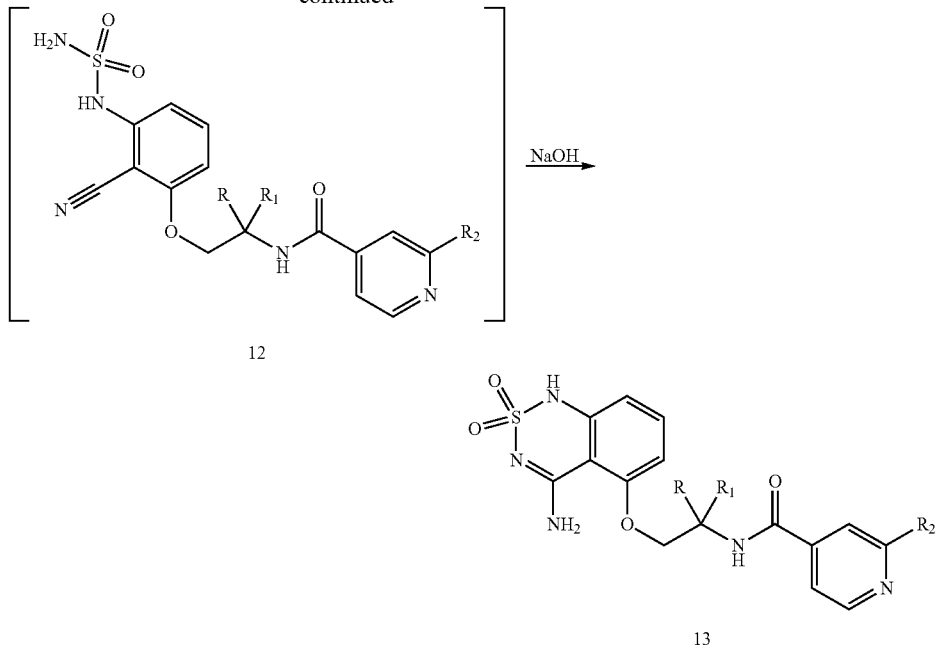

12

13

R and R₁ is independently alkyl or cycloalkyl.
R₂ is alkyl, aryl, heteroaryl, alkoxy, hydroxy, amino, amido, or sulfonyl.

Scheme 2 illustrates a synthetic route that can be used to access an advanced intermediate to generate a large number of analogs. One-pot reaction of 2,6-dinitrobenzonitrile 1 with an appropriately substituted amino alcohol in the presence of sodium hydride, followed by addition of di-tert-butyl dicarbonate provides boc-protected intermediate 4. The desired boc-protected cyclized intermediate 16 is accessed through reduction of the nitro substituent using catalytic hydrogenation or iron and acetic acid, followed by reaction with sulfamoyl chloride 11 and cyclization in the presence of NaOH. Removal of the boc-protecting group under acidic conditions provides advanced intermediate 17, which can be coupled to appropriately substituted isonicotinic acid 4 or acid chloride 5 to generate the desired compound 13.

Scheme 2:

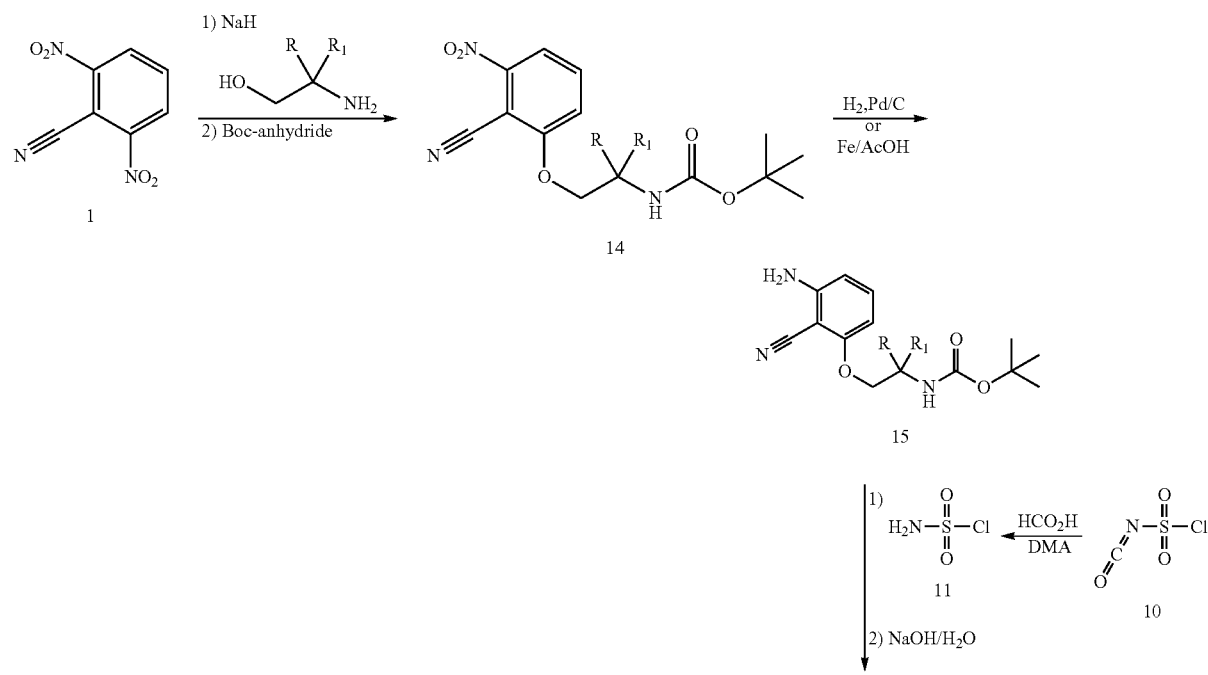

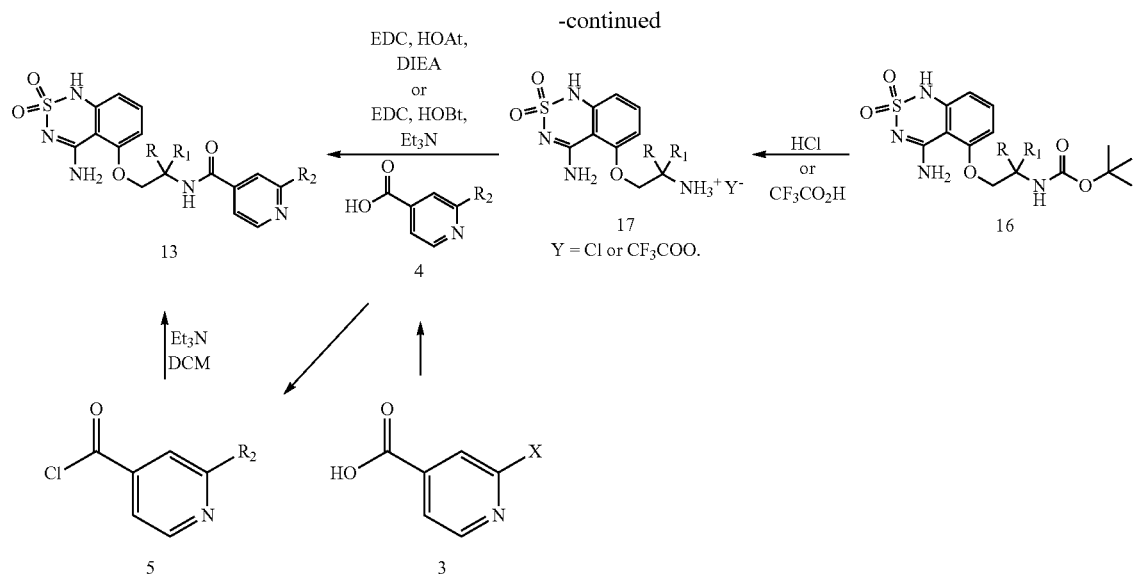

R and $R_1$ is independently alkyl or cycloalkyl.
$R_2$ = alkyl, aryl, heteroaryl, alkoxy, hydroxy, amino, amido, or sulfonyl.

Scheme 3 illustrates a route similar to that shown in Scheme 1, which demonstrates how iodo-, bromo- or chloro-isonicotinic acid 3 can be coupled directly to amines 2 or 8. Utilizing this route to access advanced intermediate 21 allows for substitution of the isonicotinic acid ring as the last step. Substitution through either direct halogen displacement or metal catalyzed coupling (Suzuki, Buchwald-Hartwig, Negishi or Ullmann coupling conditions, etc) provides the final desired compound 13.

Scheme 3:

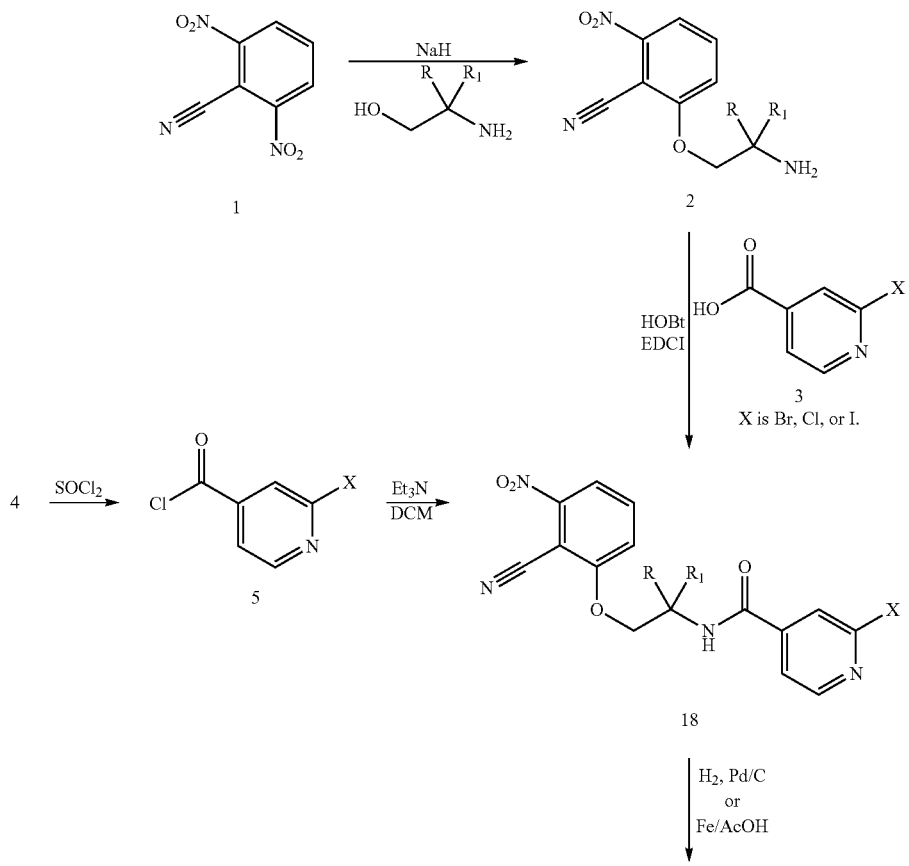

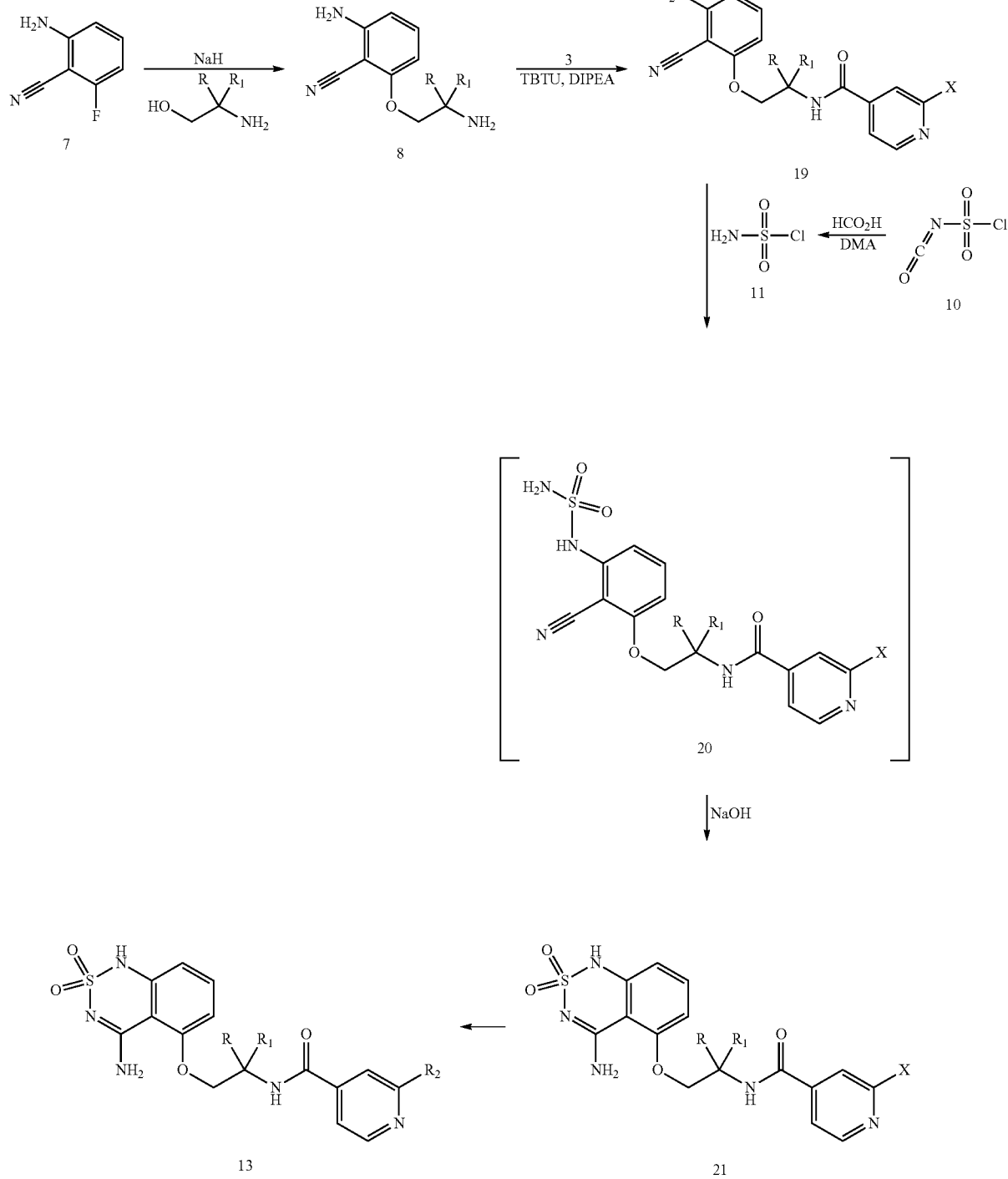

R and R₁ is independently alkyl or cycloalkyl.
R₂ is alkyl, aryl, heteroaryl, alkoxy, hydroxy, amino, amido, or sulfonyl.

EXAMPLES

Having now generally described the invention, the same will be more readily understood by reference to the following examples, which are provided by way of illustration and are not intended as limiting. It is understood that various modifications and changes can be made to the herein disclosed exemplary embodiments without departing from the spirit and scope of the invention.

Example 1

N-(1-(4-amino-2,2-dioxido-1H-benzo[c][1,2,6]thiadiazin-5-yloxy)-2-methylpropan-2-yl)isonicotinamide

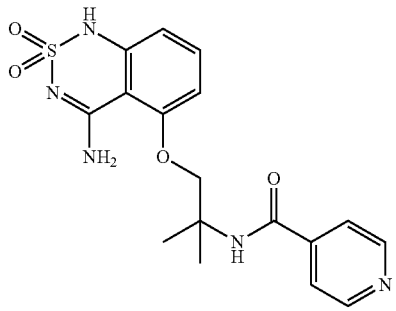 [SMILES: CC(C)(COc1cccc2c1C(N)=NS(=O)(=O)N2)NC(=O)c1ccncc1]

To a stirred suspension of 4-amino-5-(2-amino-2-methylpropoxy)-1H-benzo[c][1,2,6]thiadiazine 2,2-dioxide hydrochloride (962 mg, 3 mmol, Example 1a) in DMF (25 mL) was added triethylamine (0.834 mL, 6 mmol). After being stirred at room temperature for 10 min, a mixture of isonicotinic acid (369 mg, 3 mmol), EDCI (575 mg, 3 mmol) and HOBt (405 mg, 3 mmol) in 15 ml of DMF was added, and the reaction mixture was stirred at room temperature overnight. The resulting solution was concentrated and purified by HPLC (10-90% acetonitrile in water, reverse phase C18 column), and the product was recrystallized from ethanol/water to provide N-(1-(4-amino-2,2-dioxido-1H-benzo[c][1,2,6]thiadiazin-5-yloxy)-2-methylpropan-2-yl)isonicotinamide (760 mg, 65%) as an off white powder. M.p.: 235-238° C. $^1$H NMR (400 MHz, DMSO-$d_6$) δ 1.47 (s, 6H), 4.37 (s, 2H), 6.61 (d, J=7.6 Hz, 1H), 6.78 (d, J=7.6 Hz, 1H), 7.45 (t, J=8.4 Hz, 1H), 7.65 (d, J=6 Hz, 2H), 7.83 (s, 1H), 8.48 (s, 2H), 8.67 (d, J=6 Hz, 2H), 10.98 (s, 1H). MS 390 (MH$^+$).
Alternate Synthesis:

To a stirred suspension of N-(1-(2-cyano-3-(sulfamoylamino)phenoxy)-2-methylpropan-2-yl)isonicotinamide (12.2 g, 31.2 mmol, Example 10 in EtOH (80 mL) was added NaOH solution (2.0 N, 40 mL, 80 mmol) at room temperature. The reaction mixture was refluxed for 3 hrs, cooled to 0° C. and neutralized carefully with 2N aqueous HCl. The precipitate was collected by filtration, recrystallized from EtOH/H$_2$O and dried under high vacuum at 55° C. to provide N-(1-(4-amino-2,2-dioxido-1H-benzo[c][1,2,6]thiadiazin-5-yloxy)-2-methylpropan-2-yl)isonicotinamide (7.91 g, 65%) as a white solid. M.p.: 235-238° C. MS 390 (MH$^+$).

Example 1a 4-amino-5-(2-amino-2-methylpropoxy)-1H-benzo[c][1,2,6]thiadiazine 2,2-dioxide hydrochloride

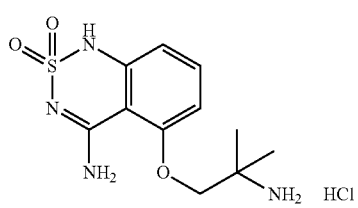 [SMILES: CC(C)(N)COc1cccc2c1C(N)=NS(=O)(=O)N2 ; Cl]

To a solution of tert-butyl(1-((4-amino-2,2-dioxido-1H-benzo[c][1,2,6]thiadiazin-5-yl)oxy)-2-methylpropan-2-yl-carbamate (114 g, 296 mmol, Example 1b) in ethanol (1 L), cooled to 0° C., was added HCl (4.0 M in dioxane, 370 mL, 1480 mmol). The mixture was stirred at 0° C. for 3 hours under nitrogen, and then allowed to warm to room temperature. The mixture was concentrated and the residue was suspended in diethyl ether (2 L) and refluxed for 1 hour. The mixture was cooled to room temperature and the solid was collected by vacuum filtration and dried under high vacuum to afford 4-amino-5-(2-amino-2-methylpropoxy)-1H-benzo[c][1,2,6]thiadiazine 2,2-dioxide hydrochloride (94 g, 100%) as a white solid. $^1$H NMR (DMSO-$d_6$), 400 MHz: δ 1.37 (s, 6H), 4.12 (s, 2H), 6.70 (d, J=8.0 Hz, 1H), 6.85 (d, J=8.0 Hz, 1H), 7.48 (t, J=8.0 Hz, 1H), 7.65 (s, 1H), 8.43 (br s, 3H), 10.9 (br s, 1H). MS 285 (MH$^+$).

Example 1b tert-butyl(1-((4-amino-2,2-dioxido-1H-benzo[c][1,2,6]thiadiazin-5-yl)oxy)-2-methylpropan-2-yl)carbamate

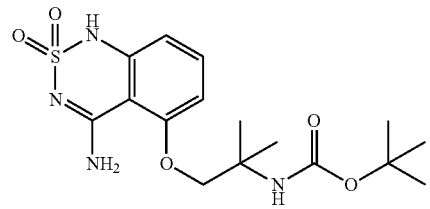 [SMILES: CC(C)(COc1cccc2c1C(N)=NS(=O)(=O)N2)NC(=O)OC(C)(C)C]

To a solution of tert-butyl(1-(2-cyano-3-(sulfamoylamino)phenoxy)-2-methylpropan-2-yl)carbamate (189 g, 492 mmol, Example 1c) in ethanol (1.5 L) was added solid NaOH (74 g, 1968 mmol), and the reaction was stirred at 115° C. for 13 hours under nitrogen. Upon completion, the mixture was cooled to 0° C. and neutralized with acetic acid. The precipitate was collected by vacuum filtration and dried under high vacuum to afford tert-butyl(1-((4-amino-2,2-dioxido-1H-benzo[c][1,2,6]thiadiazin-5-yl)oxy)-2-methylpropan-2-yl-carbamate (114 g, 61%) as a white solid. $^1$H NMR (DMSO-$d_6$), 400 MHz: δ 1.27 (s, 6H), 1.34 (s, 9H), 4.16 (s, 2H), 6.55 (d, J=8.0 Hz, 1H), 6.63 (d, J=8.0 Hz, 1H), 6.94 (br s, 1H), 7.37 (t, J=8.0 Hz, 1H), 7.75 (br s, 1H), 8.17 (br s, 1H), 10.8 (br s, 1H). MS 285 (MH$^+$).

Example 1c tert-butyl(1-(2-cyano-3-(sulfamoylamino)phenoxy)-2-methylpropan-2-yl)carbamate

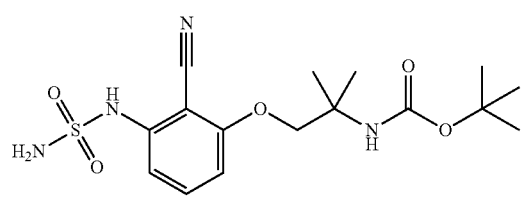 [SMILES: CC(C)(COc1cccc(NS(N)(=O)=O)c1C#N)NC(=O)OC(C)(C)C]

To a solution of tert-butyl(1-(3-amino-2-cyanophenoxy)-2-methylpropan-2-yl)carbamate (150 g, 492 mmol, Example 1d) in THF (1.8 L) was added lutidine (86 mL, 738 mmol). The mixture was cooled to −45° C. and sulfamoyl chloride (71 g, 616 mmol), dissolved in dichloromethane (400 mL), was added. After 10 min, the reaction was warmed to room temperature and stirred for 2 hours. Upon completion, solid NaHCO$_3$ (123 g, 1476 mmol) was added, and the mixture was stirred for 30 minutes, followed by concentration. The residue was diluted with ethyl acetate (1.8 L), washed with water (1 L), dried over anhydrous Na$_2$SO$_4$, filtered and concentrated in vacuo to provide tert-butyl(1-2-cyano-3-(sulfamoylamino)phenoxy)-2-methylpropan-2-yl)carbamate as a clear oil, which was used immediately in the next step. MS 285 (MH$^+$).

Example 1d tert-butyl(1-(3-amino-2-cyanophenoxy)-2-methyl-propan-2-yl)carbamate

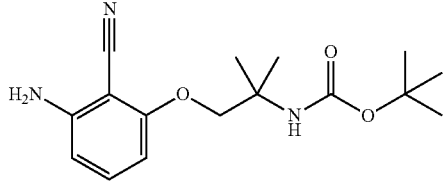

To a solution of tert-butyl(1-(2-cyano-3-nitrophenoxy)-2-methylpropan-2-yl)carbamate (45 g, 134 mmol, Example 1e) in ethyl acetate (200 mL) and ethanol (100 mL) was added 10% palladium on carbon (4.5 g). The reaction was stirred under H$_2$ at 40 psi, and upon completion, the mixture was filtered through a pad of celite, and the filtrate was concentrated in vacuo to provide tert-butyl(1-(3-amino-2-cyanophenoxy)-2-methylpropan-2-yl)carbamate (41 g, 100%) as a white solid. $^1$H NMR (DMSO-d$_6$), 400 MHz: δ 1.26 (s, 6H), 1.34 (s, 9H), 4.00 (s, 2H), 5.96 (br s, 2H), 6.15 (d, J=8.0 Hz, 1H), 6.31 (d, J=8.0 Hz, 1H), 6.63 (br s, 1H), 7.14 (t, J=8.0 Hz, 1H). MS 206 (MH$^+$).

Example 1e tert-butyl(1-(2-cyano-3-nitrophenoxy)-2-methylpropan-2-yl)carbamate

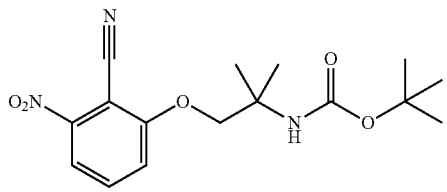 [SMILES: CC(C)(COc1cccc([N+](=O)[O-])c1C#N)NC(=O)OC(C)(C)C]

To a solution of 2-amino-2-methylpropan-1-ol (48 mL, 500 mmol) in THF (2 L) at −30° C., was added NaH (60% dispersion in oil, 22 g, 550 mmol) in one portion. The mixture was stirred for 10 minutes under nitrogen, and then warmed to room temperature. After 2 hours, the mixture was cooled −60° C. and 2,6-dinitrobenzonitrile (97 g, 500 mmol) was added. After 10 min, the solution was warmed to room temperature, and stirred for 13 h, then cooled back down to −30° C. and di-tert-butyl dicarbonate (131 g, 600 mmol) dissolved in THF (100 mL) was added. The reaction was stirred for 10 minutes at −30° C., then at room temperature for 13 hours. Upon completion, the reaction was neutralized with 10% citric acid and concentrated. The residue was diluted with ethyl acetate (1 L), washed with saturated aq. NaCl solution, dried over anhydrous Na$_2$SO$_4$ and filtered. The solvent was removed by in vacuo to obtain tert-butyl (1-(2-cyano-3-nitrophenoxy)-2-methylpropan-2-yl)carbamate as a beige solid (167 g, 100%). $^1$H NMR (DMSO-d$_6$), 400 MHz: δ 1.30 (s, 6H), 1.32 (s, 9H), 4.28 (s, 2H), 6.76 (br s, 1H), 7.68 (d, J=4.0 Hz, 1H), 7.85 (t, J=8.0 Hz, 1H), 7.91 (d, J=8.0 Hz, 1H). MS 336 (MH$^+$).

Example 1f

N-(1-(2-cyano-3-(sulfamoylamino)phenoxy)-2-methylpropan-2-yl)isonicotinamide

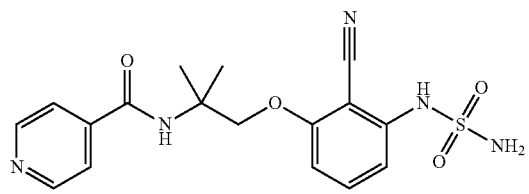 [SMILES: CC(C)(COc1cccc(NS(N)(=O)=O)c1C#N)NC(=O)c1ccncc1]

To a solution of N-(1-(3-amino-2-cyanophenoxy)-2-methylpropan-2-yl)isonicotinamide (10.76 g, 34.67 mmol, Example 1g) in DMA (35 mL) was added sulfamoyl chloride (7.98 g, 69.34 mmol) at room temperature under nitrogen. The reaction mixture was then stirred at room temperature under nitrogen overnight. The resulting solution was poured into 200 mL of ice cooled aqueous NaHCO$_3$, and stirred for 30 minutes. The precipitate was collected by filtration to afford N-(1-(2-cyano-3-(sulfamoylamino)phenoxy)-2-methylpropan-2-yl)isonicotinamide (12.2 g, 90%) as an off white solid. $^1$H NMR (400 MHz, DMSO-d$_6$) δ 1.47 (s, 6H), 4.32 (s, 2H), 6.93 (d, J=8.8 Hz, 1H), 7.12 (d, J=8.0 Hz, 1H), 7.23 (s, 2H), 7.53 (t, J=8.8 Hz, 1H), 7.67 (d, J=6 Hz, 2H), 8.29 (s, 1H), 8.66 (d, J=6.4 Hz, 2H), 9.45 (s, 1H). MS 390 (MH$^+$).

Example 1g

N-(1-(3-amino-2-cyanophenoxy)-2-methylpropan-2-yl)isonicotinamide

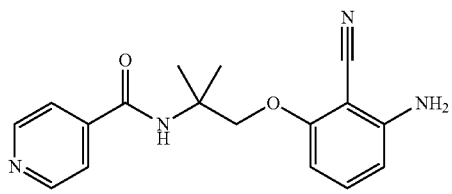 [SMILES: CC(C)(COc1cccc(N)c1C#N)NC(=O)c1ccncc1]

To a solution of N-(1-(2-cyano-3-nitrophenoxy)-2-methylpropan-2-yl)isonicotinamide (25 g, 72.27 mmol, Example 1h), acetic acid (125 mL) and THF (125 mL) was added iron powder (12.11 g, 216.8 mmol). The reaction was slowly heated to 70° C., refluxed for 1 hr, cooled to room temperature and filtered. The filtrate was concentrated under reduced pressure and purified by flash chromatography (20-30%

EtOAc in hexanes, normal phase silica gel) to provide N-(1-(3-amino-2-cyanophenoxy)-2-methylpropan-2-yl)isonicotinamide (15.8 g, 70%) as a light brown solid. MS 311 (MH+).

Example 1h

N-(1-(2-cyano-3-nitrophenoxy)-2-methylpropan-2-yl)isonicotinamide

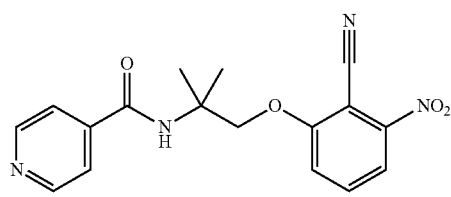 [SMILES: CC(C)(COc1cccc([N+](=O)[O-])c1C#N)NC(=O)c1ccncc1]

To a solution of isonicotinic acid (8.9 g, 72.27 mmol), EDC (13.8 g, 72.27 mmol) and HOBt (9.8 g, 72.27 mmol) in DCM (1 L) and DMF (50 mL), was added 2-(2-amino-2-methylpropoxy)-6-nitrobenzonitrile (17 g, 72.27 mmol, Example 10. The reaction was stirred at room temperature, and upon completion was diluted with DCM, washed with 0.5N aqueous HCl and water. The organic layer was dried over MgSO$_4$, filtered, and evaporated under reduced pressure to provide N-(1-(2-cyano-3-nitrophenoxy)-2-methylpropan-2-yl)isonicotinamide (25 g, 100%) as a brown gel. MS 341 (MH+).

Example 1i

Synthesis of 2-(2-amino-2-methylpropoxy)-6-nitrobenzonitrile

To a solution of 2-amino-2-methylpropan-1-ol (10.4 g, 116.51 mmol) in THF (350 mL) at 0° C. under N$_2$, was added NaH (3.26 g, 81.55 mmol, 60% dispersion in mineral oil). The mixture was stirred at room temperature for 1 hr and cooled to −5° C., at which time, 2,6-dinitrobenzonitrile (15 g, 77.67 mmol) was added in one portion. To solution was stirred at room temperature, and upon completion was concentrated, poured over ice water and the precipitate was collected by vacuum filtration to provide 2-(2-amino-2-methylpropoxy)-6-nitrobenzonitrile (17 g, 93%) as a light brown solid. $^1$H NMR (400 MHz, CDCl3) δ 1.32 (s, 6H), 3.89 (s, 2H), 7.31 (d, J=6.8 Hz, 1H), 7.70 (t, J=6.8 Hz, 1H), 7.86 (d, J=6.8 Hz, 2H). MS 236 (MH+).

Example 2

N-(1-((4-amino-2,2-dioxido-1H-benzo[c][1,2,6]thiadiazin-5-yl)oxy)-2-methylpropan-2-yl)-2-methylisonicotinamide

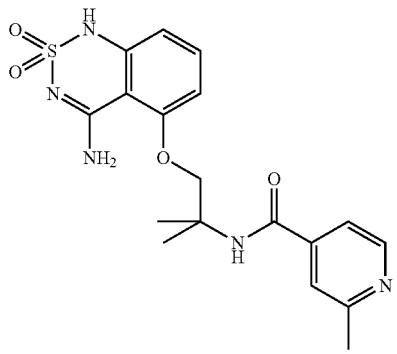 [SMILES: Cc1cc(C(=O)NC(C)(C)COc2cccc3c2C(N)=NS(=O)(=O)N3)ccn1]

Prepared as in Example 1 from 4-amino-5-(2-amino-2-methylpropoxy)-1H-benzo[c][1,2,6]thiadiazine 2,2-dioxide hydrochloride (Example 1a) and 2-methylisonicotinic acid in 80% yield. M.p.: 238-240° C. $^1$H NMR (400 MHz, DMSO-d$_6$) δ 1.48 (s, 6H), 2.52 (s, 3H), 4.39 (s, 2H), 6.63 (d, J=8.0 Hz, 1H), 6.79 (d, J=8.0 Hz, 1H), 7.45-7.49 (m, 2H), 7.52 (s, 1H), 7.83 (s, 1H), 8.43 (s, 1H), 8.50 (s, 1H), 8.54 (s, 1H), 11.00 (s, 1H). MS 404 (MH+).

Example 3

N-(1-((4-amino-2,2-dioxide-1H-benzo[c][1,2,6]thiadiazin-5-yl)oxy)-2-methylpropan-2-yl)-2,6-dimethylisonicotinamide

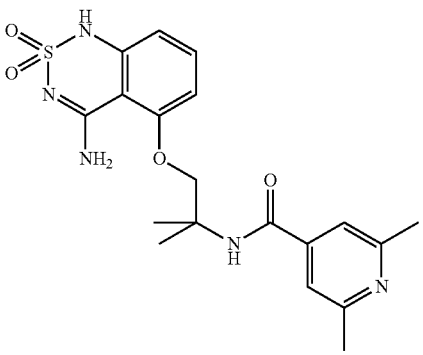 [SMILES: Cc1cc(C(=O)NC(C)(C)COc2cccc3c2C(N)=NS(=O)(=O)N3)cc(C)n1]

Prepared as in Example 1 from 4-amino-5-(2-amino-2-methylpropoxy)-1H-benzo[c][1,2,6]thiadiazine 2,2-dioxide hydrochloride (Example 1a) and 2,6-dimethylisonicotinic acid in 57% yield. M.p.: 240-241° C. $^1$H NMR (400 MHz, DMSO-d$_6$) δ 1.45 (s, 6H), 2.45 (s, 6H), 4.37 (s, 2H), 6.61 (d, J=8.0 Hz, 1H), 6.77 (d, J=8.0 Hz, 1H), 7.28 (s, 2H), 7.46 (t, J=8.0 Hz, 1H), 7.81 (s, 1H), 8.35 (s, 1H), 8.50 (s, 1H), 10.99 (s, 1H). MS 418 (MH+).

Example 4

N⁴-(1-((4-amino-2,2-dioxido-1H-benzo[c][1,2,6]thiadiazin-5-yl)oxy)-2-methylpropan-2-yl)pyridine-2,4-dicarboxamide

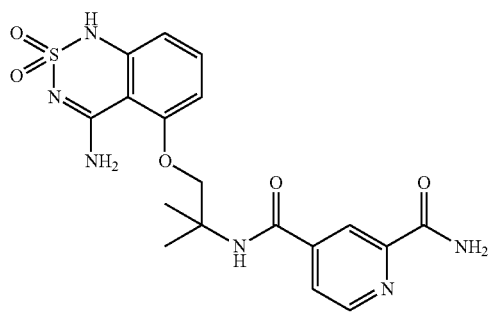 [SMILES: CC(C)(COc1cccc2c1C(N)=NS(=O)(=O)N2)NC(=O)c1ccnc(C(N)=O)c1]

To a solution of N-(1-((4-amino-2,2-dioxido-1H-benzo[c][1,2,6]thiadiazin-5-yl)oxy)-2-methylpropan-2-yl)-2-cyanoisonicotinamide (300 mg, 724 umol, Example 4a) in ethanol (20 mL) at room temperature, was added a solution of sodium hydroxide (275 mg, 7.06 mmol) in water (6 mL). The reaction was microwaved at 80° C. for five minutes, and upon completion was cooled 0° C., neutralized with 1N HCl, concentrated and purified by flash chromatography (1/9 methanol/dichloromethane, normal phase silica gel). The purified product was washed with hot ethanol and the solid was collected by vacuum filtration and dried under vacuum at 50° C. to provide N⁴-(1-((4-amino-2,2-dioxido-1H-benzo[c][1,2,6]thiadiazin-5-yl)oxy)-2-methylpropan-2-yl)pyridine-2,4-dicarboxamide (95 mg, 29%) as a white solid. ¹H NMR (DMSO-d₆, 400 MHz): δ 1.50 (s, 6H), 4.38 (s, 2H), 6.62 (d, J=0.8 Hz, 1H), 6.80 (d, J=8.4 Hz, 1H), 7.47 (t, J=8.4 Hz, 1H), 7.75 (s, 1H), 7.80 (s, 1H), 7.86 (dd, J=5.2 Hz, 1H), 8.19 (s, 1H), 8.35 (s, 1H), 8.39 (s, 1H), 8.69 (s, 1H), 8.73 (dd, J=4.8 Hz, 1H), 10.99 (s, 1H). MS 433 (MH⁺).

Example 4a

N-(1-((4-amino-2,2-dioxido-1H-benzo[c][1,2,6]thiadiazin-5-yl)oxy)-2-methylpropan-2-yl)-2-cyanoisonicotinamide

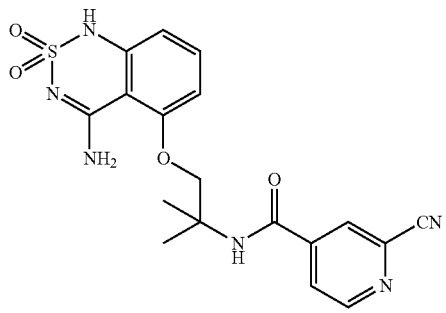 [SMILES: CC(C)(COc1cccc2c1C(N)=NS(=O)(=O)N2)NC(=O)c1ccnc(C#N)c1]

Prepared as in Example 1 from 4-amino-5-(2-amino-2-methylpropoxy)-1H-benzo[c][1,2,6]thiadiazine 2,2-dioxide hydrochloride (Example 1a) and 2-cyanoisonicotinic acid in 50% yield. ¹H NMR (DMSO-d₆, 400 MHz): δ 1.47 (s, 6H), 4.39 (s, 2H), 6.62 (d, J=8.3 Hz, 1H), 6.79 (d, J=8.5 Hz, 1H), 7.46 (t, J=8.3 Hz, 2H), 7.77 (s, 1H), 8.00 (dd, J=1.7 Hz, 1H), 8.32 (s, 1H), 8.46 (s, 1H), 8.65 (s, 1H), 8.86 (dd, J=5.1 Hz, 1H), 10.99 (s, 1H). MS 415 (MH⁺).

Example 5

N-(1-((4-amino-2,2-dioxido-1H-benzo[c][1,2,6]thiadiazin-5-yl)oxy)-2-methylpropan-2-yl)-2-(methylamino)isonicotinamide

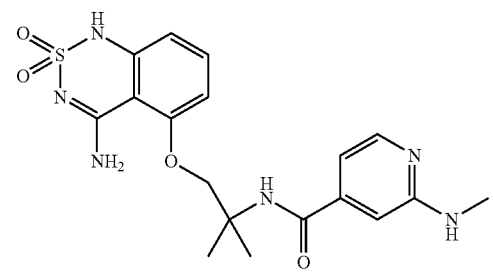 [SMILES: CNc1cc(C(=O)NC(C)(C)COc2cccc3c2C(N)=NS(=O)(=O)N3)ccn1]

Prepared as in Example 1 from 4-amino-5-(2-amino-2-methylpropoxy)-1H-benzo[c][1,2,6]thiadiazine 2,2-dioxide hydrochloride (Example 1a) and 2-(methylamino)isonicotinic acid in 56% yield. ¹H NMR (400 MHz, DMSO-d₆) δ 1.45 (s, 6H), 2.78 (d, J=4.8 Hz, 3H), 4.34 (s, 2H), 6.58-6.65 (m, 3H), 6.72 (d, J=1.2 Hz, 1H), 6.73 (d, J=1.2 Hz, 1H), 7.42 (t, J=8.0 Hz, 1H), 7.80 (br s, 1H), 8.03 (d, J=5.2 Hz, 1H), 8.23 (s, 1H), 8.30 (br s, 1H), 10.98 (br s, 1H) MS 419 (MH⁺).

Example 6

N-(1-((4-amino-2,2-dioxido-1H-benzo[c][1,2,6]thiadiazin-5-yl)oxy)-2-methylpropan-2-yl)-2-(1H-imidazol-1-yl)isonicotinamide

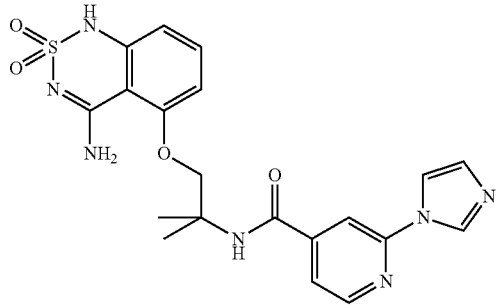 [SMILES: CC(C)(COc1cccc2c1C(N)=NS(=O)(=O)N2)NC(=O)c1ccnc(-n2ccnc2)c1]

To a solution of 2-(1H-imidazol-1-yl)isonicotinic acid (29.5 g, 156 mmol, Example 6a), N,N-diisopropylethylamine (109 mL, 626 mmol, 4 eq), and HOAt (3H-[1,2,3]triazolo[4,5-b]pyridin-3-ol) (25.5 g, 187 mmol, 1.2 eq) in anhydrous DMF (300 mL) was added under nitrogen at −5° C. N1-((ethylimino)methylene)-N3,N3-dimethylpropane-1,3-diamine hydrochloride (EDC, 35.9 g, 187 mmol, 1.2 eq). The mixture was allowed to slowly warm up to 10° C. (~1 hour) then cooled to −5° C. and 4-amino-5-(2-amino-2-methylpropoxy)-1H-benzo[c][1,2,6]thiadiazine 2,2-dioxide hydrochloride (50.0 g, 156 mmol, 1 eq, Example 1a) was added. The reaction was allowed to warm up to room temperature and stirred for 28 hours. The reaction mixture was slowly poured onto a solution of AcOH (19.23 mL, 336 mmol, 2.15 eq) in water (3200 mL) and the resultant precipitate was collected by filtration then suspended in EtOH (1000 mL), heated at reflux for sixty minutes, then cooled to room temperature. The solid material was collected by vacuum filtration and suspended in water (1000 mL). The suspension was treated with 2N aqueous NaOH until pH ~9. At this point, all the solid material has dissolved to give a brown solution. The solution was acidified at room temperature using aqueous HCl (1N) until pH 5. The precipitate that formed was collected by vacuum filtration and dried for several days under vacuum to give N-(1-((4-amino-2,2-dioxido-1H-benzo[c][1,2,6]thiadiazin-5-yl)oxy)-2-methylpropan-2-yl)-2-(1H-imidazol-1-yl)isonicotinamide as a beige solid (35.0 g, 77 mmol, 49.7%). $^1$H NMR (DMSO-$d_6$, 400 MHz): δ 1.52 (s, 6H), 4.42 (s, 2H), 6.64 (dd, J=8.0, 1.2 Hz, 1H), 6.79 (dd, J=8.4, 1.2 Hz, 1H), 7.17 (s, 1H), 7.48 (t, J=8.4 Hz, 1H), 7.65 (dd, J=5.2, 1.6 Hz, 1H), 7.84 (br. d, J=2.8 Hz, 1H), 8.02 (br. s, 1H) 8.05 (br. t, J=1.2 Hz, 1H), 8.54 (br. d, J=2.8 Hz, 1H), 8.57-8.65 (m, 3H), 11.04 (s, 1H). $^{13}$C NMR (DMSO-$d_6$, 100 MHz) δ 24.03, 53.9, 73.9, 100.2, 105.1, 110.0, 110.7, 116.9, 120.2, 130.2, 135.0, 135.5, 144.5, 145.6, 149.1, 149.4, 157.7, 160.5, 164.8.

Alternate Synthesis:

A solution of sulfamoyl chloride (5.43 g, 46.96 mmol, 1.75 equiv) in anhydrous DCM (40.5 mL) was added under nitrogen at −20° C. to a solution of N-(1-(3-amino-2-cyanophenoxy)-2-methylpropan-2-yl)-2-(1H-imidazol-1-yl) isonicotinamide (10.1 g, 26.83 mmol, 1 equiv, Example 6b) in anhydrous DMA (40.5 mL). The reaction temperature was maintained between −20° C. and −10° C. during this addition. The mixture was then allowed to stir at room temperature for 45 minutes, cooled back to −20° C., and 1-butanol (121 mL) was added. The cold bath was removed and the reaction was washed with 3.3% aqueous NaHCO$_3$ (2×243 mL). The organic layer was treated slowly with NaOH (3M, 89.5 mL, 10 equiv) and heated in a 50° C. bath for 76 hours. The layers were separated and the organic layer was cooled to 0° C. and acidified to pH 3 using 1M aqueous HCl solution. The precipitate was collected by vacuum filtration and rinsed with a small amount of butanol, then dried under vacuum to give a beige powder. This material was dissolved in aqueous NaOH (0.3M, 152 mL). While stirring vigorously, the mixture was acidified using 0.75M aqueous HCl solution to pH 5. The precipitate was filtered, washed with water and dried under vacuum to give N-(1-((4-amino-2,2-dioxido-1H-benzo[c][1,2,6]thiadiazin-5-yl)oxy)-2-methylpropan-2-yl)-2-(1H-imidazol-1-yl)isonicotinamide as off white solid (7.62 g, 62.4%). MS 456 (MH$^+$).

Example 6a 2-(1H-imidazol-1-yl)isonicotinic acid

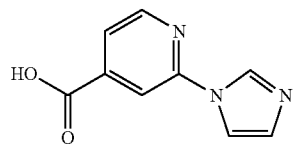 [SMILES: O=C(O)c1ccnc(-n2ccnc2)c1]

A solution of 2-chloroisonicotinic acid (60.0 g, 380.8 mmol) and 1H-imidazole (150 g, 2203.3 mmol) in water (75 mL) was stirred for 30 min at room temperature then heated to 170° C. (internal temperature) in a pressure vessel. After 6 hours the reaction mixture cooled to room temperature and water (1500 mL) was added. The resulting solution was acidified by dropwise addition of aqueous HCl (5N) until pH 4.5. The reaction was further diluted with water (1000 mL) and the precipitate was collected and washed with ice water. The solid was air dried overnight, collected and further dried under vacuum to give 2-(1H-imidazol-1-yl)isonicotinic acid as a beige solid (59.6 g, 315.06 mmol, 83%). $^1$H NMR (400 MHz, DMSO-$d_6$) δ 7.15 (br. t, J=1.2 Hz, 1H), 7.74 (dd, J=4.8, 1.2 Hz, 1H), 8.07 (br. t, J=1.20 Hz, 1H), 8.17 (br. t, J=1.20 Hz, 1H), 8.62-8.70 (m, 2H). MS 190 (MH$^+$).

Example 6b

N-(1-(3-amino-2-cyanophenoxy)-2-methylpropan-2-yl)-2-(1H-imidazol-1-yl) isonicotinamide

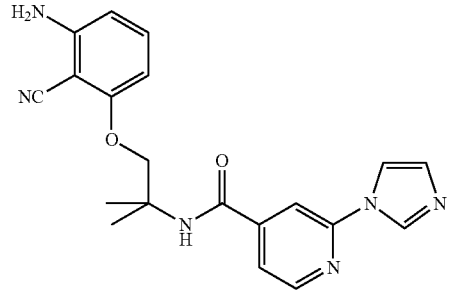 [SMILES: CC(C)(COc1cccc(N)c1C#N)NC(=O)c1ccnc(-n2ccnc2)c1]

Diisopropylethyl amine (49.7 mL, 285 mmol, 3 equiv.) was added under nitrogen to a suspension of 2-(1H-imidazol-1-yl)isonicotinic acid (18.0 g, 95.2 mmol, 1 equiv., Example 6a) in anhydrous DMF (200 mL) and stirred at room temperature until complete dissolution. The mixture was cooled to −10° C. and TBTU (36.66 g, 114 mmol, 1.2 equiv.) was added. It was then allowed to warm up slowly to 0° C. over a period of 30 minutes and cooled back down to −10° C. A solution of 2-Amino-6-(2-amino-2-methylpropoxy)benzonitrile (19.54 g, 95.2 mmol, 1 equiv., Example 6c) in anhydrous DMF (100 mL) was added at a rate which kept the reaction temperature below 0° C. The reaction temperature was maintained at 0° C. for 4 hours. The mixture was then poured into water (3000 mL), stirred vigorously for 30 minutes, and the precipitated product was collected by vacuum filtration, washed with water and dried under vacuum to provide N-(1-(3-amino-2-cyanophenoxy)-2-methylpropan-2-yl)-2-(1H-imidazol-1-yl) isonicotinamide as a beige solid (35.8 g, 100% yield). $^1$H NMR (400 MHz, DMSO-$d_6$) δ 1.49 (s, 6H), 4.25 (s, 2H), 6.01 (br. s, 2H), 6.23 (dd, J=8.4, 0.8, Hz, 1H), 6.33 (dd, J=8.4, 0.8, Hz, 1H), 7.14-7.20 (m, 2H), 7.64 (dd, J=4.8, 0.8, Hz, 1H), 8.02 (dm, J=8.8 Hz, 2H), 8.38 (s, 1H), 8.56-8.61 (m, 2H). MS 377 (MH$^+$).

Example 6c

2-Amino-6-(2-amino-2-methylpropoxy)benzonitrile

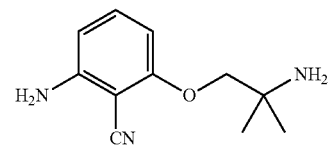

2-Amino-2-methylpropan-1-ol (17.29 g, 193.93 mmol) in anhydrous dioxane (200 mL) was added dropewise to a solution of sodium hydride (7.75 g, 193.93 mmol, 60% suspension in mineral oil) in anhydrous dioxane (100 mL). After the addition was completed the mixture was stirred at room temperature for 1 h and cooled to 10° C. A solution of 2-amino-6-fluorobenzonitrile (22 g, 160.34 mmol) in anhydrous dioxane (200 mL) was added dropewise while keeping the temperature below 15° C. The cooling bath was removed and the reaction was slowly heated to reflux and stirred for 2 h. The reaction was cooled to RT, quenched with saturated sodium bicarbonate and extracted with Dioxane/EtOAc/Et$_2$O 5:1:1. The combined extract was dried over Na$_2$SO$_4$ and partially concentrated. The precipitate that formed was filtered, washed with Et$_2$O and dried under vacuum to give 18.1 g of 2-Amino-6-(2-amino-2-methylpropoxy)benzonitrile. The filtrate was concentrated and purified by chromatography over silica gel using 10% MeOH/DCM to give 7.78 g of additional 2-Amino-6-(2-amino-2-methylpropoxy)benzonitrile. (79% yield). $^1$H NMR (400 MHz, DMSO-d$_6$) δ 1.10 (s, 6H), 1.51 (br. s, 2H), 3.66 (s, 2H), 6.01 (br. s, 2H), 6.16 (dd, J=8.4, 0.8 Hz, 1H), 6.33 (dd, J=8.4, 0.8 Hz, 1H), 7.17 (t, J=8.4 Hz, 1H). MS 236 (MH$^+$).

Example 7

N-(1-((4-amino-2,2-dioxido-1H-benzo[c][1,2,6]thiadiazin-5-yl)oxy)-2-methylpropan-2-yl)-2-(1H-1,2,4-triazol-1-yl)isonicotinamide

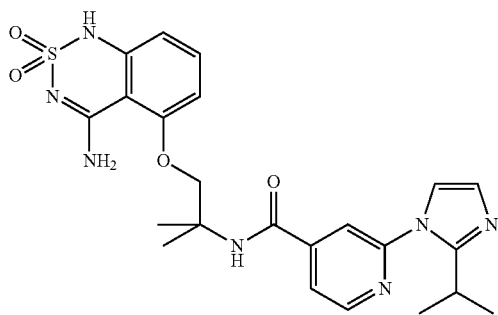 [SMILES: CC(C)c1nccn1-c1cc(C(=O)NC(C)(C)COc2cccc3c2C(N)=NS(=O)(=O)N3)ccn1]

Prepared as in Example 1 from 4-amino-5-(2-amino-2-methylpropoxy)-1H-benzo[c][1,2,6]thiadiazine 2,2-dioxide hydrochloride (Example 1a) and 2-(2-isopropyl-1H-imidazol-1-yl)isonicotinic acid (Example 7a) in 23% yield. $^1$H NMR (DMSO-d$_6$, 400 MHz): δ 1.15 (d, J=6.4 Hz, 6H), 1.49 (s, 6H), 3.46 (m, J=6.4 Hz, 1H), 4.38 (s, 2H), 6.61 (d, J=8.4 Hz, 1H), 6.79 (d, J=8.0 Hz, 1H), 6.94 (s, 1H), 7.46 (t, J=8.4 Hz, 1H), 7.52 (s, 1H), 7.74 (dd, J=3.6 Hz, 1H), 7.81 (s, 2H), 8.66 (dd, J=4.8 Hz, 1H), 11.00. MS 498 (MH$^+$).

Example 7a 2-(2-isopropyl-1H-imidazol-1-yl)isonicotinic acid

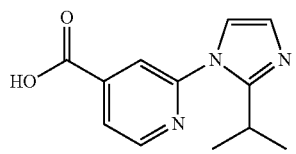 [SMILES: CC(C)c1nccn1-c1cc(C(=O)O)ccn1]

A mixture of methyl 2-bromoisonicotinate (2.00 g, 9.26 mmol), 2-isopropyl-1H-imidazole (1.12 g, 10.2 mmol), cesium carbonate (6.03 g, 18.5 mmol) and copper(1) Iodide (176 mg, 926 umol) in DMSO was heated to 120° C. for eighteen hours, under nitrogen. The crude material was filtered, purified by preparative HPLC (10-90% CH$_3$CN in water, reverse phase C18 column), and concentrated under reduced pressure to provide 2-(2-isopropyl-1H-imidazol-1-yl)isonicotinic acid (1.18 g, 55% yield) as a white solid. MS 232 (MH$^+$).

Example 8

N-(1-((4-amino-2,2-dioxido-1H-benzo[c][1,2,6]thiadiazin-5-yl)oxy)-2-methylpropan-2-yl)-2-(1H-1,2,4-triazol-1-yl)isonicotinamide

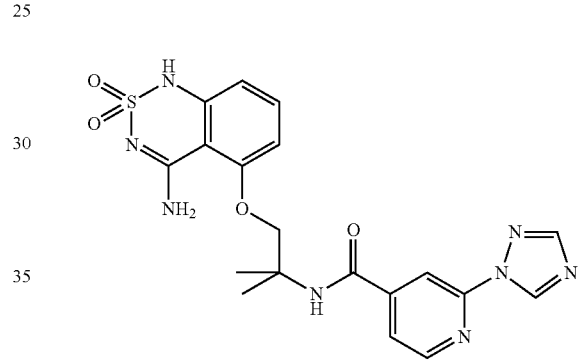

A mixture of N-(1-((4-amino-2,2-dioxido-1H-benzo[c][1,2,6]thiadiazin-5-yl)oxy)-2-methylpropan-2-yl)-2-bromoisonicotinamide (750 mg, 1.60 mmol, Example 8a), 1H-1,2,4-triazole (122 mg, 1.76 mmol), cesium carbonate (782 mg, 2.40 mmol) and copper(1) Iodide (76.2 mg, 0.400 mmol) in DMF was heated to 120° C. for eighteen hours, under nitrogen. The crude material was filtered, purified by preparative HPLC (10-90% acetonitrile in water, reverse phase C18 column), followed by flash chromatography (7/93 methanol/dichloromethane, normal phase silica gel). The purified product was suspended in water (3 mL) and sodium carbonate was added (86.4 mg, 815 umol). The suspension was heated to 70° C. until fully dissolved, cooled to room temperature and neutralized with 1N HCl. The precipitate was collected by vacuum filtration and dried under vacuum at 60° C. to provide N-(1-((4-amino-2,2-dioxido-1H-benzo[c][1,2,6]thiadiazin-5-yl)oxy)-2-methylpropan-2-yl)-2-bromoisonicotinamide (155 mg, 21%) as a white solid. $^1$H NMR (DMSO-d$_6$, 400 MHz): δ 1.49 (s, 6H), 4.39 (s, 2H), 6.61 (d, J=7.6 Hz, 1H), 6.79 (d, J=8.0 Hz, 1H), 7.46 (t, J=8.0 Hz, 1H), 7.76 (dd, J=4.4 Hz, 1H), 7.78 (s, 1H), 8.15 (s, 1H), 8.33 (s, 1H), 8.37 (s, 1H), 8.63 (dd, J=6.0 Hz, 1H), 8.71 (s, 1H), 9.40 (s, 1H), 10.98 (s, 1H). MS 457 (MH$^+$).

Example 8a

N-(1-((4-amino-2,2-dioxido-1H-benzo[c][1,2,6]thiadiazin-5-yl)oxy)-2-methylpropan-2-yl)-2-bromoisonicotinamide

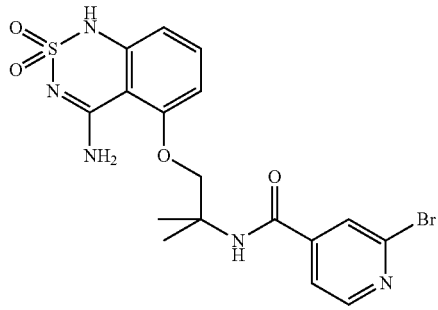 [SMILES: CC(C)(COc1cccc2c1C(N)=NS(=O)(=O)N2)NC(=O)c1ccnc(Br)c1]

Prepared as in Example 1 from 4-amino-5-(2-amino-2-methylpropoxy)-1H-benzo[c][1,2,6]thiadiazine 2,2-dioxide hydrochloride (Example 1a) and 2-bromoisonicotinic acid as a light orange solid in 62% yield. $^1$H NMR (DMSO-d$_6$), 400 MHz: δ 1.47 (s, 6H), 4.36 (s, 2H), 6.62 (d, J=8.0 Hz, 1H), 6.80 (d, J=8.0 Hz, 1H), 7.46 (t, J=8.0 Hz, 1H), 7.71 (d, J=4.0 Hz, 1H), 7.77 (br s, 1H), 7.93 (m, 1H), 8.45 (br s, 1H), 8.50 (d, J=4.0 Hz, 1H), 8.58 (s, 1H), 11.0 (br s, 1H). MS 468 (MH$^+$).

Example 9

N-(1-(((4-amino-2,2-dioxido-1H-benzo[c][1,2,6]thiadiazin-5-yl)oxy)methyl)cyclopentyl)isonicotinamide

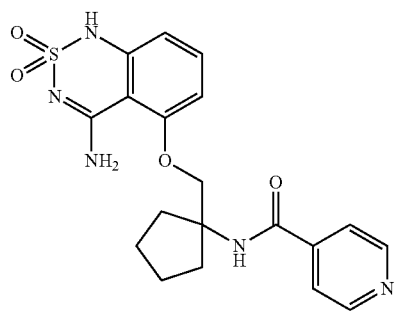 [SMILES: NC1=NS(=O)(=O)Nc2cccc(OCC3(NC(=O)c4ccncc4)CCCC3)c21]

Prepared as in Example 1 from 4-amino-5-((1-aminocyclopentyl)methoxy)-1H-benzo[c][1,2,6]thiadiazine 2,2-dioxide hydrochloride (Example 9a) and isonicotinic acid in 72% yield. M.p.: >250° C. $^1$H NMR (400 MHz, DMSO-d$_6$) δ 1.65-1.67 (m, 2H), 1.75-1.78 (m, 2H), 1.83-1.88 (m, 2H), 2.19-2.24 (m, 2H), 4.43 (s, 2H), 6.59 (d, J=8.0 Hz, 1H), 6.79 (d, J=8.0 Hz, 1H), 7.43 (t, J=8.0 Hz, 1H), 7.66 (d, J=8.0 Hz, 2H), 7.85 (s, 1H), 8.43 (s, 1H), 8.56 (s, 1H), 8.66 (d, J=8 Hz, 2H), 10.96 (s, 1H). MS 416 (MH$^+$).

Example 9a 4-amino-5-(1-aminocyclopentyl)methoxy)-1H-benzo[c][1,2,6]thiadiazine 2,2-dioxide hydrochloride

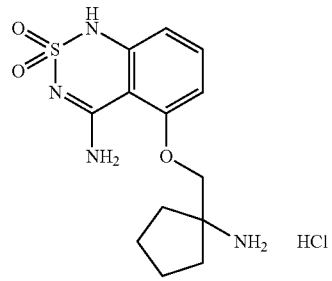 [SMILES: NC1=NS(=O)(=O)Nc2cccc(OCC3(N)CCCC3)c21 ; Cl]

Prepared as in Example 1a from tert-butyl(3-(((4-amino-2,2-dioxido-1H-benzo[c][1,2,6]thiadiazin-5-yl)oxy)methyl)cyclopentyl)carbamate (Example 9b) in 64% yield. MS 311 (MH$^+$).

Example 9b tert-butyl(3-(((4-amino-2,2-dioxido-1H-benzo[c][1,2,6]thiadiazin-5-yl)oxy)methyl)cyclopentyl)carbamate

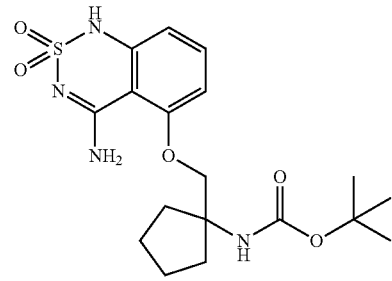 [SMILES: CC(C)(C)OC(=O)NC1(COc2cccc3c2C(N)=NS(=O)(=O)N3)CCCC1]

Prepared as in Example 1b from tert-butyl(1-((2-cyano-3-(sulfamoylamino)phenoxy)methyl)cyclopentyl)carbamate (Example 9c) as a white solid in 49% yield. MS 411 (MH$^+$).

Example 9c tert-butyl(1-((2-cyano-3-sulfamoylamino)phenoxy)methyl)cyclopentyl)carbamate

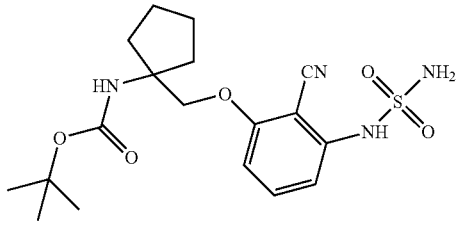 [SMILES: CC(C)(C)OC(=O)NC1(COc2cccc(NS(N)(=O)=O)c2C#N)CCCC1]

To a solution of tert-butyl(1-(((3-amino-2-cyanophenoxy)methyl)cyclopentyl)carbamate (1.00 g, 3.02 mmol, Example 9d) in DMA (24 mL), was added pyridine (733 uL, 9.06 mmol) followed by sulfamoyl chloride (523 mg, 4.53 mmol) at room temperature. The reaction was stirred at room temperature under nitrogen for 1 hr., neutralized with saturated sodium bicarbonate, diluted with water and extracted with EtOAc. The organic layer was dried over sodium sulfate, filtered and concentrated under reduced pressure to provide tert-butyl(1-((2-cyano-3-sulfamoylamino)phenoxy)methyl)cyclopentyl)carbamate (939 mg, 100%). MS 311 (MH$^+$).

Example 9d tert-butyl(1-((3-amino-2-cyanophenoxy)methyl)cyclopentyl)carbamate

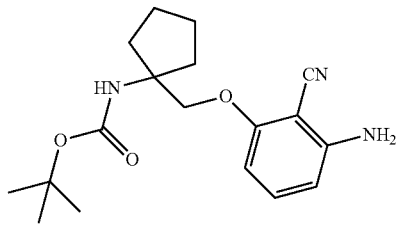 [SMILES: CC(C)(C)OC(=O)NC1(COc2cccc([N+](=O)[O-])c2C#N)CCCC1]

Prepared as in Example 1d from tert-butyl(1-((2-cyano-3-nitrophenoxy)methyl)cyclopentyl)carbamate (Example 9e) in 100% yield. MS 232 (MH$^+$ w/o Boc group).

Example 9e tert-butyl(1-((2-cyano-3-nitrophenoxy)methyl)cyclopentyl)carbamate

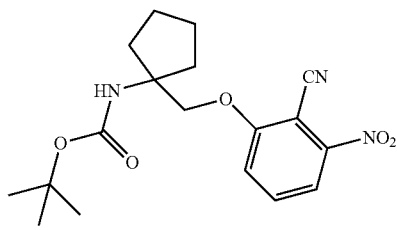

To a mixture of tert-butyl(1-(hydroxymethyl)cyclopentyl)carbamate (5.00 g, 23.2 mmol) and 2,6-dinitrobenzonitrile (4.48 g, 23.2 mmol) in THF (210 mL) was added sodium hydride (60% in mineral oil, 1.02 g, 25.5 mmol). The reaction was slowly warmed to room temperature and stirred for 18 hrs., under nitrogen. Upon completion, the reaction was quenched with water, extracted with EtOAc, and the organic layer was dried over sodium sulfate, filtered and concentrated. The crude residue was purified by flash chromatography (3/7 EtOAc/hexane, normal phase silica gel) to provide tert-butyl(1-((2-cyano-3-nitrophenoxy)methyl)cyclopentyl)carbamate (7.09 g, 85%) as a yellow solid. MS 262 (MH$^+$ w/o Boc group).

Example 10

Synthesis of N-(1-(((4-amino-2,2-dioxido-1H-benzo[c][1,2,6]thiadiazin-5-yl)oxy)methyl)cyclopentyl)-2-methylisonicotinamide

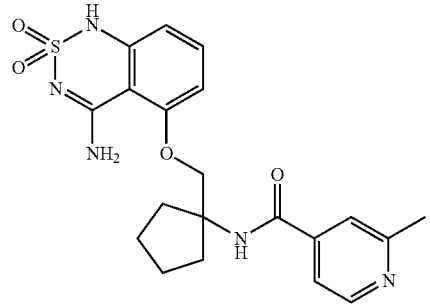 [SMILES: Cc1cc(C(=O)NC2(COc3cccc4c3C(N)=NS(=O)(=O)N4)CCCC2)ccn1]

Prepared as in Example 1 from 4-amino-5-(1-aminocyclopentyl)methoxy)-1H-benzo[c][1,2,6]thiadiazine-2,2-dioxide hydrochloride (Example 9a) and 2-methylpyridine-4-carboxylic acid in 40% yield. $^1$H NMR (400 MHz, DMSO-d$_6$) δ 1.66 (m, 2H), 1.74 (m, 2H), 1.82 (m, 2H), 2.19 (m, 2H), 2.50 (s, 3H), 4.42 (s, 2H), 6.59 (d, J=8.4 Hz, 1H), 6.77 (d, J=8.4 Hz, 1H), 7.42 (t, J=8.4 Hz, 1H), 7.44 (m, 1H), 7.51 (s, 1H), 7.83 (br s, 1H), 8.40 (br s, 1H), 8.49 (s, 1H), 8.51 (d, J=5.1 Hz, 1H), 10.95 (br s, 1H). MS 430 (MH$^+$).

Example 11

N-(1-(((4-amino-2,2-dioxido-1H-benzo[c][1,2,6]thiadiazin-5-yl)oxy)methyl)cyclopentyl)-2-(methylamino)isonicotinamide

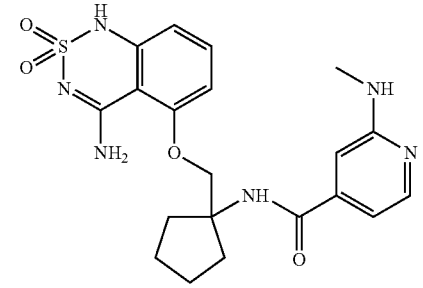 [SMILES: CNc1cc(C(=O)NC2(COc3cccc4c3C(N)=NS(=O)(=O)N4)CCCC2)ccn1]

Prepared as in Example 1 from 4-amino-5-((1-aminocyclopentyl)methoxy)-1H-benzo[c][1,2,6]thiadiazine 2,2-dioxide hydrochloride (Example 9a) and 2-(methylamino)isonicotinic acid in 34% yield. $^1$H NMR (400 MHz, DMSO-d$_6$) δ 1.62-1.84 (m, 6H), 2.15-2.21 (m, 2H), 2.76 (J=4.8 Hz, 3H), 4.40 (s, 2H), 6.59-6.64 (m, 3H), 6.70-6.72 (m, 1H), 6.77 (d, J=8.0 Hz, 1H), 7.43 (t, J=8.8 Hz, 1H), 7.88 (s, 1H), 8.00 (d, J=5.2 Hz, 1H), 8.33 (s, 1H), 8.38 (s, 1H), 10.97 (s, 1H). MS 445 (MH$^+$).

Example 12

N-(1-((4-amino-2,2-dioxido-1H-benzo[c][1,2,6]thia-diazin-5-yl)oxy)-2-methylpropan-2-yl)-2-(4-methyl-1H-imidazol-1-yl)isonicotinamide

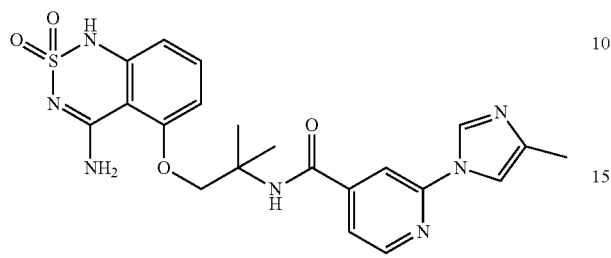

Prepared as in Example 1 from 4-amino-5-(2-amino-2-methylpropoxy)-1H-benzo[c][1,2,6]thiadiazine 2,2-dioxide hydrochloride (Example 1a) and 2-(4-methyl-1H-imidazol-1-yl)isonicotinic acid (Example 12a) in 37% yield. $^1$H NMR (DMSO-$d_6$, 400 MHz): δ 1.51 (s, 6H), 2.18 (s, 3H), 4.41 (s, 2H), 6.62 (d, J=8.0 Hz, 1H), 6.79 (d, J=8.0 Hz, 1H), 7.47 (t, J=8.0 Hz, 1H), 7.60 (dd, J=5.2, 1.2 Hz, 1H), 7.69 (s, 1H), 7.81 (s br, 1H), 7.96 (s, 1H), 8.45 (d, J=1.2 Hz, 1H), 8.49 (s br, 1H), 8.55 (d, J=5.2 Hz, 1H), 8.57 (s, 1H), 11.00 (s, 1H). MS 470 (MH$^+$).

Example 12a 2-(4-methyl-1H-imidazol-1-yl)isonicotinic acid

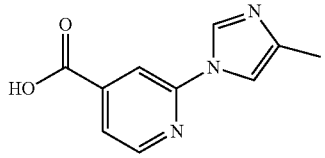

Methyl 2-(4-methyl-1H-imidazol-1-yl)isonicotinate (310 mg, 1.43 mmol, Example 12b) and an aqueous solution of 2 M sodium hydroxide (858 uL, 1.72 mmol) in ethanol (5 mL) were heated to 120° C. in the microwave for 10 minutes, cooled to room temperature, neutralized with an aqueous solution of 5 M hydrochloric acid and concentrated to provide 2-(4-methyl-1H-imidazol-1-yl)isonicotinic acid in quantitative yield. MS 204 (MH+).

Example 12b methyl 2-(4-methyl-1H-imidazol-1-yl)isonicotinate

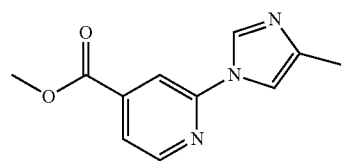

To a solution of methyl 2-bromoisonicotinate (1.06 g, 4.89 mmol), 4-methyl-1H-imidazole (401 mg, 4.89 mmol) and Cs$_2$CO$_3$ (1.92 g, 5.88 mmol) in DMF (20 mL), was added CuI (280 mg, 1.47 mmol). The mixture was heated to 100° C., stirred for 18 hours, cooled to room temperature and concentrated under reduced pressure. The residue was suspended in ethyl acetate (50 mL) and washed with water (50 mL). The aqueous phase was extracted with ethyl acetate (2×), and the combined organic layers were dried over anhydrous Na$_2$SO$_4$, filtered, concentrated under reduced pressure and purified by flash chromatography (5-10% methanol in dichloromethane, normal phase silica gel) to provide methyl 2-(4-methyl-1H-imidazol-1-yl)isonicotinate (315 mg, 30%) as a white solid. MS 218 (MH$^+$).

Example 13

N-(1-((4-amino-2,2-dioxido-1H-benzo[c][1,2,6]thia-diazin-5-yl)oxy)-2-methylpropan-2-yl)-2-(piperidin-1-yl)isonicotinamide

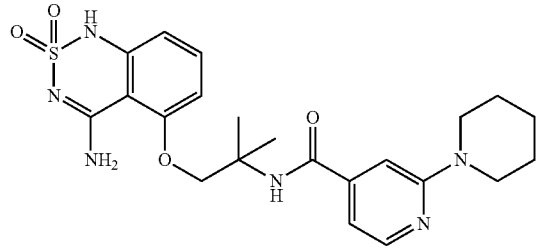 [SMILES: CC(C)(COc1cccc2c1C(N)=NS(=O)(=O)N2)NC(=O)c1ccnc(N2CCCCC2)c1]

N-(1-((4-amino-2,2-dioxido-1H-benzo[c][1,2,6]thiadi-azin-5-yl)oxy)-2-methylpropan-2-yl)-2-bromoisonicotinamide (300 mg, 0.641 mmol, Example 8a) in piperidine (2.5 mL) was heated at 130° C. in the microwave for 30 minutes. The reaction was cooled to room temperature and purified by preparative HPLC (10-90% acetonitrile in water, reverse phase C18 column) The purified product was suspended in a mixture of water (5 mL) and Na$_2$CO$_3$ (100 mg), heated to 75° C. for 10 minutes, cooled to room temperature, neutralized with 1N HCl solution and further cooled to 0° C. The resulting precipitate was collected by vacuum filtration and dried at 40° C. under vacuum to provide N-(1-((4-amino-2,2-dioxido-1H-benzo[c][1,2,6]thiadiazin-5-yl)oxy)-2-methylpropan-2-yl)-2-(piperidin-1-yl)isonicotinamide (184 mg, 61%). $^1$H NMR (400 MHz, DMSO-$d_6$) δ 1.47 (s, 6H), 1.51-1.64 (m, 6H), 3.51-3.59 (m, 4H), 4.36 (s, 2H), 6.61 (d, J=12.0 Hz, 1H), 6.77 (d, J=8.0 Hz, 1H), 6.87 (d, J=8.0 Hz, 1H), 7.07 (s br, 1H), 7.46 (t, J=8.0 Hz, 1H), 7.81 (s, 1H), 8.10 (d, J=4.0 Hz, 1H), 8.36 (s, 1H), 8.45 (s, 1H), 10.99 (s, 1H). MS 473 (MH$^+$).

Example 14

N-(1-((4-amino-2,2-dioxido-1H-benzo[c][1,2,6]thia-diazin-5-yl)oxy)-2-methylpropan-2-yl)-2-(2-methyl-1H-benzo[d]imidazol-1-yl)isonicotinamide

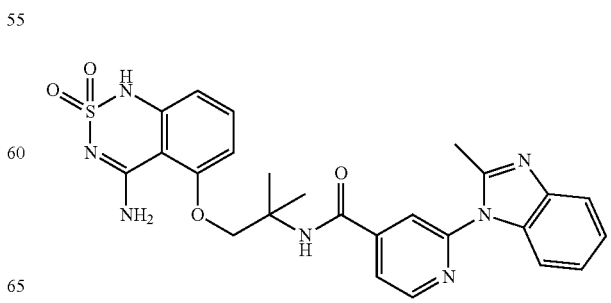

Prepared as in Example 1 from 4-amino-5-(2-amino-2-methylpropoxy)-1H-benzo[c][1,2,6]thiadiazine 2,2-dioxide hydrochloride (Example 1a) and 2-(2-methyl-1H-benzo[d]imidazol-1-yl)isonicotinic acid (Example 14a) to provide N-(1-((4-amino-2,2-dioxido-1H-benzo[c][1,2,6]thiadiazin-5-yl)oxy)-2-methylpropan-2-yl)-2-(2-methyl-1H-benzo[d]imidazol-1-yl)isonicotinamide (22% yield). $^1$H NMR (DMSO-d$_6$, 400 MHz): δ 1.50 (s, 6H), 2.55 (s, 3H), 4.39 (s, 2H), 6.60 (d, J=8.0 Hz, 1H), 6.77 (d, J=8.0 Hz, 1H), 7.23 (m, 2H), 7.39 (m, 1H), 7.44 (t, J=8.0 Hz, 1H), 7.62 (m, 1H), 7.80 (s br, 1H), 7.87 (dd, J=8.0, 1.2 Hz, 1H), 8.0 (m, 1H), 8.41 (s br, 1H), 8.59 (s, 1H), 8.80 (dd, J=8.0, 0.8 Hz, 1H), 11.00 (s, 1H). MS 520 (MH$^+$).

Example 14a 2-(2-methyl-1H-benzo[d]imidazol-1-yl)isonicotinic acid

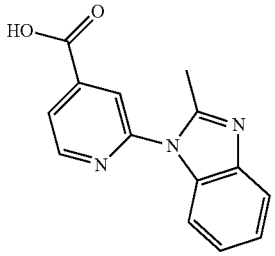 [SMILES: Cc1nc2ccccc2n1-c1cc(C(=O)O)ccn1]

Prepared as in Example 7a from methyl 2-bromoisonicotinate and 2-methyl-1H-benzo[d]imidazole in 20% yield. MS 254 (MH$^+$).

Example 15

N-(1-((4-amino-2,2-dioxido-1H-benzo[c][1,2,6]thiadiazin-5-yl)oxy)-2-methylpropan-2-yl)-2-(1H-benzo[d]imidazol-1-yl)isonicotinamide

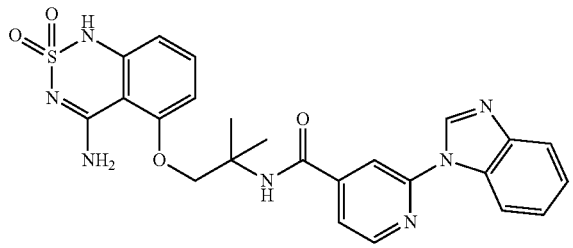 [SMILES: CC(C)(COc1cccc2c1C(N)=NS(=O)(=O)N2)NC(=O)c1ccnc(-n2cnc3ccccc32)c1]

Prepared as in Example 1 from 5-(2-amino-2-methylpropoxy)-1H-benzo[c][1,2,6]thiadiazin-4-amine-2,2-dioxide hydrochloride (Example 1a) and 2-(1H-benzo[d]imidazol-1-yl)isonicotinic acid (Example 15a) to provide N-(1-((4-amino-2,2-dioxido-1H-benzo[c][1,2,6]thiadiazin-5-yl)oxy)-2-methylpropan-2-yl)-2-(1H-benzo[d]imidazol-1-yl)isonicotinamide (17% yield). $^1$H NMR (80° C., 400 MHz, DMSO-d$_6$) δ 1.54 (s, 6H), 4.43 (s, 2H), 6.60 (d, J=8.0 Hz, 1H), 6.69 (d, J=8.0 Hz, 1H), 7.29-7.42 (m, 3H), 7.70 (d, J=4.0 Hz, 1H), 7.76 (d, J=8.0 Hz, 2H), 7.79 (s br, 1H), 8.13 (s, 1H), 8.26 (d, J=8.0 Hz, 1H), 8.32 (s br, 1H), 8.71 (d, J=8.0 Hz, 1H), 8.92 (s, 1H), 10.70 (s, 1H). MS 506 (MH$^+$).

Example 15a 2-(1H-benzo[d]imidazol-1-yl)isonicotinic acid

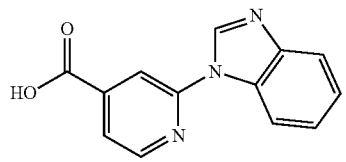 [SMILES: O=C(O)c1ccnc(-n2cnc3ccccc32)c1]

Prepared as in Example 7a from methyl 2-bromoisonicotinate and 1H-benzo[d]imidazole to provide 2-(1H-benzo[d]imidazol-1-yl)isonicotinic acid (54% yield). MS 240 (MH$^+$).

Example 16

N-(1-((4-amino-2,2-dioxido-1H-benzo[c][1,2,6]thiadiazin-5-yl)oxy)-2-methylpropan-2-yl)-2-(diethylamino)isonicotinamide

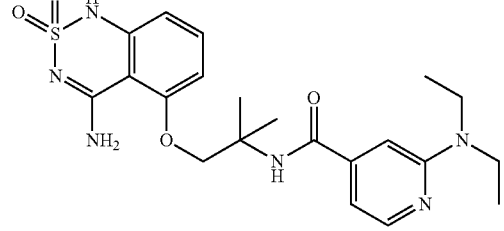

To a solution of N-(1-((4-amino-2,2-dioxido-1H-benzo[c][1,2,6]thiadiazin-5-yl)oxy)-2-methylpropan-2-yl)-2-bromoisonicotinamide (400 mg, 0.85 mmol, Example 8a) in CH$_3$CN (5 mL), were added diethylamine (4.25 mL) and triethylamine (237 uL, 1.7 mmol). The mixture was irradiated in the microwave for 4.5 h at 150° C., and upon completion, was diluted with water and the solution was neutralized with conc. HCl. The mixture was extracted with EtOAc (3×), and the combined organics were dried over Na$_2$SO$_4$, filtered, concentrated and purified by preparative HPLC (10-90% acetonitrile in water, reverse phase C18 column) The residue was dissolved in a hot NaHCO$_3$ solution (100 mg of NaHCO$_3$ in 3 mL water at 85° C.), cooled to 0° C. and neutralized with 1N aqueous HCl. The resulting precipitate was collected by vacuum filtration, suspended in boiling Et$_2$O, filtered hot, and washed extensively with water. The solid was once again dissolved in a hot NaHCO$_3$ solution (100 mg of NaHCO$_3$ in 3 mL water at 85° C.), cooled to 0° C. and neutralized with 1N HCl. The precipitate was collected by vacuum filtration and dried to provide N-(1-((4-amino-2,2-dioxido-1H-benzo[c][1,2,6]thiadiazin-5-yl)oxy)-2-methylpropan-2-yl)-2-(diethylamino)isonicotinamide (109 mg, 28%) as an off-white solid. $^1$H NMR (DMSO-d$_6$, 400 MHz): δ 1.08 (t, 6H, J=7.0 Hz), 1.47 (s, 6H), 3.49 (q, 4H, J=6.9 Hz), 4.36 (s, 2H), 6.62 (d, 1H, J=7.9 Hz), 6.73 (br s, 1H), 6.76 (m, 1H), 6.78 (d, 1H, J=8.2 Hz), 7.46 (t, 1H, J=8.2 Hz), 7.84 (br s, 1H), 8.09 (d, 1H, J=5.3 Hz), 8.25 (s, 1H), 8.46 (m, 1H), 10.99 (s, 1H). MS 461 (MH$^+$).

Example 17

N-(1-((4-amino-2,2-dioxido-1H-benzo[c][1,2,6]thiadiazin-5-yl)oxy)-2-methylpropan-2-yl)-2-morpholinoisonicotinamide

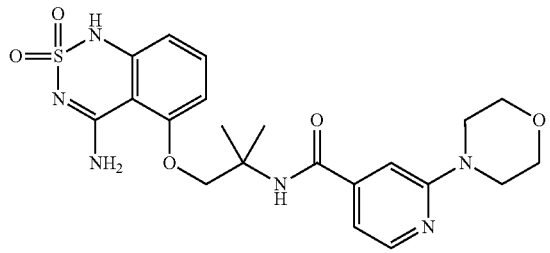 [SMILES: CC(C)(COc1cccc2c1C(N)=NS(=O)(=O)N2)NC(=O)c1ccnc(N2CCOCC2)c1]

Prepared as in Example 1 from 4-amino-5-(2-amino-2-methylpropoxy)-1H-benzo[c][1,2,6]thiadiazine 2,2-dioxide hydrochloride (Example 1a) and 2-morpholinoisonicotinic acid in 16% yield. $^1$H NMR (DMSO-d$_6$, 400 MHz): δ 1.48 (s, 6H), 3.44-3.48 (m, 4H), 3.68-3.72 (m, 4H), 4.37 (s, 2H), 6.63 (d, J=8.0 Hz, 1H), 6.78 (d, J=8.0 Hz, 1H), 6.94 (dd, J=4.0 Hz, J=8.0 Hz, 1H), 7.01 (s, 1H), 7.47 (t, J=8.0 Hz, 1H), 7.83 (s, 1H), 8.19 (d, J=4.0 Hz, 1H), 8.34 (s, 1H), 8.49 (s, 1H), 11.00 (s, 1H). MS 475 (MH$^+$).

Example 18

N-(1-((4-amino-2,2-dioxido-1H-benzo[c][1,2,6]thiadiazin-5-yl)oxy)-2-methylpropan-2-yl)-2-(pyrrolidin-1-yl)isonicotinamide

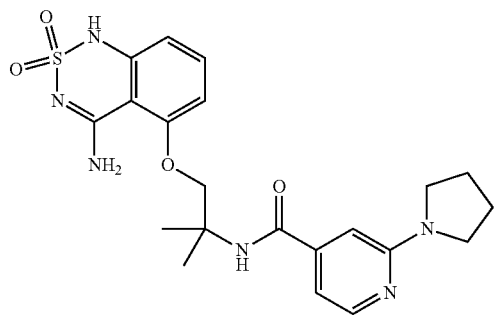 [SMILES: CC(C)(COc1cccc2c1C(N)=NS(=O)(=O)N2)NC(=O)c1ccnc(N2CCCC2)c1]

Prepared as in Example 16 from 2-amino-N-(1-((4-amino-2,2-dioxido-1H-benzo[c][1,2,6]thiadiazin-5-yl)oxy)-2-methylpropan-2-yl-2-bromoisonicotinamide (Example 8a) and pyrrolidine in 23% yield. $^1$H NMR (DMSO-d$_6$, 400 MHz): δ 1.47 (s, 6H), 1.94 (m, 4H), 3.40 (m, 4H), 4.36 (s, 2H), 6.62 (d, J=8.0 Hz, 1H), 6.77 (s, 1H), 6.79 (m, 2H), 7.46 (t, J=8.0 Hz, 1H), 7.82 (br s, 1H), 8.09 (d, J=4.0 Hz, 1H), 8.29 (s, 1H), 8.48 (s, 1H), 11.00 (s, 1H). MS 459 (MH$^+$).

Example 19

N-(1-((4-amino-2,2-dioxido-1H-benzo[c][1,2,6]thiadiazin-5-yl)oxy)-2-methylpropan-2-yl)-2-(4-fluorophenyl)isonicotinamide

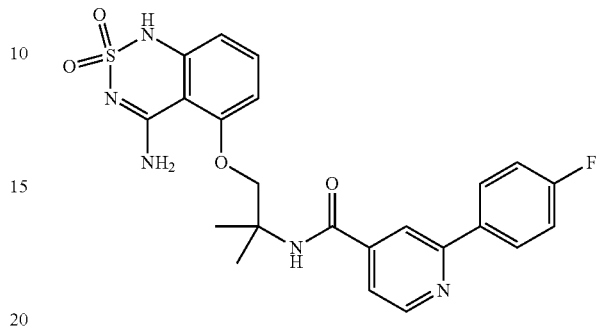

To a solution of N-(1-((4-amino-2,2-dioxido-1H-benzo[c][1,2,6]thiadiazin-5-yl)oxy)-2-methylpropan-2-yl)-2-bromoisonicotinamide (370 mg, 0.770 mmol, Example 8a), in DMF (3 mL) and water (2 mL) at room temperature, were added (4-fluorophenyl)boronic acid (108 mg, 0.770 mmol), palladium tetrakis triphenylphosphine (89 mg, 0.07 mmol), and potassium carbonate (320 mg, 2.31 mmol). The reaction was microwaved at 150° C. for ten minutes, and upon completion was cooled to room temperature, filtered, and the filtrate was neutralized with 1N HCl and extracted with ethyl acetate. The organic layer was dried over Na$_2$SO$_4$, filtered and concentrated. The crude residue was purified by HPLC (10-90% acetonitrile in water, reverse phase C18 column), and the purified product was dissolved in a hot Na$_2$CO$_3$ solution (120 mg of Na$_2$CO$_3$ in 5 mL water at 60° C.), cooled to 0° C. and neutralized with 1N HCl. The precipitate was collected by vacuum filtration and dried to provide N-(1-((4-amino-2,2-dioxido-1H-benzo[c][1,2,6]thiadiazin-5-yl)oxy)-2-methylpropan-2-yl)-2-(4-fluorophenyl)isonicotinamide (120 mg, 30%) as a white solid. $^1$H NMR (DMSO-d$_6$, 400 MHz): δ 1.51 (s, 6H), 4.40 (s, 2H), 6.61 (d, J=12.0 Hz, 1H), 6.72 (d, J=8.0 Hz, 1H), 7.30 (dd, 8.0 Hz, 2H), 7.40 (t, J=8.0 Hz, 1H), 7.61 (d, J=4.0 Hz, 1H), 7.88 (br s, 2H), 8.15 (m, 3H), 8.30 (s, 1H), 8.73 (d, J=4.0 Hz, 1H), 10.7 (s, 1H). MS 484 (MH$^+$).

Example 20

N-(1-((4-amino-2,2-dioxido-1H-benzo[c][1,2,6]thiadiazin-5-yl)oxy)-2-methylpropan-2-yl)-2-(3-hydroxyphenyl)isonicotinamide

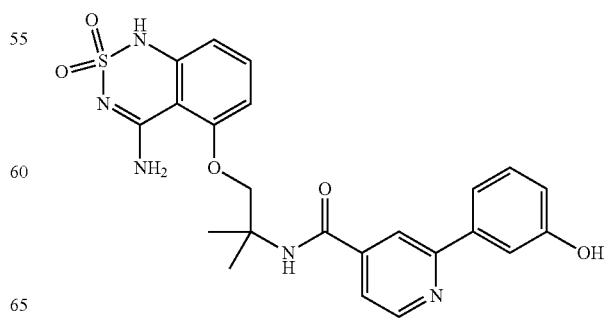

Prepared as in Example 19 from N-(1-((4-amino-2,2-dioxido-1H-benzo[c][1,2,6]thiadiazin-5-yl)oxy)-2-methylpropan-2-yl)-2-bromoisonicotinamide (Example 8a) and (3-hydroxyphenyl)boronic acid in 30% yield. ¹H NMR (DMSO-d₆, 400 MHz): δ 1.53 (s, 6H), 4.40 (s, 2H), 6.56 (d, J=8.0 Hz, 1H), 6.62 (d, J=8.0 Hz, 1H), 6.84 (dd, 8.0 Hz, 1H), 7.30 (t, J=8.0 Hz, 1H), 7.34 (t, J=8.0 Hz, 1H), 7.52 (m, 2H), 7.59 (d, J=4.0 Hz, 1H), 7.65 (br s, 2H), 8.00 (s, 1H), 8.26 (s, 1H), 8.70 (d, J=4.0 Hz, 1H), 9.30 (s, 1H), 10.6 (br s, 1H). MS 482 (MH⁺).

Example 21

N-(1-((4-amino-2,2-dioxido-1H-benzo[c][1,2,6]thiadiazin-5-yl)oxy)-2-methylpropan-2-yl)-2-(2-hydroxyphenyl)isonicotinamide

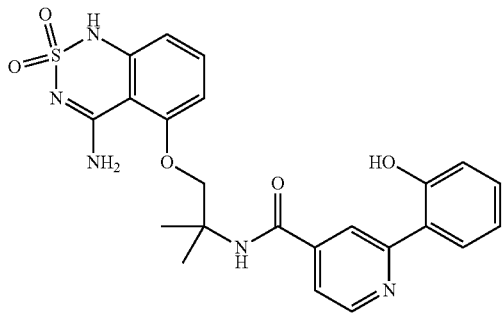 [SMILES: CC(C)(COc1cccc2c1C(N)=NS(=O)(=O)N2)NC(=O)c1ccnc(-c2ccccc2O)c1]

Prepared as in Example 19 from N-(1-((4-amino-2,2-dioxido-1H-benzo[c][1,2,6]thiadiazin-5-yl)oxy)-2-methylpropan-2-yl)-2-bromoisonicotinamide (Example 8a) and (2-hydroxyphenyl)boronic acid in 35% yield. ¹H NMR (DMSO-d₆, 400 MHz): δ 1.52 (s, 6H), 4.40 (s, 2H), 6.61 (d, J=7.6 Hz, 1H), 6.80 (d, J=7.6 Hz, 1H), 6.92 (d, J=9.6 Hz, 1H), 6.97 (t, J=9.2 Hz, 1H), 7.32 (t, J=8.0 Hz, 1H), 7.46 (t, J=8.0 Hz, 1H), 7.67 (dd, J=8.0 Hz, 1H), 8.38 (s, 1H), 8.49 (s, 1H), 8.66 (s, 1H), 8.71 (d, J=5.6 Hz, 1H), 11.00 (s, 1H), 13.72 (s, 1H). MS 482 (MH⁺).

Example 22

N-(1-((4-amino-2,2-dioxido-1H-benzo[c][1,2,6]thiadiazin-5-yl)oxy)-2-methylpropan-2-yl)-2-(3-fluorophenyl)isonicotinamide

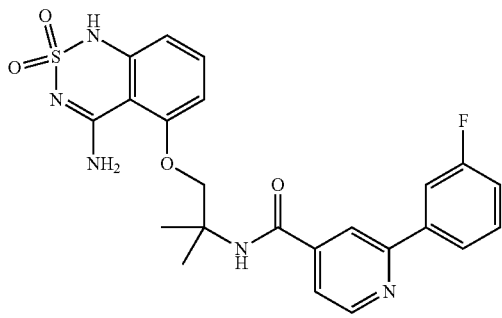 [SMILES: CC(C)(COc1cccc2c1C(N)=NS(=O)(=O)N2)NC(=O)c1ccnc(-c2cccc(F)c2)c1]

Prepared as in Example 19 from N-(1-((4-amino-2,2-dioxido-1H-benzo[c][1,2,6]thiadiazin-5-yl)oxy)-2-methylpropan-2-yl)-2-bromoisonicotinamide (Example 8a) and (3-fluorophenyl)boronic acid in 22% yield. ¹H NMR (DMSO-d₆, 400 MHz): δ 1.51 (s, 6H), 4.40 (s, 2H), 6.61 (d, J=8.0 Hz, 1H), 6.79 (d, J=8.0 Hz, 1H), 7.30 (t, 9.2 Hz, 1H), 7.47 (t, J=8.8 Hz, 1H), 7.46 (q, J=6.4 Hz, 1H), 7.67 (dd, J=4.4 Hz, 1H), 7.85 (s, 1H), 7.93 (d, J=8.8 Hz, 1H), 7.98 (d, J=8.8 Hz, 1H), 8.22 (s, 1H), 8.50 (s, 1H), 8.56 (s, 1H), 8.77 (s, 1H), 10.99 (s, 1H). MS 484 (MH⁺).

Example 23

N-(1-((4-amino-2,2-dioxido-1H-benzo[c][1,2,6]thiadiazin-5-yl)oxy)-2-methylpropan-2-yl)-2-(2-methyl-1H-imidazol-1-yl)isonicotinamide

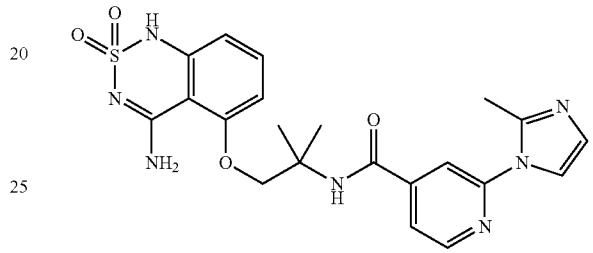

Prepared as in Example 8 from N-(1-((4-amino-2,2-dioxido-1H-benzo[c][1,2,6]thiadiazin-5-yl)oxy)-2-methylpropan-2-yl)-2-bromoisonicotinamide (Example 8a) and 2-methyl-1H-imidazole in 25% yield. ¹H NMR (DMSO-d₆, 400 MHz): δ 1.50 (s, 6H), 2.49 (s, 3H), 4.35 (s, 2H), 6.52 (d, J=8.0 Hz, 1H), 6.56 (d, J=8.0 Hz, 1H), 6.90 (s, 1H), 7.30 (t, J=8.0 Hz, 1H), 7.56 (m, 3H), 7.70 (d, J=4.0 Hz, 1H), 7.80 (s, 1H), 8.33 (s, 1H), 8.62 (d, J=8.0 Hz, 1H), 10.75 (br s, 1H). MS 470 (MH⁺).

Example 24

N-(1-((4-amino-2,2-dioxido-1H-benzo[c][1,2,6]thiadiazin-5-yl)oxy)-2-methylpropan-2-yl)-2-(dimethylamino)isonicotinamide

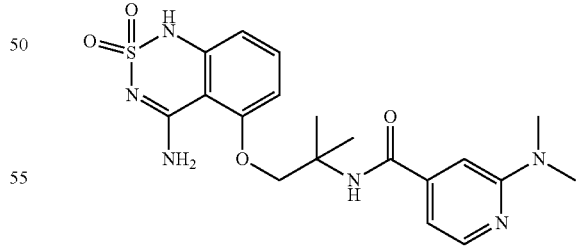

Prepared as in Example 1 from 4-amino-5-(2-amino-2-methylpropoxy)-1H-benzo[c][1,2,6]thiadiazine 2,2-dioxide hydrochloride (Example 1a) and 2-(dimethylamino)isonicotinic acid hydrochloride in 30% yield. ¹H NMR (DMSO-d₆, 400 MHz): 1.48 (s, 6H), 3.04 (s, 6H), 4.35 (s, 2H), 6.60 (d, 1H, J=8.0 Hz), 6.71 (d, 1H, J=8.8 Hz), 6.83 (m, 2H), 7.45 (t, 1H, J=8.0 Hz), 7.76 (br s, 1H), 8.11 (m, 1H), 8.27 (s, 1H), 8.33 (br s, 1H), 10.96 (s, 1H). MS 433 (MH⁺).

Example 25

N-(1-((4-amino-2,2-dioxido-1H-benzo[c][1,2,6]thiadiazin-5-yl)oxy)-2-methylpropan-2-yl)imidazo[1,2-a]pyridine-7-carboxamide

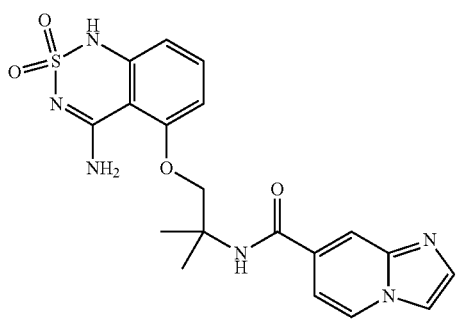 [SMILES: CC(C)(COc1cccc2c1C(N)=NS(=O)(=O)N2)NC(=O)c1ccn2ccnc2c1]

Prepared as in Example 1 from 5-(2-amino-2-methylpropoxy)-1H-benzo[c][1,2,6]thiadiazin-4-amine-2,2-dioxide hydrochloride (Example 1a) and imidazo[1,2-a]pyridine-7-carboxylic acid in 25% yield. $^1$H NMR (400 MHz, DMSO-$d_6$) δ 1.51 (s, 6H), 4.40 (s, 2H), 6.63 (d, J=8.0 Hz, 1H), 6.80 (d, J=8.0 Hz, 1H), 7.24-7.26 (m, 1H), 7.48 (t, J=6.8 Hz, 1H), 7.71 (s, 1H), 7.87 (s, 1H), 8.05 (s, 1H), 8.15 (s, 1H), 8.37 (s, 1H), 8.47 (s, 1H), 8.57 (d, J=5.6 Hz, 1H), 10.99 (s, 1H). MS 429 (MH$^+$).

Example 26

N-(1-(((4-amino-2,2-dioxido-1H-benzo[c][1,2,6]thiadiazin-5-yl)oxy)methyl)cyclopentyl)-2-(dimethylamino)isonicotinamide

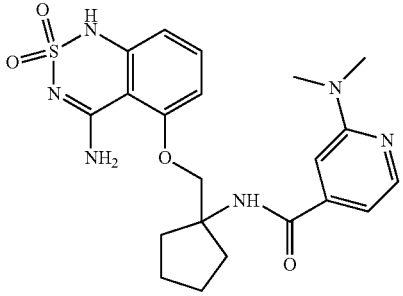 [SMILES: CN(C)c1cc(C(=O)NC2(COc3cccc4c3C(N)=NS(=O)(=O)N4)CCCC2)ccn1]

Prepared as in Example 1 from 4-amino-5-((1-aminocyclopentyl)methoxy)-1H-benzo[c][1,2,6]thiadiazine 2,2-dioxide hydrochloride (Example 9a) and 2-(dimethylamino)isonicotinic acid in 35% yield. $^1$H NMR (400 MHz, DMSO-$d_6$) δ 1.59-1.89 (m, 6H), 2.14-2.24 (m, 2H), 3.03 (s, 6H), 4.41 (s, 2H), 6.60 (d, J=8.0 Hz, 1H), 6.76-6.84 (m, 3H), 7.44 (t, J=8.0 Hz, 1H), 7.85 (s, 1H), 8.12 (d, J=4.0 Hz, 1H), 8.37 (s, 1H), 8.42 (s, 1H), 10.96 (s, 1H). MS 459 (MH$^+$).

Example 27

N-(1-((4-amino-2,2-dioxido-1H-benzo[c][1,2,6]thiadiazin-5-yl)oxy)-2-methylpropan-2-yl)pyrimidine-4-carboxamide

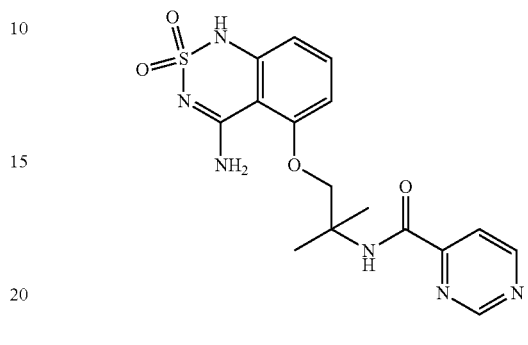

Prepared as in Example 1 from 4-amino-5-(2-amino-2-methylpropoxy)-1H-benzo[c][1,2,6]thiadiazine 2,2-dioxide hydrochloride (Example 1a) and pyrimidine-4-carboxylic acid in 28% yield. $^1$H NMR (DMSO-$d_6$, 400 MHz, 80° C.): δ 1.50 (s, 6H), 4.40 (s, 2H), 6.61 (d, J=8.0 Hz, 1H), 6.79 (d, J=9.2 Hz, 1H), 7.45 (t, J=8.8 Hz, 1H), 7.70 (s, 1H), 7.95 (dd, J=4.4 Hz, 1H), 8.31 (s, 1H), 8.57 (s, 1H), 9.04 (dd, J=5.6 Hz, 1H), 9.30 (s, 1H), 10.95 (s, 1H), 8.64 (d, J=5.2 Hz, 2H), 10.67 (s, 1H), MS 391 (MH$^+$).

Example 28

N-(1-((4-amino-2,2-dioxido-1H-benzo[c][1,2,6]thiadiazin-5-yl)oxy)-2-methylpropan-2-yl)-2-(1H-pyrazole-1-yl)isonicotinamide

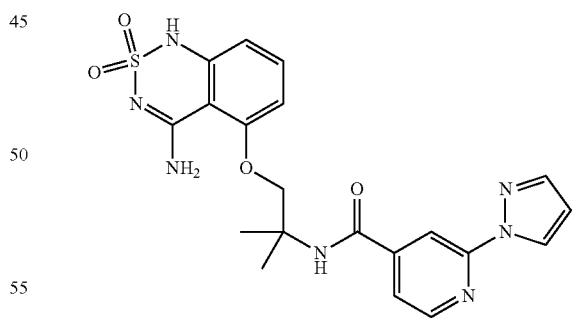

Prepared as in Example 1 from 4-amino-5-(2-amino-2-methylpropoxy)-1H-benzo[c][1,2,6]thiadiazine 2,2-dioxide hydrochloride (Example 1a) and 2-(1H-pyrazol-1-yl)isonicotinic acid (Example 28a) in 20% yield. $^1$H NMR (DMSO-$d_6$, 400 MHz): δ 1.51 (s, 6H), 4.39 (s, 2H), 6.60 (m, 2H), 6.79 (d, J=8.4 Hz, 1H), 7.46 (t, J=7.2 Hz, 1H), 7.63 (dd, J=9.2 Hz, 1H), 7.79 (br s, 1H), 7.86 (s, 1H), 8.21 (s, 1H), 8.36 (br s, 1H), 8.56 (dd, J=6.8 Hz, 1H), 8.64 (s, 1H), 8.68 (s, 1H), 10.98 (s, 1H). m.p. 175.3-176.2° C.

Example 28a 2-(1H-pyrazol-1-yl)isonicotinic acid

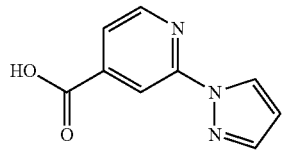 [SMILES: O=C(O)c1ccnc(-n2cccn2)c1]

Prepared as in Example 7a from 2-bromoisonicotinic acid and 1H-pyrazole in 100% yield. MS 190 (MH$^+$).

Example 29

N-(3-(((4-amino-2,2-dioxido-1H-benzo[c][1,2,6]thiadiazin-5-yl)oxy)methyl)pentan-3-yl)isonicotinamide

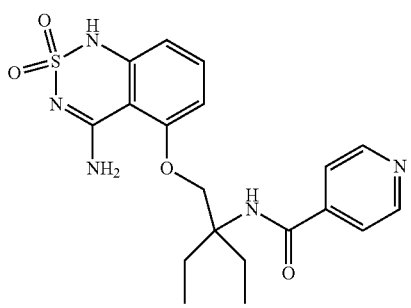 [SMILES: CCC(CC)(COc1cccc2c1C(N)=NS(=O)(=O)N2)NC(=O)c1ccncc1]

Prepared as in Example 1 from 4-amino-5-(2-amino-2-ethylbutoxy)-1H-benzo[c][1,2,6]thiadiazine-2,2-doxide hydrochloride (Example 29a) and isonicotinic acid in 31% yield. $^1$H NMR (400 MHz, DMSO-d$_6$) δ 0.84 (t, J=7.2 Hz, 6H), 1.77 (m, 2H), 1.95 (m, 2H), 4.43 (s, 2H), 6.61 (d, J=8.4 Hz, 1H), 6.83 (d, J=8.0 Hz, 1H), 7.45 (t, J=8.0 Hz, 1H), 7.79 (s, 1H), 8.17 (s, 1H), 8.47 (s, 1H), 8.67 (d, J=4.8 Hz, 1H), 10.98 (s, 1H). MS 418 (MH$^+$).

Example 29a 4-amino-5-(2-amino-2-ethylbutoxy)-1H-benzo[c][1,2,6]thiadiazine-2,2-dioxide hydrochloride

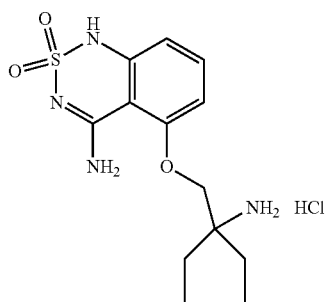 [SMILES: CCC(N)(CC)COc1cccc2c1C(N)=NS(=O)(=O)N2 ; Cl]

Prepared as in Example 1a from tert-butyl(3-(((4-amino-2,2-dioxido-1H-benzo[c][1,2,6]thiadiazin-5-yl)oxy)methyl)pentan-3-yl)carbamate (Example 29b) in 86% yield. MS 313 (MH$^+$).

Example 29b tert-butyl(3-(((4-amino-2,2-dioxido-1H-benzo[c][1,2,6]thiadiazin-5-yl)oxy)methyl)pentan-3-yl)carbamate

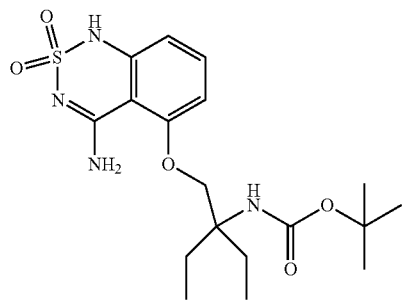 [SMILES: CCC(CC)(COc1cccc2c1C(N)=NS(=O)(=O)N2)NC(=O)OC(C)(C)C]

Prepared as in Example 1b from tert-butyl(3-((2-cyano-3-(sulfamoylamino)phenoxy)methyl)pentan-3-yl) (Example 29c) in 100% yield. MS 313 (MH$^+$).

Example 29c tert-butyl(3-(((4-amino-2,2-dioxido-1H-benzo[c][1,2,6]thiadiazin-5-yl)oxy)methyl)pentan-3-yl)carbamate

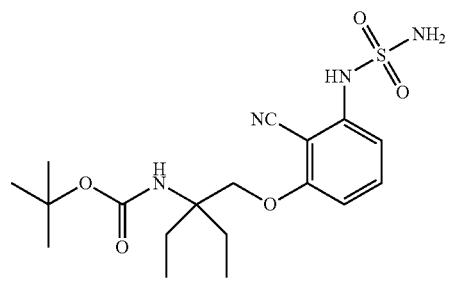 [SMILES: CCC(CC)(COc1cccc(NS(N)(=O)=O)c1C#N)NC(=O)OC(C)(C)C]

Prepared as in Example 9c from tert-butyl(3-((3-amino-2-cyanophenoxy)methyl)pentan-3-yl)carbamate (Example 29d) in 100% yield. MS 313 (MH$^+$).

Example 29d tert-butyl(3-((3-amino-2-cyanophenoxy)methyl)pentan-3-yl)carbamate

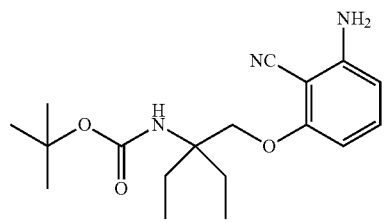

Prepared as in Example 1g from tert-butyl(3-((2-cyano-3-nitrophenoxy)methyl)pentan-3-yl)carbamate (Example 29e) in 56% yield. MS 234 (MH+ w/o Boc group).

Example 29e tert-butyl(3-((2-cyano-3-nitrophenoxy)methyl)pentan-3-yl)carbamate

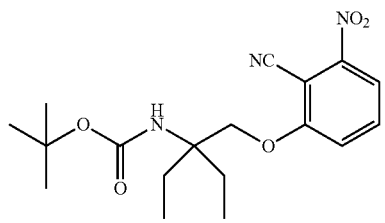 [SMILES: CCC(CC)(COc1cccc([N+](=O)[O-])c1C#N)NC(=O)OC(C)(C)C]

Prepared as in Example 9e from tert-butyl(3-(hydroxymethyl)pentan-3-yl)carbamate and 2,6-dinitrobenzonitrile in 76% yield. MS 264 (MH+ w/o Boc group).

Example 30

N-(3-(((4-amino-2,2-dioxido-1H-benzo[c][1,2,6]thiadiazin-5-yl)oxy)methyl)pentan-3-yl)-2-methyl-isonicotinamide

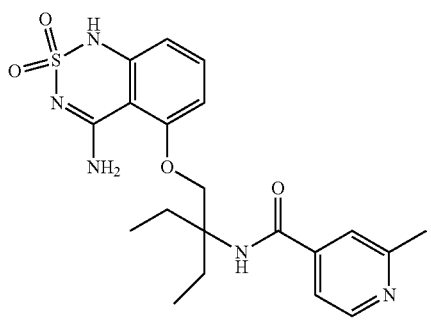 [SMILES: CCC(CC)(COc1cccc2c1C(N)=NS(=O)(=O)N2)NC(=O)c1ccnc(C)c1]

Prepared as in Example 1 from 4-amino-5-(2-amino-2-ethylbutoxy)-1H-benzo[c][1,2,6]thiadiazine 2,2-dioxide hydrochloride (Example 29a) and 2-methylisonicotinic in 24% yield. $^1$H NMR (DMSO-d$_6$, 400 MHz): δ 0.84 (t, J=7.2 Hz, 3H), 1.77 (m, 2H), 1.94 (m, 2H), 2.51 (s, 3H), 4.44 (s, 2H), 6.62 (d, J=8.0 Hz, 1H), 6.83 (d, J=8.4 Hz, 1H), 7.43 (t, J=5.2 Hz, 1H), 7.46 (s, 1H), 7.49 (m, 1H), 7.75 (s, 1H), 8.11 (s, 1H), 8.50 (s, 1H), 8.52 (d, J=5.6 Hz, 1H), 11.00 (s, 1H). MS 432 (MH+).

Example 31

N-(3-(((4-amino-2,2-dioxido-1H-benzo[c][1,2,6]thiadiazin-5-yl)oxy)methyl)pentan-3-yl)-2-methyl-amino)isonicotinamide

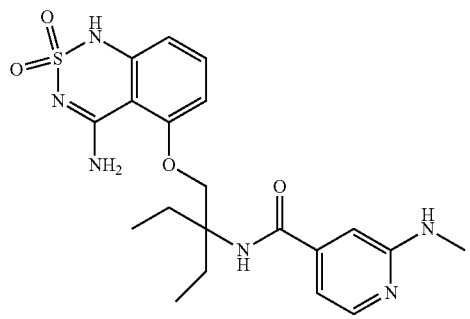 [SMILES: CCC(CC)(COc1cccc2c1C(N)=NS(=O)(=O)N2)NC(=O)c1ccnc(NC)c1]

Prepared as in Example 1 from 4-amino-5-(2-amino-2-ethylbutoxy)-1H-benzo[c][1,2,6]thiadiazine 2,2-dioxide hydrochloride (Example 29a) and 2-(methylamino)isonicotinic acid in 28% yield. $^1$H NMR (DMSO-d$_6$, 400 MHz): δ 0.82 (t, J=7.6 Hz, 3H), 1.75 (m, 2H), 1.93 (m, 2H), 2.77 (d, J=5.2 Hz, 3H), 4.41 (s, 2H), 6.59-6.62 (m, 3H), 6.69 (dd, J=5.6 Hz, 1H), 6.82 (d, J=8.8 Hz, 1H), 7.46 (t, J=8.4 Hz, 1H), 7.81 (s, 1H), 7.94 (s, 1H), 8.02 (dd, J=5.2 Hz, 1H), 8.45 (s, 1H), 11.00 (s, 1H). MS 447 (MH+).

Example 32

N-(1-(((4-amino-2,2-dioxido-1H-benzo[c][1,2,6]thiadiazin-5-yl)oxy)methyl)cyclohexyl)isonicotinamide

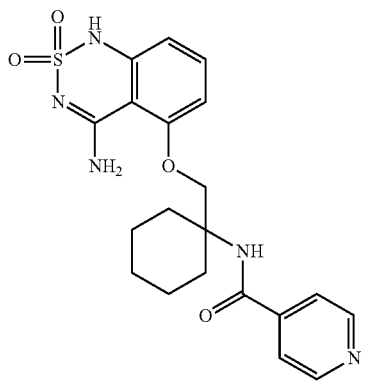 [SMILES: NC1=NS(=O)(=O)Nc2cccc(OCC3(NC(=O)c4ccncc4)CCCCC3)c21]

Prepared as in Example 1 from 4-amino-5-((1-aminocyclohexyl)methoxy)-1H-benzo[c][1,2,6]thiadiazine 2,2-dioxide hydrochloride (Example 32a) and isonicotinic acid in 38% yield. $^1$H NMR (DMSO-d$_6$, 400 MHz): 1.29 (br s, 1H), 1.52 (m, 7H), 2.37 (m, 2H), 4.39 (s, 2H), 6.60 (m, 1H), 6.81 (d, 1H, J=8.0 Hz), 7.45 (t, 1H, J=8.4 Hz), 7.66 (m, 2H), 7.83 (br s, 1H), 8.19 (s, 1H), 8.32 (br s, 1H), 8.67 (dd, 2H, J=4.8, 2.0 Hz), 10.94 (s, 1H). MS 430 (MH+).

Example 32a 4-amino-5-((1-aminocyclohexyl)methoxy)-1H-benzo[c][1,2,6]thiadiazine 2,2-dioxide hydrochloride

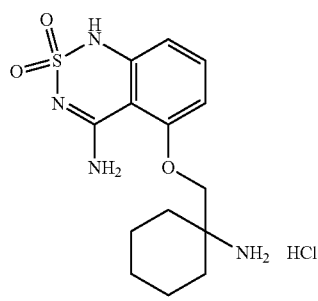 [SMILES: NC1=NS(=O)(=O)Nc2cccc(OCC3(N)CCCCC3)c21 ; Cl]

Prepared as in Example 1a from tert-butyl(1-(((4-amino-2,2-dioxido-1H-benzo[c][1,2,6]thiadiazin-5-yl)oxy)methyl)cyclohexyl)carbamate (Example 32b) in 40% yield. MS 361 (MH$^+$).

Example 32b tert-butyl(1-(((4-amino-2,2-dioxido-1H-benzo[c][1,2,6]thiadiazin-5-yl)oxy)methyl)cyclohexyl)carbamate

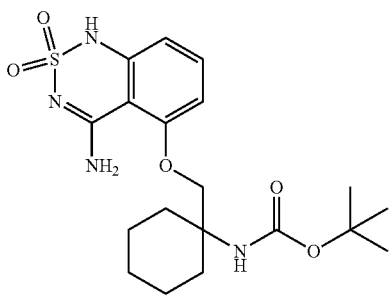 [SMILES: CC(C)(C)OC(=O)NC1(COc2cccc3c2C(N)=NS(=O)(=O)N3)CCCCC1]

Prepared as in Example 1b from tert-butyl(1-((2-cyano-3-(sulfamoylamino)phenoxy)methyl)cyclohexyl)carbamate (Example 32c) in 79% yield. MS 325 (MH$^+$, −Boc).

Example 32c tert-butyl(1-((2-cyano-3-(sulfamoylamino)phenoxy)methyl)cyclohexyl)carbamate

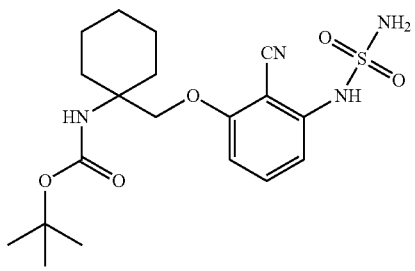 [SMILES: CC(C)(C)OC(=O)NC1(COc2cccc(NS(N)(=O)=O)c2C#N)CCCCC1]

Prepared as in Example 9c from tert-butyl(1-((3-amino-2-cyanophenoxy)methyl)cyclohexyl)carbamate (Example 32d) in 100% yield. MS 325 (MH$^+$, −Boc).

Example 32d tert-butyl(1-((3-amino-2-cyanophenoxy)methyl)cyclohexyl)carbamate

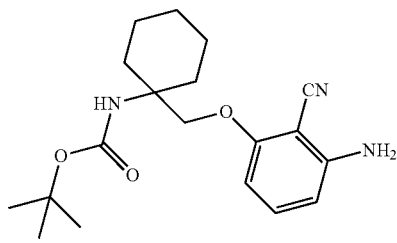 [SMILES: CC(C)(C)OC(=O)NC1(COc2cccc(N)c2C#N)CCCCC1]

Prepared as in Example 1d from tert-butyl(1-((2-cyano-3-nitrophenoxy)methyl)cyclohexyl)carbamate (Example 32e) in 27% yield. MS 246 (MH$^+$, −Boc).

Example 32e tert-butyl(1-((2-cyano-3-nitrophenoxy)methyl)cyclohexyl)carbamate

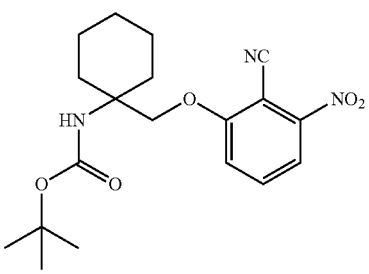 [SMILES: CC(C)(C)OC(=O)NC1(COc2cccc([N+](=O)[O-])c2C#N)CCCCC1]

Prepared as in Example 9e from 2,6-dinitrobenzonitrile and tert-butyl(1-(hydroxymethyl)cyclohexyl)carbamate in 99% yield. MS 276 (MH$^+$, −Boc).

Example 33

N-(1-((4-amino-2,2-dioxido-1H-benzo[c][1,2,6]thiadiazin-5-yl)oxy)-2-methylpropan-2-yl)-2-(2-ethyl-1H-imidazol-1-yl)isonicotinamide

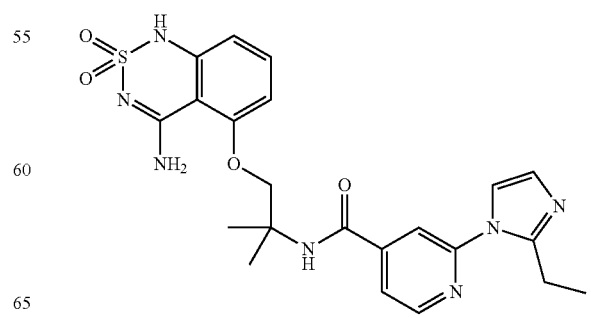

Prepared as in Example 1 from 4-amino-5-(2-amino-2-methylpropoxy)-1H-benzo[c][1,2,6]thiadiazine 2,2-dioxide hydrochloride (Example 1a) and 2-(2-ethyl-1H-imidazol-1-yl)isonicotinic acid (Example 33a) in 18% yield. $^1$H NMR (DMSO-$d_6$, 400 MHz): δ 1.15 (t, J=7.2 Hz, 3H), 1.49 (s, 6H), 2.87 (q, J=7.2 Hz, 2H), 4.38 (s, 2H), 6.61 (d, J=8.4 Hz, 1H), 6.78 (d, J=8.8 Hz, 1H), 6.95 (s, 1H), 7.46 (t, J=8.0 Hz, 1H), 7.59 (s, 1H), 7.71 (dd, J=4.8 Hz, 1H), 7.79 (s, 1H), 7.81 (s, 1H), 8.46 (s, 1H), 8.56 (s, 1H), 8.65 (dd, J=4.8 Hz, 1H), 11.00 (s, 1H). MS 484 (MH$^+$).

Example 33a 2-(2-ethyl-1H-imidazol-1-yl)isonicotinic acid

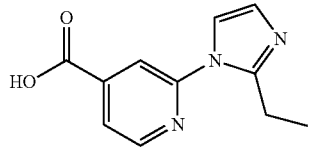 [SMILES: CCc1nccn1-c1cc(C(=O)O)ccn1]

Prepared as in Example 7a from methyl-2-bromoisonicotinate and 2-ethyl-1H-imidazole in 84% yield. MS 218 (MH$^+$).

Example 34

N-(1-((4-amino-2,2-dioxido-1H-benzo[c][1,2,6]thiadiazin-5-yl)oxy)-2-methylpropan-2-yl)-2-(2,4-dimethyl-1H-imidazol-1-yl)isonicotinamide

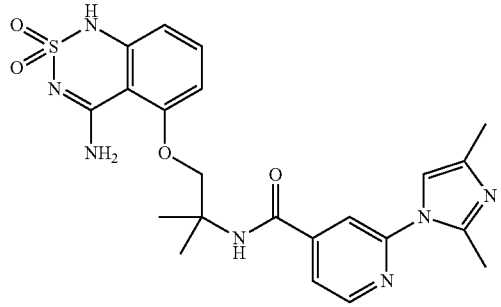 [SMILES: Cc1cn(-c2cc(C(=O)NC(C)(C)COc3cccc4c3C(N)=NS(=O)(=O)N4)ccn2)c(C)n1]

Prepared as in Example 1 from 4-amino-5-(2-amino-2-methylpropoxy)-1H-benzo[c][1,2,6]thiadiazine 2,2-dioxide hydrochloride (Example 1a) and 2-(2,4-dimethyl-1H-imidazol-1-yl)isonicotinic acid (Example 34a) in 20% yield. $^1$H NMR (DMSO-$d_6$, 400 MHz): δ 1.15 (d, J=6.4 Hz, 6H), 1.49 (s, 6H), 2.09 (s, 1H), 2.44 (s, 3H), 4.37 (s, 2H), 6.61 (d, J=7.6 Hz, 1H), 6.78 (d, J=8.4 Hz, 1H), 7.31 (s, 1H), 7.46 (t, J=8.4 Hz, 1H), 7.77 (s, 1H), 7.80 (s, 2H), 8.47 (s, 1H), 8.54 (s, 1H), 8.61 (dd, J=4.4 Hz, 1H), 11.00 (s, 1H). MS 484 (MH$^+$).

Example 34a 2-(2,4-dimethyl-1H-imidazol-1-yl)isonicotinic acid

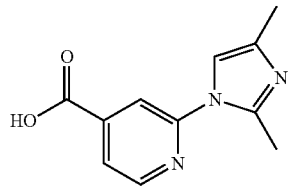 [SMILES: Cc1cn(-c2cc(C(=O)O)ccn2)c(C)n1]

Prepared as in Example 7a from 2-bromoisonicotinic acid and 2,4-dimethyl-1H-imidazole in 50% yield. MS 218 (MH$^+$).

Example 35

N-(1-((4-amino-2,2-dioxido-1H-benzo[c][1,2,6]thiadiazin-5-yl)oxy)-2-methylpropan-2-yl)-2-(2-propyl-1H-imidazol-1-yl)isonicotinamide

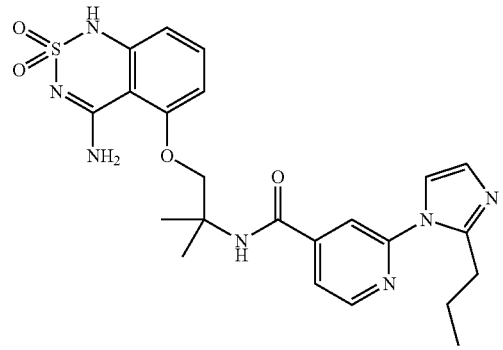 [SMILES: CCCc1nccn1-c1cc(C(=O)NC(C)(C)COc2cccc3c2C(N)=NS(=O)(=O)N3)ccn1]

Prepared as in Example 1 from 4-amino-5-(2-amino-2-methylpropoxy)-1H-benzo[c][1,2,6]thiadiazine 2,2-dioxide hydrochloride (Example 1a) and 2-(2-propyl-1H-imidazol-1-yl)isonicotinic acid (Example 35a) in 20% yield. $^1$H NMR (DMSO-$d_6$, 400 MHz): $^1$H NMR (DMSO-$d_6$, 400 MHz): δ 0.82 (t, J=7.6 Hz, 3H), 1.48 (s, 6H), 1.58 (sext, J=7.6 Hz, 2H), 2.83 (t, J=7.5 Hz, 2H), 4.37 (s, 2H), 6.60 (d, J=8.4 Hz, 1H), 6.77 (d, J=8.2 Hz, 1H), 6.94 (m, 1H), 7.44 (t, J=8.4 Hz, 1H), 7.57 (m, 1H), 7.71 (dd, J=4.9, 1.2 Hz, 1H), 7.78 (br s, 1H), 7.80 (s, 1H), 8.44 (br s, 1H), 8.56 (s, 1H), 8.65 (d, J=5.1 Hz, 1H), 10.99 (s, 1H). MS 498 (MH$^+$).

Example 35a 2-(2-propyl-1H-imidazol-1-yl)isonicotinic acid

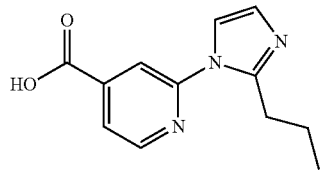 [SMILES: CCCc1nccn1-c1cc(C(=O)O)ccn1]

Prepared as in Example 7a from 2-bromoisonicotinic acid and 2-propyl-1H-imidazole in 75% yield. MS 232 (MH$^+$).

Example 36

N-(1-((4-amino-2,2-dioxido-1H-benzo[c][1,2,6]thiadiazin-5-yl)oxy)-2-methylpropan-2-yl)-2-(4-(hydroxymethyl)-1H-imidazol-1-yl)isonicotinamide

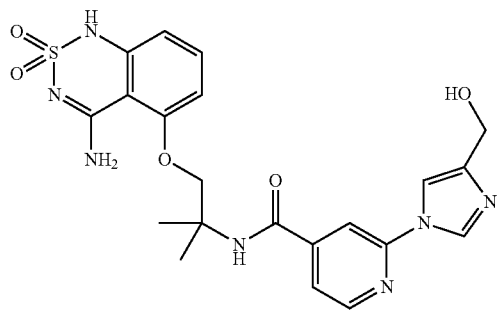 [SMILES: CC(C)(COc1cccc2c1C(N)=NS(=O)(=O)N2)NC(=O)c1ccnc(-n2cnc(CO)c2)c1]

To a suspension of N-(1-((4-amino-2,2-dioxido-1H-benzo[c][1,2,6]thiadiazin-5-yl)oxy)-2-methylpropan-2-yl)-2-(4-formyl-1H-imidazol-1-yl)isonicotinamide (255 mg, 527 umol, Example 36a) in MeOH (5 mL) at room temperature, was added sodium borohydride (59.8 mg, 1.58 mmol) in portions. The reaction was stirred at room temperature for thirty minutes, and upon completion was quenched with water. The solution was concentrated under reduced pressure and purified by flash chromatography (15% methanol in dichloromethane, normal phase silica gel), followed by preparative HPLC (10-80% acetonitrile in water, reverse phase C18 column) The purified product was precipitated from DMSO/water, suspended in aqueous $Na_2CO_3$ (50 mg in 50 mL water), heated at 45° C. to completely dissolve the solid and carefully neutralized with 1N HCl while at 45° C. The mixture was cooled to room temperature, and the white solid was collected by vacuum filtration and dried under vacuum to provide N-(1-((4-amino-2,2-dioxido-1H-benzo[c][1,2,6]thiadiazin-5-yl)oxy)-2-methylpropan-2-yl)-2-(4-(hydroxymethyl)-1H-imidazol-1-yl)isonicotinamide (90 mg, 35%) as a white solid. M.p.>200° C. $^1H$ NMR (DMSO-$d_6$, 400 MHz): δ 1.50 (s, 6H), 4.41 (m, 4H), 5.03 (t, J=6.0 Hz, 1H), 6.61 (d, J=7.6 Hz, 1H), 6.79 (d, J=8.0 Hz, 1H), 7.46 (t, J=8.4 Hz, 1H), 7.60 (dd, J=6.4 Hz, 1H), 7.81 (m, 2H), 8.00 (s, 1H), 8.49 (m, 2H), 8.53 (s, 1H), 8.56 (dd, J=4.4 Hz, 1H), 10.99 (s, 1H). MS=486 (MH$^+$).

Example 36a

N-(1-((4-amino-2,2-dioxido-1H-benzo[c][1,2,6]thiadiazin-5-yl)oxy)-2-methylpropan-2-yl)-2-(4-formyl-1H-imidazol-1-yl)isonicotinamide

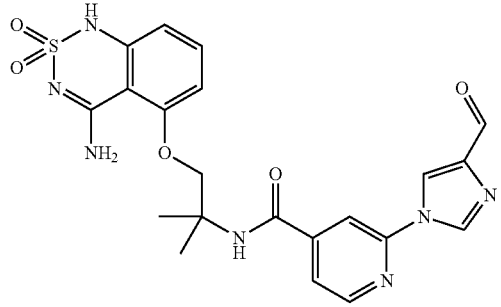 [SMILES: CC(C)(COc1cccc2c1C(N)=NS(=O)(=O)N2)NC(=O)c1ccnc(-n2cnc(C=O)c2)c1]

Prepared as in Example 1 from 4-amino-5-(2-amino-2-methylpropoxy)-1H-benzo[c][1,2,6]thiadiazine 2,2-dioxide hydrochloride (Example 1a) and 2-(4-formyl-1H-imidazol-1-yl)isonicotinic acid (Example 36b) as a white solid in 29% yield. MS=484 (MH$^+$).

Example 36b 2-(4-formyl-1H-imidazol-1-yl)isonicotinic acid

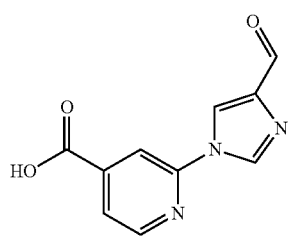 [SMILES: O=Cc1cn(-c2cc(C(=O)O)ccn2)cn1]

Prepared as in Example 7a from 2-bromoisonicotinic acid and 1H-imidazole-4-carbaldehyde in 40% yield. MS 218 (MH$^+$).

Example 37

1-(4-((1-((4-amino-2,2-dioxido-1H-benzo[c][1,2,6]thiadiazin-5-yl)oxy)-2-methylpropan-2-yl)carbamoyl)pyridine-2yl)1H-imidazole-4-carboxylic acid

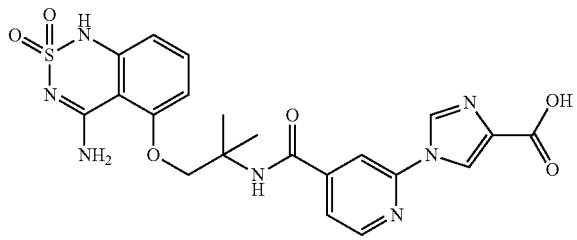 [SMILES: CC(C)(COc1cccc2c1C(N)=NS(=O)(=O)N2)NC(=O)c1ccnc(-n2cnc(C(=O)O)c2)c1]

A mixture of methyl 1-(4-((1-((4-amino-2,2-dioxido-1H-benzo[c][1,2,6]thiadiazin-5-yl)oxy)-2-methylpropan-2-yl)carbamoyl)pyridin-2-yl)-1H-imidazole-4-carboxylate (489 mg, 0.95 mmol, Example 37a) and $Na_2CO_3$ (800 mg, 7.55 mmol) was suspended in water (8 mL). The suspension was heated to 90° C., carefully acidified to pH 4.0 with 1N HCl and cooled to room temperature. The white solid was collected by vacuum filtration and dried under vacuum at 50° C. to provide 1-(4-((1-((4-amino-2,2-dioxido-1H-benzo[c][1,2,6]thiadiazin-5-yl)oxy)-2-methylpropan-2-yl)carbamoyl)pyridine-2yl)1H-imidazole-4-carboxylic acid (430 mg, 91% yield) as a white solid. m.p.>200° C. $^1H$ NMR (DMSO-$d_6$, 400 MHz): δ 1.50 (s, 6H), 4.41 (s, 2H), 6.62 (d, J=8.0 Hz, 1H), 6.79 (d, J=8.0 Hz, 1H), 7.46 (t, J=8.0 Hz, 1H), 7.70 (d, J=4.0 Hz, 1H), 7.78 (br s, 1H), 8.20 (s, 1H), 8.48 (br s, 1H), 8.55 (s, 1H), 8.61 (s, 1H), 8.63 (d, J=8.0 Hz, 1H), 8.67 (s, 1H), 11.00 (s, 1H). MS 500 (MH+).

Example 37a 1-(4-((1-((4-amino-2,2-dioxido-1H-benzo[c][1,2,6]thiadiazin-5-yl)oxy)-2-methylpropan-2-yl)carbamoyl)pyridin-2-yl)-1H-imidazole-4-carboxylate

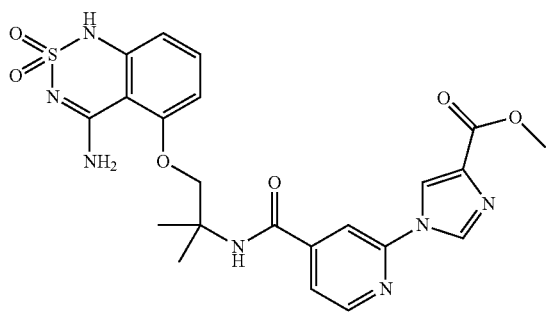 [SMILES: COC(=O)c1cn(-c2cc(C(=O)NC(C)(C)COc3cccc4c3C(N)=NS(=O)(=O)N4)ccn2)cn1]

Prepared as in Example 1 from 4-amino-5-(2-amino-2-methylpropoxy)-1H-benzo[c][1,2,6]thiadiazine 2,2-dioxide hydrochloride (Example 1a) and 2-(4-(methoxycarbonyl)-1H-imidazol-1-yl)isonicotinic acid (Example 37b) in 40% yield. $^1$H NMR (DMSO-d$_6$, 400 MHz): δ 1.50 (s, 6H), 3.80 (s, 3H), 4.42 (s, 2H), 6.61 (d, J=8.3 Hz, 1H), 6.79 (d, J=8.3 Hz, 1H), 7.46 (t, J=8.3 Hz, 1H), 7.71 (dd, J=5.1, 1.2 Hz, 1H), 7.78 (br s, 1H), 8.20 (s, 1H), 8.47 (br s, 1H), 8.53 (s, 1H), 8.62 (d, J=5.2 Hz, 1H), 8.66 (m, 2H), 10.99 (s, 1H). MS 514 (MH+).

Example 37b 2-(4-(methoxycarbonyl)-1H-imidazol-1-yl)isonicotinic acid

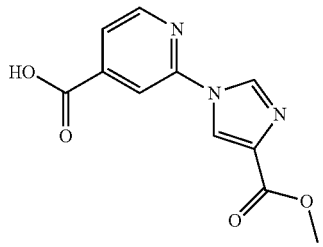 [SMILES: COC(=O)c1cn(-c2cc(C(=O)O)ccn2)cn1]

Prepared as in Example 7a from 2-bromoisonicotinic acid and methyl 1H-imidazole-4-carboxylate in 50% yield. MS 247 (MH+).

Example 38

N-(1-((4-amino-2,2-dioxido-1H-benzo[c][1,2,6]thiadiazin-5-yl)oxy)-2-methylpropan-2-yl)-2-isobutyramidoisonicotinamide

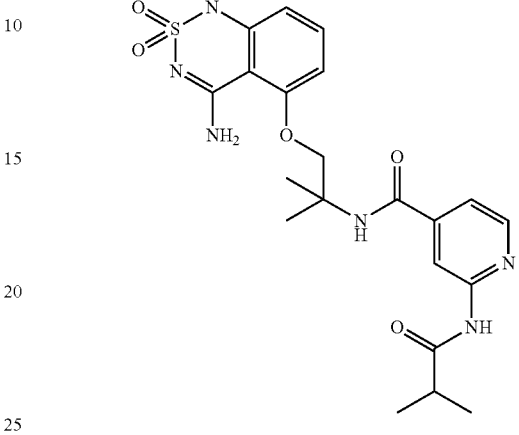

Prepared as in Example 1 from 4-amino-5-(2-amino-2-methylpropoxy)-1H-benzo[c][1,2,6]thiadiazine 2,2-dioxide hydrochloride (Example 1a) and 2-isobutyramidoisonicotinic acid (Example 38a) in 23% yield. $^1$H NMR (DMSO-d$_6$, 400 MHz): δ 1.07 (d, J=6.8 Hz, 6H), 1.47 (s, 6H), 2.74 (m, 1H), 4.36 (s, 1H), 6.61 (d, J=8.4 Hz, 1H), 6.78 (d, J=8.4 Hz, 1H), 7.32 (dd, J=5.2 Hz, 1H), 7.45 (t, J=8.4 Hz, 1H), 7.83 (s, 1H), 8.31 (s, 1H), 8.33 (s, 1H), 8.36 (dd, J=5.6 Hz, 1H), 8.47 (s, 1H), 10.53 (s, 1H), 10.98 (s, 1H). MS 475 (MH+).

Example 38b 2-isobutyramidoisonicotinic acid

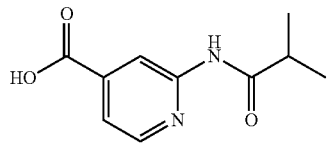

Prepared as in Example 12a from methyl 2-isobutyramidoisonicotinate (Example 38c) in 79% yield. MS 209 (MH+).

Example 38c methyl 2-isobutyramidoisonicotinate

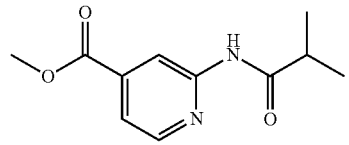 [SMILES: COC(=O)c1ccnc(NC(=O)C(C)C)c1]

To a solution of methyl 2-aminoisonicotinate (1.00 g, 6.57 mmol) in pyridine (12 mL) at 0° C. was slowly added isobutyryl chloride (763 uL, 7.23 mmol). The reaction was warmed to room temperature and stirred for 18 hours, at which time, the reaction was cooled to 0° C. again and a second portion of isobutyryl chloride (763 uL, 7.23 mmol) was added. The reaction was warmed to room temperature, stirred for 4 hours, diluted with water and extracted with EtOAc. The combined organic layers were dried over $Na_2SO_4$, filtered, concentrated and purified by flash chromatography (25/75 ethyl acetate/hexane, normal phase silica gel) to provide methyl 2-isobutyramidoisonicotinate (523 mg, 36% yield) as a white solid. MS 223 (MH$^+$).

Example 39

4-amino-5-(N-(1-hydroxy-2-methylpropan-2-yl)-2-phenylisonicotinamide)-1H-benzo[c][1,2,6]thiadiazine 2,2-dioxide

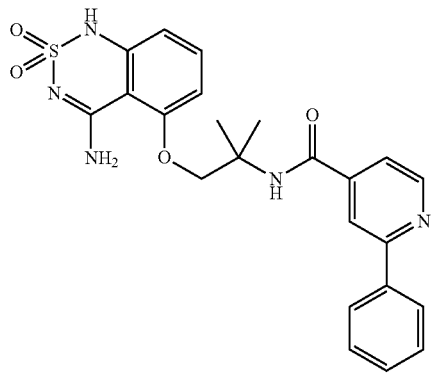 [SMILES: CC(C)(COc1cccc2c1C(N)=NS(=O)(=O)N2)NC(=O)c1ccnc(-c2ccccc2)c1]

Prepared as in Example 1 from 4-amino-5-(2-amino-2-methylpropoxy)-1H-benzo[c][1,2,6]thiadiazine-2,2-dioxide-hydrochloride (Example 1a) and 2-phenylisonicotinic acid in 52% yield. $^1$H NMR (400 MHz, DMSO-d$_6$) δ 1.51 (s, 6H), 4.40 (s, 2H), 6.62 (d, J=8.0 Hz, 1H), 6.80 (d, J=8.0 Hz, 1H), 7.41-7.55 (m, 4H), 7.63 (dd, J=4.0, 8.0 Hz, 1H), 7.86 (s, 1H), 8.08-8.14 (m, 2H), 8.16-8.18 (m, 1H), 8.57 (s, 1H), 8.76 (dd, J=4.0, 8.0 Hz, 1H). MS 466 (MH$^+$).

Example 40

N-(1-((4-amino-2,2-dioxido-1H-benzo[c][1,2,6]thiadiazin-5-yl)oxy)-2-methylpropan-2-yl)-2-ethylisonicotinamide

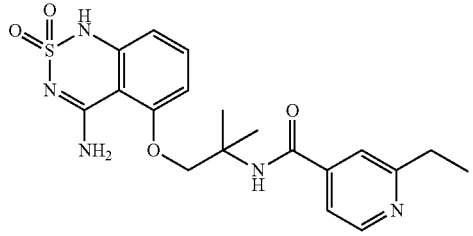 [SMILES: CCc1cc(C(=O)NC(C)(C)COc2cccc3c2C(N)=NS(=O)(=O)N3)ccn1]

Prepared as in Example 1 from 4-amino-5-(2-amino-2-methylpropoxy)-1H-benzo[c][1,2,6]thiadiazine 2,2-dioxide hydrochloride (Example 1a) and 2-ethylisonicotinic acid in 18% yield. $^1$H NMR (400 MHz, DMSO-d$_6$) δ 1.23 (t, J=8.0 Hz, 3H), 1.48 (s, 6H), 2.79 (q, J=8.0 Hz, 2H), 4.38 (s, 2H), 6.61 (d, J=8.0 Hz, 1H), 6.76 (d, J=8.0 Hz, 1H), 7.40-7.49 (m, 2H), 7.51 (s, 1H), 7.80 (s, 1H), 8.43 (s, 2H), 8.56 (d, J=8.0 Hz, 1H), 11.00 (s, 1H). MS 418 (MH$^+$).

Example 41

N-(1-((4-amino-2,2-dioxido-1H-benzo[c][1,2,6]thiadiazin-5-yl)oxy)-2-methylpropan-2-yl)-2-isopropylisonicotinamide

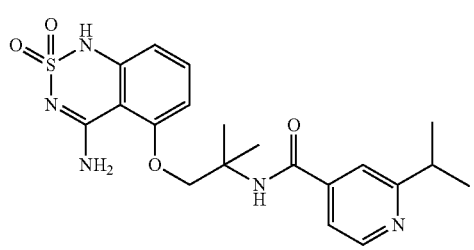 [SMILES: CC(C)c1cc(C(=O)NC(C)(C)COc2cccc3c2C(N)=NS(=O)(=O)N3)ccn1]

Prepared as in Example 1 from 4-amino-5-(2-amino-2-methylpropoxy)-1H-benzo[c][1,2,6]thiadiazine 2,2-dioxide hydrochloride (Example 1a) and 2-isopropylisonicotinic acid in 17% yield. $^1$H NMR (400 MHz, DMSO-d$_6$) δ 1.22 (d, J=8.0 Hz, 6H), 1.47 (s, 6H), 3.06 (hept, J=8.0 Hz, 1H), 4.36 (s, 2H), 6.59 (d, J=8.0 Hz, 1H), 6.74 (d, J=8.0 Hz, 1H), 7.40-7.48 (m, 2H), 7.50 (s, 1H), 7.79 (s br, 1H), 8.41 (s, 2H), 8.56 (d, J=4.0 Hz, 1H), 10.99 (s, 1H). MS 432 (MH$^+$).

Example 42

N-(1-(((4-amino-2,2-dioxido-1H-benzo[c][1,2,6]thiadiazin-5-yl)oxy)methyl)cyclobutyl)-2-(dimethylamino)isonicotinamide

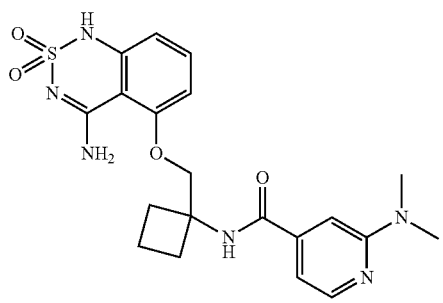 [SMILES: CN(C)c1cc(C(=O)NC2(COc3cccc4c3C(N)=NS(=O)(=O)N4)CCC2)ccn1]

Prepared as in Example 1 from 4-amino-5-((1-aminocyclobutyl)methoxy)-1H-benzo[c][1,2,6]thiadiazine 2,2-dioxide hydrochloride (Example 42a) and 2-(dimethylamino)isonicotinic acid in 30% yield. $^1$H NMR (DMSO-d$_6$, 400 MHz): δ 1.92 (m, 2H), 2.25 (m, 2H), 2.41 (m, 2H), 3.03 (s, 6H), 4.47 (s, 2H), 6.60 (d, J=7.6 Hz, 1H), 6.82 (d, J=8.4 Hz, 1H), 6.87 (d, J=5.6 Hz, 1H), 6.89 (s, 1H), 7.44 (t, J=8.0 Hz, 1H), 7.95 (s, 1H), 8.13 (dd, J=4.8 Hz, 1H), 8.37 (s, 1H), 8.86 (s, 1H), 10.93 (s, 1H). MS 445 (MH$^+$).

Example 42a 4-amino-5-((1-aminocyclobutyl)methoxy)-1H-benzo[c][1,2,6]thiadiazine 2,2-dioxide hydrochloride

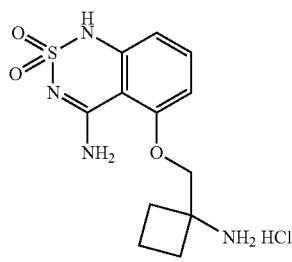

Prepared as in Example 1a from (1-(((4-amino-2,2-dioxido-1H-benzo[c][1,2,6]thiadiazin-5-yl)oxy)methyl)cyclobutyl)carbamate (Example 42b) in 86% yield. MS 297 (MH+).

Example 42b (1-(((4-amino-2,2-dioxido-1H-benzo[c][1,2,6]thiadiazin-5-yl)oxy)methyl)cyclobutyl)carbamate

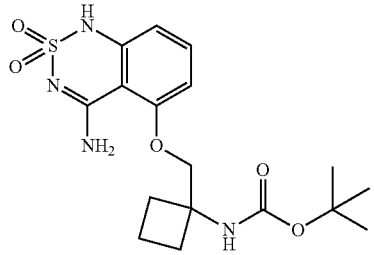 [SMILES: CC(C)(C)OC(=O)NC1(COc2cccc3c2C(N)=NS(=O)(=O)N3)CCC1]

Prepared as in Example 1b from tert-butyl(1-((2-cyano-3-(sulfamoylamino)phenoxy)methyl)cyclobutyl)carbamate (Example 42c) in 79% yield. MS 297 (MH+, –Boc).

Example 42c tert-butyl(1-((2-cyano-3-(sulfamoylamino)phenoxy)methyl)cyclobutyl)carbamate

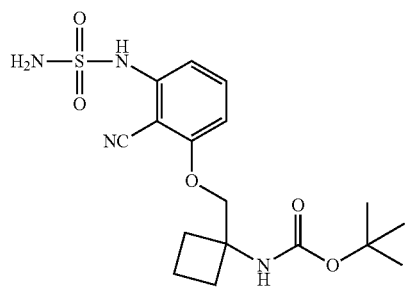 [SMILES: CC(C)(C)OC(=O)NC1(COc2cccc(NS(N)(=O)=O)c2C#N)CCC1]

Prepared as in Example 9c from tert-butyl(1-((3-amino-2-cyanophenoxy)methyl)cyclobutyl)carbamate (Example 42d) in 100% yield. MS 297 (MH+, –Boc).

Example 42d tert-butyl(1-((3-amino-2-cyanophenoxy)methyl)cyclobutyl)carbamate

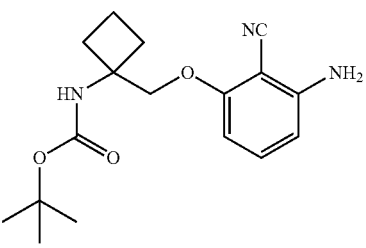

Prepared as in Example 1g from tert-butyl(1-((2-cyano-3-nitrophenoxy)methyl)cyclobutyl)carbamate (Example 42e) in 80% yield. MS 218 (MH+, –Boc)

Example 42e tert-butyl(1-((2-cyano-3-nitrophenoxy)methyl)cyclobutyl)carbamate

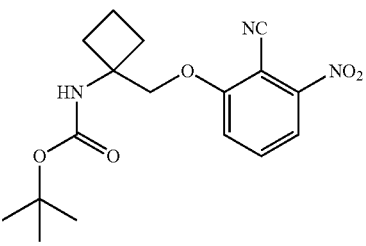 [SMILES: CC(C)(C)OC(=O)NC1(COc2cccc(N)c2C#N)CCC1]

Prepared as in Example 9e from 2,6-dinitrobenzonitrile and tert-butyl(1-(hydroxymethyl)cyclobutyl) in 77% yield. MS 248 (MH+, –Boc).

Example 43

N-(1-(((4-amino-2,2-dioxido-1H-benzo[c][1,2,6]thiadiazin-5-yl)oxy)methyl)cyclobutyl)-2-methylisonicotinamide

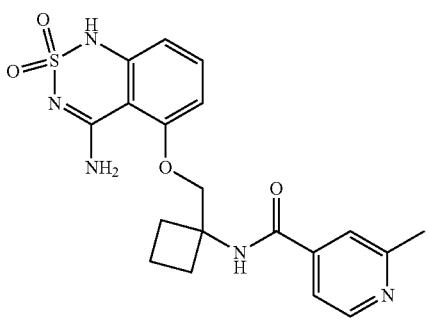 [SMILES: Cc1cc(C(=O)NC2(COc3cccc4c3C(N)=NS(=O)(=O)N4)CCC2)ccn1]

Prepared as in Example 1 from 4-amino-5-((1-aminocyclobutyl)methoxy)-1H-benzo[c][1,2,6]thiadiazine 2,2-dioxide hydrochloride (Example 42a) and 2-methylisonicotinic acid in 21% yield. ¹H NMR (DMSO-d₆, 400 MHz): δ 1.91 (m, 2H), 2.25 (m, 2H), 2.41 (m, 2H), 2.51 (s, 3H), 4.47 (s, 2H), 6.60 (d, J=8.0 Hz, 1H), 6.83 (d, J=8.4 Hz, 1H), 7.44 (d, J=8.0 Hz, 1H), 7.49 (dd, J=5.2 Hz, 1H), 7.55 (s, 1H), 7.93 (s, 1H), 8.39 (s, 1H), 8.53 (dd, J=4.8 Hz, 1H), 9.00 (s, 1H), 10.94 (s, 1H). MS 416 (MH⁺).

Example 44

N-(1-(((4-amino-2,2-dioxido-1H-benzo[c][1,2,6]thiadiazin-5-yl)oxy)methyl)cyclohexyl)-2-(dimethylamino)isonicotinamide

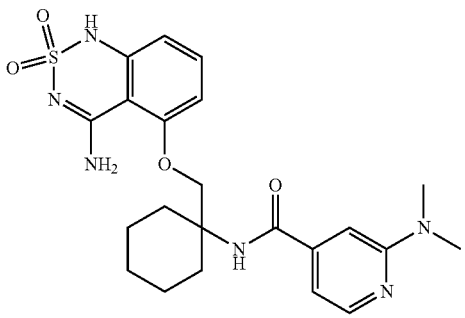 [SMILES: CN(C)c1cc(C(=O)NC2(COc3cccc4c3C(N)=NS(=O)(=O)N4)CCCCC2)ccn1]

Prepared as in Example 1 from 4-amino-5-(1-aminocyclohexyl)methoxy)-1H-benzo[c][1,2,6]thiadiazine 2,2-dioxide hydrochloride (Example 32a) and 2-(dimethylamino)isonicotinic acid hydrochloride in 13% yield. ¹H NMR (DMSO-d₆, 400 MHz): δ 1.29 (br s, 1H), 1.46-1.61 (br m, 7H), 2.37 (br s, 2H), 3.03 (s, 6H), 4.38 (s, 2H), 6.59 (d, J=8.0 Hz, 1H), 6.79 (s, 1H), 6.81-6.84 (m, 2H), 7.43 (t, J=8.4 Hz, 1H), 7.85 (s, 1H), 7.98 (s, 1H), 8.12 (dd, J=5.2, 1H), 8.34 (s, 1H), 10.95 (s, 1H). MS 473 (MH⁺).

Example 45

N-(1-(((4-amino-2,2-dioxido-1H-benzo[c][1,2,6]thiadiazin-5-yl)oxy)methyl)cyclopropyl)-2-(dimethylamino)isonicotinamide

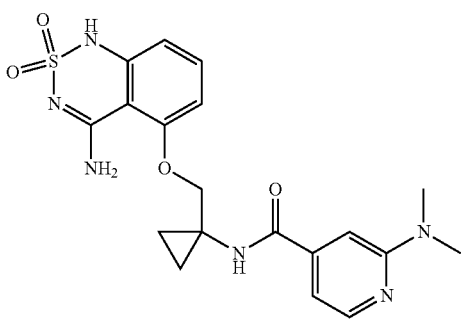 [SMILES: CN(C)c1cc(C(=O)NC2(COc3cccc4c3C(N)=NS(=O)(=O)N4)CC2)ccn1]

Prepared as in Example 1 from 4-amino-5-((1-aminocyclopropyl)methoxy)-1H-benzo[c][1,2,6]thiadiazine 2,2-dioxide hydrochloride (Example 45a) and 3-(dimethylamino)isonicotinic acid hydrochloride in 19% yield. ¹H NMR (DMSO-d₆, 400 MHz): δ 0.97 (m, 2H), 1.02 (m, 2H), 3.03 (s, 3H), 4.24 (s, 6H), 6.58 (t, J=8.4 Hz, 1H), 6.70 (dd, J=5.6 Hz, 1H), 8.30 (s, 1H), 8.38 (s, 1H), 9.10 (s, 1H), 10.89 (s, 1H). MS 431 (MH⁺).

Example 45a 4-amino-5-((1-aminocyclopropyl)methoxy)-1H-benzo[c][1,2,6]thiadiazine 2,2-dioxide hydrochloride

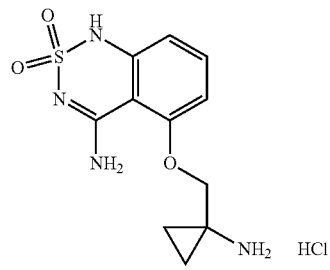 [SMILES: NC1=NS(=O)(=O)Nc2cccc(OCC3(N)CC3)c21 ; Cl]

Prepared as in Example 1a from tert-butyl(1-(((4-amino-2,2-dioxido-1H-benzo[c][1,2,6]thiadiazin-5-yl)oxy)methyl)cyclopropyl)carbamate (Example 45b) in 88% yield. MS 283 (MH⁺).

Example 45b tert-butyl(1-(((4-amino-2,2-dioxido-1H-benzo[c][1,2,6]thiadiazin-5-yl)oxy)methyl)cyclopropyl)carbamate

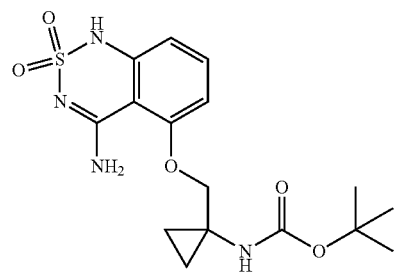 [SMILES: CC(C)(C)OC(=O)NC1(COc2cccc3c2C(N)=NS(=O)(=O)N3)CC1]

Prepared as in Example 1b from tert-butyl(1-((2-cyano-3-(sulfamoylamino)phenoxy)methyl)cyclopropyl)carbamate (Example 45c) as a white solid in 75% yield. MS 327 (MH⁺, –tBu).

Example 45c tert-butyl(1-((2-cyano-3-(sulfamoylamino)phenoxy)methyl)cyclopropyl)carbamate

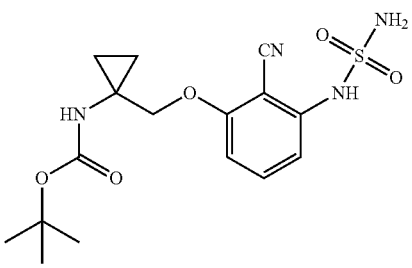 [SMILES: CC(C)(C)OC(=O)NC1(COc2cccc(NS(N)(=O)=O)c2C#N)CC1]

Prepared as in Example 9c from tert-butyl(1-((3-amino-2-cyanophenoxy)methyl)cyclopropyl)carbamate (Example 45d) in 100% yield. MS 283 (MH+, −Boc).

Example 45d tert-butyl(1-((3-amino-2-cyanophenoxy)methyl)cyclopropyl)carbamate

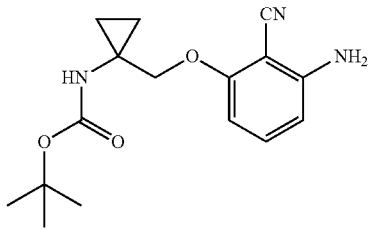 [SMILES: CC(C)(C)OC(=O)NC1(COc2cccc(N)c2C#N)CC1]

Prepared as in Example 29d from tert-butyl(1-((2-cyano-3-nitrophenoxy)methyl)cyclopropyl)carbamate (Example 45e) in 99% yield. MS 204 (MH+, −Boc).

Example 45e tert-butyl(1-((2-cyano-3-nitrophenoxy)methyl)cyclopropyl)carbamate

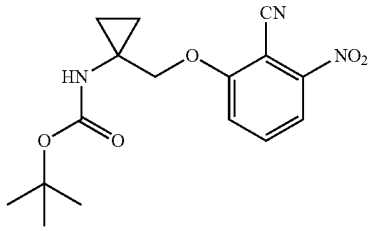 [SMILES: CC(C)(C)OC(=O)NC1(COc2cccc([N+](=O)[O-])c2C#N)CC1]

Prepared as in Example 9e from 2,6-dinitrobenzonitrile and tert-butyl(1-(hydroxymethyl)cyclopropyl)carbamate in 51% yield. MS 234 (MH+, −Boc).

Example 46

N-(1-(((4-amino-2,2-dioxido-1H-benzo[c][1,2,6]thiadiazin-5-yl)oxy)methyl)cyclopropyl)-2-methylisonicotinamide

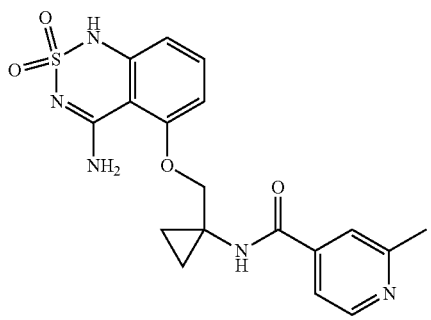 [SMILES: Cc1cc(C(=O)NC2(COc3cccc4c3C(N)=NS(=O)(=O)N4)CC2)ccn1]

Prepared as in Example 1 from 4-amino-5-((1-aminocyclopropyl)methoxy)-1H-benzo[c][1,2,6]thiadiazine 2,2-dioxide hydrochloride (Example 45a) and 2-methylisonicotinic acid hydrochloride in 5% yield. $^1$H NMR (DMSO-d$_6$, 400 MHz): δ 0.97 (m, 2H), 1.03 (m, 2H), 2.50 (s, 3H), 3.03 (s, 6H), 4.24 (s, 2H), 6.58 (d, J=9.2 Hz, 1H), 6.70 (d, J=8.0 Hz, 1H), 7.40 (t, J=8.4 Hz, 1H), 7.50 (dd, J=3.6 Hz, 1H), 7.57 (s, 1H), 8.27 (s, 1H), 8.39 (s, 1H), 8.54 (dd, J=5.6 Hz, 1H), 9.23 (s, 1H), 10.90 (s, 1H). MS 402 (MH+).

Example 47

2-Amino-1-(4-((1-(((4-amino-2,2-dioxido-1H-benzo[c][1,2,6]thiadiazin-5-yl)oxy)-2-methylpropan-2-yl)carbamoyl)pyridin-2-yl)-1H-imidazol-3-ium chloride

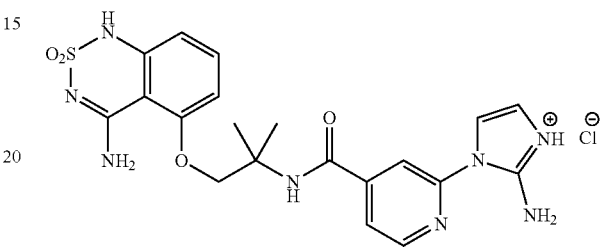

To a suspension of 2-(2-amino-1H-imidazol-1-yl)-N-(1-((4-amino-2,2-dioxido-1H-benzo[c][1,2,6]thiadiazin-5-yl)oxy)-2-methylpropan-2-yl)isonicotinamide (0.31 g, 0.65 mmol) in EtOH (30 mL) was added drop wise a 1.5M aqueous HCl solution (1.50 mL) at room temperature. The reaction mixture was stirred at room temperature for 1 hour and the obtained precipitate was filtered, washed with EtOH, dried under high vacuum and suspended in EtOH.

The suspension was stirred and heated at 80° C. for 30 min, filtered hot and the obtained solid was washed with EtOH and dried under high vacuum to provide 2-Amino-1-(4-((1-((4-amino-2,2-dioxido-1H-benzo[c][1,2,6]thiadiazin-5-yl)oxy)-2-methylpropan-2-yl)carbamoyl)pyridin-2-yl)-1H-imidazol-3-ium chloride (0.23 g 71%) as a pale white solid. m.p.=235-237° C. (decomposed). $^1$H-NMR (400 MHz, DMSO-d$_6$) δ 12.46 (broad s, 1H), 11.04 (broad s, 1H), 8.77 (s, 1H), 8.68 (broad s, 2H), 8.65 (dd, J=5.2, 0.7 Hz, 1H), 8.43 (d, J=3.0 Hz, 1H), 8.15-8.10 (m, 1H), 7.86 (d, J=2.7 Hz, 1H), 7.82 (d, J=3.0 Hz, 1H), 7.78 (dd, J=5.2, 1.3 Hz, 1H), 7.48 (t, J=8.2 Hz, 1H), 7.19 (d, J=2.7 Hz, 1H), 6.81 (dd, J=8.5, 1.0 Hz, 1H), 6.64 (dd, J=8.2, 0.9 Hz, 1H), 4.43 (s, 2H), 1.52 (s, 6H). MS 471 (MH+).

Example 47a 2-(2-Amino-1H-imidazol-1-yl)-N-(1-((4-amino-2,2-dioxido-1H-benzo[c][1,2,6]thiadiazin-5-yl)oxy)-2-methylpropan-2-yl)isonicotinamide

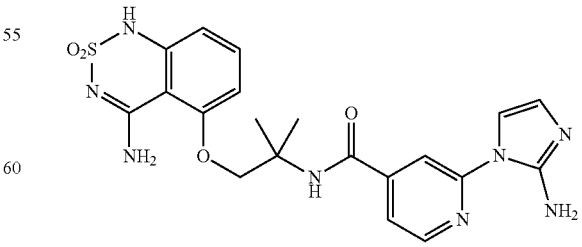

Prepared as in Example 1 from 4-amino-5-(2-amino-2-methylpropoxy)-1H-benzo[c][1,2,6]thiadiazine 2,2-dioxide hydrochloride (Example 1a) and 2-(2-amino-1H-imidazol-1-yl)isonicotinic acid (Example 47b) in 26% yield. $^1$H-NMR (400 MHz, DMSO-$d_6$) δ 11.03 (broad s, 1H), 8.57 (s, 1H), 8.55 (dd, J=5.2, 0.7 Hz, 1H), 8.45 (broad s, 1H), 7.84-7.79 (m, 1H), 7.80 (broad s, 1H), 7.54 (dd, J=5.2, 1.3 Hz, 1H), 7.46 (t, J=8.3 Hz, 1H), 7.36 (d, J=1.9 Hz, 1H), 6.79 (dd, J=8.4, 1.0 Hz, 1H), 6.74 (brad s, 2H), 6.62 (dd, J=8.2, 0.9 Hz, 1H), 6.59 (d, J=1.8 Hz, 1H), 4.40 (s, 2H), 1.51 (s, 6H). MS 471 (MH$^+$).

Example 47b 2-(2-Amino-1H-imidazol-1-yl)isonicotinic acid

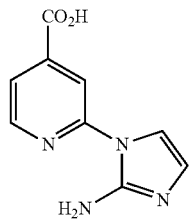 [SMILES: Nc1nccn1-c1cc(C(=O)O)ccn1]

A solution of 2-bromopyridine-4-carboxylic acid (1.30 g, 6.45 mmol), 2-aminoimidazole sulfate (0.94 g, 7.09 mmol), 8-hydroxyquinoline (0.14 g, 0.97 mmol), CuI (0.12 g, 0.64 mmol) and Cs$_2$CO$_3$ (3.15 g, 9.67 mmol) in dry t-BuOH (48.0 mL) was heated at 110° C. for 20 hours. The reaction mixture was cooled to room temperature, diluted with a mixture of EtOAc-MeOH (1:1, 100 mL) and filtered. The obtained cake was washed several times with a mixture of EtOAc-MeOH (1:1) and the filtrate was evaporated. The residue was treated with MeOH (100 mL), and the obtained suspension was again filtered and the cake was washed with MeOH. The collected filtrate was evaporated, the residue was dissolved in a mixture of water and EtOH (1:1, 100 mL) and the pH was adjusted to 1-2 with a 1.5M aqueous HCl solution. The product was isolated by preparative HPLC (10-90% acetonitrile in water, reverse phase C18 column) and dried under high vacuum to provide 2-(2-Amino-1H-imidazol-1-yl)isonicotinic acid (0.59 g, 44%) as a pale white solid. $^1$H-NMR (400 MHz, DMSO-$d_6$) 8.61 (dd, J=5.0, 0.8 Hz, 1H), 8.00-7.96 (m, 1H), 7.71 (dd, J=5.0, 1.2 Hz, 1H), 7.53 (d, J=2.1 Hz, 1H), 7.33 (brad s, 2H), 6.75 (d, J=2.1 Hz, 1H). MS 205 (MH$^+$).

The compounds in Table A below were synthesized following the procedures similar to those described in the above Examples.

TABLE A

| Compound | MS (MH$^+$) |
|---|---|
| N-(1-((4-amino-2,2-dioxido-1H-benzo[c][1,2,6]thiadiazin-5-yl)oxy)-2-methylpropan-2-yl)-2-(1H-imidazol-1-yl)-6-methoxyisonicotinamide | 486 |
| N-(1-((4-amino-2,2-dioxido-1H-benzo[c][1,2,6]thiadiazin-5-yl)oxy)-2-methylpropan-2-yl)-2-(cyclopentylamino)isnicotinamide | 473 |
| N-(1-((4-amino-2,2-dioxido-1H-benzo[c][1,2,6]thiadiazin-5-yl)oxy)-2-methylpropan-2-yl)-2,6-di(1H-imidazol-1-yl)isonicotinamide | 522 |
| N-(1-((4-amino-2,2-dioxido-1H-benzo[c][1,2,6]thiadiazin-5-yl)oxy)-2-methylpropan-2-yl)-2-ethoxyisnicotinamide | 434 |
| N-(1-(((4-amino-2,2-dioxido-1H-benzo[c][1,2,6]thiadiazin-5-yl)oxy)methyl)cyclohexyl)-2-methylisonicotinamide | 444 |

TABLE A-continued

| Compound | MS (MH+) |
|---|---|
| N-(1-((4-amino-2,2-dioxido-1H-benzo[c][1,2,6]thiadiazin-5-yl)oxy)-2-methylpropan-2-yl)-2-(2-methoxyacetamido)isnicotinamide | 477 |
| N-(1-(((4-amino-2,2-dioxido-1H-benzo[c][1,2,6]thiadiazin-5-yl)oxy)methyl)cyclobutyl)isonicotinamide | 402 |
| N-(1-((4-amino-2,2-dioxido-1H-benzo[c][1,2,6]thiadiazin-5-yl)oxy)-2-methylpropan-2-yl)-4-methylpicolinamide | 404 |
| N-(3-(((4-amino-2,2-dioxido-1H-benzo[c][1,2,6]thiadiazin-5-yl)oxy)methyl)pentan-3-yl)-2,6-dimethylisonicotinamide | 446 |
| N-(1-((4-amino-2,2-dioxido-1H-benzo[c][1,2,6]thiadiazin-5-yl)oxy)-2-methylpropan-2-yl)-2-(furan-2-yl)isonicotinamide | 456 |
| N-(1-((4-amino-2,2-dioxido-1H-benzo[c][1,2,6]thiadiazin-5-yl)oxy)-2-methylpropan-2-yl)-2-(2,5-dimethyl-1H-imidazol-1-yl)isonicotinamide | 484 |
| N-(1-((4-amino-2,2-dioxido-1H-benzo[c][1,2,6]thiadiazin-5-yl)oxy)-2-methylpropan-2-yl)-6-fluoro-2-methylquinoline-4-carboxamide | 472 |
| N-(1-((4-amino-2,2-dioxido-1H-benzo[c][1,2,6]thiadiazin-5-yl)oxy)-2-methylpropan-2-yl)-2-(2-(methoxymethyl)-1H-imidazol-1-yl)isonicotinamide | 500 |

TABLE A-continued

| Compound | MS (MH+) |
|---|---|
| N-(1-((4-amino-2,2-dioxido-1H-benzo[c][1,2,6]thiadiazin-5-yl)oxy)-2-methylpropan-2-yl)-3-methyl-6,7-dihydro-5H-cyclopenta[b]isoxazolo[4,5-e]pyridine-4-carboxamide | 485 |
| N-(1-((4-amino-2,2-dioxido-1H-benzo[c][1,2,6]thiadiazin-5-yl)oxy)-2-methylpropan-2-yl)-2-(5-(hydroxymethyl)-4-methyl-1H-imidazol-1-yl)isonicotinamide | 500 |
| N-(1-((4-amino-2,2-dioxido-1H-benzo[c][1,2,6]thiadiazin-5-yl)oxy)-2-methylpropan-2-yl)-1,3,6-trimethyl-1H-pyrazolo[3,4-b]pyridine-4-carboxamide | 472 |
| N-(1-((4-amino-2,2-dioxido-1H-benzo[c][1,2,6]thiadiazin-5-yl)oxy)-2-methylpropan-2-yl)-2-(hydroxymethyl)isonicotinamide | 420 |
| N-(1-((4-amino-2,2-dioxido-1H-benzo[c][1,2,6]thiadiazin-5-yl)oxy)-2-methylpropan-2-yl)-2-methylquinoline-4-carboxamide | 454 |
| N-(1-((4-amino-2,2-dioxido-1H-benzo[c][1,2,6]thiadiazin-5-yl)oxy)-2-methylpropan-2-yl)-2-(hydroxymethyl)isonicotinamide | 434 |
| N-(1-((4-amino-2,2-dioxido-1H-benzo[c][1,2,6]thiadiazin-5-yl)oxy)-2-methylpropan-2-yl)-2-methoxyquinoline-4-carboxamide | 470 |
| N-(1-((4-amino-2,2-dioxido-1H-benzo[c][1,2,6]thiadiazin-5-yl)oxy)-2-methylpropan-2-yl)-2-((2-propyl-1H-imidazol-1-yl)methyl)isonicotinamide | 512 |

TABLE A-continued

| Compound | MS (MH+) |
|---|---|
| N-(1-((4-amino-2,2-dioxido-1H-benzo[c][1,2,6]thiadiazin-5-yl)oxy)-2-methylpropan-2-yl)-2-methylnicotinamide | 404 |
| 2-((1H-imidazol-1-yl)methyl)-N-(1-((4-amino-2,2-dioxido-1H-benzo[c][1,2,6]thiadiazin-5-yl)oxy)-2-methylpropan-2-yl)isonicotinamide | 470 |
| N-(1-((4-amino-2,2-dioxido-1H-benzo[c][1,2,6]thiadiazin-5-yl)oxy)-2-methylpropan-2-yl)-2-fluoroisonicotinamide | 408 |
| N-(1-((4-amino-2,2-dioxido-1H-benzo[c][1,2,6]thiadiazin-5-yl)oxy)-2-methylpropan-2-yl)-2-(1-methyl-1H-imidazol-2-yl)isonicotinamide | 470 |
| N-(1-((4-amino-2,2-dioxido-1H-benzo[c][1,2,6]thiadiazin-5-yl)oxy)-2-methylpropan-2-yl)-6-cyclopropyl-3-methylisoxazolo[5,4-b]pyridine-4-carboxamide | 485 |
| N-(1-((4-amino-2,2-dioxido-1H-benzo[c][1,2,6]thiadiazin-5-yl)oxy)-2-methylpropan-2-yl)-2-(3,5-dimethyl-1H-pyrazol-1-yl)isonicotinamide | 484 |
| N-(1-((4-amino-2,2-dioxido-1H-benzo[c][1,2,6]thiadiazin-5-yl)oxy)-2-methylpropan-2-yl)-2,6-dimethylquinoline-4-carboxamide | 468 |
| N-(1-((4-amino-2,2-dioxido-1H-benzo[c][1,2,6]thiadiazin-5-yl)oxy)-2-methylpropan-2-yl)-2-((2-methoxyethyl)amino)isonicotinamide | 463 |

TABLE A-continued

| Compound | MS (MH+) |
|---|---|
| 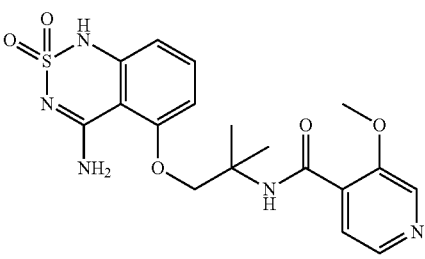<br>N-(1-((4-amino-2,2-dioxido-1H-benzo[c][1,2,6]thiadiazin-5-yl)oxy)-2-methylpropan-2-yl)-2-methoxynicotinamide | 420 |
| 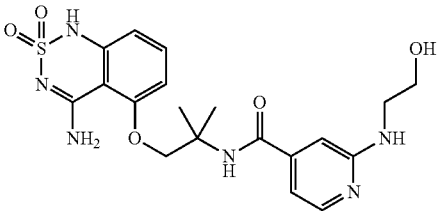<br>N-(1-((4-amino-2,2-dioxido-1H-benzo[c][1,2,6]thiadiazin-5-yl)oxy)-2-methylpropan-2-yl)-2-((2-hydroxyethyl)amino)isonicotinamide | 449 |
| 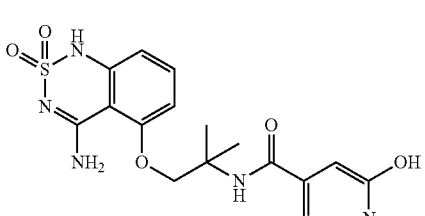<br>N-(1-((4-amino-2,2-dioxido-1H-benzo[c][1,2,6]thiadiazin-5-yl)oxy)-2-methylpropan-2-yl)-2-hydroxyisonicotinamide | 406 |
| 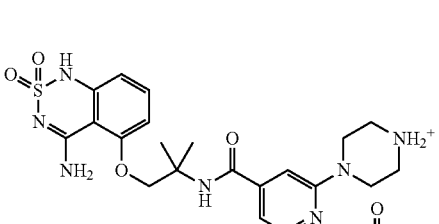<br>4-(4-((1-((4-amino-2,2-dioxido-1H-benzo[c][1,2,6]thiadiazin-5-yl)oxy)-2-methylpropan-2-yl)carbamoyl)pyridin-2-yl)piperazin-1-ium 2,2,2-trifluoroacetate | 588 |
| 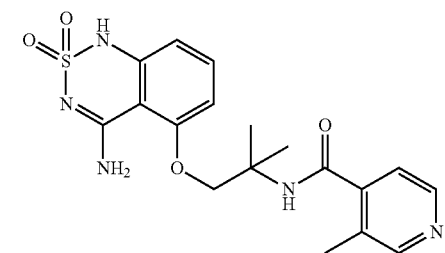<br>N-(1-((4-amino-2,2-dioxido-1H-benzo[c][1,2,6]thiadiazin-5-yl)oxy)-2-methylpropan-2-yl)quinoline-4-carboxamide | 440 |
| 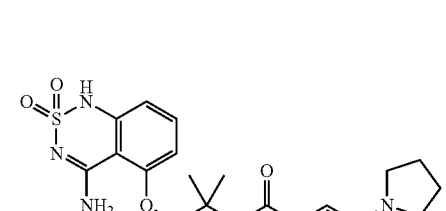<br>N-(1-((4-amino-2,2-dioxido-1H-benzo[c][1,2,6]thiadiazin-5-yl)oxy)-2-methylpropan-2-yl)-2-(2-oxopyrrolidin-1-yl)isonicotinamide | 473 |
| 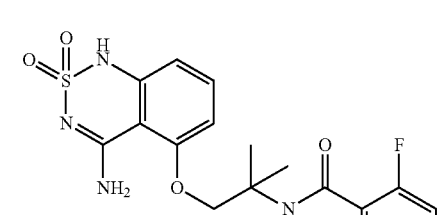<br>N-(1-((4-amino-2,2-dioxido-1H-benzo[c][1,2,6]thiadiazin-5-yl)oxy)-2-methylpropan-2-yl)-3-fluoroisonicotinamide | 408 |
| 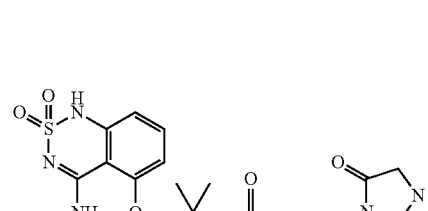<br>N-(1-((4-amino-2,2-dioxido-1H-benzo[c][1,2,6]thiadiazin-5-yl)oxy)-2-methylpropan-2-yl)-2-(3-methyl-2,5-dioxoimidazolidin-1-yl)isonicotinamide | 502 |

TABLE A-continued

| Compound | MS (MH+) |
|---|---|
| 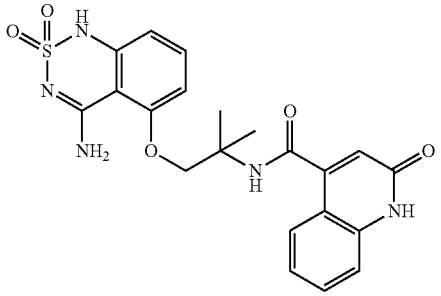 N-(1-((4-amino-2,2-dioxido-1H-benzo[c][1,2,6]thiadiazin-5-yl)oxy)-2-methylpropan-2-yl)-2-oxo-1,2-dihydroquinoline-4-carboxamide | 456 |
| 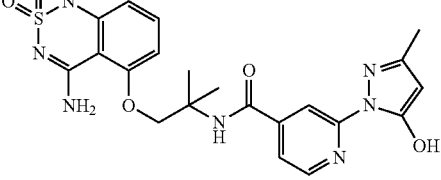 N-(1-((4-amino-2,2-dioxido-1H-benzo[c][1,2,6]thiadiazin-5-yl)oxy)-2-methylpropan-2-yl)-2-(5-hydroxy-3-methyl-1H-pyrazol-1-yl)isonicotinamide | 486 |
| 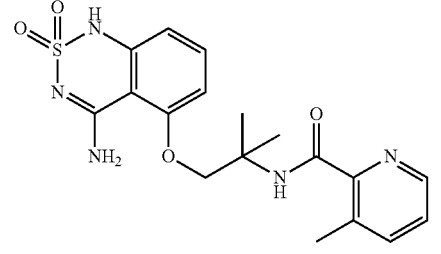 N-(1-((4-amino-2,2-dioxido-1H-benzo[c][1,2,6]thiadiazin-5-yl)oxy)-2-methylpropan-2-yl)-3-methylpicolinamide | 404 |
| 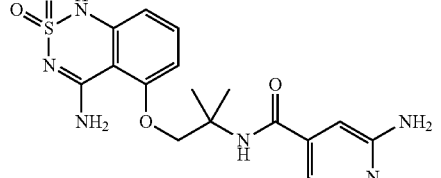 2-amino-N-(1-((4-amino-2,2-dioxido-1H-benzo[b][1,2,6]thiadiazin-5-yl)oxy)-2-methylpropan-2-yl)isonicotinamide | 405 |
| 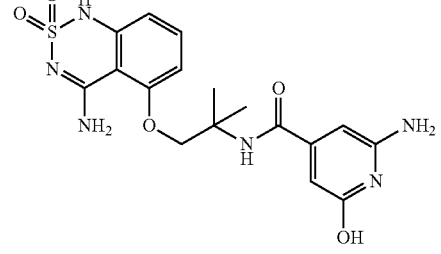 N-(1-((4-amino-2,2-dioxido-1H-benzo[c][1,2,6]thiadiazin-5-yl)oxy)-2-methylpropan-2-yl)-2,6-dihydroxyisonicotinamide | 422 |
| 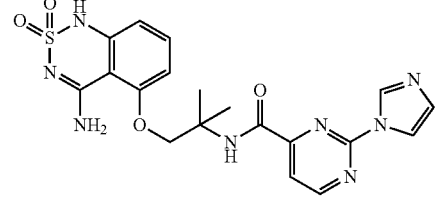 N-(1-((4-amino-2,2-dioxido-1H-benzo[c][1,2,6]thiadiazin-5-yl)oxy)-2-methylpropan-2-yl)-2-(1H-imidazol-1-yl)pyrimidine-4-carboxamide | 456 |
| 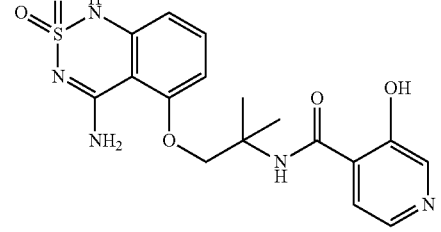 N-(1-((4-amino-2,2-dioxido-1H-benzo[c][1,2,6]thiadiazin-5-yl)oxy)-2-methylpropan-2-yl)-3-hydroxyisonicotinamide | 406 |
| 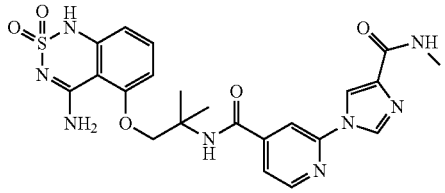 N-(1-((4-amino-2,2-dioxido-1H-benzo[b][1,2,6]thiadiazin-5-yl)oxy)-2-methylpropan-2-yl)-2-(4-(methylcarbamoyl)-1H-imidazol-1-yl)isonicotinamide | 513 |

TABLE A-continued

| Compound | MS (MH+) |
|---|---|
| 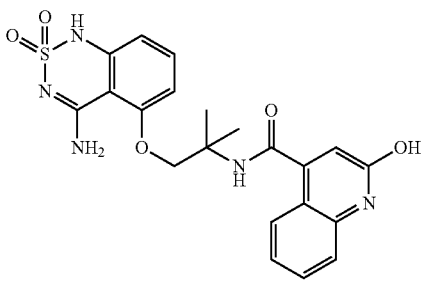<br>N-(1-((4-amino-2,2-dioxido-1H-benzo[c][1,2,6]thiadiazin-5-yl)oxy)-2-methylpropan-2-yl)-2-hydroxyquinoline-4-carboxamide | 456 |
| 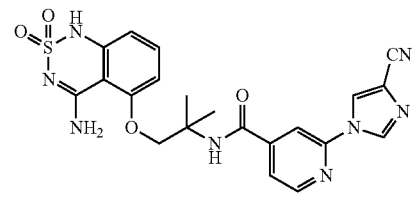<br>N-(1-((4-amino-2,2-dioxido-1H-benzo[c][1,2,6]thiadiazin-5-yl)oxy)-2-methylpropan-2-yl)-2-(4-cyano-1H-imidazol-1-yl)isonicotinamide | 481 |
| 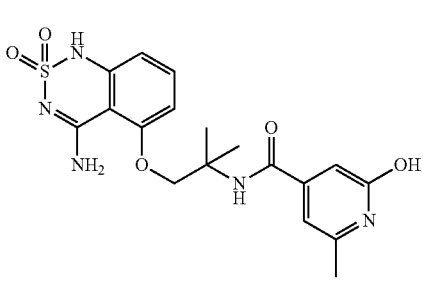<br>N-(1-((4-amino-2,2-dioxido-1H-benzo[c][1,2,6]thiadiazin-5-yl)oxy)-2-methylpropan-2-yl)-2-hydroxy-6-methylisonicotinamide | 420 |
| 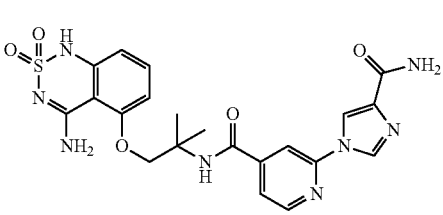<br>N-(1-((4-amino-2,2-dioxido-1H-benzo[c][1,2,6]thiadiazin-5-yl)oxy)-2-methylpropan-2-yl)-2-(4-carbamoyl-1H-imidazol-1-yl)isnicotinamide | 499 |
| 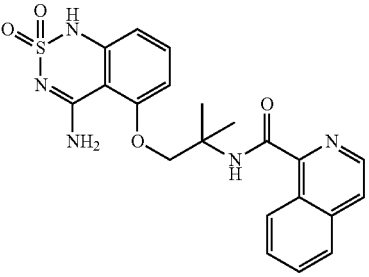<br>N-(1-((4-amino-2,2-dioxido-1H-benzo[c][1,2,6]thiadiazin-5-yl)oxy)-2-methylpropan-2-yl)isoquinoline-1-carboxamide | 440 |
| 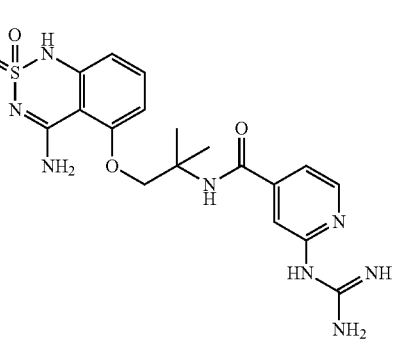<br>N-(1-((4-amino-2,2-dioxido-1H-benzo[c][1,2,6]thiadiazin-5-yl)oxy)-2-methylpropan-2-yl)-2-guanidinoisonicotinamide | 447 |
| 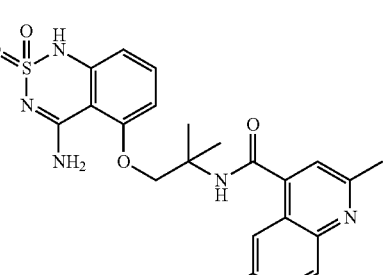<br>N-(1-((4-amino-2,2-dioxido-1H-benzo[c][1,2,6]thiadiazin-5-yl)oxy)-2-methylpropan-2-yl)-6-hydroxy-2-methylquinoline-4-carboxamide | 470 |
| 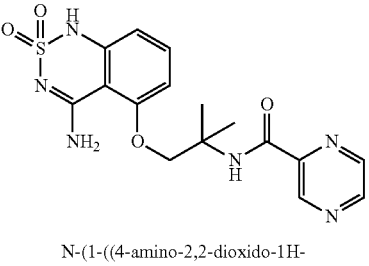<br>N-(1-((4-amino-2,2-dioxido-1H-benzo[c][1,2,6]thiadiazin-5-yl)oxy)-2-methylpropan-2-yl)pyrazine-2-carboxamide | 391 |

TABLE A-continued

| Compound | MS (MH⁺) |
|---|---|
| 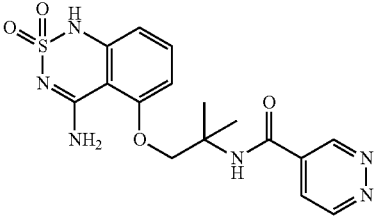<br>N-(1-((4-amino-2,2-dioxido-1H-benzo[c][1,2,6]thiadiazin-5-yl)oxy)-2-methylpropan-2-yl)pyridazine-4-carboxamide | 391 |
| 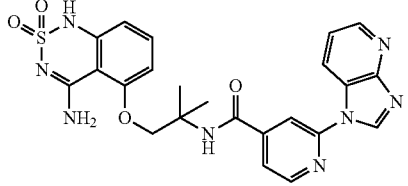<br>N-(1-((4-amino-2,2-dioxido-1H-benzo[c][1,2,6]thiadiazin-5-yl)oxy)-2-methylpropan-2-yl)-2-(1H-imidazo[4,5-b]pyridazin-1-yl)isonicotinamide | 507 |
| 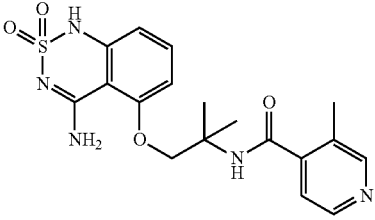<br>N-(1-((4-amino-2,2-dioxido-1H-benzo[c][1,2,6]thiadiazin-5-yl)oxy)-2-methylpropan-2-yl)-3-methylisonicotinamide | 404 |
| 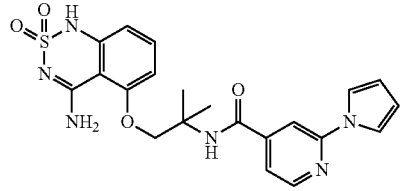<br>N-(1-((4-amino-2,2-dioxido-1H-benzo[c][1,2,6]thiadiazin-5-yl)oxy)-2-methylpropan-2-yl)-2-(1H-pyrrol-1-yl)isonicotinamide | 455 |
| 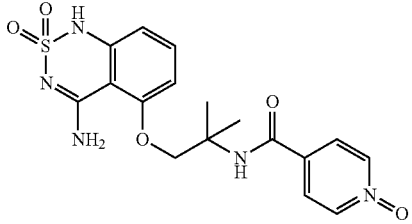<br>4-((1-((4-amino-2,2-dioxido-1H-benzo[c][1,2,6]thiadiazin-5-yl)oxy)-2-methylpropan-2-yl)carbamoyl)pyridine 1-oxide | 406 |
| 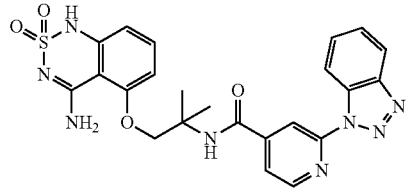<br>N-(1-((4-amino-2,2-dioxido-1H-benzo[c][1,2,6]thiadiazin-5-yl)oxy)-2-methylpropan-2-yl)-2-(1H-benzo[d][1,2,3]triazol-1-yl)isonicotinamide | 507 |
| 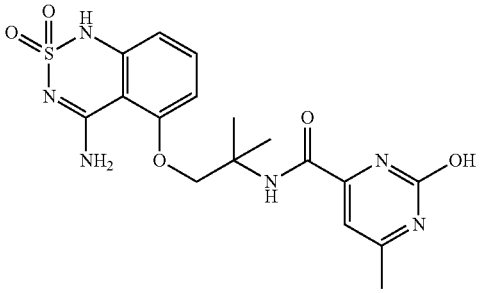<br>N-(1-((4-amino-2,2-dioxido-1H-benzo[c][1,2,6]thiadiazin-5-yl)oxy)-2-methylpropan-2-yl)-2-hydroxy-6-methylpyrimidine-4-carboxamide | 421 |
| 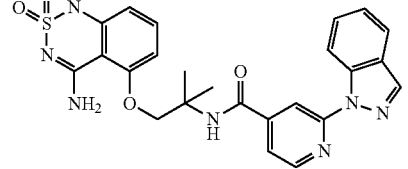<br>N-(1-((4-amino-2,2-dioxido-1H-benzo[c][1,2,6]thiadiazin-5-yl)oxy)-2-methylpropan-2-yl)-2-(1H-indazol-1-yl)isonicotinamide | 506 |

TABLE A-continued

| Compound | MS (MH+) |
|---|---|
| N-(1-((4-amino-2,2-dioxido-1H-benzo[c][1,2,6]thiadiazin-5-yl)oxy)-2-methylpropan-2-yl)-2-(4-methylpiperazin-1-yl)isonicotinamide | 488 |
| N-(1-((4-amino-2,2-dioxido-1H-benzo[c][1,2,6]thiadiazin-5-yl)oxy)-2-methylpropan-2-yl)-2-(1H-indol-1-yl)isonicotinamide | 505 |
| N-(1-((4-amino-2,2-dioxido-1H-benzo[c][1,2,6]thiadiazin-5-yl)oxy)-2-methylpropan-2-yl)-2-(methylsulfonyl)isnicotinamide | 468 |
| N-(1-((4-amino-2,2-dioxido-1H-benzo[c][1,2,6]thiadiazin-5-yl)oxy)-2-methylpropan-2-yl)-2-propionamidoisonicotinamide | 461 |
| N-(1-((4-amino-2,2-dioxido-1H-benzo[c][1,2,6]thiadiazin-5-yl)oxy)-2-methylpropan-2-yl)-2-((tetrahydro-2H-pyran-4-yl)amino)isonicotinamide | 489 |
| N-(1-((4-amino-2,2-dioxido-1H-benzo[c][1,2,6]thiadiazin-5-yl)oxy)-2-methylpropan-2-yl)-2-(cyclopropanecarboxamido)isonicotinamide | 473 |
| N-(1-((4-amino-2,2-dioxido-1H-benzo[c][1,2,6]thiadiazin-5-yl)oxy)-2-methylpropan-2-yl)-2-(2H-1,2,3-triazol-2-yl)isonicotinamide | 457 |
| N-(1-((4-amino-2,2-dioxido-1H-benzo[c][1,2,6]thiadiazin-5-yl)oxy)-2-methylpropan-2-yl)-2-phenoxyisonicotinamide | 482 |
| N-(1-((4-amino-2,2-dioxido-1H-benzo[c][1,2,6]thiadiazin-5-yl)oxy)-2-methylpropan-2-yl)-2-(1H-1,2,3-triazol-1-yl)isonicotinamide | 457 |

TABLE A-continued

| Compound | MS (MH⁺) |
|---|---|
| 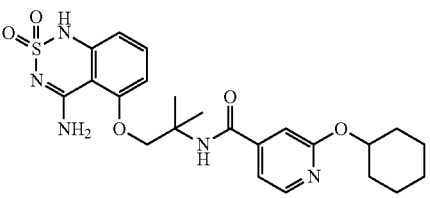<br>N-(1-((4-amino-2,2-dioxido-1H-benzo[c][1,2,6]thiadiazin-5-yl)oxy)-2-methylpropan-2-yl)-2-(cyclohexyloxy)isonicotinamide | 488 |
| 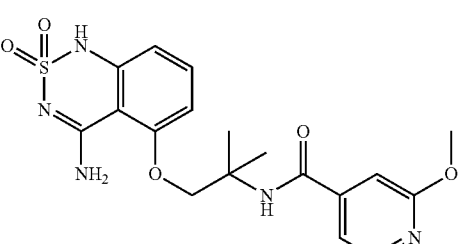<br>N-(1-((4-amino-2,2-dioxido-1H-benzo[c][1,2,6]thiadiazin-5-yl)oxy)-2-methylpropan-2-yl)-2-methoxyisonicotinamide | 420 |
| 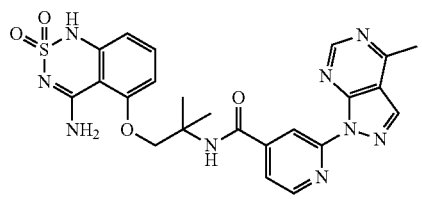<br>N-(1-((4-amino-2,2-dioxido-1H-benzo[c][1,2,6]thiadiazin-5-yl)oxy)-2-methylpropan-2-yl)-2-(6-methyl-9H-purin-9-yl)isonicotinamide | 522 |
| 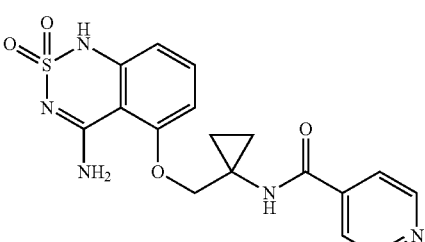<br>N-(1-(((4-amino-2,2-dioxido-1H-benzo[c][1,2,6]thiadiazin-5-yl)oxy)methyl)cyclopropyl)isonicotinamide | 388 |

TABLE A-continued

| Compound | MS (MH⁺) |
|---|---|
| 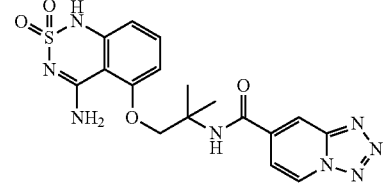<br>N-(1-((4-amino-2,2-dioxido-1H-benzo[c][1,2,6]thiadiazin-5-yl)oxy)-2-methylpropan-2-yl)tetrazolo[1,5-a]pyridine-7-carboxamide | 431 |
| 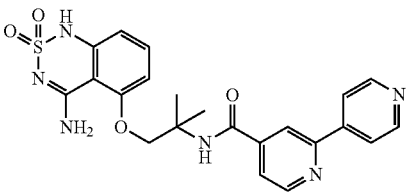<br>N-(1-((4-amino-2,2-dioxido-1H-benzo[c][1,2,6]thiadiazin-5-yl)oxy)-2-methylpropan-2-yl)-[2,4'-bipyridin]-4-carboxamide | 467 |
| 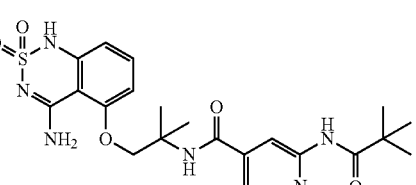<br>N-(1-((4-amino-2,2-dioxido-1H-benzo[c][1,2,6]thiadiazin-5-yl)oxy)-2-methylpropan-2-yl)-2-pivalamidoisonicotinamide | 489 |
| 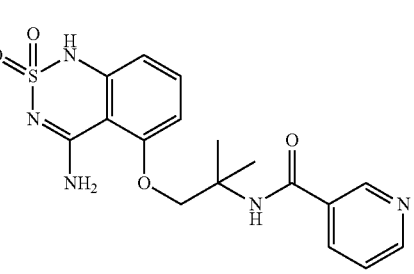<br>N-(1-((4-amino-2,2-dioxido-1H-benzo[c][1,2,6]thiadiazin-5-yl)oxy)-2-methylpropan-2-yl)nicotinamide | 390 |

Biological Tests

The present compounds have been tested and shown sweet taste enhancing activities. Specifically, the present compounds have demonstrated activation of the T1R2/T1R3 receptor and potentiation or enhancement of the activation of the T1R2/T1R3 receptor as well as sweet taste enhancing activities for sweetener, such as sucrose and fructose. Compounds A1 to A9 and B1 to B7 in Experiment 1 below for the human taste tests are selected compounds described above. For example, Compound A1 is Example 1.

EXPERIMENT 1

Sweet Flavor and Sweet Flavor Enhancement Measurement Using Human Panelists Conducting a Paired Comparison Test Test samples containing experimental compounds were presented in pairs to the panelist and they were asked to determine which of the sample is sweeter. The present compounds showed sweet flavor enhancement in medium with a wide range of pH value, and this Experiment provided results for samples tested at pH of about 2.8 or 7.1. A group of 10-16 or more panelists participated in each test. Subjects refrained from eating or drinking (except water) for at least 1 hour prior to the test. Subjects rinsed with water several times to clean the mouth.

Taste tests were performed with sucrose or HFCS as the sweetener in the presence or absence of compound. A 0.2% stock solution of compound in water with sodium bicarbonate was prepared and then this stock solution was diluted in the final sample to achieve the targeted final concentration of compound. For the sample evaluated at pH 2.8 the pH of the solution is decreased to about pH 2.8 using citric acid. Taste samples were also prepared in a low sodium phosphate buffer (pH 7.1; "LSB") lacking sucrose or HFCS to evaluate the taste of the compound alone. Low sodium phosphate buffer consists of 0.3 mM KCl, 0.5 mM $Na_2HPO_4$, and 0.175 mM $KH_2PO_4$. Sample volumes are usually 20 ml.

In one paired comparison test, the panelist was presented with two different samples and asked to identify the sample which is sweeter. The samples within a paired comparison test were presented in a randomized, counterbalanced order. Panelists had up to a 1 minute delay between taste tests to clear the mouth of any tastes.

Binomial probability tables were used to determine the probability of the correct number of responses occurring for each test at alpha=0.05

The results of human taste tests with Compound A1 are found below. Table 1-a indicates that panelists perceived 6% sucrose+10 ppm Compound A1 as being not significantly different in sweetness than a solution of 10% sucrose at pH 7.1. Table 1-b indicates that panelists perceived 6% sucrose+5 ppm Compound A1 as being not significantly different in sweetness than a solution of 11% sucrose at pH 2.8. Table 1-c indicates that panelists perceived 6% High Fructose Corn Syrup+5 ppm Compound A1 as being not significantly different in sweetness than a solution of 9% High Fructose Corn Syrup at pH 2.8. Table 1-d indicates that 25 ppm Compound A1 alone is as sweet as a 1% sucrose solution.

TABLE 1-a

Sample selected as sweeter by panelists,
n = 32 (16 panelists x 2 reps). pH 7.1

| Samples | Total |
|---|---|
| 10% Sucrose | 14 |
| 6% Sucrose + 10 ppm Compound A1 | 18 |
| Total | 32 |
| 10% Sucrose (p-value) | 0.597 |

TABLE 1-b

Sample selected as sweeter by panelists,
n = 33 (141 panelists x 3 reps). pH 2.8

| Samples | Total |
|---|---|
| 11% Sucrose | 21 |
| 6% Sucrose + 5 ppm Compound A1 | 12 |
| Total | 42 |
| 11% Sucrose (p-value) | 0.163 |

TABLE 1-c

Sample selected as sweeter by panelists,
n = 32 (16 panelists x 2 reps). pH 2.8

| Samples | Total |
|---|---|
| 9% High Fructose Corn Syrup | 20 |
| 6% High Fructose Corn Syrup + 20 ppm Compound A1 | 12 |
| Total | 32 |
| 9% High Fructose Corn Syrup (p-value) | 0.215 |

TABLE 1-d

Sample selected as sweeter by panelists,
n = 26 (13 panelists x 2 reps).

| Samples | Total |
|---|---|
| 1% Sucrose | 14 |
| LSB + 25 ppm Compound A1 | 12 |
| Total | 26 |
| 1% Sucrose (p-value) | 0.845 |

The results of human taste tests with Compound A6 are found below. Table 2-a indicates that panelists perceived 6% sucrose+5 ppm Compound A6 as being not significantly different in sweetness than a solution of 11% sucrose at pH 7.1. Table 2-b indicates that panelists perceived 6% sucrose+5 ppm Compound A6 as being not significantly different in sweetness than a solution of 12% sucrose at pH 2.8. Table 2-c indicates that panelists perceived 6% High Fructose Corn Syrup+10 ppm Compound A6 as being not significantly different in sweetness than a solution of 9% High Fructose Corn Syrup at pH 2.8. Table 2-d indicates that 10 ppm Compound A6 alone is as sweet as a 1% sucrose solution.

TABLE 2-a

Sample selected as sweeter by panelists,
n = 48 (16 panelists x 3 reps). pH 7.1

| Samples | Total |
|---|---|
| 11% Sucrose | 24 |
| 6% Sucrose + 5 ppm Compound A6 | 24 |
| Total | 48 |
| 11% Sucrose (p-value) | >0.885 |

TABLE 2-b

Sample selected as sweeter by panelists,
n = 48 (16 panelists x 3 reps). pH 2.8

| Samples | Total |
|---|---|
| 12% Sucrose | 22 |
| 6% Sucrose + 5 ppm Compound A6 | 26 |
| Total | 48 |
| 12% Sucrose (p-value) | 0.665 |

TABLE 2-c

Sample selected as sweeter by panelists,
n = 30 (10 panelists x 3 reps). pH 2.8

| Samples | Total |
|---|---|
| 9% High Fructose Corn Syrup | 18 |
| 6% High Fructose Corn Syrup + 10 ppm Compound A6 | 12 |
| Total | 30 |
| 9% High Fructose Corn Syrup (p-value) | 0.362 |

TABLE 2-d

Sample selected as sweeter by panelists,
n = 30 (10 panelists x 3 reps).

| Samples | Total |
|---|---|
| 1% Sucrose | 18 |
| LSB + 10 ppm Compound A6 | 12 |
| Total | 30 |
| 1% Sucrose (p-value) | 0.362 |

Compounds A2, A3, A4, A5, A7, A8, A9, and B1 to B7 have been evaluated as described above and the data is summarized in Table A, B, C and D:

A. Sweetness Threshold: Paired comparison taste test for sweetness with LSB + compound vs. 1% sucrose.

| Compound | Results |
|---|---|
| A2 | 10 ppm less sweet than 1% sucrose |
| A3 | 10 ppm less sweet than 1% sucrose |
| A4 | 10 ppm less sweet than 1% sucrose |
| A5 | 10 ppm less sweet than 1% sucrose |
| A7 | 10 ppm less sweet than 1% sucrose |
| A8 | 10 ppm less sweet than 1% sucrose |
| A9 | 15 ppm equivalent to 1% sucrose |
| B1 | 25 ppm equivalent to 1% sucrose |
| B2 | 5 ppm less sweet than 1% sucrose |
| B3 | 10 ppm equivalent to 1% sucrose |
| B4 | 8 ppm equivalent to 1% sucrose |
| B5 | 8 ppm equivalent to 1% sucrose |
| B6 | 8 ppm equivalent to 1% sucrose |
| B7 | 10 ppm equivalent to 1% sucrose |

B. Enhancement of Sucrose at pH 7.1: Paired comparison taste test with 6% sucrose + compound at pH 7.1 vs. 10%, 11% or 12% Sucrose at pH 7.1

| Compound | Results |
|---|---|
| A2 | 5 ppm in 6% sucrose is equivalent to 10% sucrose |
| A3 | 5 ppm in 6% sucrose is equivalent to 10% sucrose |
| A4 | 5 ppm in 6% sucrose is equivalent to 10% sucrose |
| A5 | 5 ppm in 6% sucrose is equivalent to 10% sucrose |
| A7 | 5 ppm in 6% sucrose is equivalent to 10% sucrose |
| A8 | 5 ppm in 6% sucrose is equivalent to 10% sucrose |
| A9 | 15 ppm in 6% sucrose is equivalent to 12% sucrose |
| | 10 ppm in 6% sucrose is equivalent to 10% sucrose |
| B1 | 5 ppm in 6% sucrose is equivalent to 10% sucrose |
| B2 | 5 ppm in 6% sucrose is equivalent to 10% sucrose |
| B3 | 5 ppm in 6% sucrose is equivalent to 10% sucrose |
| B4 | 5 ppm in 6% sucrose is equivalent to 11% sucrose |
| B5 | 5 ppm in 6% sucrose is equivalent to 10% sucrose |
| B6 | 5 ppm in 6% sucrose is equivalent to 10% sucrose |
| B7 | 5 ppm in 6% sucrose is equivalent to 10% sucrose |

C. Enhancement of Sucrose at pH 2.8: Paired comparison taste test with 6% sucrose + compound at pH 2.8 vs. 10%, 11% or 12% Sucrose at pH 2.8

| Compound | Results |
|---|---|
| A2 | 5 ppm in 6% sucrose is equivalent to 12% sucrose |
| A5 | 5 ppm in 6% sucrose is equivalent to 12% sucrose |
| A7 | 5 ppm in 6% sucrose is equivalent to 12% sucrose |
| A9 | 7 ppm in 6% sucrose is equivalent to 12% sucrose |
| | 5 ppm + 6% in 6% sucrose is equivalent to 10% sucrose |
| B2 | 5 ppm in 6% sucrose is equivalent to 12% sucrose |
| B3 | 5 ppm in 6% sucrose is equivalent to 12% sucrose |
| B6 | 5 ppm in 6% sucrose is equivalent to 12% sucrose |

D. Enhancement of HFCS at pH 2.8: Paired comparison taste test with 6% HFCS + compound at pH 2.8 vs. 8% or 9% HFCS at pH 2.8

| Compound | Results |
|---|---|
| A2 | 10 ppm in 6% HFCS is equivalent to 8% HFCS |
| A3 | 10 ppm in 6% HFCS is equivalent to 8% HFCS |
| A5 | 10 ppm in 6% HFCS is equivalent to 8% HFCS |
| A7 | 10 ppm in 6% HFCS is equivalent to 8% HFCS |
| A8 | 10 ppm in 6% HFCS is equivalent to 8% HFCS |
| A9 | 15 ppm in 6% HFCS is equivalent to 8% HFCS |
| B3 | 10 ppm in 6% HFCS is equivalent to 8% HFCS |
| B4 | 8 ppm in 6% HFCS is equivalent to 8% HFCS |
| B5 | 8 ppm in 6% HFCS is equivalent to 8% HFCS |
| B6 | 8 ppm in 6% HFCS is equivalent to 8% HFCS |
| B7 | 10 ppm in 6% HFCS is equivalent to 8% HFCS |

All publications and patent applications herein are incorporated by reference to the same extent as if each individual publication or patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A compound represented by structural Formula (Ia):

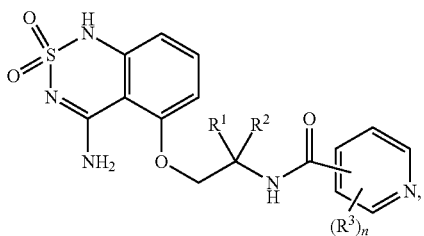

or a salt or solvate thereof; wherein, $R^1$ and $R^2$ are independently C1 to C2 alkyl; or alternatively, $R^1$ and $R^2$, together with the carbon atom to which they are attached, form a C3 to C6 cycloalkyl;

n is 0, 1, or 2; and $R^3$ is halo, cyano, hydroxyl, amine, substituted amine, alkoxy, substituted alkoxy, aryloxy, substituted aryloxy, acyl, sulfonamide, ester, alkyl, substituted alkyl, aryl, substituted aryl, arylalkyl, substituted arylalkyl, heteroaryl, substituted heteroaryl, heteroarylalkyl, substituted heteroarylalkyl, carbocyclyl, substituted carbocyclyl, heterocyclyl, or substituted heterocyclyl, wherein the substituents of a moiety indicated as substituted are selected from the group consisting of —$R^a$, halo, =O, —$OR^b$, —$SR^b$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2OR^b$, —OS$(O)_2R^b$, —$OS(O)_2OR^b$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O (oxygen), N (nitrogen) and S (sulfur).

2. The compound of claim 1, wherein $R^1$ and $R^2$ are both methyl, or ethyl.

3. The compound of claim 1, wherein R' and $R^2$, together with the carbon atom to which they are attached, form cyclopropyl, cyclobutyl, or cyclohexyl.

4. The compound of claim 1, which is represented by structural Formula (Ib):

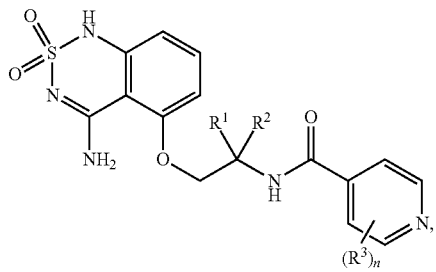

or a salt or solvate thereof; wherein, $R^1$ and $R^2$ are both methyl, or ethyl; or alternatively, $R^1$ and $R^2$, together with the carbon atom to which they are attached, form cyclopropyl, cyclobutyl, or cyclohexyl;

n is 0, 1, or 2; and $R^3$ is halo, cyano, hydroxyl, amine, substituted amine, alkoxy, substituted alkoxy, aryloxy, substituted aryloxy, acyl, sulfonamide, ester, alkyl, substituted alkyl, aryl, substituted aryl, arylalkyl, substituted arylalkyl, heteroaryl, substituted heteroaryl, heteroarylalkyl, substituted heteroarylalkyl, carbocyclyl, substituted carbocyclyl, heterocyclyl, or substituted heterocyclyl.

5. A compound selected from the group consisting of

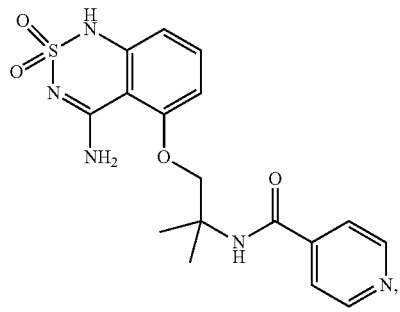

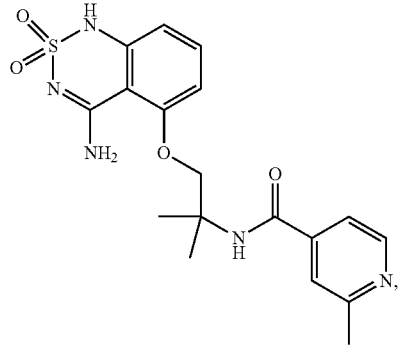

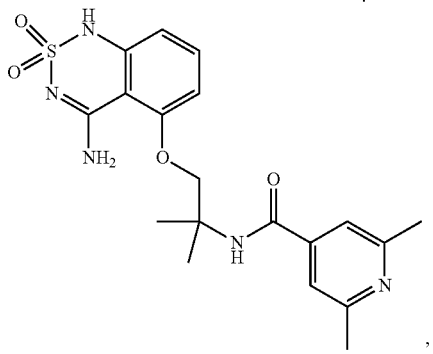

127
-continued
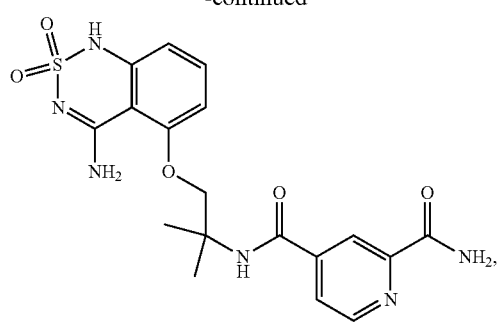
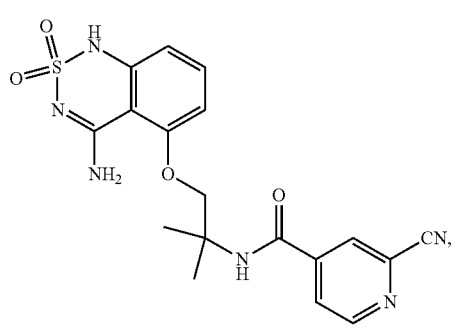
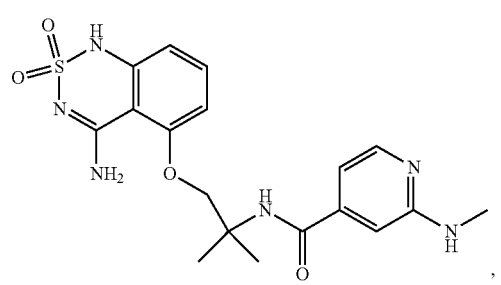
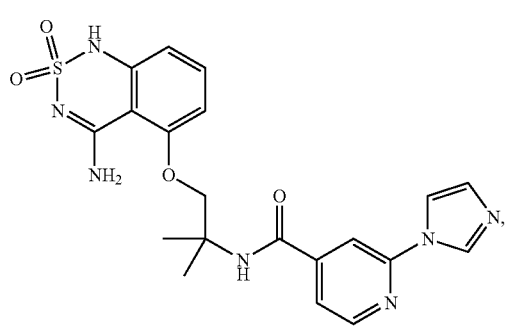
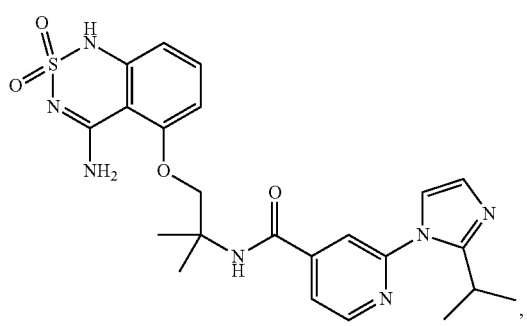
128
-continued
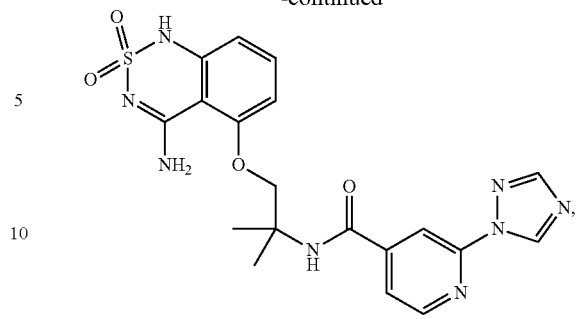
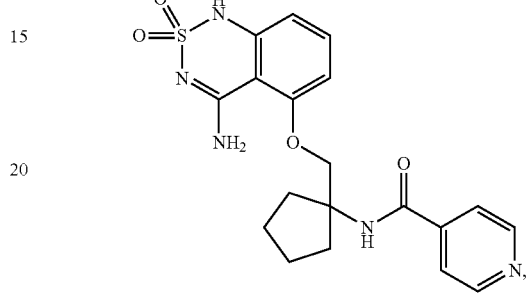
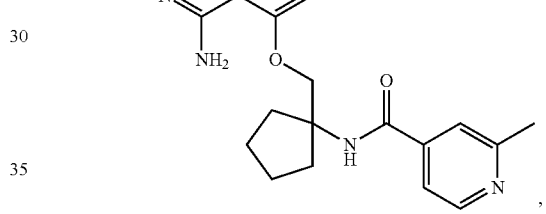
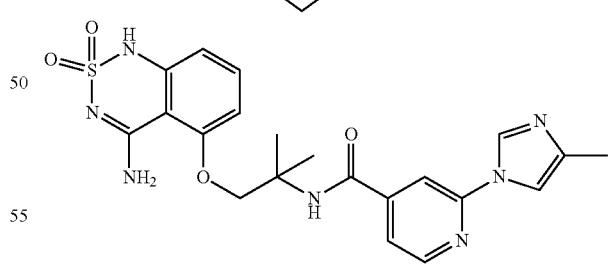
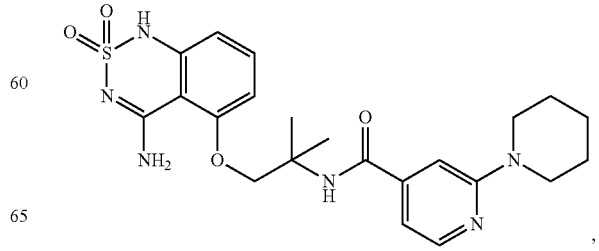

129
-continued
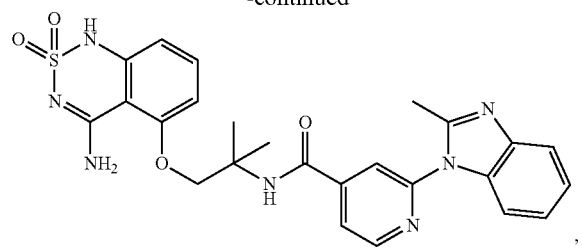
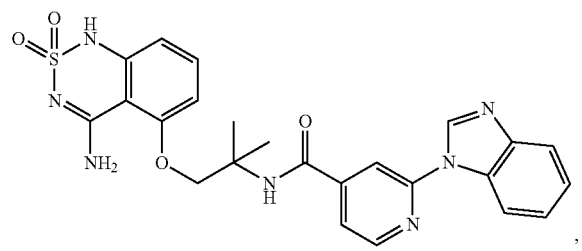
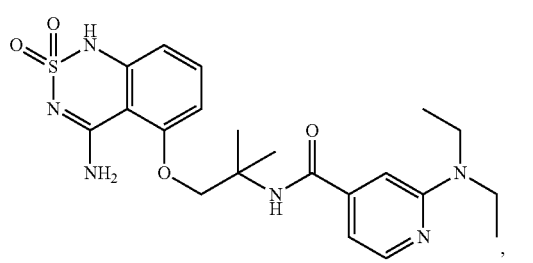
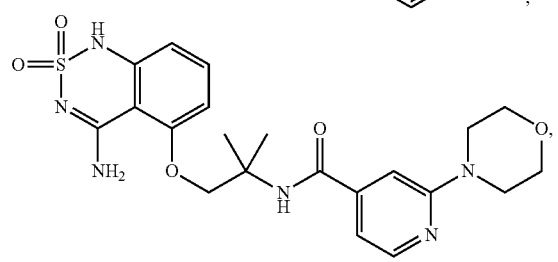
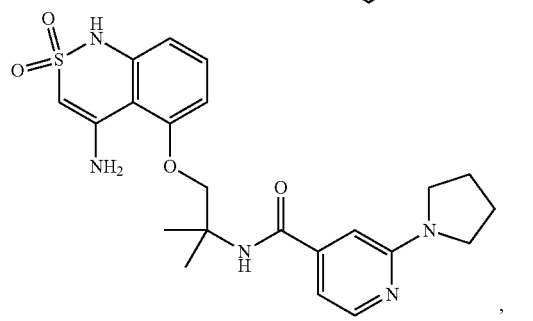
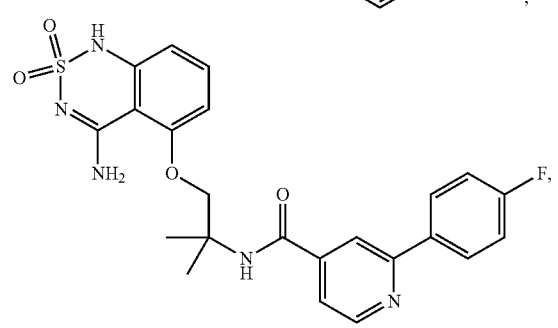
130
-continued
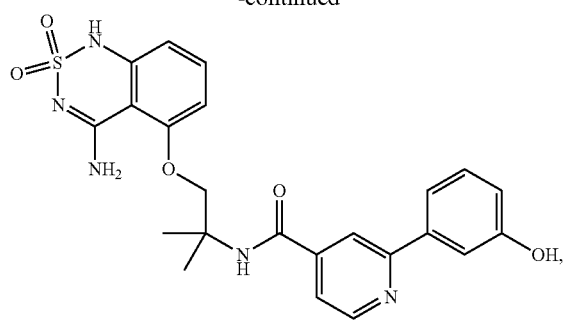
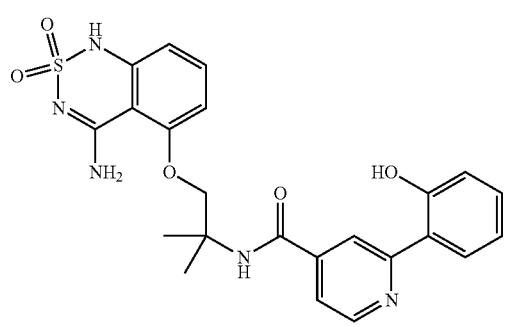
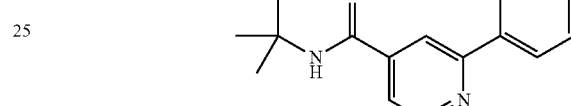
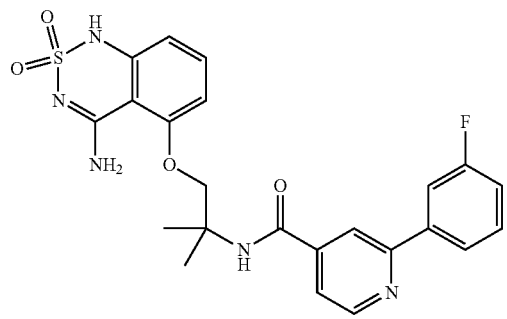
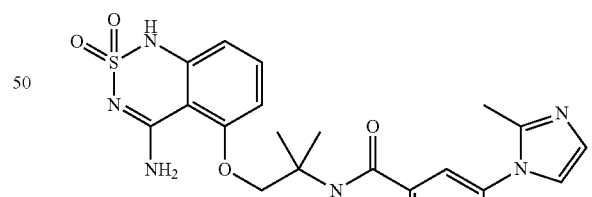
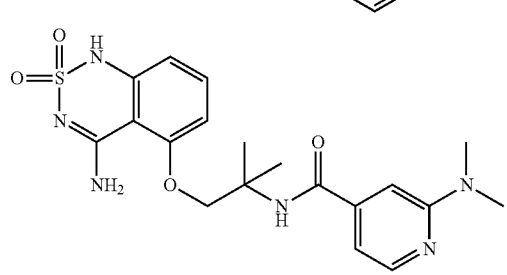

131
-continued
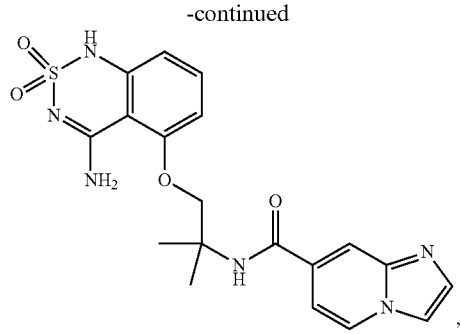
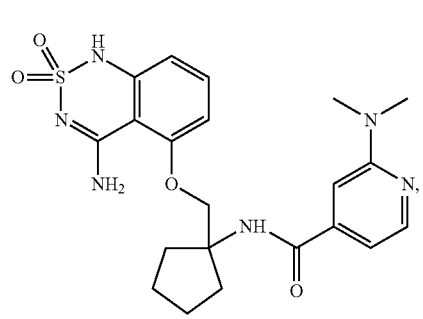
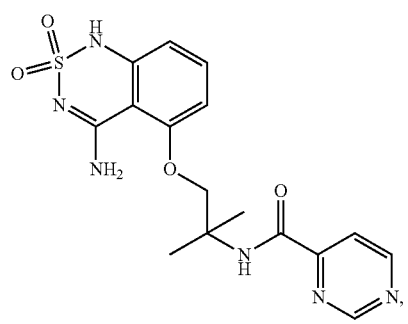
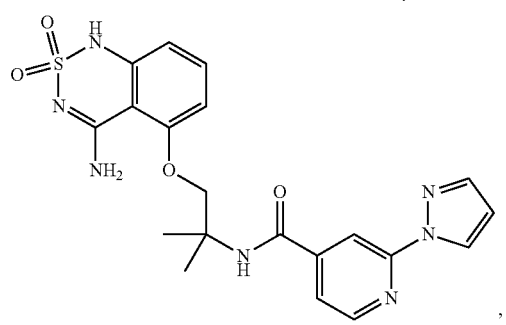
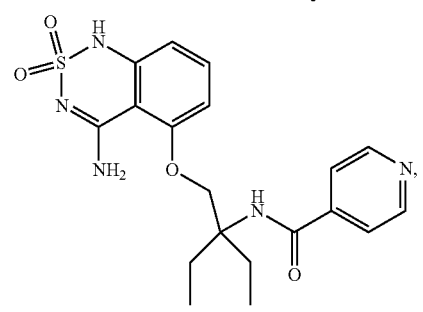
132
-continued
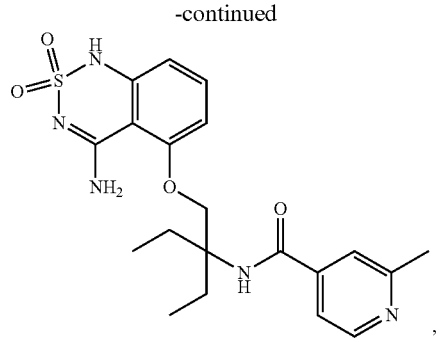
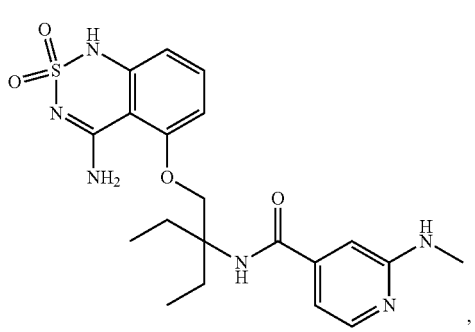
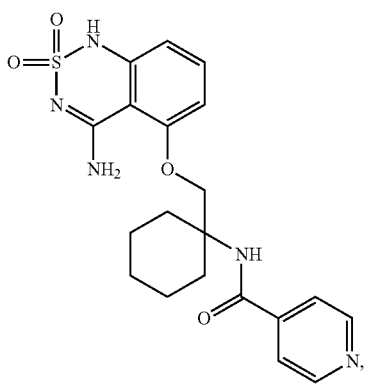
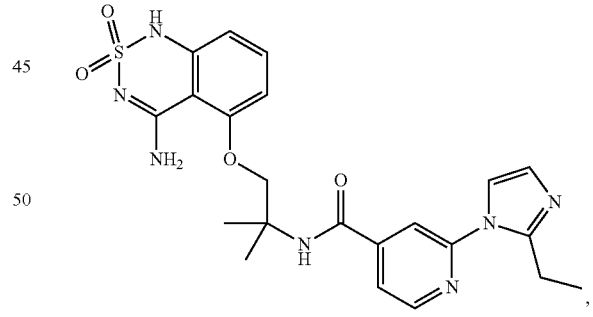
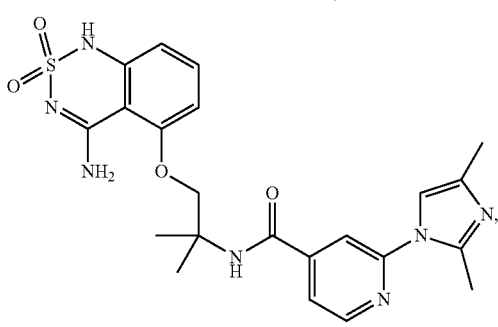

133
-continued
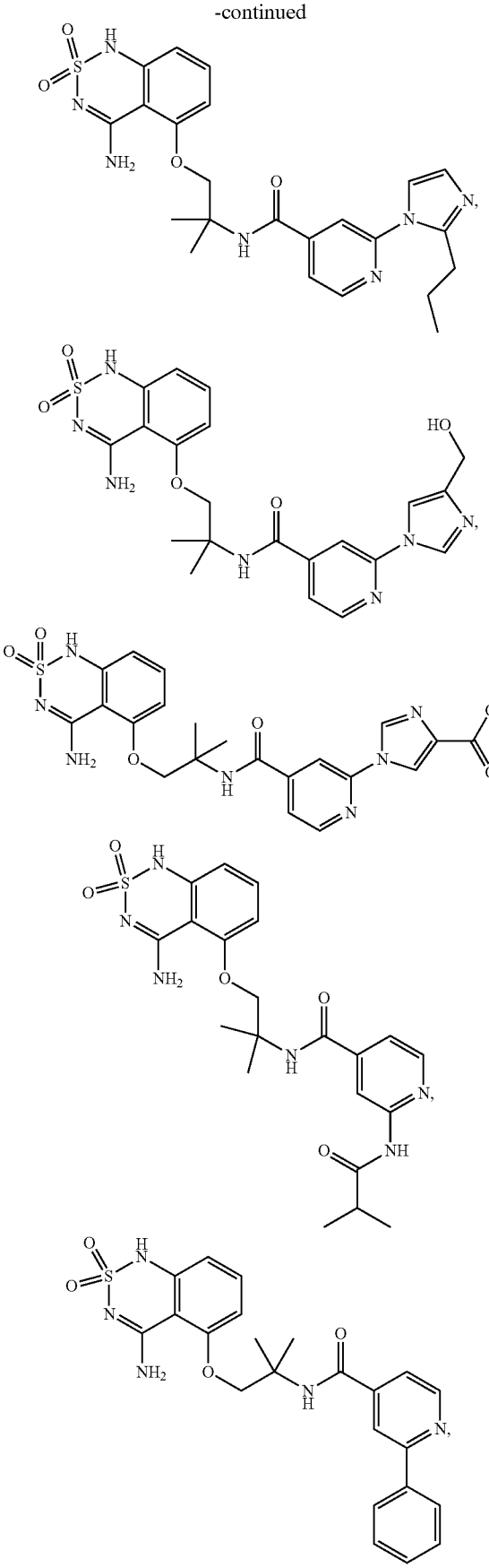
134
-continued
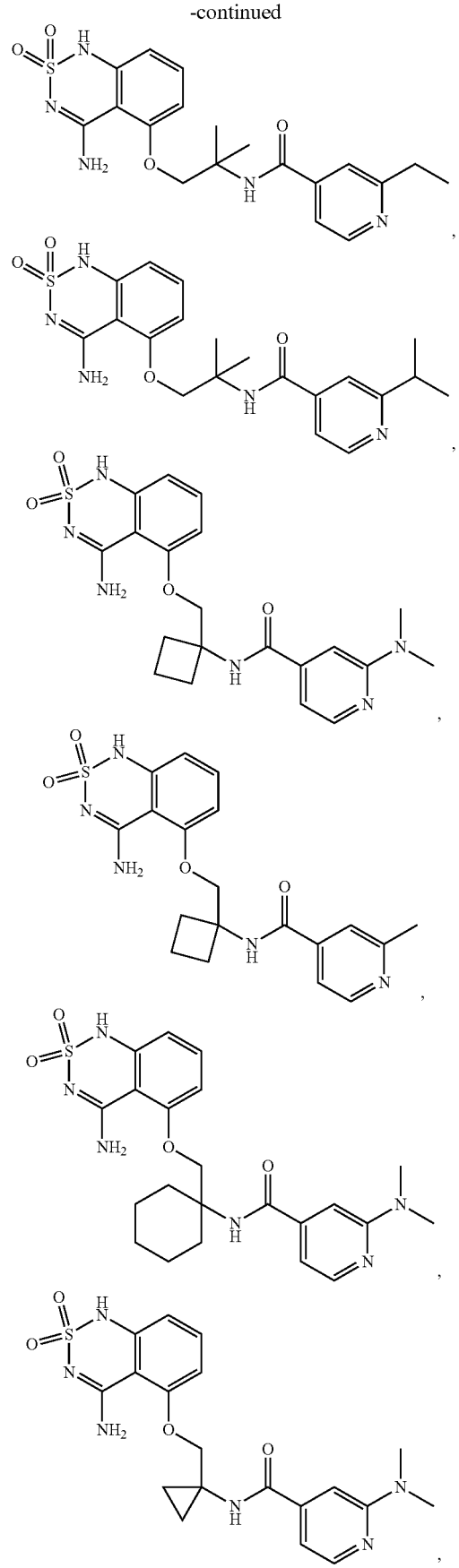

135
-continued
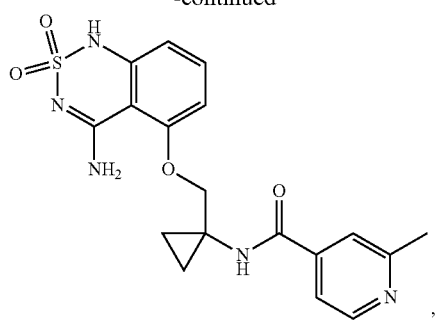
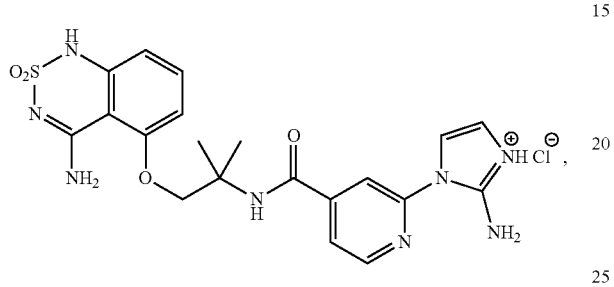
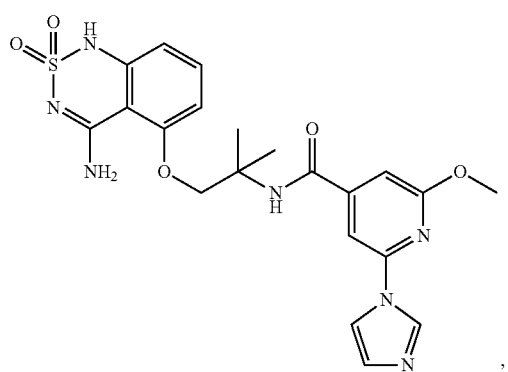
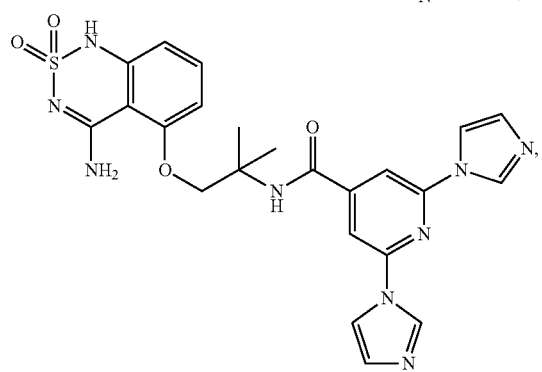
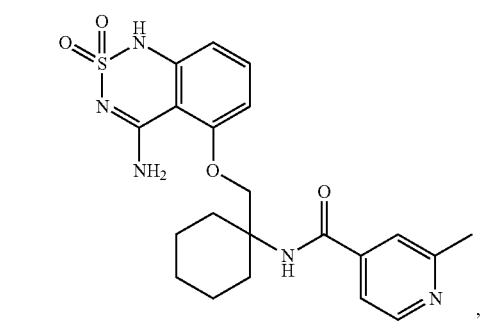
136
-continued
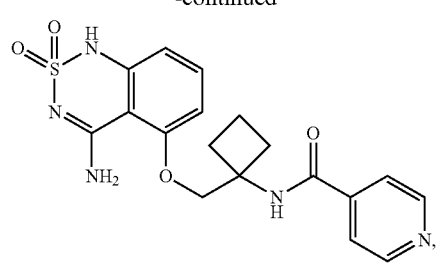
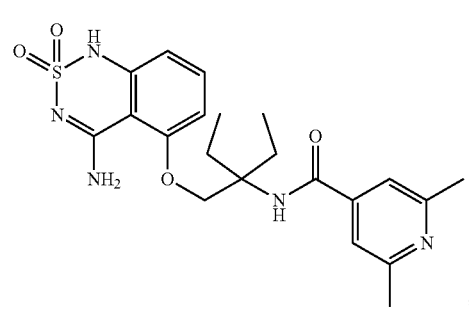
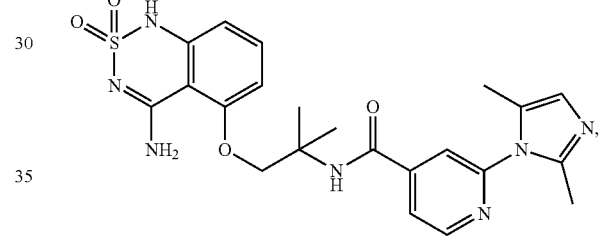
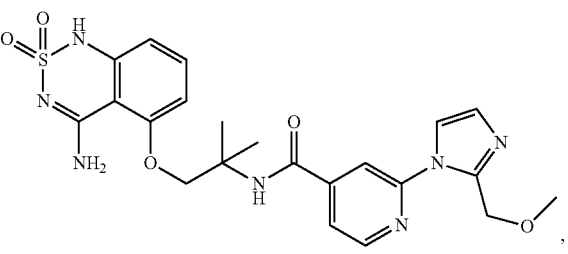
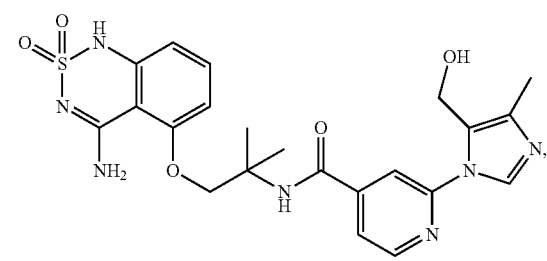
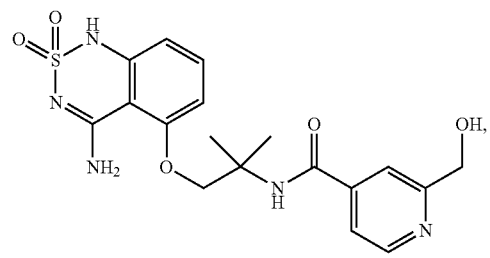

137
-continued
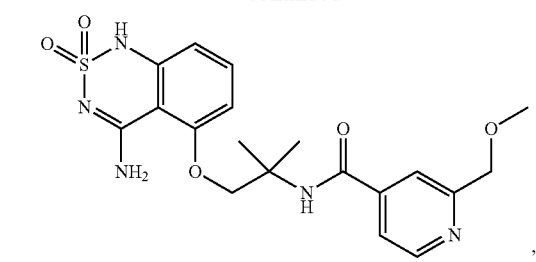
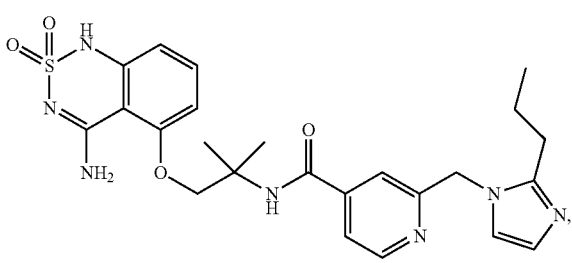
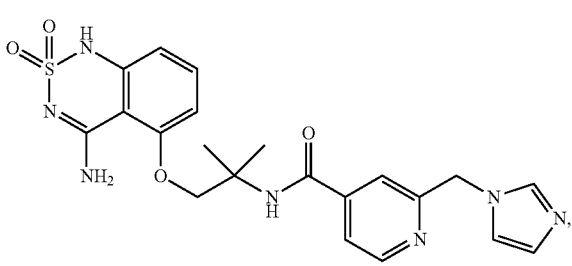
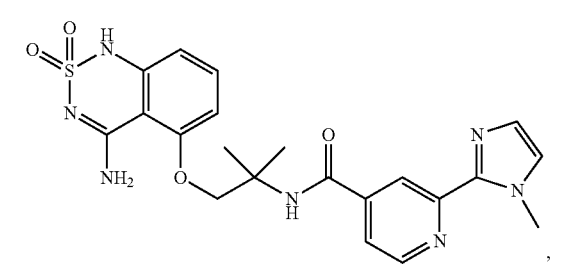
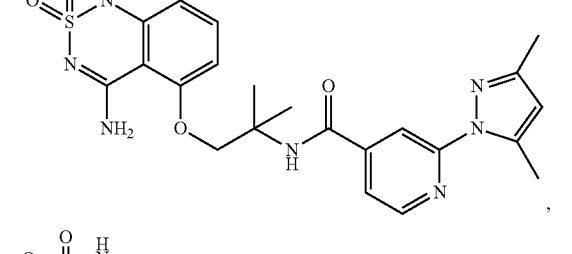
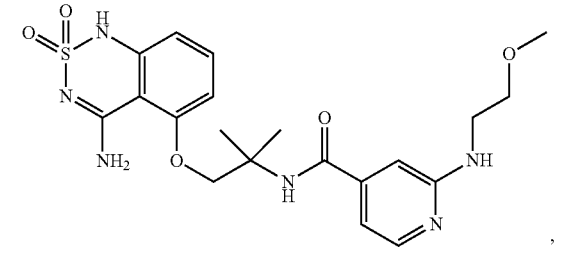
138
-continued
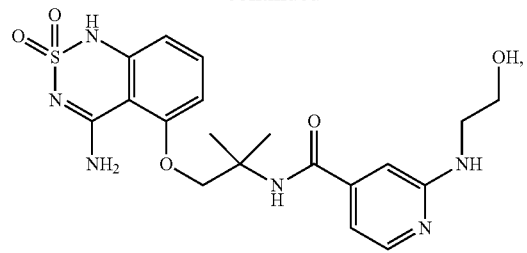
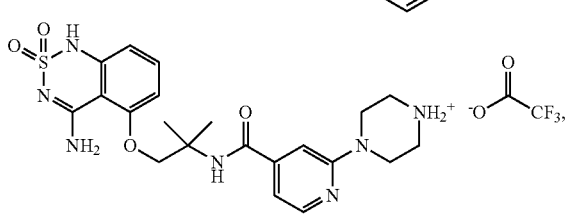
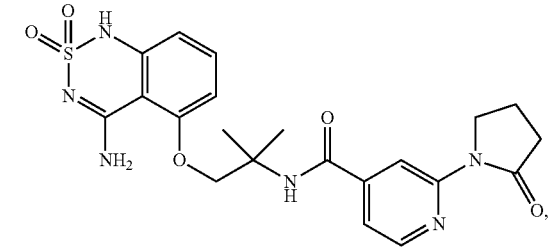
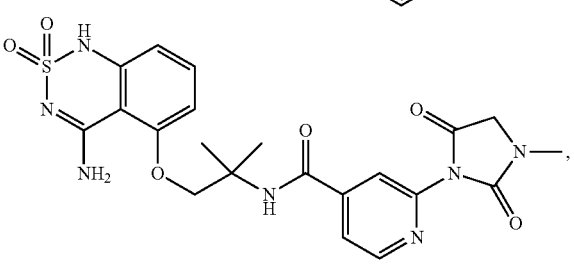
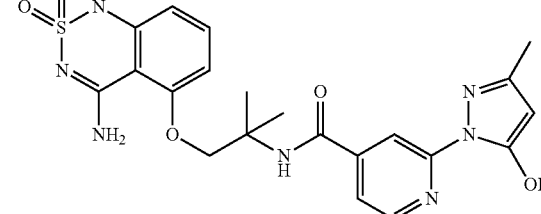
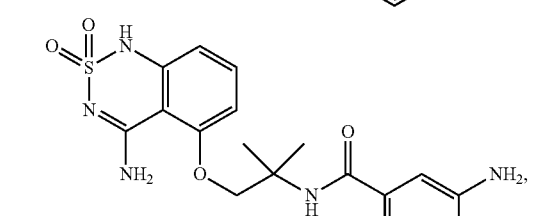
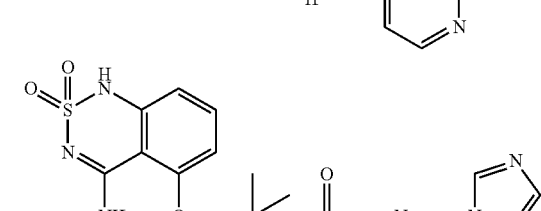
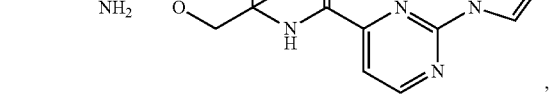

139
-continued
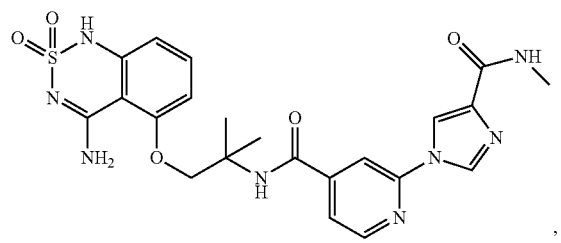
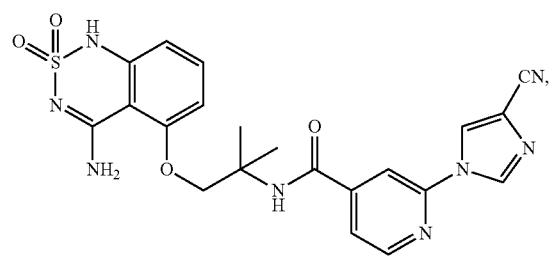
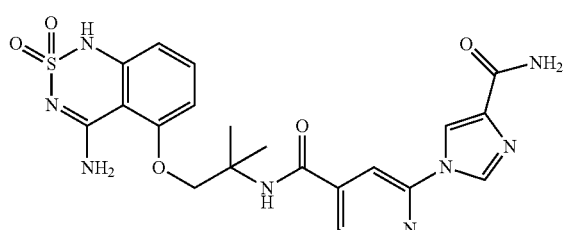
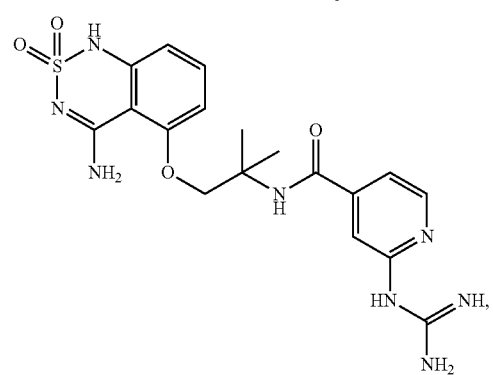
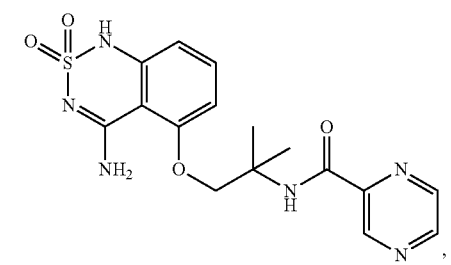
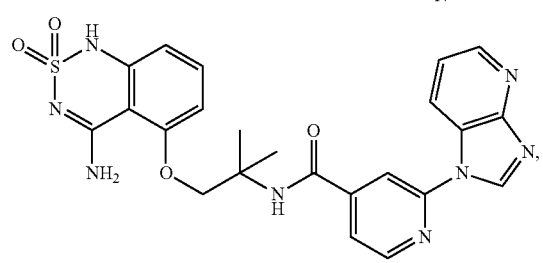
140
-continued 141
-continued
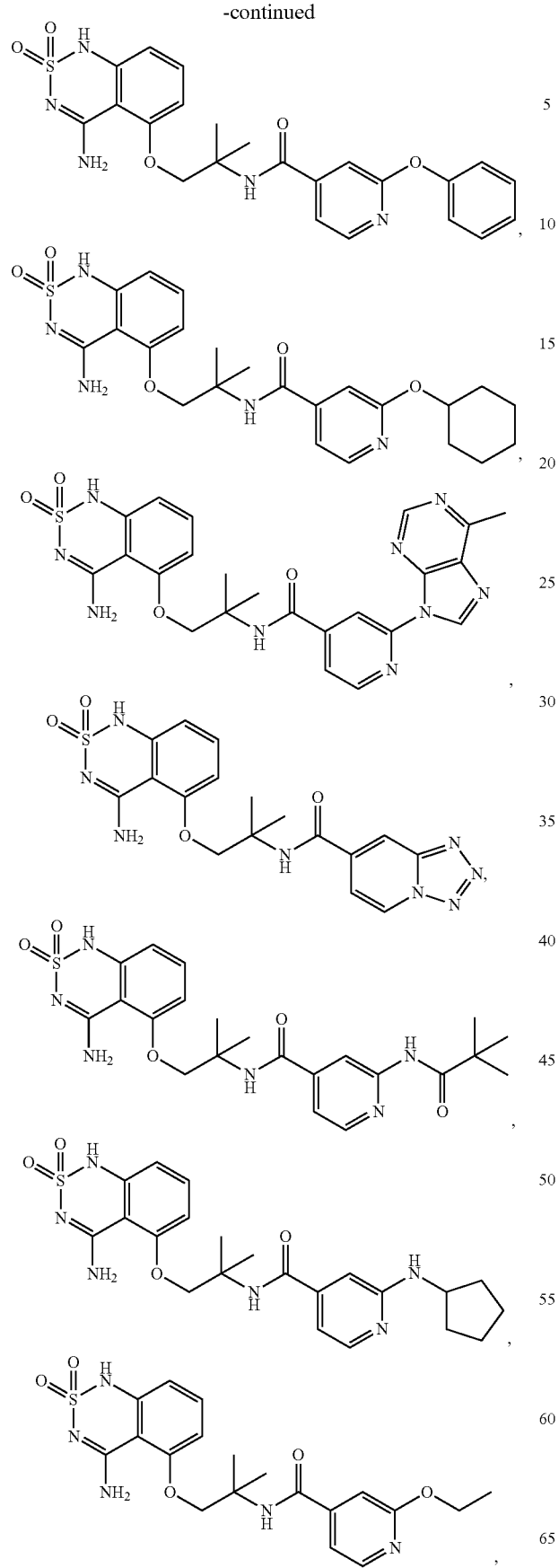
142
-continued
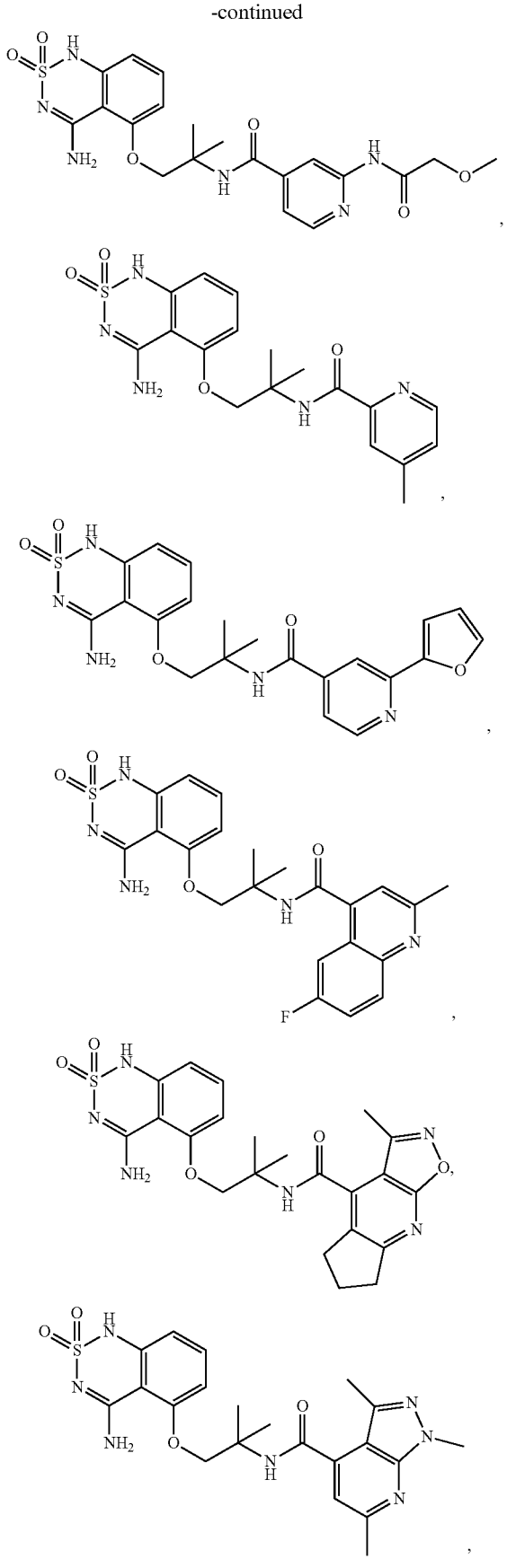

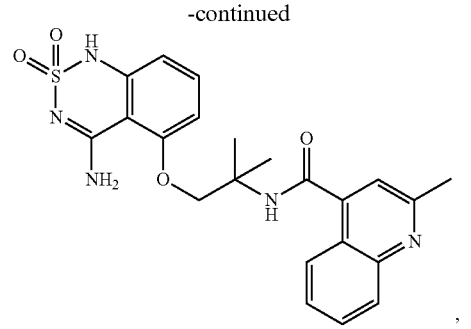
,
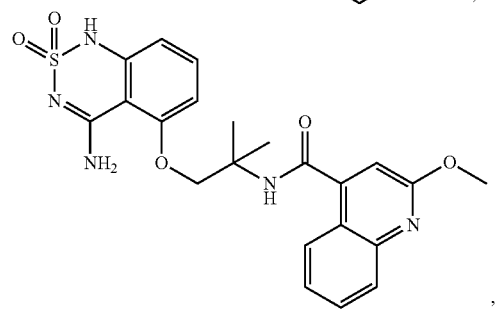
,
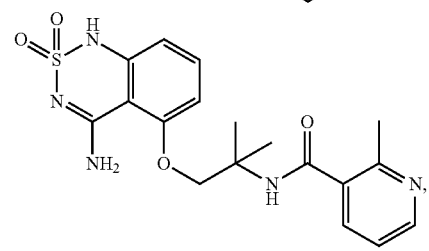
,
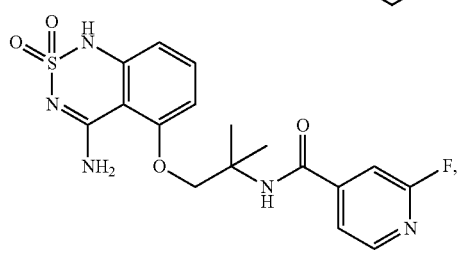
,
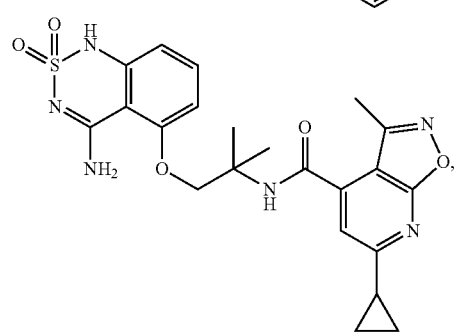
,
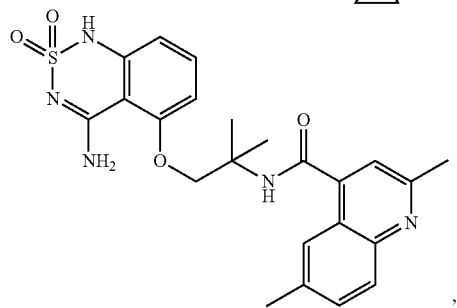
,
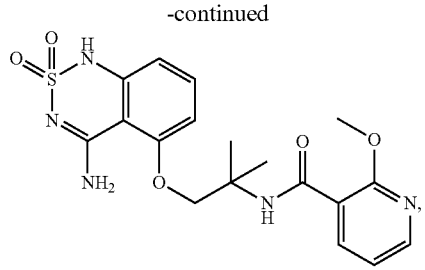
,
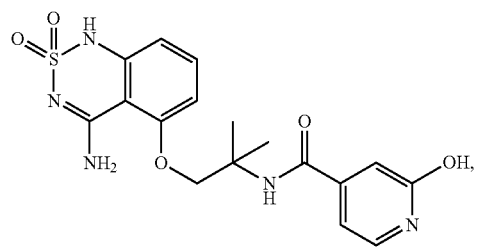
,
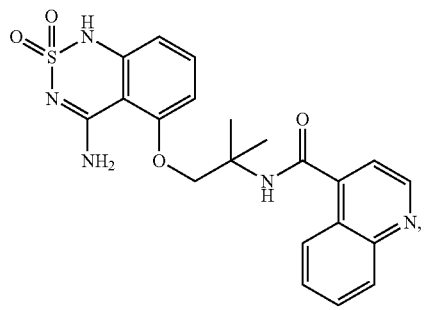
,
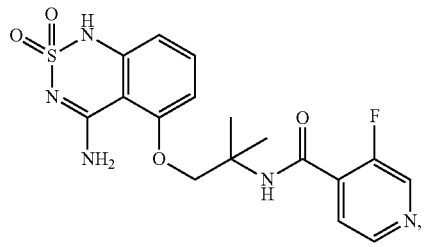
,
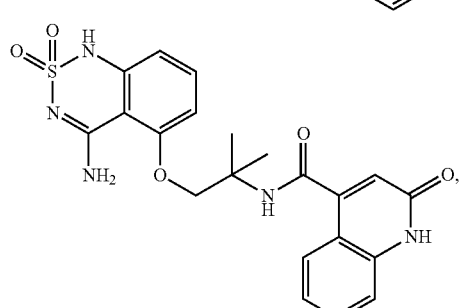
,
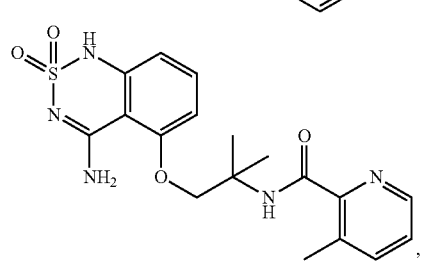
, 145
-continued
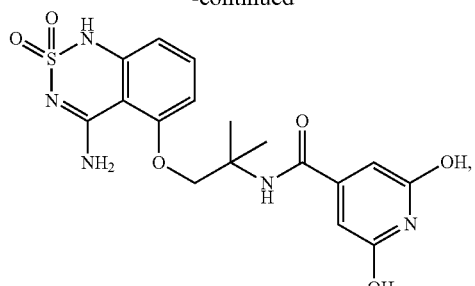
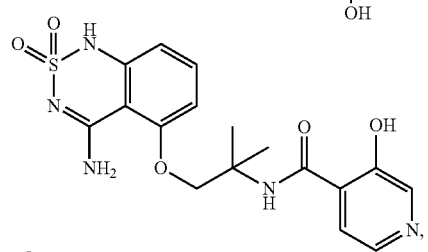
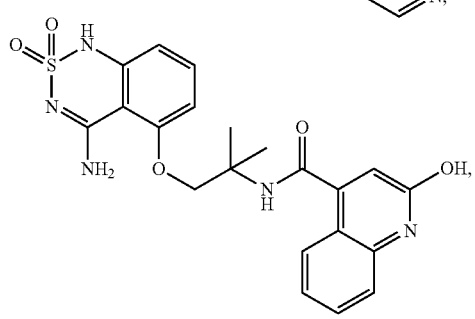
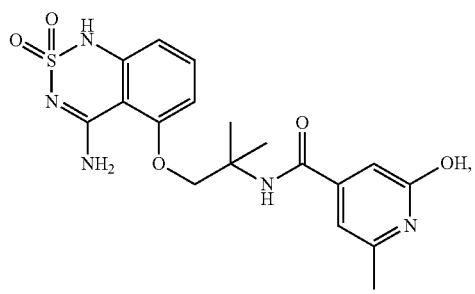
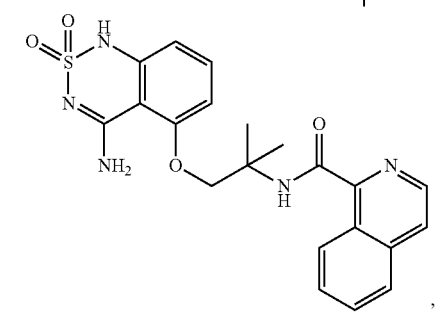
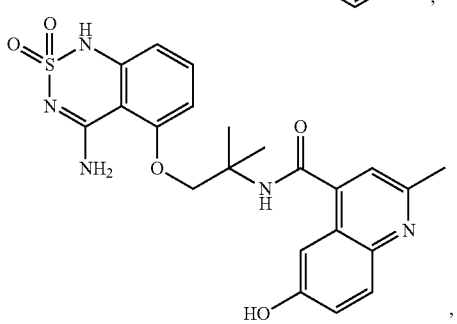
146
-continued
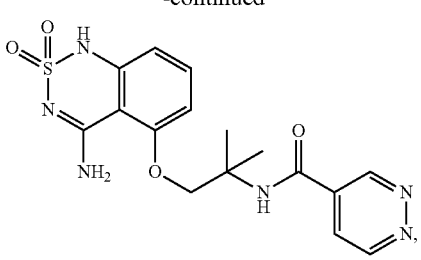
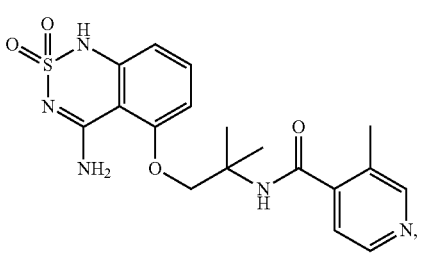
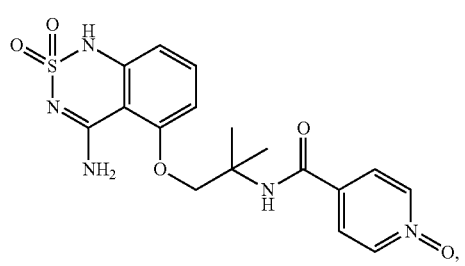
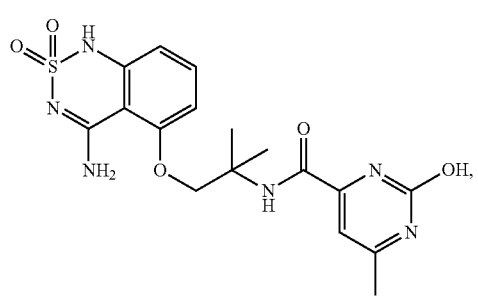
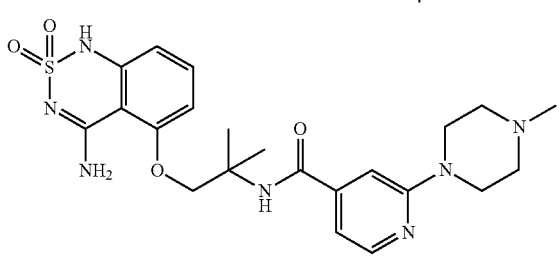
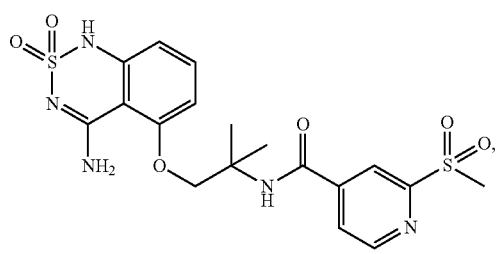

-continued

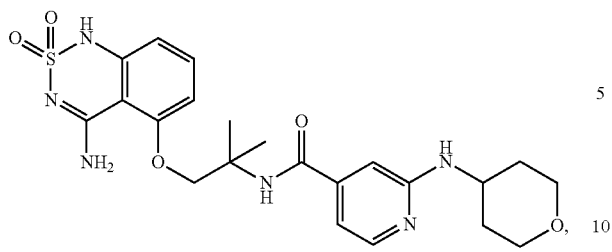

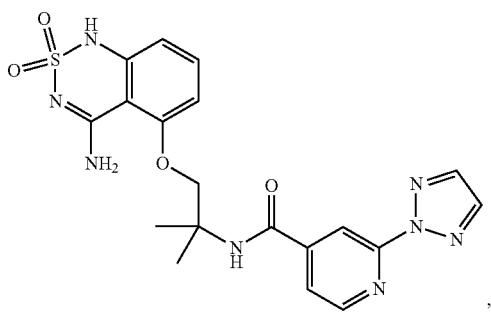

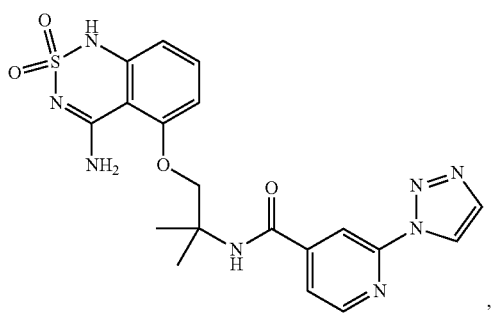

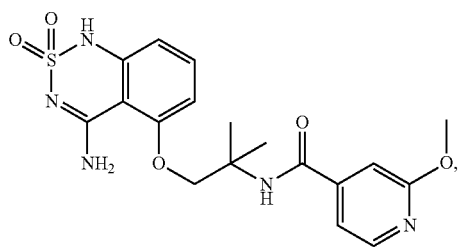

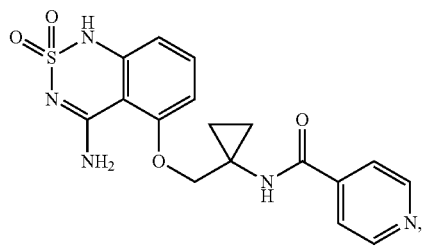

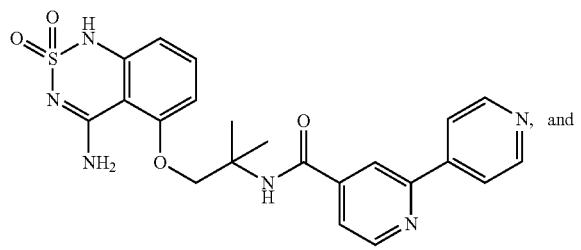

-continued

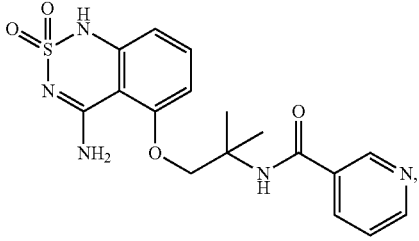 [SMILES: CC(C)(COc1cccc2c1C(N)=NS(=O)(=O)N2)NC(=O)c1cccnc1]

or a salt or solvate thereof.

6. The compound of claim 1, wherein when a group is indicated as substituted the substituent is one or more selected from the group consisting of —R$^a$, halo, =O, —OR$^b$, —NR$^c$R$^c$, —CN, —S(O)$_2$R$^b$, and —C(O)NR$^c$R$^c$, where R$^a$ is selected from the group consisting of alkyl, cycloalkyl, cycloheteroalkyl, aryl, arylalkyl, heteroaryl and heteroarylalkyl; each R$^b$ is independently hydrogen or R$^a$; and each R$^c$ is independently R$^b$ or alternatively, the two R$^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O (oxygen), N (nitrogen) and S (sulfur).

7. The compound of claim 5, which is selected from the group consisting of

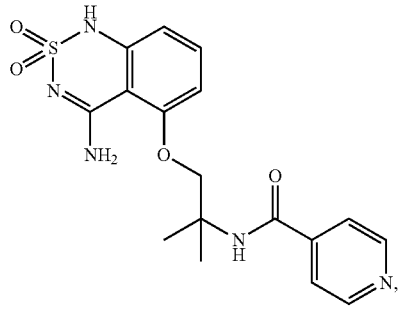

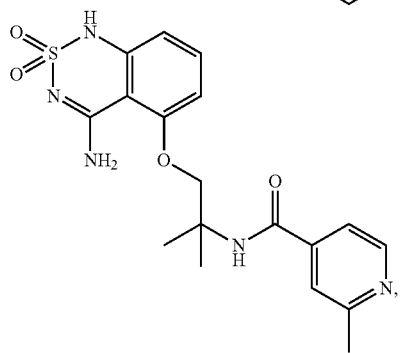

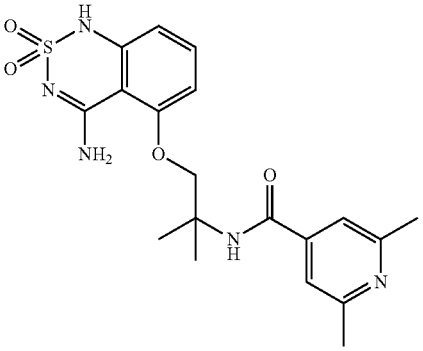

-continued
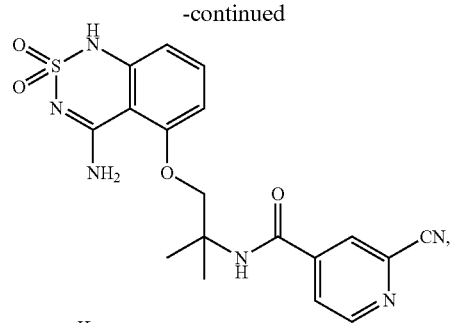
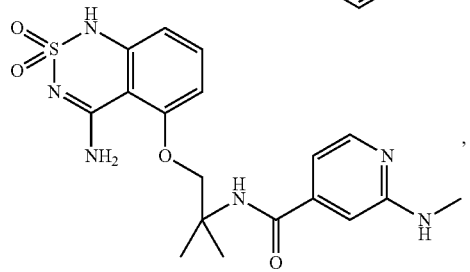
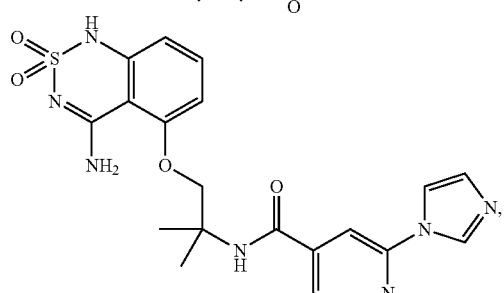
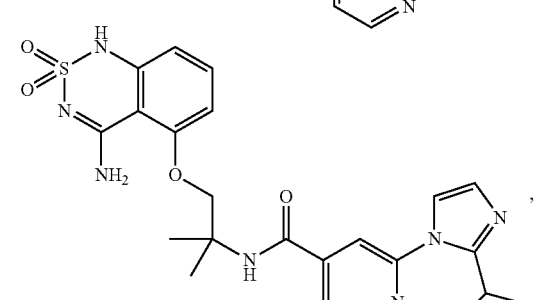
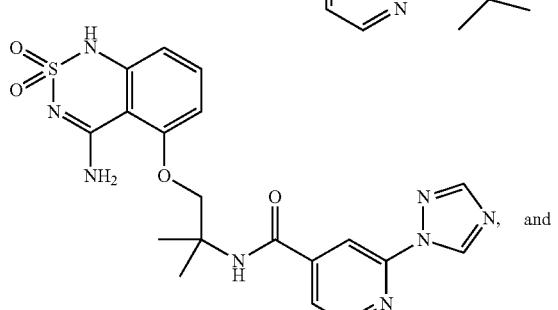
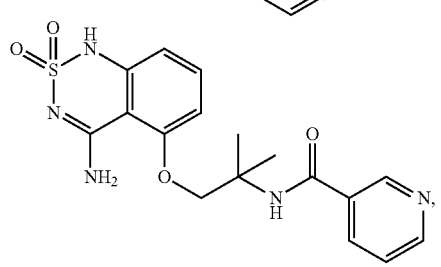
or a salt or solvate thereof.
8. The compound of claim 5, which is selected from the group consisting of
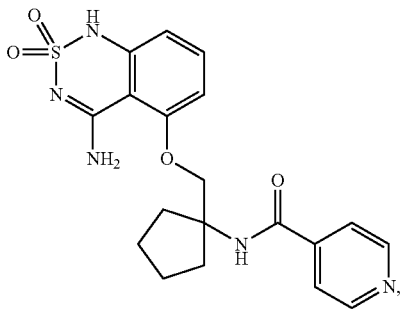
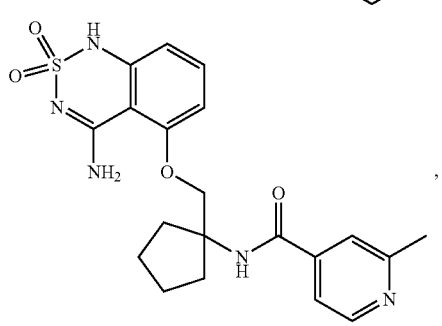
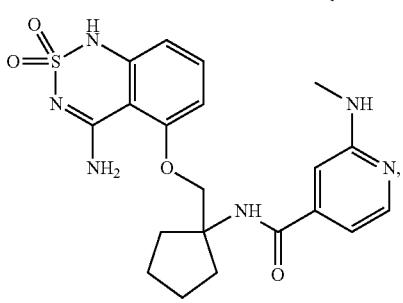
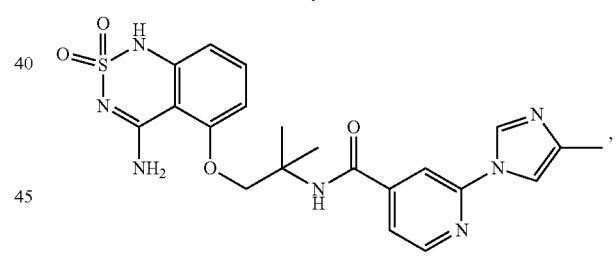
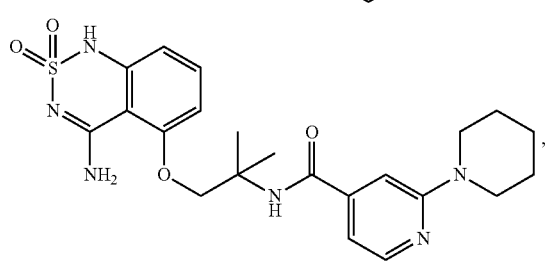
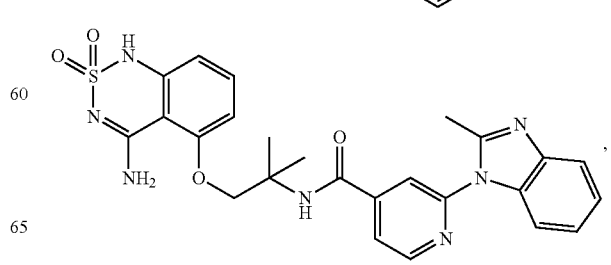

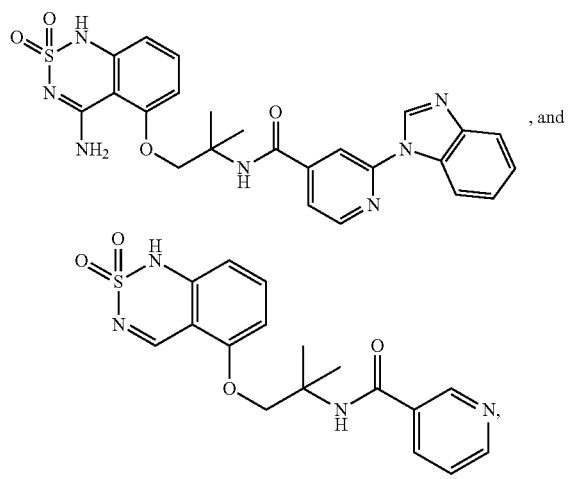
or a salt or solvate thereof.
9. The compound of claim 5, which is selected from the group consisting of
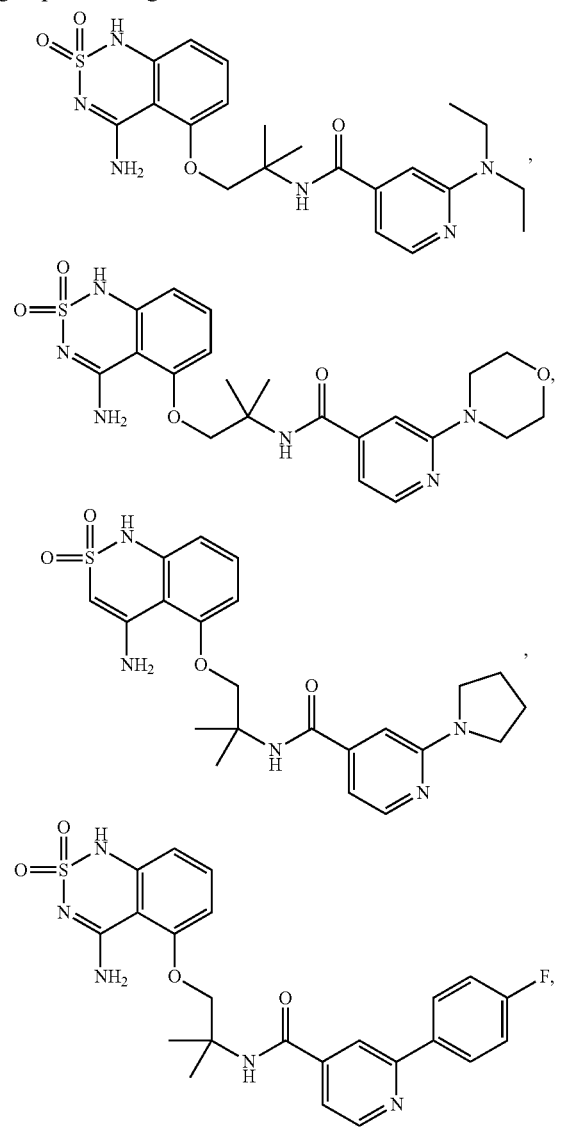
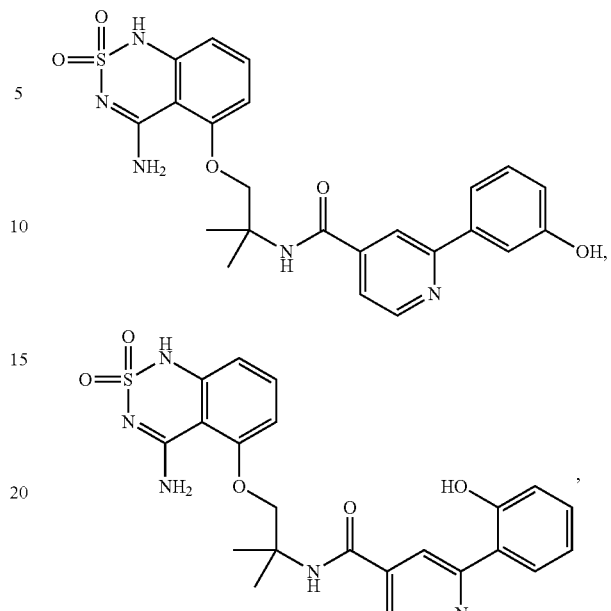
or a salt or solvate thereof.
10. The compound of claim 5, which is selected from the group consisting of

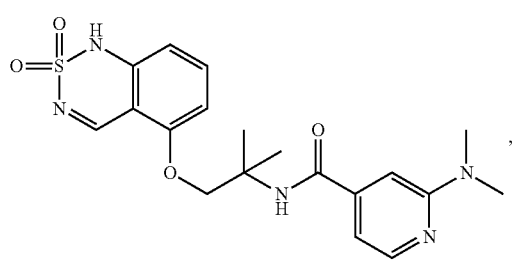
,
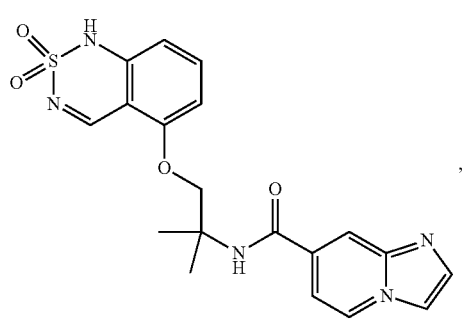
,
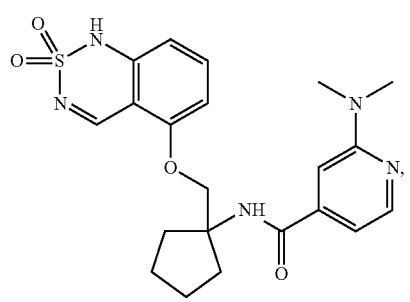
,
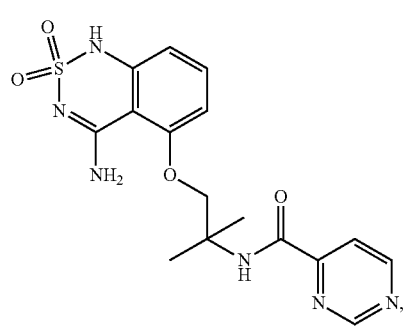
,
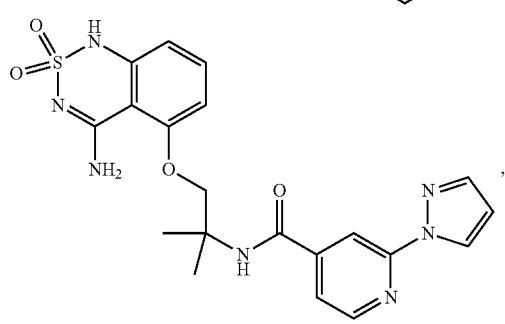
,
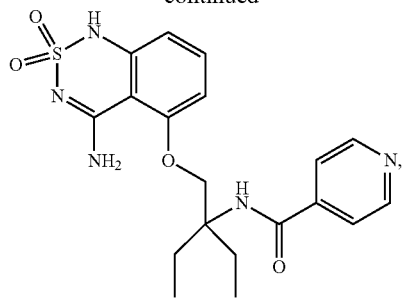
,
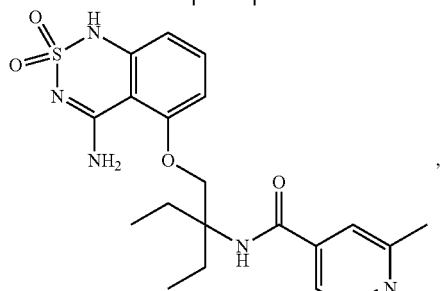
,
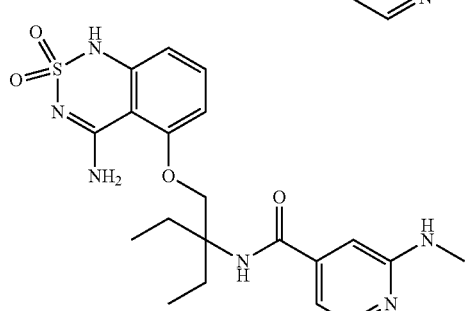
, and
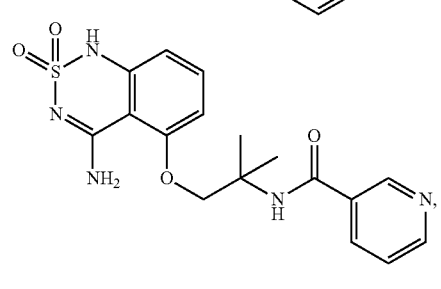
or a salt or solvate thereof.
11. The compound of claim 5, which is selected from the group consisting of
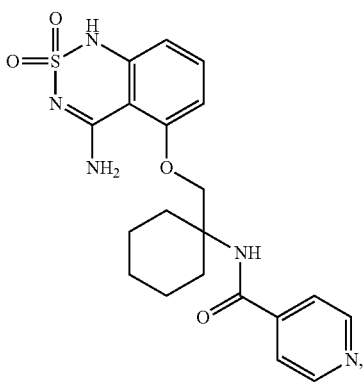
,

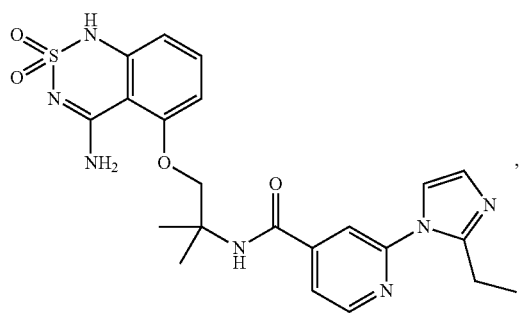
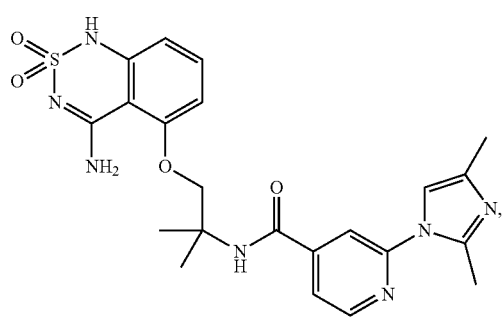
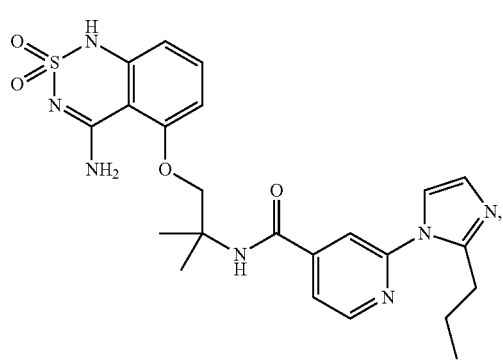
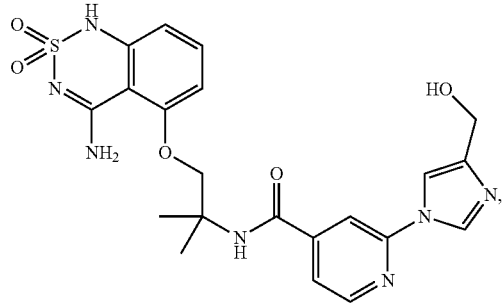
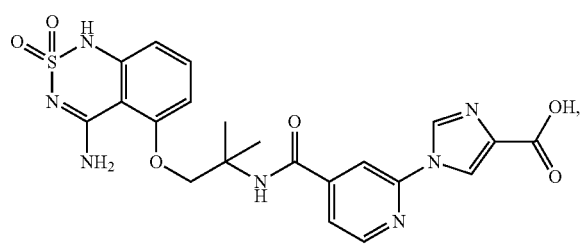
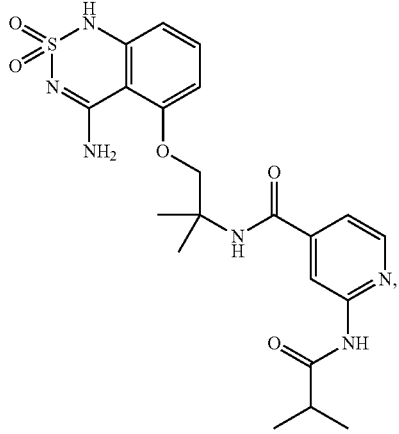
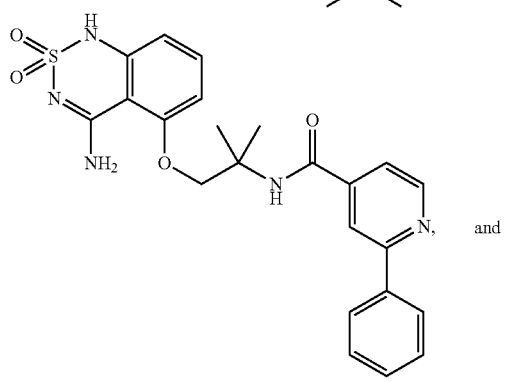
and
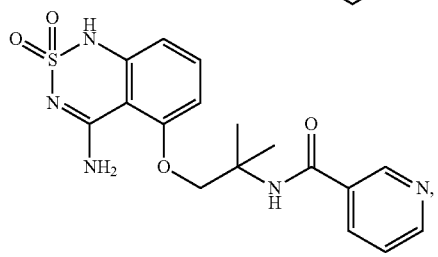
or a salt or solvate thereof.
12. The compound of claim 5, which is selected from the group consisting of
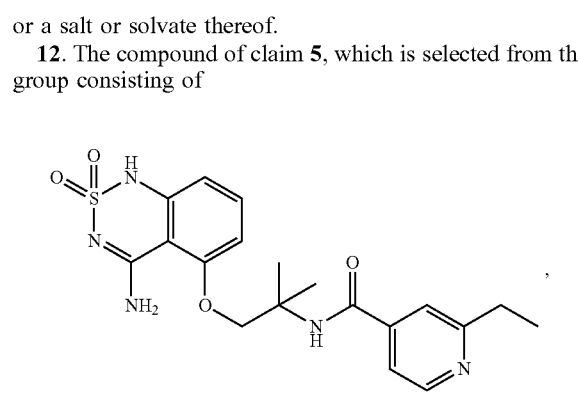
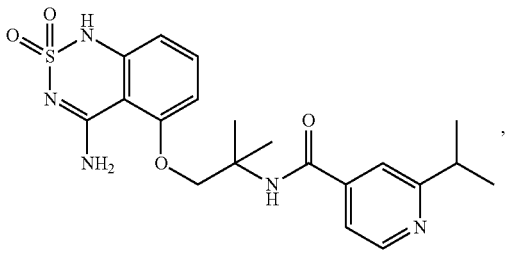

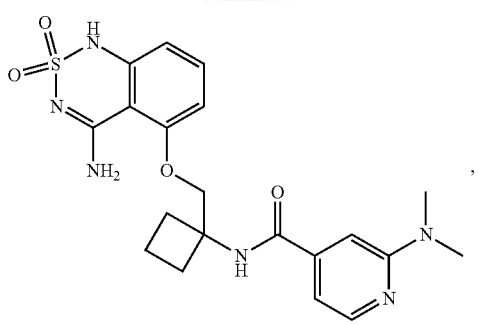
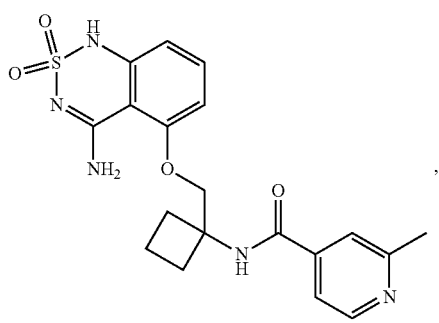
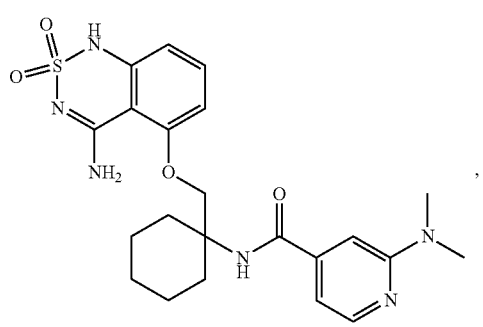
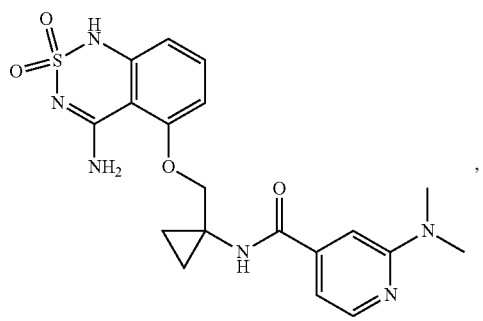
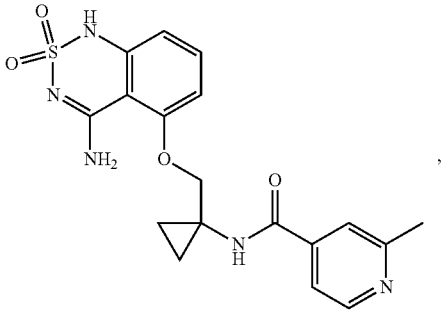
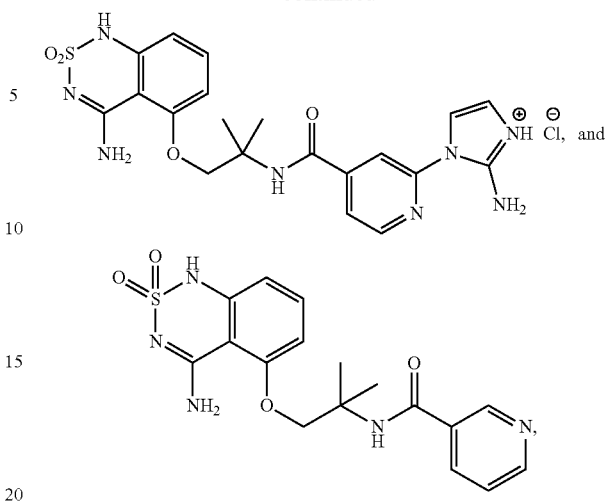
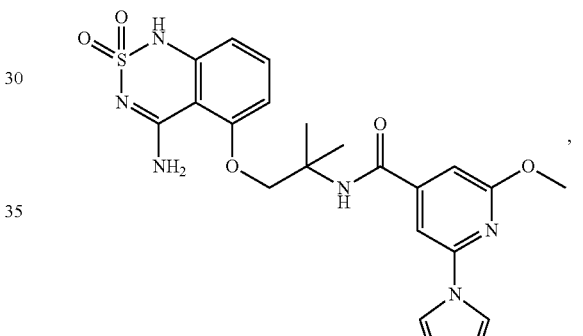
or a salt or solvate thereof.
13. The compound of claim 5, which is selected from the group consisting of
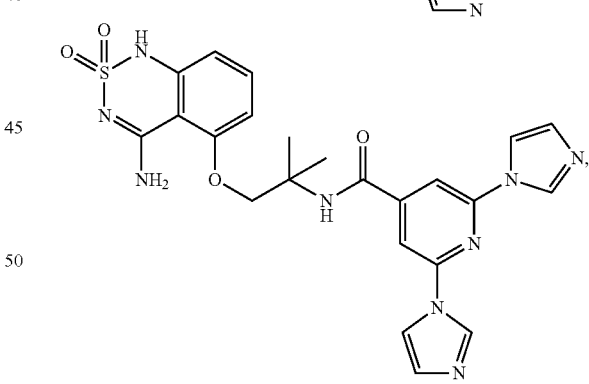
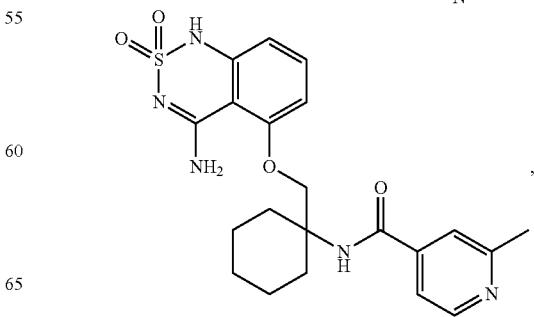

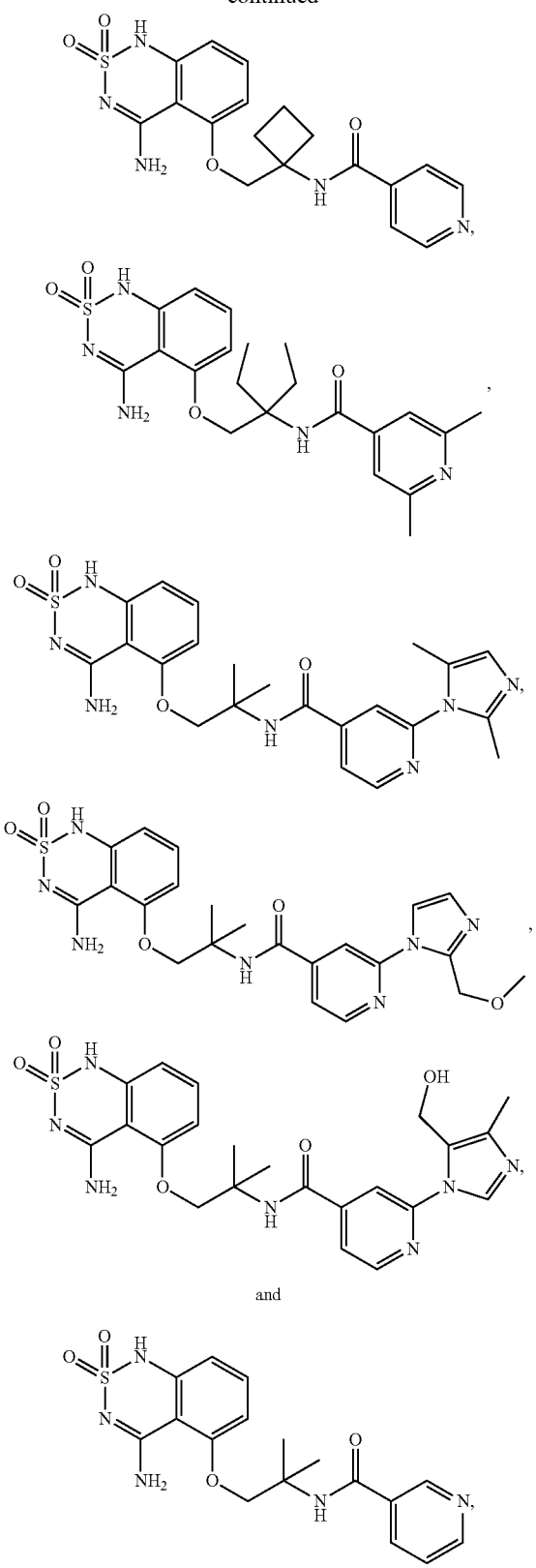
or a salt or solvate thereof.
14. The compound of claim 5, which is selected from the group consisting of

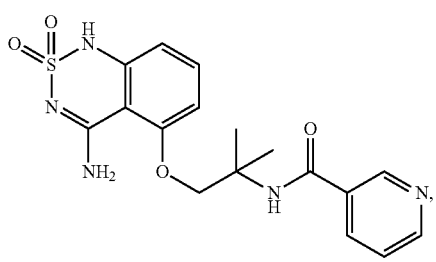
or a salt or solvate thereof.
15. The compound of claim 5, which is selected from the group consisting of
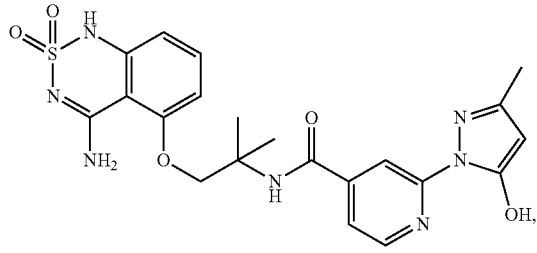
and
or a salt or solvate thereof.
16. The compound of claim 5, which is selected from the group consisting of -continued
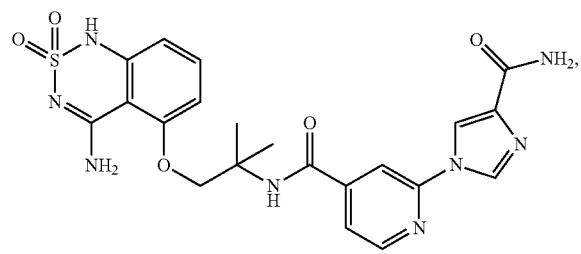
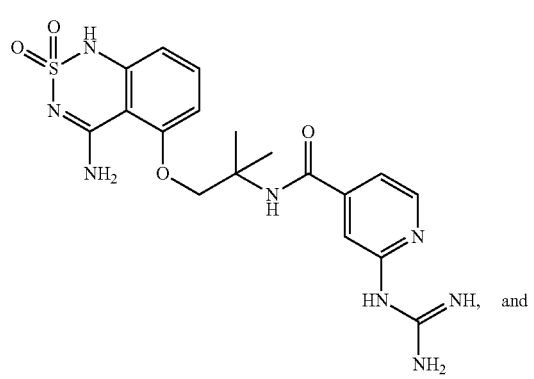
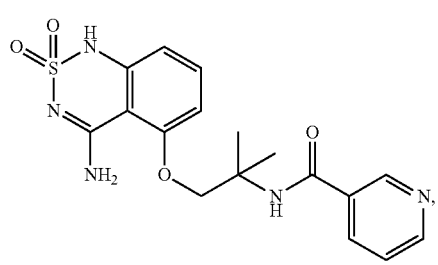 [SMILES: CC(C)(COc1cccc2c1C(N)=NS(=O)(=O)N2)NC(=O)c1cccnc1]
or a salt or solvate thereof.
17. The compound of claim 5, which is selected from the group consisting of
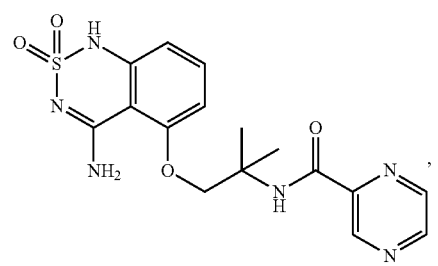
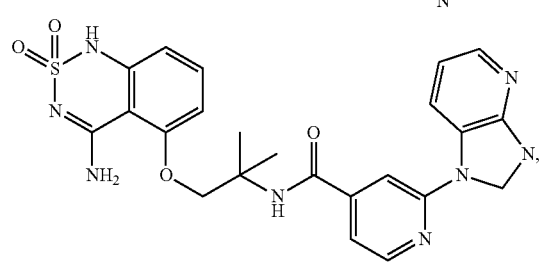
-continued
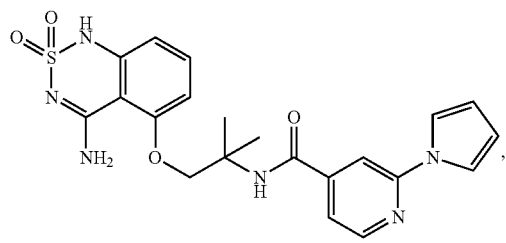
or a salt or solvate thereof.
18. The compound of claim 5, which is selected from the group consisting of

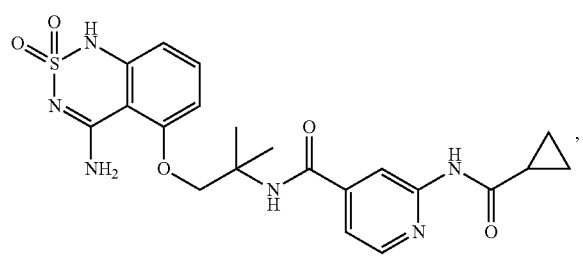
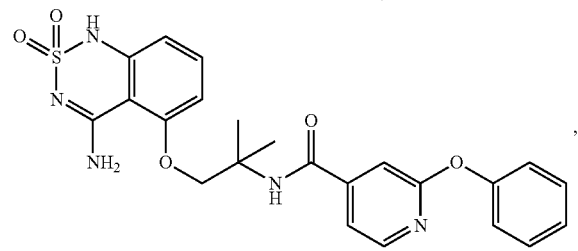
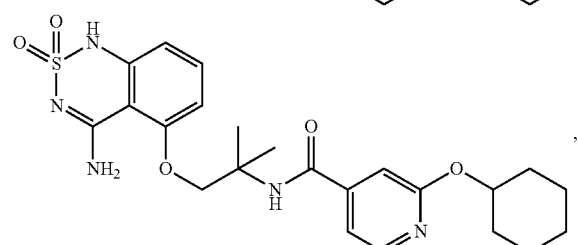
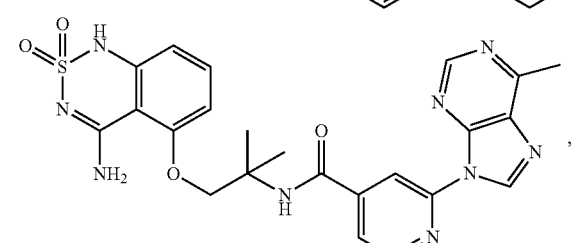
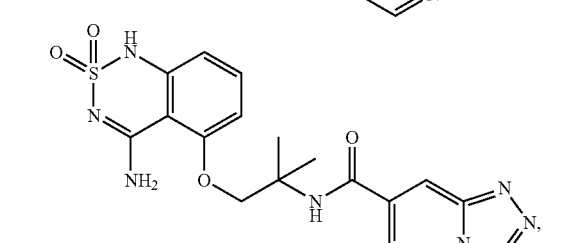
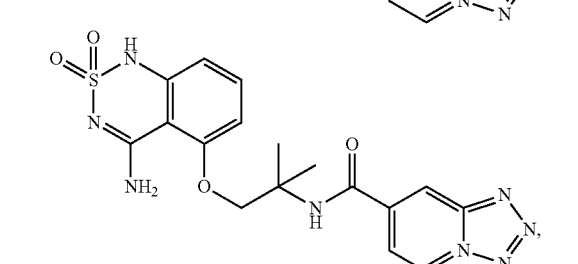
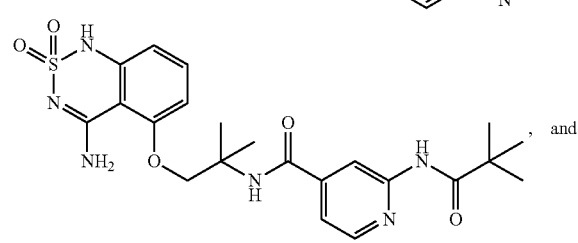
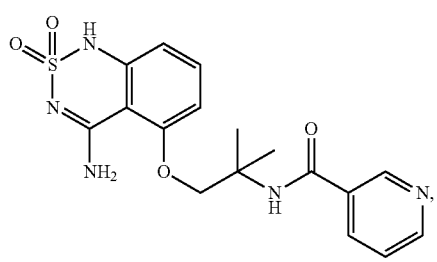 [SMILES: CC(C)(COc1cccc2c1C(N)=NS(=O)(=O)N2)NC(=O)c1cccnc1]
or a salt or solvate thereof.
19. The compound of claim 5, which is selected from the group consisting of
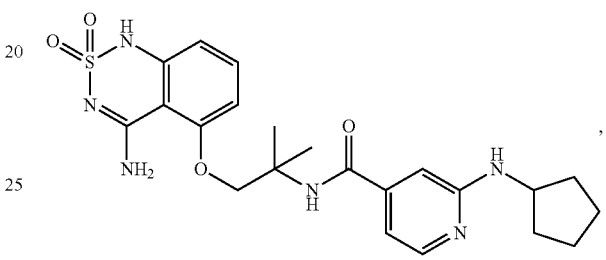
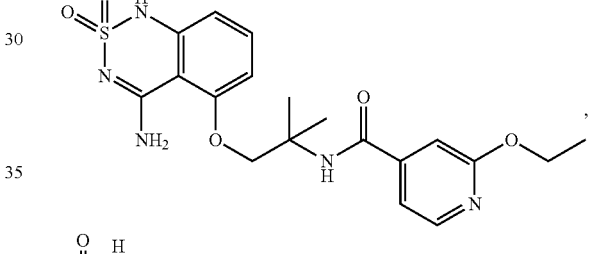
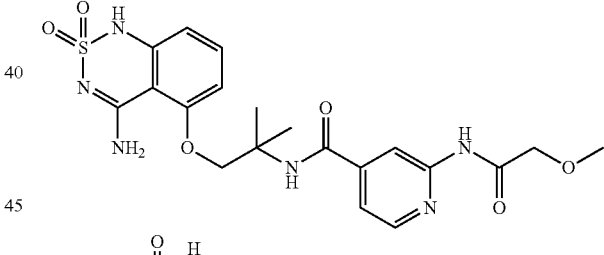
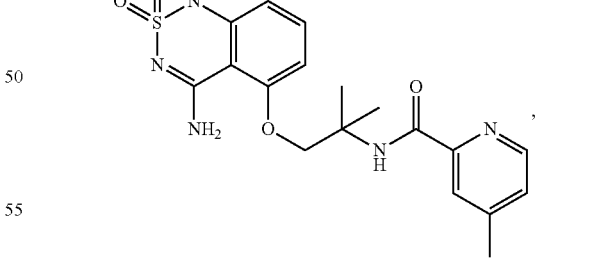
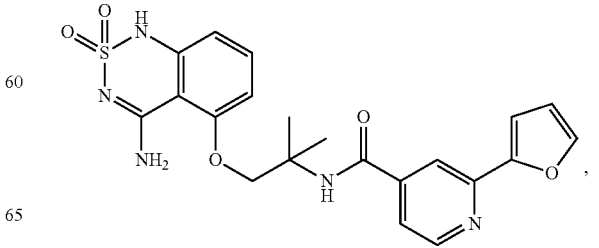

-continued
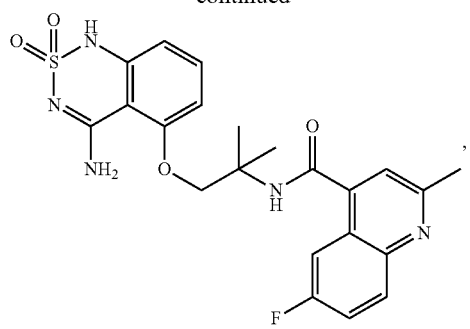
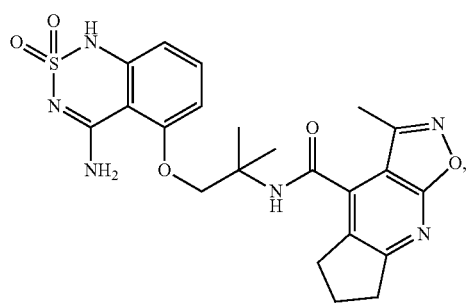
and
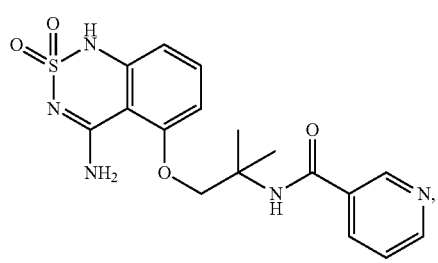
or a salt or solvate thereof.
20. The compound of claim 5, which is selected from the group consisting of
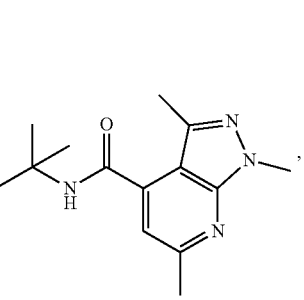
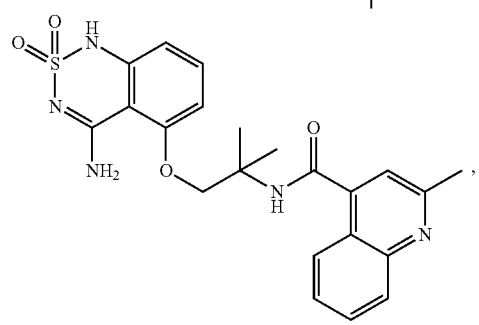
-continued
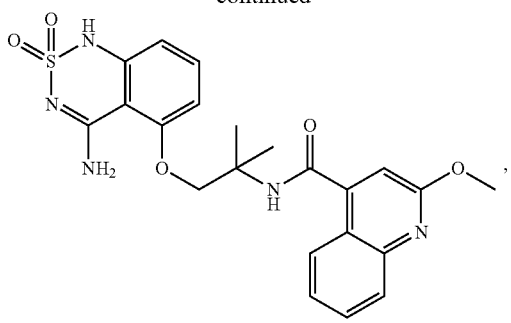
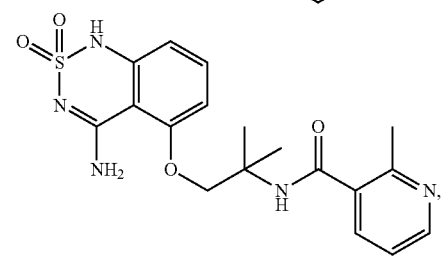
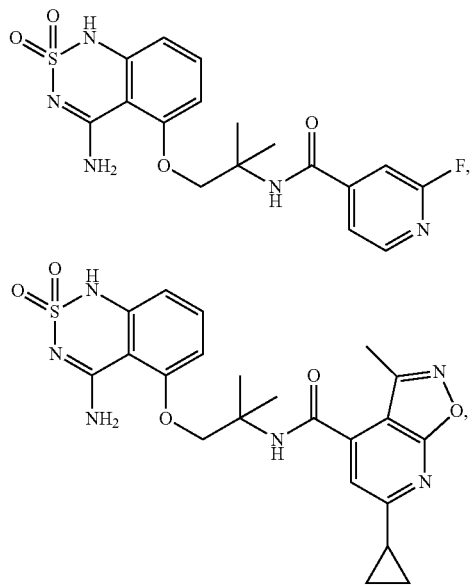
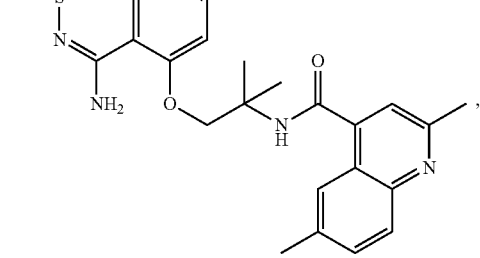
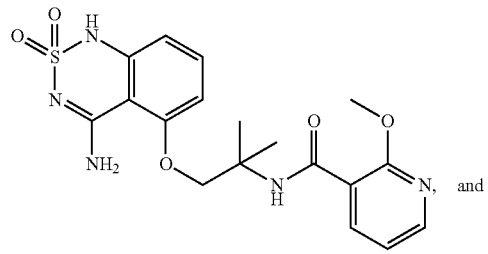
and

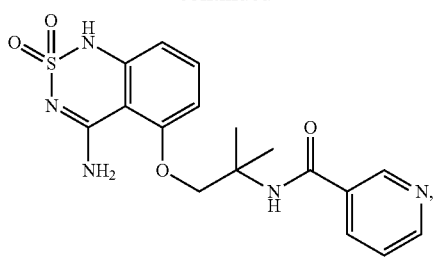
or a salt or solvate thereof.
21. The compound of claim 5, which is selected from the group consisting of
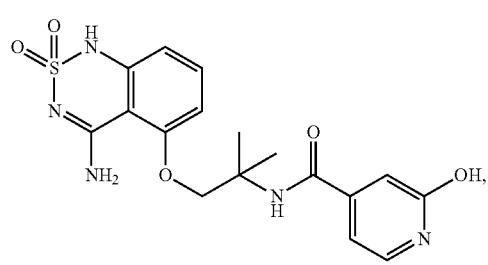
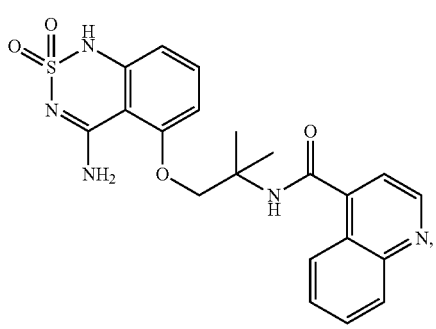
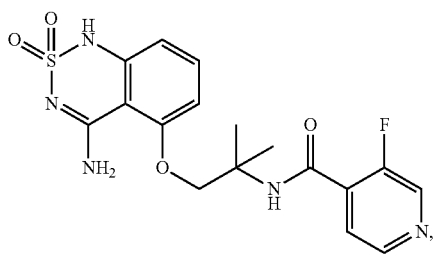
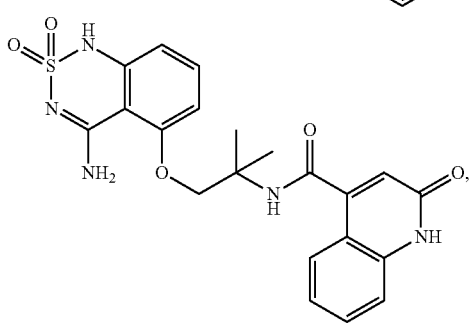
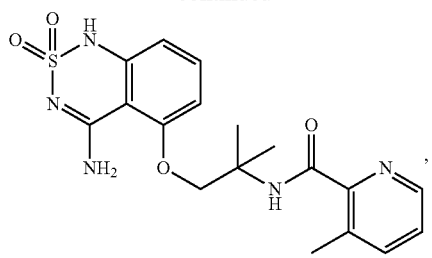
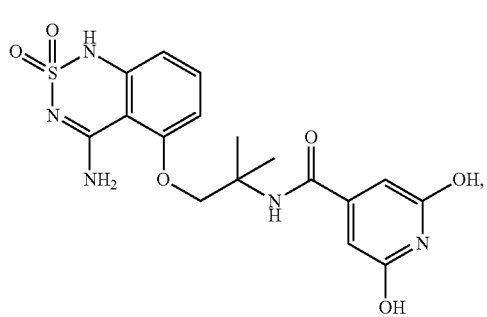
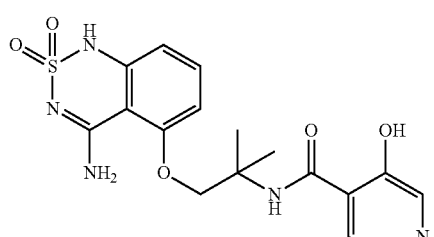
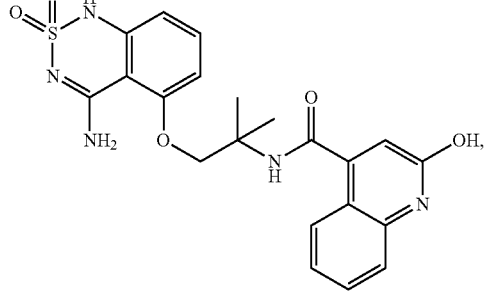
and
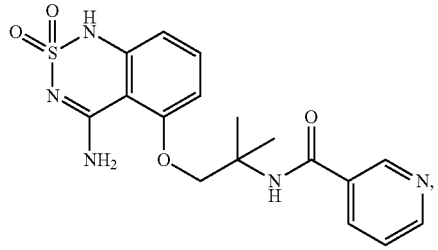 [SMILES: CC(C)(COc1cccc2c1C(N)=NS(=O)(=O)N2)NC(=O)c1cccnc1]
or a salt or solvate thereof.
22. The compound of claim 5, which is selected from the group consisting of

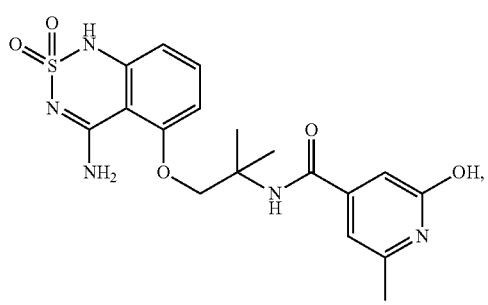
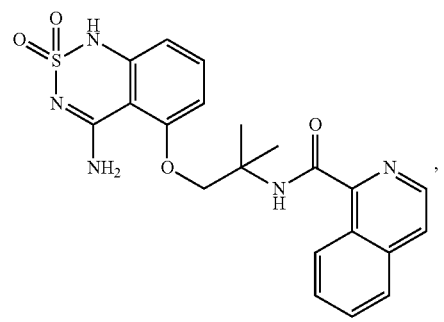
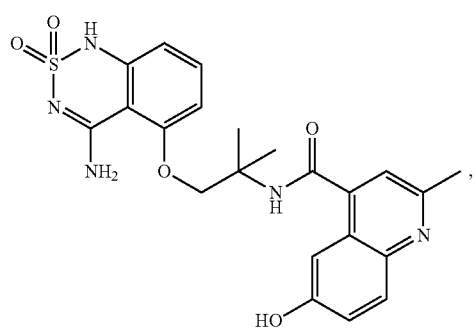
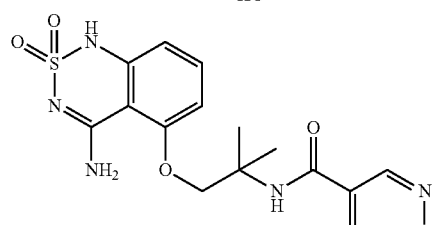
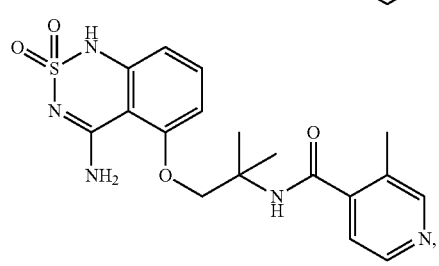
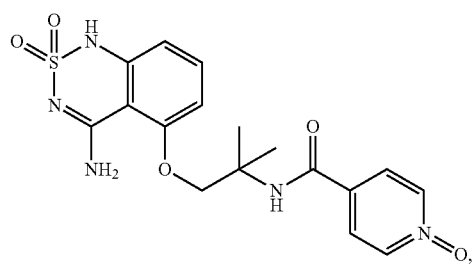
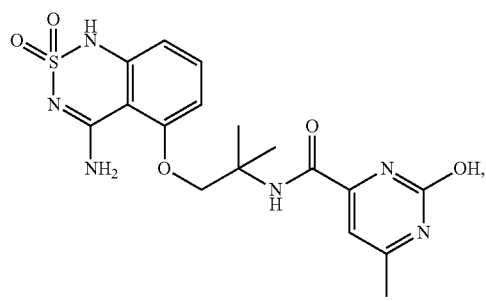
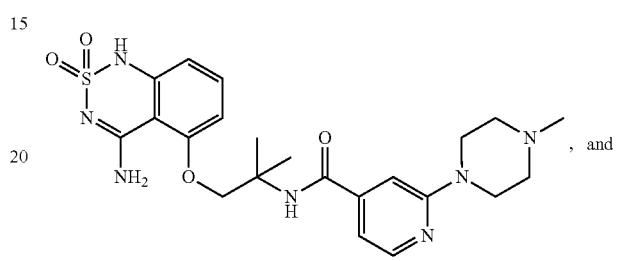
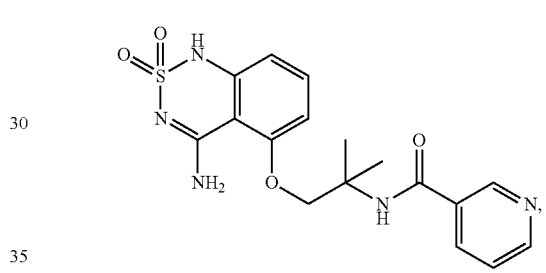
or a salt or solvate thereof.
23. The compound of claim 5, which is selected from the group consisting of
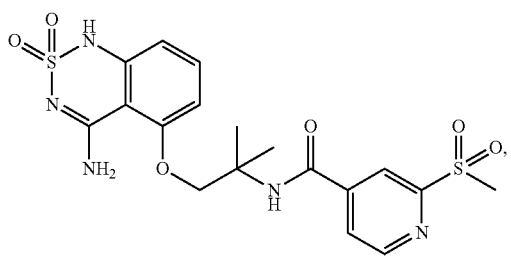
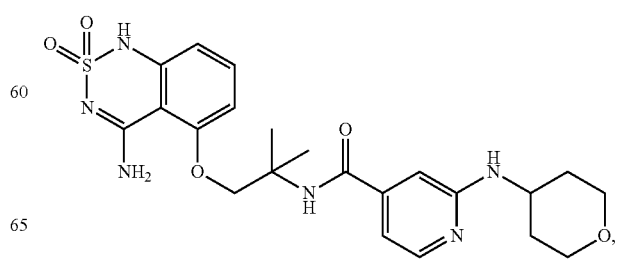

-continued
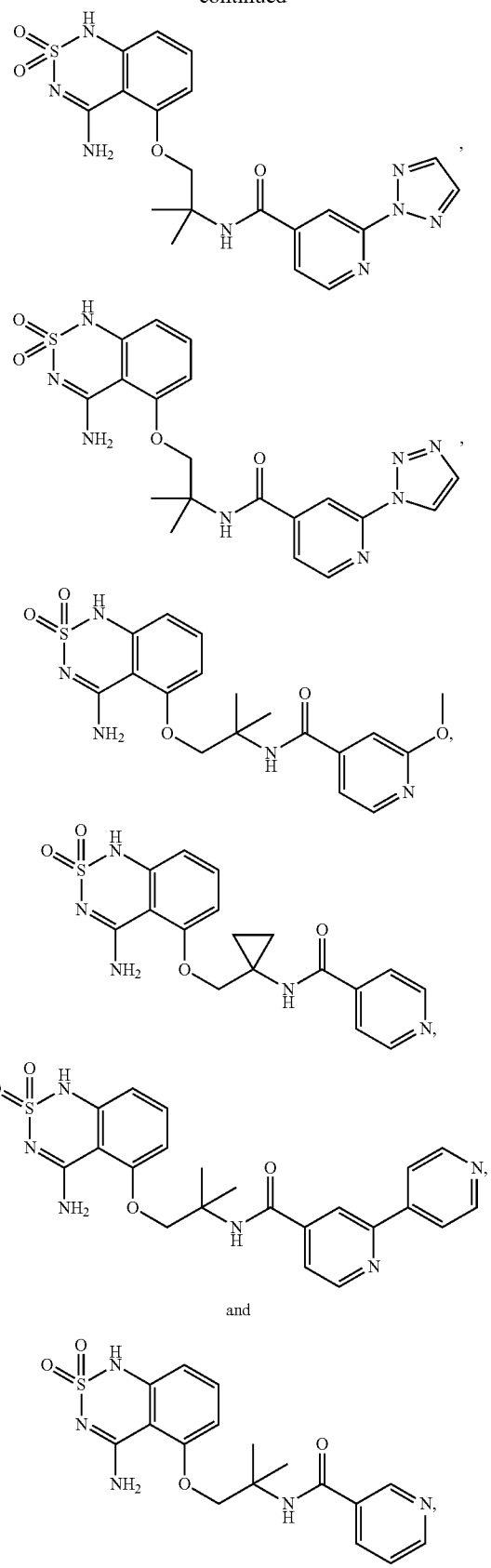
or a salt or solvate thereof.
24. The compound of claim 5, which is selected from the group consisting of
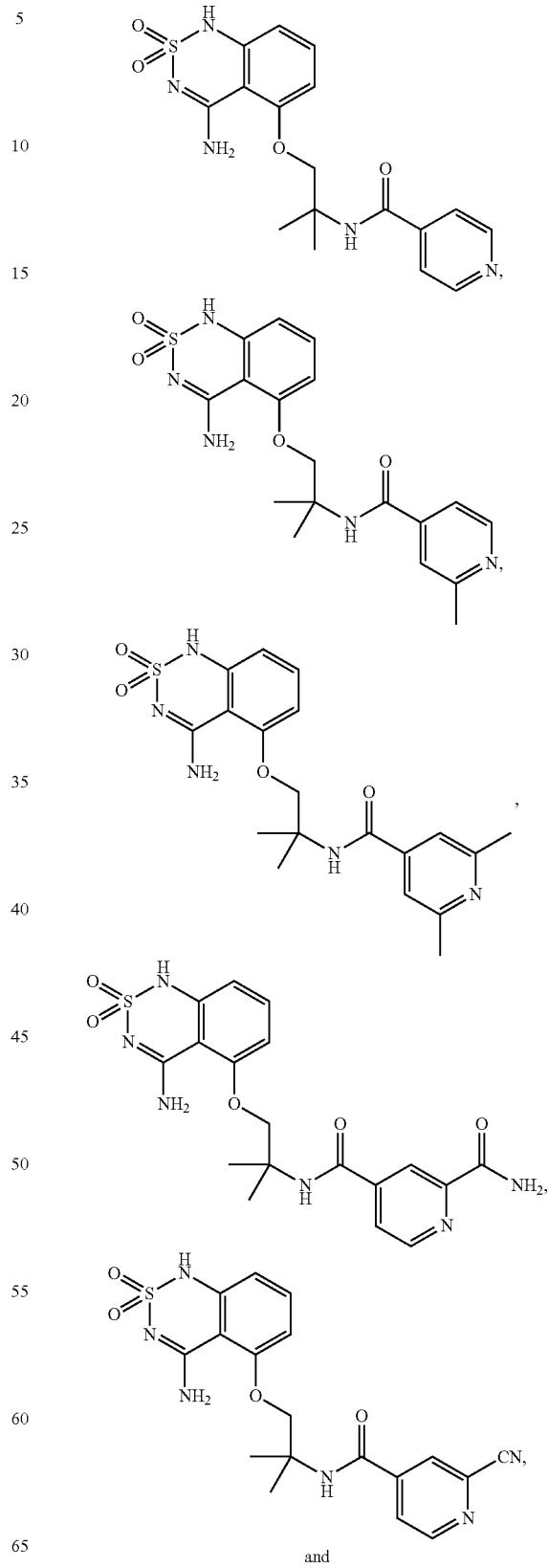
and -continued

[chemical structure]

or a salt or solvate thereof.

25. The compound of claim 5, which is selected from the group consisting of

[chemical structures]

and

-continued

[chemical structure]

or a salt or solvate thereof.

26. The compound of claim 5, which is selected from the group consisting of

[chemical structures]

and

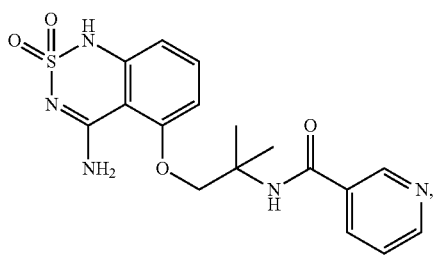
or a salt or solvate thereof.
27. The compound of claim 5, which is selected from the group consisting of
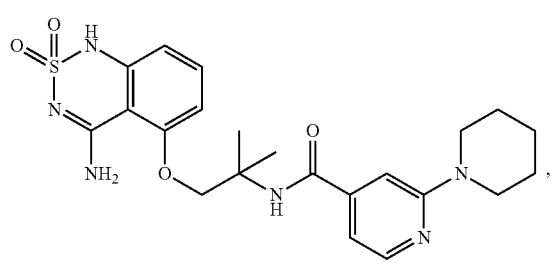
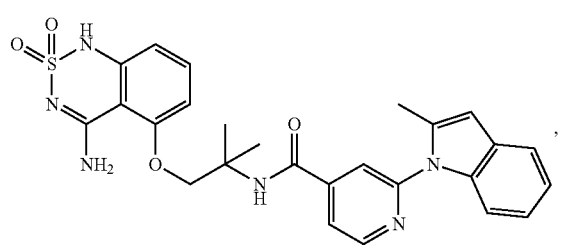
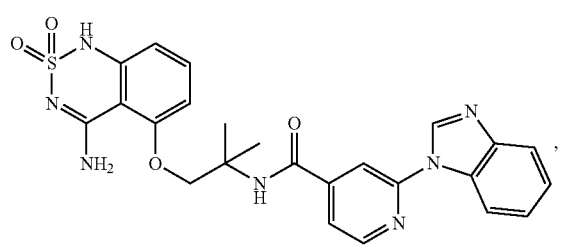
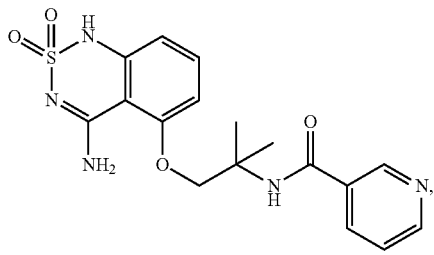
and
28. The compound of claim 5, which is selected from the group consisting of
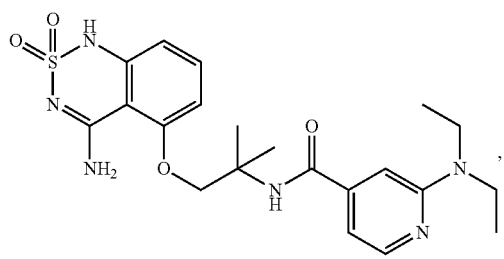
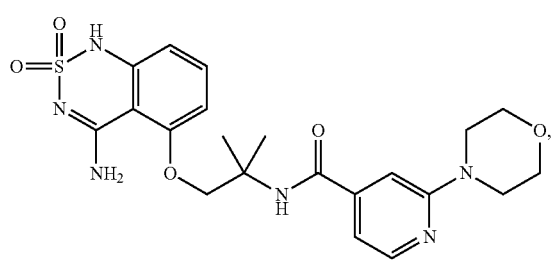
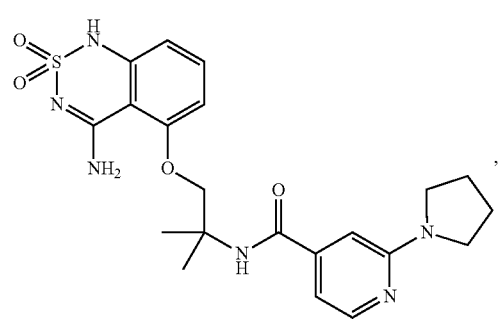
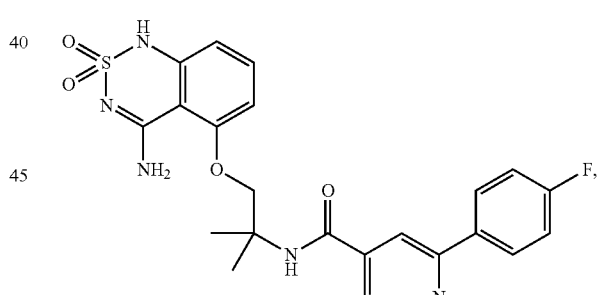
and
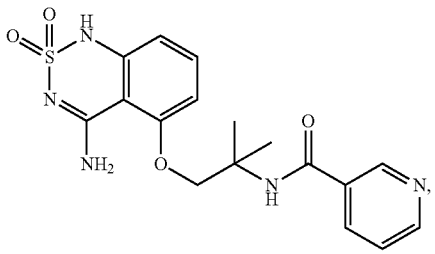 [SMILES: CC(C)(COc1cccc2c1C(N)=NS(=O)(=O)N2)NC(=O)c1cccnc1]
or a salt or solvate thereof.
29. The compound of claim 5, which is selected from the group consisting of

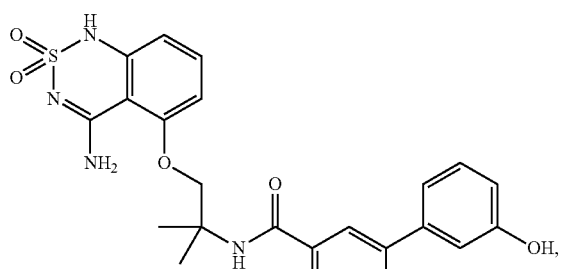
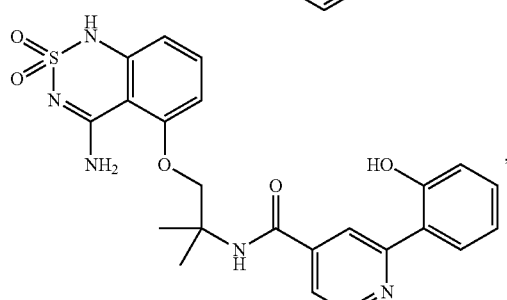
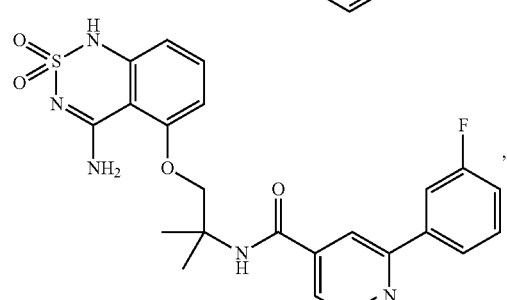
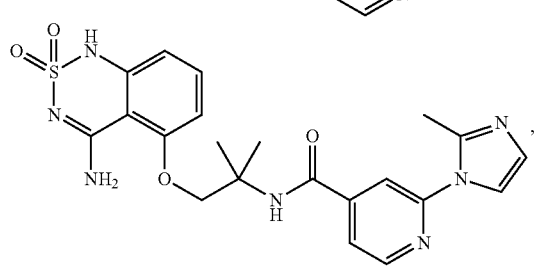
and
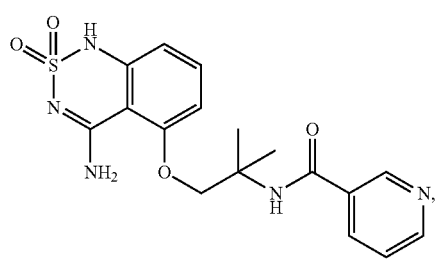
or a salt or solvate thereof.
30. The compound of claim 5, which is selected from the group consisting of
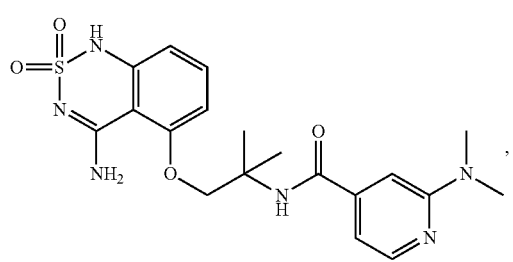
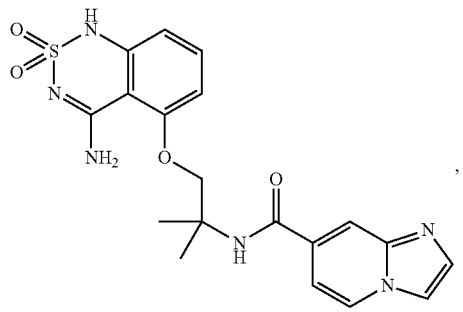
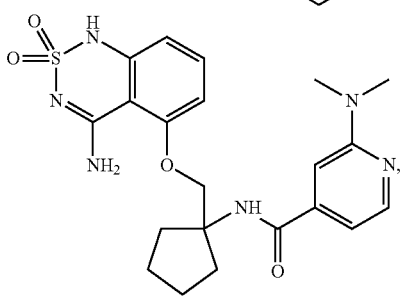
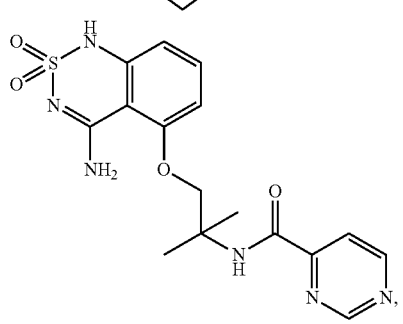
and
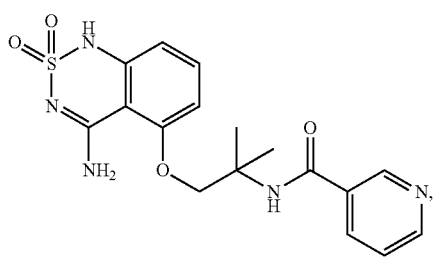
or a salt or solvate thereof.
\* \* \* \* \*